US009920097B2

(12) United States Patent
Zhong et al.

(10) Patent No.: US 9,920,097 B2
(45) Date of Patent: *Mar. 20, 2018

(54) CAPSID-MODIFIED RAAV VECTOR COMPOSITIONS HAVING IMPROVED TRANSDUCTION EFFICIENCIES, AND METHODS OF USE

(71) Applicant: University of Florida Research Foundation, Inc., Gainesville, FL (US)

(72) Inventors: Li Zhong, Gainesville, FL (US); Sergei Zolotukhin, Gainesville, FL (US); Lakshmanan Govindasamy, Gainesville, FL (US); Mavis Agbandje-McKenna, Gainesville, FL (US); Arun Srivastava, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 726 days.

This patent is subject to a terminal disclaimer.

(21) Appl. No.: 13/899,481

(22) Filed: May 21, 2013

(65) Prior Publication Data

US 2014/0050701 A1    Feb. 20, 2014

Related U.S. Application Data

(63) Continuation-in-part of application No. 12/595,196, filed as application No. PCT/US2008/059647 on Apr. 8, 2008, now Pat. No. 8,445,267.

(60) Provisional application No. 60/910,798, filed on Apr. 9, 2007.

(51) Int. Cl.
*C07K 14/005* (2006.01)
*C12N 15/86* (2006.01)
*A61K 48/00* (2006.01)

(52) U.S. Cl.
CPC ........ *C07K 14/005* (2013.01); *A61K 48/0008* (2013.01); *C12N 15/86* (2013.01); *C12N 2750/14122* (2013.01); *C12N 2750/14145* (2013.01); *C12N 2750/14171* (2013.01); *C12N 2810/6027* (2013.01)

(58) Field of Classification Search
None
See application file for complete search history.

(56) References Cited

U.S. PATENT DOCUMENTS

| 6,156,303 | A  | 12/2000 | Russell et al. |
| 7,052,692 | B1 | 5/2006 | Srivastava et al. |
| 8,445,267 | B2 | 5/2013 | Zhong et al. |
| 8,802,440 | B2 | 8/2014 | Zhong et al. |
| 9,157,098 | B2 | 10/2015 | Zhong et al. |
| 9,611,302 | B2 | 4/2017 | Srivastava et al. |
| 2003/0219733 | A1 | 11/2003 | Clark et al. |
| 2006/0292117 | A1 | 12/2006 | Loiler et al. |
| 2010/0104561 | A1 | 4/2010 | Zhong et al. |
| 2013/0203841 | A1 | 8/2013 | Zhong et al. |
| 2013/0216501 | A1 | 8/2013 | Zhong et al. |
| 2013/0224836 | A1 | 8/2013 | Muramatsu |
| 2013/0310443 | A1 | 11/2013 | Srivastava et al. |
| 2014/0341852 | A1 | 11/2014 | Srivastava et al. |
| 2015/0133530 | A1 | 5/2015 | Srivastava et al. |
| 2016/0106865 | A1 | 4/2016 | Zhong et al. |
| 2016/0333372 | A1 | 11/2016 | Srivastava et al. |

FOREIGN PATENT DOCUMENTS

| EP | 1310571 A2 | 5/2003 |
| WO | 03/006616 A2 | 1/2003 |
| WO | WO 03/052052 A2 | 6/2003 |
| WO | WO 2004/027019 A2 | 4/2004 |
| WO | WO 2004/111248 A2 | 12/2004 |
| WO | WO 2006/110689 A2 | 10/2006 |
| WO | WO 2006/119150 A2 | 11/2006 |
| WO | WO 2008/145400 A2 | 12/2008 |
| WO | WO 2012/057363 A2 | 5/2012 |

OTHER PUBLICATIONS

International Preliminary Report on Patentability of the International Bureau of WIPO dated Oct. 13, 2009, and Written Opinion of the International Searching Authority issued in priority application PCT/US2008/059647.
EP Examination Report dated Jan. 27, 2011, issued in EP 08733161.7-2405 (3 pages).
Response to EP Examination Report dated Jul. 25, 2011, issued in EP 08733161.7-2405 (8 pages).
Le Meur, G. et al., "Restoration of vision in RPE65-deficient Briard dogs using an AAV serotype 4 vector that specifically targets the retinal pigmented epithelium," Gene Therapy 14(4):292-303 (Feb. 2007), 12 pages.
Zhong, Li et al., "Evaluation of Primitive Murine Hematopoietic Stem and Progenitor Cell Transduction In Vitro and In Vivo by Recombinant Adeno-Associated Virus Vector Serotypes 1 Through 5," Human Gene Therapy 17(3):321-333 (Mar. 2006), 13 pages.

(Continued)

*Primary Examiner* — Nancy A Treptow
(74) *Attorney, Agent, or Firm* — Wolf, Greenfield & Sacks, P.C.

(57) ABSTRACT

Disclosed are capsid-modified rAAV expression vectors, as well as infectious virions, compositions, and pharmaceutical formulations that include them. Also disclosed are methods of preparing and using novel capsid-protein-mutated rAAV vector constructs in a variety of diagnostic and therapeutic applications including, inter alia, as delivery agents for diagnosis, treatment, or amelioration of one or more symptoms of disease or abnormal conditions via in situ and/or ex vivo mammalian gene therapy methods. Also disclosed are large-scale production methods for capsid-modified rAAV expression vectors, viral particles, and infectious virions having improved transduction efficiencies over those of the corresponding, un-modified, rAAV vectors, as well as use of the disclosed compositions in the manufacture of medicaments for a variety of in vitro and/or in vivo applications.

10 Claims, 54 Drawing Sheets

(56) References Cited

OTHER PUBLICATIONS

Yan, Ziying et al. "Ubiquitination of both Adeno-Associated Virus Type 2 and 5 Capsid Proteins Affects the Transduction Efficiency of Recombinant Vectors," Journal of Virology 76(5):2043-2053 (Mar. 2002), 11 pages.
Lochrie, Michael A. et al., "Mutations on the External Surfaces of Adeno-Associated Virus Type 2 Capsids That Affect Transduction and Neutralization," Journal of Virology 80(2):821-834 (Jan. 2006), 14 pages.
Zhong, Li et al., "A Dual Role of EGFR Protein Tyrosine Kinase Signaling in Ubiquitination of AAV2 Capsids and Viral Second-strand DNA Synthesis," The American Society of Gene Therapy, Molecular Therapy 15(7):1323-1330 (Jul. 2007), 8 pages.
Zhong, Li et al., "Next generation of adeno-associated virus 2 vectors: Point mutations in tyrosines lead to high-efficiency transduction at lower doses," Proceedings of the National Academy of Sciences of the United States of America 105(22):7827-7832 (Jun. 2008), 7 pages.
International Search Report and Written Opinion of the International Searching Authority dated Sep. 10, 2008, issued in International Application No. PCT/US2008/059647, 20 pages.
Dalkara, D., et al., "Enhanced Gene Delivery to the Neonatal Retina Through Systemic Administration of Tyrosine-Mutated AAV9," © 2012 Macmillan Publishers Limited (0969-7128/12), www.nature.com/gt, Gene Therapy (2012) 19, pp. 176-181.
Doroudchi, M. Mehdi, et al., "Virally Delivered Channelrhodopsin-2 Safely and Effectively Restores Visual Function in Multiple Mouse Models of Blindness," © The American Society of Gene & Cell Therapy, www.moleculartherapy.org, vol. 19, No. 7, Jul. 2011, pp. 1220-1229.
Horowitz, Eric D., et al., "Tyrosine Cross-Linking Reveals Interfacial Dynamics in Adeno-Associated Viral Capsids During Infection," ACS Chemical Biology, pubs.acs.org/acschemicalbiology, ACS Publications, © American Chemical Society, dx.doi.org/10.1021/cb3000265, Mar. 29, 2012, pp. A-H.
Kauss, M. Ariel, et al., "Enhanced Long-Term Transduction and Multilineage Engraftment of Human Hematopoietic Stem Cells Transduced With Tyrosine-Modified Recombinant Adeno-Associated Virus Serotype 2," Human Gene Therapy 21:1129-1136 (Sep. 2010), © Mary Ann Liebert, Inc., doi: 10.1089/hum.2010.016, pp. 1129-1136.
Ku, Cristy A., et al., "Gene Therapy Using Self-Complementary T733F Capsid Mutant AAV2/8 Restores Vision in a Model of Early Onset Leber Congenital Amaurosis," © The Author 2011, Published by Oxford University Press, Human Molecular Genetics, 2011, doi: 10.1093/hmg/ddr391, pp. 1-13.
Locke, Michelle, et al., "Transduction of Human Adipose-Derived Mesenchymal Stem Cells by Recombinant Adeno-Associated Virus Vectors," © Mary Ann Liebert, Inc., DOI: 10.1089/ten.tec.2011.0153, Tissue Engineering: Part C; vol. 17, No. 9, 2011, pp. 949-959.
Pang, Ji-Jing, et al., "Long-Term Retinal Function and Structure Rescue Using Capsid Mutant AAV8 Vector in the rd10 Mouse, a Model or Recessive Retinitis Pigmentosa," © The American Society of Gene & Cell Therapy, Molecular Therapy, pp. 1-9.
Petrs-Silva, Hilda, et al., "High-Efficiency Transduction of the Mouse Retina by Tyrosine-Mutant AAV Serotype Vectors" © The American Society of Gene & Cell Therapy, www.moleculartherapy.org, Molecular Therapy, vol. 17, No. 3, pp. 463-471, Mar. 2009.
Petrs-Silva, Hilda, et al., "Novel Properties of Tyrosine-Mutant AAV2 Vectors in the Mouse Retina," © The American Society of Gene & Cell Therapy, Molecular Therapy, www.moleculartherapy.org, pp. 1-9.
Qi, YanFei, et al., "Comparison of Transduction Efficiency of Tyrosine-Mutant AAV Serotype Vectors in Kidney," © 2012 The Authors Clinical and Experimental Pharmacology and Physiology, © 2012 Wiley Publishing Asia Pty Ltd., doi: 10.1111/1440-1681.12037, 8 pages.

Qiao, Chunping, et al., "Adeno-Associated Virus Serotype 6 Capsid Tyrosine-to-Phenylalanine Mutations Improve Gene Transfer to Skeletal Muscle," Human Gene Therapy 21:1343-1348 (Oct. 2010), © Mary Ann Liebert, Inc., doi: 10.1089/hum.2010.003, pp. 1343-1348.
Qiao, Chunping, et al., "Single Tyrosine Mutation in AAV8 and AAV9 Capsids Is Insufficient to Enhance Gene Delivery to Skeletal Muscle and Heart," Human Gene Therapy Methods: Part B 23:29-37 (Feb. 2012), © Mary Ann Liebert, Inc., doi: 10.1089/hgtb.2011.229, pp. 29-37.
Ruan, Qing, et al., "Development of an Anti-Angiogenic Therapeutic Model Combining scAAV2-delivered siRNAs and Noninvasive Photoacoustic Imaging of Tumor Vasculature Development," Cancer Lett. (2012), http://dx.doi.org/10.1016/j.canlet.2012.11.016, Dec. 4, 2012, 10 pages.
Ryals, Renee C., et al., "Quantifying Transduction Efficiencies of Unmodified and Tyrosine Capsid Mutant AAV Vectors in Vitro Using Two Ocular Cell Lines," Molecular Vision 2011; 17:1090-1102 (http://www.molvis.org/molvis/v17/a124), Apr. 29, 2011, pp. 1090-1102.
Shin, Jin-Hong, et al., "A Simplified Immune Suppression Scheme Leads to Persistent Micro-Dystrophin Expression in Duchenne Muscular Dystrophy Dogs," Human Gene Therapy 23:202-209 (Feb. 2012), © Mary Ann Libert, Inc., doi: 10.1089/hum.2011.147, pp. 202-209.
Ussher, James E., et al., "Optimized Transduction of Human Monocyte-Derived Dendritic Cells by Recombinant Adeno-Associated Virus Serotype 6," Human Gene Therapy 21:1675-1686 (Dec. 2010), © Mary Ann Liebert, Inc., doi: 10.1089/hum.2010.078, pp. 1675-1686.
Aslanidi, George V. et al, "High-Efficiency Transduction of Human Monocyte-Derived Dendritic Cells by Capsid-Modified Recombinant AAV2 Vectors," Vaccine 30:3908-3917 (2012), © 2012 Elsevier Ltd., pp. 3908-3917.
Aslanidi, George V. et al, "Optimization of the Capsid of Recombinant Adeno-Associated Virus 2 (AAV2) Vectors: The Final Threshold?," PLoS ONE 8(3): e59142 (Mar. 2013), 12 pages.
Cheng, Binbin et al, "Development of Optimized AAV3 Serotype Vectors: Mechanism of High-Efficiency Transduction of Human Liver Cancer Cells," Gene Ther. Apr. 2012; 19(4): 375-384, 24 pages.
Jayandharan, Giridhara R. et al., "Activation of the NF-kB Pathway by Adeno-Associated Virus (AAV) Vectors and its Implications in Immune Response and Gene Therapy," PNAS, Mar. 1, 2011, vol. 108, No. 9, pp. 3743-3748.
Markusic, David M. et al., "High-Efficiency Transduction and Correction of Murine Hemophelia B Using AAV2 Vectors Devoid of Multiple Surface-Exposed Tyrosines," Molecular Therapy (Dec. 2010), vol. 18, No. 12, pp. 2048-2056.
Examination Report dated Oct. 22, 2013, issued in CIPO 2,720,097 (2 pages).
International Search Report and Written Opinion for Application No. PCT/US2013/041234 dated Feb. 13, 2014.
International Preliminary Report on Patentability for Application No. PCT/US2013/041234 dated Nov. 27, 2014.
International Search Report and Written Opinion for Application No. PCT/US2014/039015 dated Nov. 24, 2014.
Gabriel et al., Targeted Mutagenesis of Ubiquitin-Binding Lysine Residues on the Adeno-Associated Virus (AAV)2 Capsid Improves Its Transduction Efficiency. Mol Ther. 2012;20(Supp 1):S146.
Kay et al., Targeting photoreceptors via intravitreal delivery using novel, capsid-mutated AAV vectors. PLoS One. Apr. 26, 2013;8(4):e62097. doi: 10.1371/journal.pone.0062097. Print 2013.
Kern et al., Identification of a heparin-binding motif on adeno-associated virus type 2 capsids. J Virol. Oct. 2003;77(20):11072-81.
Li et al., Site-Directed Mutagenesis of Surface-Exposed Lysine Residues Leads To Improved Transduction By Recombinant Aav2 and Aav8 Vectors in Murine Hepatocytes in Vivo. Mol Ther. 2013;21(Supp 1):S208-9.
Ling et al, Selective in vivo targeting of human liver tumors by optimized AAV3 vectors in a murine xenograft model. Hum Gene Ther. Dec. 2014;25(12):1023-34. doi: 10.1089/hum.2014.099.

(56) References Cited

OTHER PUBLICATIONS

Opie et al., Identification of amino acid residues in the capsid proteins of adeno-associated virus type 2 that contribute to heparan sulfate proteoglycan binding. J Virol. Jun. 2003;77(12):6995-7006.
Pandya et al., Rationally designed capsid and transgene cassette of AAV6 vectors for dendritic cell-based cancer immunotherapy. Immunol Cell Biol. Feb. 2014;92(2):116-23. doi: 10.1038/icb.2013.74. Epub Nov. 12, 2013.
Song et al., High-efficiency transduction of primary human hematopoietic stem cells and erythroid lineage-restricted expression by optimized AAV6 serotype vectors in vitro and in a murine xenograft model in vivo. PLoS One. 2013;8(3):e58757. doi: 10.1371/journal.pone.0058757. Epub Mar. 14, 2013.
U.S. Appl. No. 13/855,640, filed Apr. 2, 2013, Zhong et al.
U.S. Appl. No. 13/840,224, filed Mar. 15, 2013, Srivastava et al.
U.S. Appl. No. 14/401,442, filed Nov. 14, 2014, Srivastava et al.
U.S. Appl. No. 14/214,011, filed Mar. 14, 2014, Srivastava et al.
U.S. Appl. No. 14/847,528, filed Sep. 8, 2015, Zhong et al.
International Preliminary Report on Patentability for Application No. PCT/US2014/039015 dated Dec. 3, 2015.
Chiorini et al., Capsid Protein [Adeno-associated virus -5] Genbank Accession No. YP-068409 Dec. 8, 2008.
Schaffer et al., GenBank Submission: ADW24587. Apr. 7, 2005.
Vandenberghe et al., Naturally occurring singleton residues in AAV capsid impact performance and illustrate structural constraints. Submitted 2007. EMBL/GenBank/DDBJ databases. Accession No. B4Y882_9VIRU.
Aslanidi et al., Abstract C240: Modification on the capsid of recombinant adeno-associated virus vectors (rAAV) leads to high-efficiency transduction of human monocyte-derived dendritic cells (moDCs). Mol Cancer Ther. Nov. 10, 2011(11): Abstract C240. 3 pages.
Bantel-Schaal et al., Human adeno-associated virus type 5 is only distantly related to other known primate helper-dependent parvoviruses. J Virol. Feb. 1999;73(2):939-47.
Vandenberghe et al., B4Y882_9VIRU sequence alignment, Submitted Sep. 23, 2008.

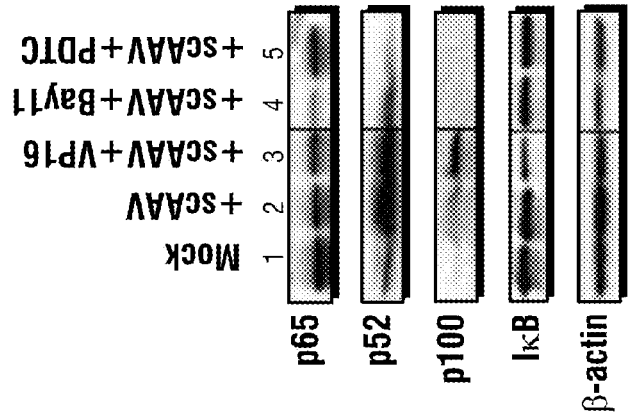
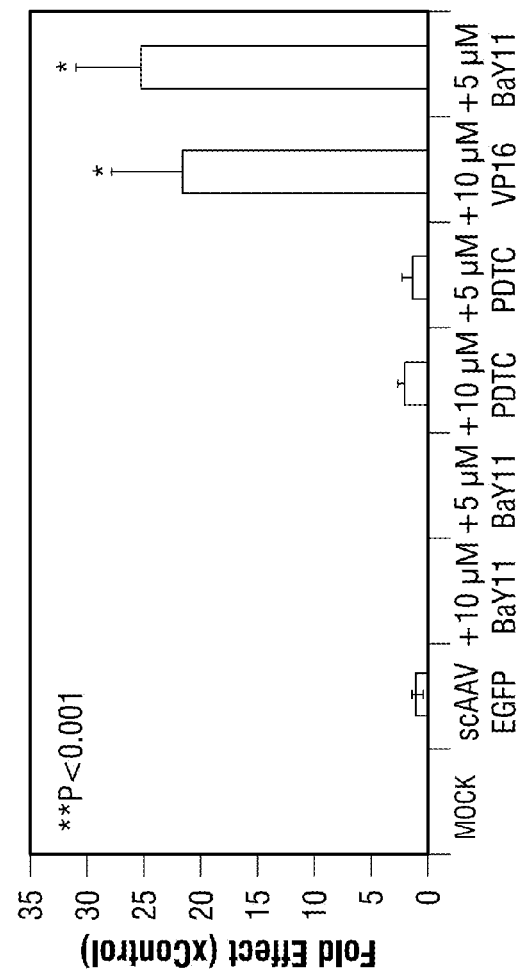
FIG. 1A
FIG. 1B
FIG. 1C

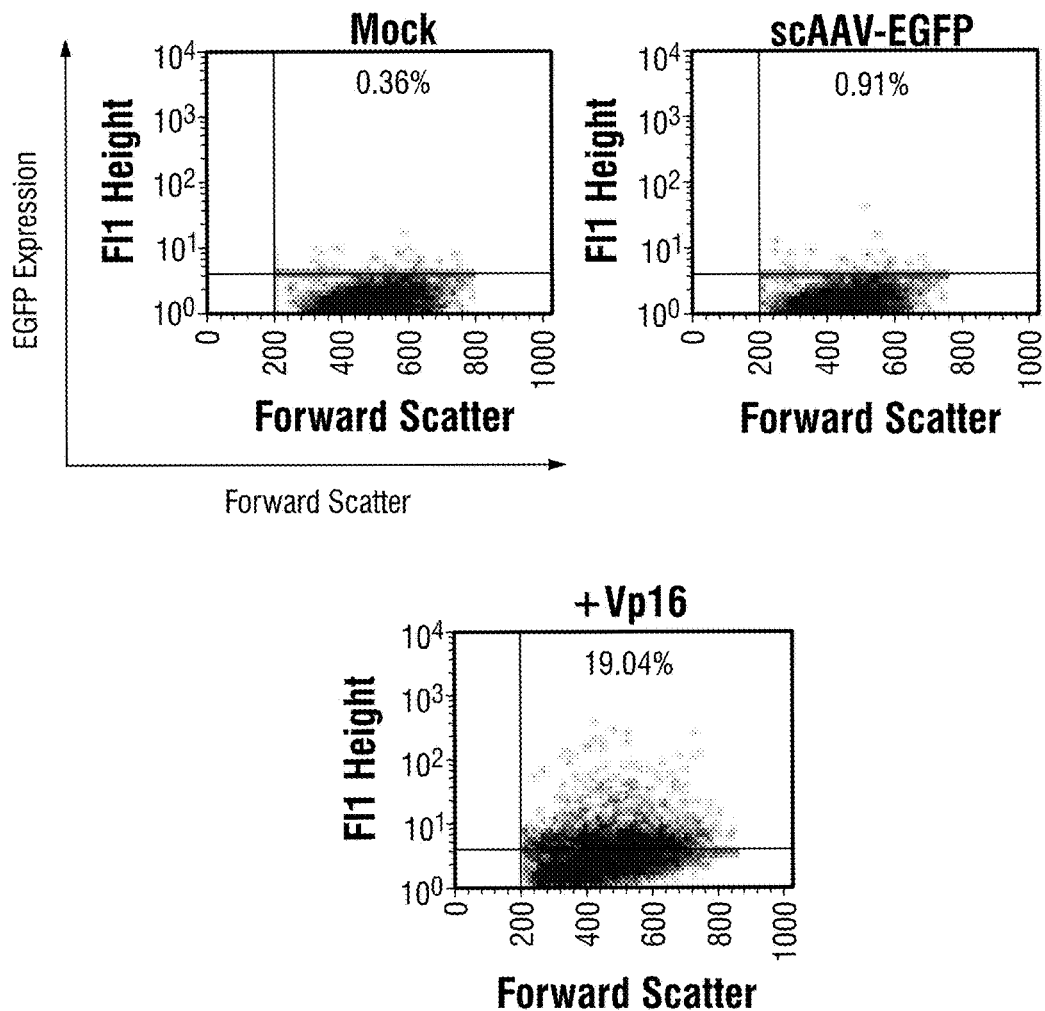
FIG. 2A
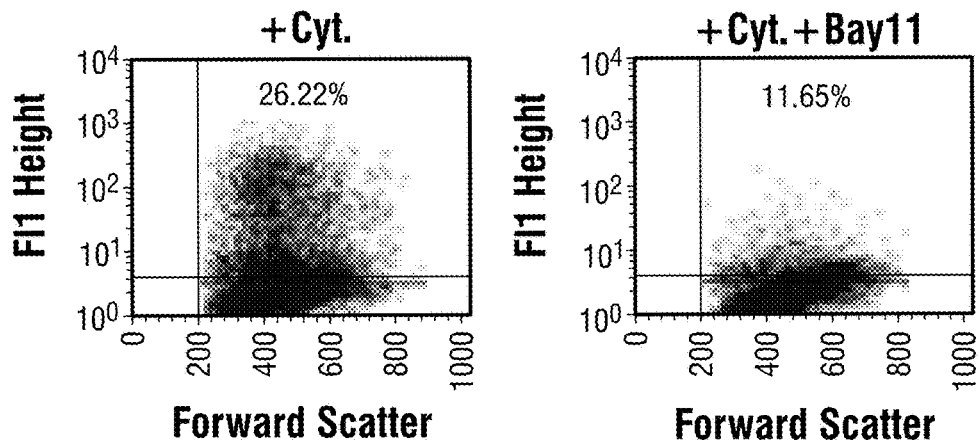

1
AGGAACCCCTAGTGATGGAGTTGGCCACTCCCTCTCTGCCCGCTCGGCTCGCTCACTGAGGCCGGGCGACCAAAG
D-SEQUENCE

75
GTCGGCCCGACGCCCGGGCTTTGCCCGGGGGCCCTCAGTGAGCGAGCGAGCGCGCAGAGAGGGAGTGGCCAA
                                                       125              145

| Transcription factor | No. of binding sites |
|---|---|
| p300 | 4 |
| TFIIB | 4 |
| SpII | 1 |

FIG. 5

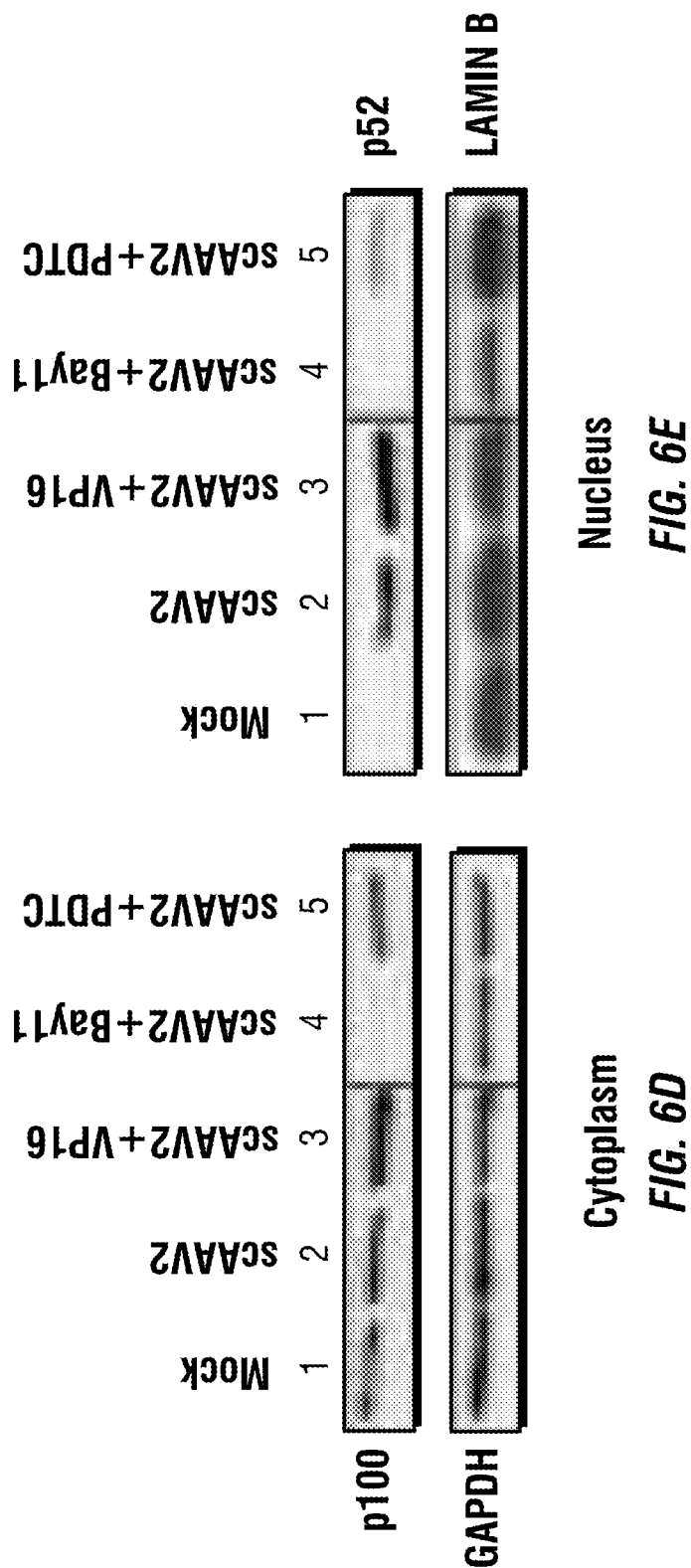

| Strand | Sequence |
|---|---|
| ssD[-]: | 5'-CTC CA TCACTA G GGGT TCCT-3' |
| dsD[±]: | 5'-CTC CA TCACTA G GGGT TCCT-3'<br>3'-GAGG TAGT GAT CCC AAGGA-5' |
| ssD[+]: | 5'-GAGGTA GTGAT CC CCAAGGA-3' |

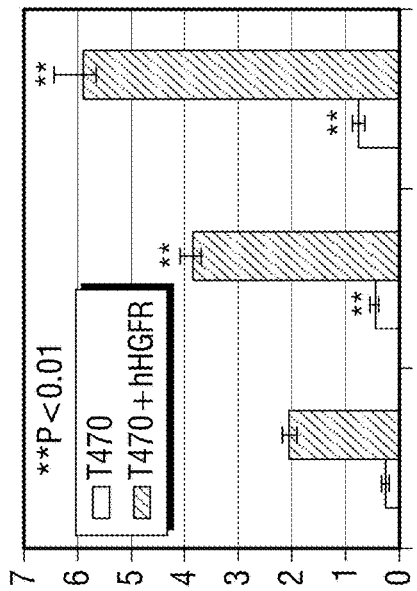
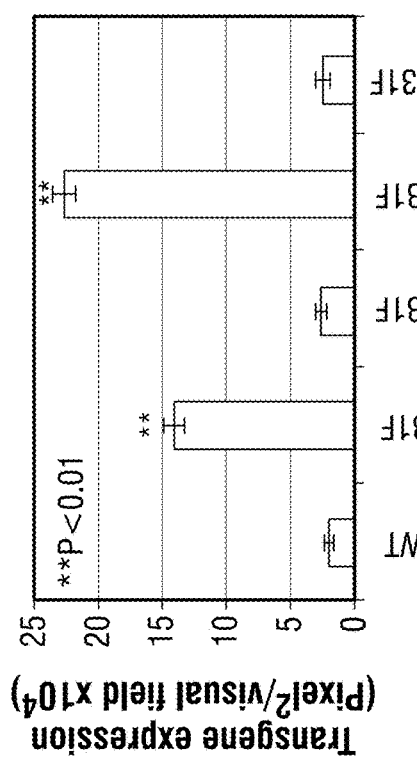
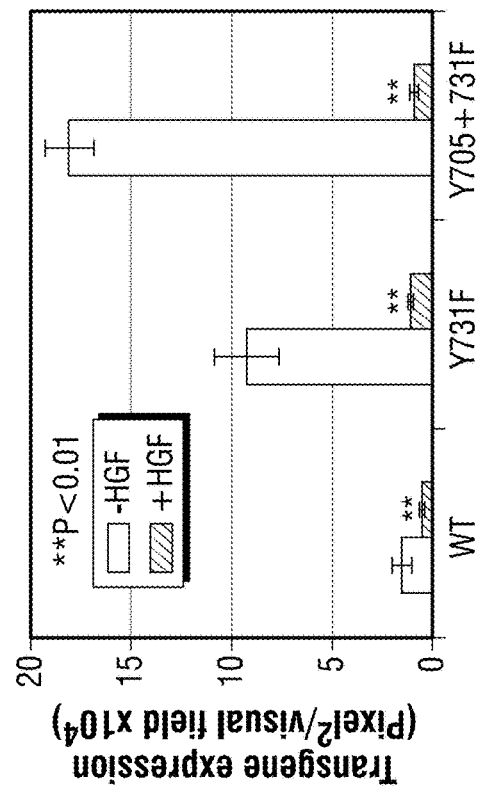
FIG. 16A
FIG. 16B
FIG. 16C

Huh7 Tumors

Hep293TT Tumors

WT-AAV3

Y705+731F-AAV3

Color Key
- S458
- S492
- S662
- DE Loop(aa319-333) ⎫
- HI Loop(aa651-670) ⎬ PANEL B WT 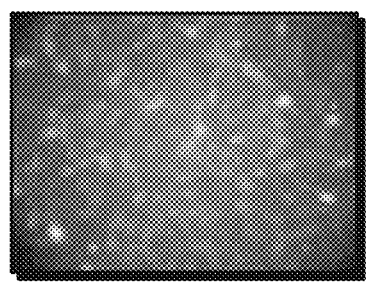 T455V 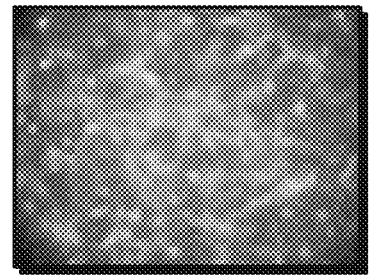
T491V 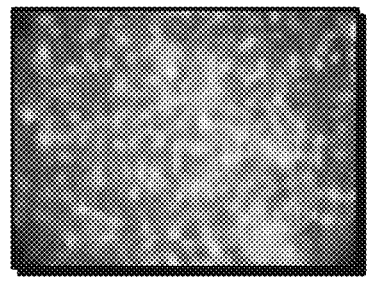
T550V 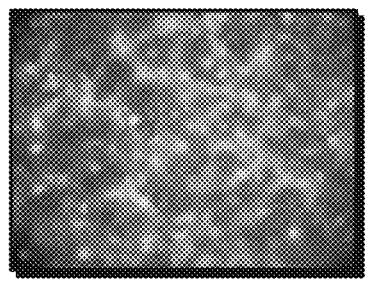 T659V 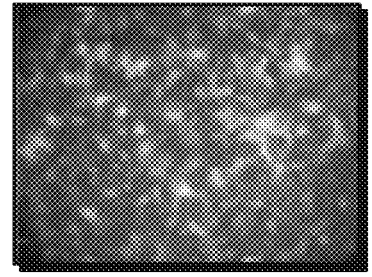
*FIG. 26A*

WT 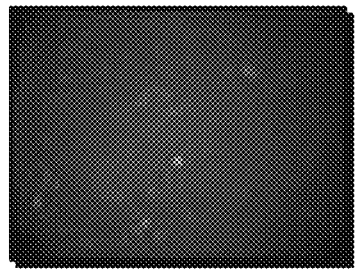
Y444+500+730F 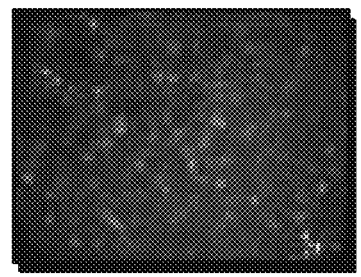
Y444+500+
730F+T491V 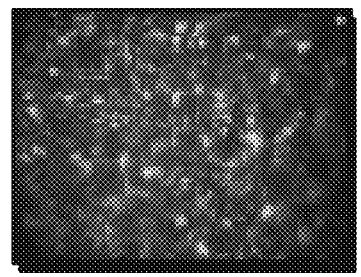
Y444+500+730F+S662V 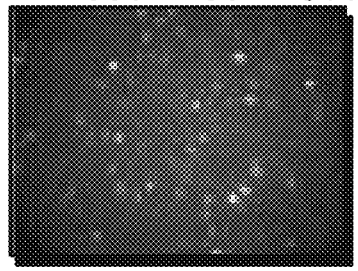
Y444+500+730F
T491V+S662V 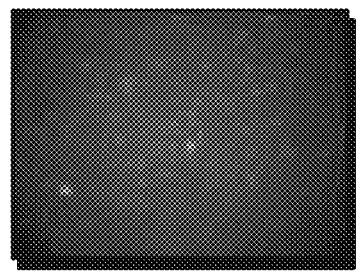
FIG. 28A

Serine and Threonine residue alignment in AAV serotype capsids

```
CAPSID                                                                                                         100
AAV1   (1)  MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF
AAV2   (1)  MAADGYLPDWLEDTLSEGIRQWWKLKPGPPPKPAERHKDESRGLVLPGYKYLGPFNGLDKGEPVNEADAAALEHDKAYDRQLDSGDNPYLKYNHADAEF
AAV3   (1)  MAADGYLPDWLEDNLSEGIREWWALKPGAPKPKANQQHQDNARGLVLPGYKYLGPGNGLDKGEPVNEADAAALEHDKAYDQQLKAGDNPYLKYNHADAEF
AAV4   (1)  -MTDGYLPDWLEDNLSEGIREWWDLKPGAPKPKANQQHQDNARGLVLPGYKYLGPGNGLDKGEPVNAADAAALEHDKAYDQQLKAGDNPYLKYNHADAEF
AAV5   (1)  MSFVDHPPDWLEEVG-EGLREFLGLEAGPPKPKPNQQHQDQARGLVLPGYNYLGPGNGLDRGEPVNRADEVAREHDISYNEQLEAGDNPYLKYNHADAEF
AAV6   (1)  MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF
AAV7   (1)  MAADGYLPDWLEDNLSEGIREWWDLKPGAPKPKANQQKQDNQRGLVLPGYKYLGPFNGLDKGEPVNAADAAALEHDKAYDQQLKAGDNPYLRYNHADAEF
AAV8   (1)  MAADGYLPDWLEDNLSEGIREWWALKPGAPKPKANQQKQDDGRGLVLPGYKYLGPFNGLDKGEPVNAADAAALEHDKAYDQQLQAGDNPYLRYNHADAEF
AAV9   (1)  MAADGYLPDWLEDNLSEGIREWWALKPGAPQPKANQQHQDNARGLVLPGYKYLGPFNGLDKGEPVNAADAAALEHDKAYDQQLKAGDNPYLKYNHADAEF
AAV10  (1)  MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF

200
AAV1   (101) QERLQEDTSFGGNLGRAVFQAKKRVLEPLGLVEEGAKTAPGKKRPVEQSPQE-PDSSSGIGKTGQQPAKKRLNFGQTGDSESVPDPQPLGEPPATPAAVG
AAV2   (101) QERLKEDTSFGGNLGRAVFQAKKRVLEPLGLVEEPVKTAPGKKRPVEHSPVE-PDSSSGTGKAGQQPARKRLNFGQTGDSADSVPDPQPLGQPPAAPSGLG
AAV3   (101) QERLQEDTSFGGNLGRAVFQAKKRILEPLGLVEEAAKTAPGKKAPGKKRPVEHSPQE-PDSSSGVGKSEKQPARKRLNFGQTGDSESVPDPQPLGEPPAAPTSLG
AAV4   (100) QQRLQGDTSFGGNLGRAVFQAKKRVLEPLGLVEQAGETAPGKKRPLIESPQQ--PDSSTGIGKKKQPAKKKLVFEDETGAGDGP---PEGSTSGAMSDDS
AAV5   (100) QERLADDTSFGGNLGKAVFQAKKRVLEPFGLVEEGAKTAPGKKRPLEPFGLVEEGAKTAPGKKRPLEPF--------KKARTEEDSKPSTSSDAEAGPSGS-QOLQIPAQPASSLG
AAV6   (101) QERLQEDTSFGGNLGRAVFQAKKRVLEPLGLVEEGAKTAPGKKRPVEQSPQE-PDSSSGIGKTGQQPAKKRLNFGQTGDSESVPDPQPLGEPPATPAAVG
AAV7   (101) QERLQEDTSFGGNLGRAVFQAKKRVLEPLGLVEEGAKTAPAKKRPVEPSPQRSPDSSTGIGKKGQQPARKRLNFGQTGDSESVPDPQPLGEPPAAPSSVG
AAV8   (101) QERLQEDTSFGGNLGRAVFQAKKRVLEPLGLVEEGAKTAPGKKRPVEPSPQRSPDSSTGIGKKQQPAKKRLNFGQTGDSESVPDPQPLGEPPAAPSGVG
AAV9   (101) QERLKEDTSFGGNLGRAVFCQAKKRLLEPLGLVEEAAKTAPGKKRPVEQSPQE-PDSSAGIGKSGAQPAKKRLNFGQTGDTESVPDPQPIGEPPAAPSGVG
AAV10  (101) QERLQEDTSFGGNLGRAVFQAKKRVLEPLGLVEEGAKTAPGKKRPVEPSPQRSPDSSTGIGKKGQQPAKKRLNFGQTGDSESVPDPQPIGEPPAGPSGLG

300
AAV1   (200) PTTMASGGGAPMADNNEGADGVGNASGNWHCDSTWLGDRVITTSTRTWALPTYNNHLYKQISS-I-GASNDNHYFGYSTPWGYFDFNRFHCHFSPRDWQ
AAV2   (200) TNTMATGSGAPMADNNEGADGVGNSSGNWHCDSTWMGDRVITTSTRTWALPTYNNHLYKQISS-----GASNDNHYFGYSTPWGYFDFNRFHCHFSPRDWQ
AAV3   (200) SNTMASGGGAPMADNNEGADGVGNSSGNWHCDSTWLGDRVITTSTRTWALPTYNNHLYKQISS-S---GASNDNHYFGYSTPWGYFDFNRFHCHFSPRDWQ
AAV4   (196) EMRAAAGGAAVEGG--QGADGVGNASGDWHCDSTWSEGHVTTTSTRTWVLPTYNNHLYKRLGESLQ-----SNTYNGFSTPWGYFDFNRFHCHFSPRDWQ
AAV5   (190) ADTMSAGGGPLGDNNQGADGVGNASGDWHCDSTWMGDRVVTKSTRTWVLPSYNNHQYREIKS-S---VDGSNANAYFGYSTPWGYFDFNRFHSHWSPRDWQ
AAV6   (200) PTTMASGGGAPMADNNEGADGVGNASGNWHCDSTWLGDRVITTSTRTWALPTYNNHLYKQISS-I-GASNDNHYFGYSTPWGYFDFNRFHCHFSPRDWQ
AAV7   (201) SGTVAAGGGAPMADNNEGADGVGSSSGNWHCDSTWLGDRVITTSTRTWALPTYNNHLYKQISETAG-STNDNTYFGYSTPWGYFDFNRFHCHFSPRDWQ
AAV8   (201) PNTMAAGGGAPMADNNEGADGVGSSSGNWHCDSTWLGDRVITTSTRTWAIPTYNNHLYKQISNGTSGGATNDNTYFGYSTPWGYFDFNRFHCHFSPRDWQ
AAV9   (200) SLTMASGGGAPVADNNEGADGVGSSSGNWHCDSQWLGDRVITTSTRTWALPTYNNHLYKQISNSTSGGSSNDNAYFGYSTPWGYFDFNRFHCHFSPRDWQ
AAV10  (201) SGTMAAGGGAPMADNNEGADGVGSSSGNWHCDSTWLGDRVITTSTRTWALPTYNNHLYKQISNGTSGGSTNDNTYFGYSTPWGYFDFNRFHCHFSPRDWQ
```

```
           601         *                                                       ◇**  ◇   *           700
AAV1  (587) SSTDPATGDVHAMGALPGMVWQDRDVYLQGPIWAKIPHTDGHFHPSPLMGGFGLKNPPPQILIKNTPVPANPPAEFSATKFASFITQYSTGQVSVEIEWE
AAV2  (586) GNRQAATADVNTQGVLPGMVWQDRDVYLQGPIWAKIPHTDGHFHPSPLMGGFGLKHPPPQILIKNTPVPANPSTTFSAAKFASFITQYSTGQVSVEIEWE
AAV3  (587) SNTAPTTGTVNHQGALPGMVWQDRDVYLQGPIWAKIPHTDGHFHPSPLMGGFGLKHPPPQIMIKNTPVPANPPTTFSPAKFASFITQYSTGQVSVEIEWE
AAV4  (585) NSNLPTVDRLTALGAVPGMVWQNRDIYYQGPIWAKIPHTDGHFHPSPLIGGFGLKHPPPQIFIKNTPVPANPATTFSSTPVNSFITQYSTGQVSVQIDWE
AAV5  (576) STTAPATGTYNLQEIVPGSVWMERDVYLQGPIWAKIPETGAHFHPSPAMGGFGLKHPPPMMLIKNTPVPGN-ITSFSDVPVSSFITQYSTGQVTVEMEWE
AAV6  (587) SSTDPATGDVHVMCALPGMVWQDRDVYLQGPIWAKIPHTDGHFHPSPLMGGFGLKHPPPQILIKNTPVPANPPAEFSATKFASFITQYSTGQVSVEIEWE
AAV7  (588) ANTAAQTQVVNNQGALPGMVWQNRDVYLQGPIWAKIPHTDGNFHPSPLMGGFGLKHPPPQILIKNTPVPANPPEVFTPAKFASFITQYSTGQVSVEIEWE
AAV8  (589) QNTAPQIGTVNSQGALPGMVWQNQGILPGMVWQNRDVYLQGPIWAKIPHTDGNFHPSPLMGGFGLKHPPPQILIKNTPVPADPPTTFNQSKLNSFITQYSTGQVSVEIEWE
AAV9  (587) AQAQAQTGWVQNQGILPGMVWQNRDVYLQGPIWAKIPHTDGNFHPSPLMGGFGMKHPPPQILIKNTPVPADPPTAFNKDKLNSFITQYSTGQVSVEIEWE
AAV10 (589) QNAAPIVGAVNSQGALPGMVWQNRDVYLQGPIWAKIPHTDGNFHPSPLMGGFGLKHPPPQILIKNTPVPADPPTTFSQAKLASFITQYSTGQVSVEIEWE

701        *         *              ◇                               751
AAV1  (687) LQKENSKRWNPEIQYTSNYAKSANVDFTVDNNGLYTEPRPIGTRYLTRPL-  SEQ ID NO: 1
AAV2  (686) LQKENSKRWNPEIQYTSNYNKSVNVDFTVDTNGVYSEPRPIGTRYLTRNL-  SEQ ID NO: 2
AAV3  (687) LQKENSKRWNPEIQYTSNYNKSVNVDFTVDTNGVYSEPRPIGTRYLTRNL-  SEQ ID NO: 3
AAV4  (685) IQKERSKRWNPEVQFTSNYGQQNSLLWAPDAAGKYTEPRAIGTRYLTHHL-  SEQ ID NO: 4
AAV5  (675) LKKENSKRWNPEIQYTNNYNDPQFVDFAPDSTGEYRTTRPIGTRYLTRPL-  SEQ ID NO: 5
AAV6  (687) LQKENSKRWNPEVQYTSNYAKSANVDFTVDNNGLYTEPRPIGTRYLTRPL-  SEQ ID NO: 6
AAV7  (688) LQKENSKRWNPEIQYTSNFEKQTGVDFAVDSQGVSEPRPIGTRYLTRNL-   SEQ ID NO: 7
AAV8  (689) LQKENSKRWNPEIQYTSNYYKSTSVDFAVNTEGVYSEPRPIGTRYLTRNL-  SEQ ID NO: 8
AAV9  (687) LQKENSKRWNPEIQYTSNNVEFAVNTEGVYSEPRPIGTRYLTRNL-       SEQ ID NO: 9
AAV10 (689) LQKENSKRWNPEIQYTSNYYKSTNVDFAVNTDGTYSEPRPIGTRYLTRNL-  SEQ ID NO: 10
```

FIG. 33B-3

Tyrosine residue alignment in AAV serotype capsids

```
CAPSID        1                                                                                                   100
AAV1    (1)   MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF
AAV2    (1)   MAADGYLPDWLEDTLSEGIRQWWKLKPGPPPPKPAERHKDDSRGLVLPGYKYLGPFNGLDKGEPVNEADAAALEHDKAYDRQLDSGDNPYLKYNHADAEF
AAV3    (1)   MAADGYLPDWLEDNLSEGIREWWALKPGAPQPKANQQHQDNARGLVLPGYKYLGPGNGLDKGEPVNAADAAALEHDKAYDQQLKAGDNPYLKYNHADAEF
AAV4    (1)   -MTDGYLPDWLEDNLSEGIREWWALQPGAPKPKANQQHQDNARGLVLPGYNYLGPGNGLDKGEPVNRADEVAREHDISYNEQLEAGDNPYLKYNHADAEF
AAV5    (1)   -MSFVDHPPDWLEEVG-EGLREFLGLEAGPPKPKPNQQHQDQARGLVLPGYNYLGPGNGLDRGEPVNRADEVAREHDISYNEQLEAGDNPYLKYNHADAEF
AAV6    (1)   MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF
AAV7    (1)   MAADGYLPDWLEDNLSEGIREWWALKPGAPKPKANQQKQDDGRGLVLPGYKYLGPFNGLDKGEPVNAADAAALEHDKAYDQQLKAGDNPYLRYNHADAEF
AAV8    (1)   MAADGYLPDWLEDNLSEGIREWWALKPGAPQPKANQQHQDNARGLVLPGYKYLGPFNGLDKGEPVNAADAAALEHDKAYDQQLQAGDNPYLRYNHADAEF
AAV9    (1)   MAADGYLPDWLEDNLSEGIREWWALKPGAPQPKANQQHQDNARGLVLPGYKYLGPFNGLDKGEPVNAADAAALEHDKAYDQQLKAGDNPYLKYNHADAEF
AAV10   (1)   MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF 101                                                                                                 200
AAV1  (101)   QERLQEDTSFGGNLGRAVFQAKKRVLEPLGLVEEGAKTAPGKKRPVEQSPQE-PDSSSGIGKTGQQPAKKRLNFGQTGDSESVPDPQPLGEPPATPAAVG
AAV2  (101)   QERLKEDTSFGGNLGRAVFQAKKRVLEPLGLVEEPVKTAPGKKRPVEHSPVE-PDSSSGTGKAGQQPARKRLNFGQTGDADSVPDPQPLGQPPAAPSGLG
AAV3  (101)   QERLQEDTSFGGNLGRAVFQAKKRILEPLGLVEEAAKTAPGKKGADQSPQE-PDSSSGVGKSGKQPARKRLNFGQTGDSESVPDPQPLGEPPAAPTSLG
AAV4  (100)   CQRLQGDTSFGGNLGRAVFQAKKRVLEPLGLVEQAGETAPGKKRPLLESPQQ-PDSSTGIGKKGKQPAKKKLVFEDETGAGDGP---PEGSTSGAMSDDS
AAV5  (100)   QEKLADDTSFGGNLGKAVFQAKKRVLEPFGLVEPFGLVEEGAKTAPTGKRIDDHFPKR--------KKARTEEDSKPSTSSDALAGPSGS--QQLQIPAQPASSLG
AAV6  (101)   QERLQEDTSFGGNLGRAVFQAKKRVLEPLGLVEEGAKTAPAKKRPVEQSPQE-PDSSSGIGKTGQQPAKKRLNFGQTGDSESVPDPQPLGEPPATPAAVG
AAV7  (101)   QERLQEDTSFGGNLGRAVFQAKKRVLEPLGLVEEGAKTAPGKKRPVEPSPQRSPDSSTGIGKKGQQPARKRLNFGQTGDSESVPDPQPLGEPPAAPSGVG
AAV8  (101)   QERLQEDTSFGGNLGRAVFQAKKRVLEPLGLVEEGAKTAPGKKRPVEPSPQRSPDSSTGIGKKGQQPARKRLNFGQTGDSESVPDPQPLGEPPAAPSGVG
AAV9  (101)   QERLKEDTSFGGNLGRAVFQAKKRVLEPLGLVEEAAKTAPGKKRPVEQSPQE-PDSSAGIGKSGAQPAKKRLNFGQTGDTDSVPDPQPLGEPPAAPSGVG
AAV10 (101)   QERLQEDTSFGGNLGRAVFQAKKRVLEPLGLVEEGAKTAPGKKRPVEPSPQRSPDSSTGIGKKGQQPAKKRLNFGQTGDSESVPDPQPLGEPPAGPSGLG 201                                                                                                 300
AAV1  (200)   PTTMASGGGAPMADNNEGADGVGNASGNWHCDSTWLGDRVITTSTRTWALPTYNNHLYKQISSAST-GASNDNHYFGYSTPWGYFDFNRFHCHFSPRDWQ
AAV2  (200)   TNTMATGSGAPMADNNEGADGVGNSSGNWHCDSTWMGDRVITTSTRTWALPTYNNHLYKQISSQS--GASNDNHYFGYSTPWGYFDFNRFHCHFSPRDWQ
AAV3  (200)   SNTMASGGGAPMADNNEGADGVGNASGNWHCDSQWLGDRVITTSTRTWALPTYNNHLYKQISSQS--GASNDNHYFGYSTPWGYFDFNRFHCHFSPRDWQ
AAV4  (196)   EMRAAAGGAAVEGG--QGADGVGNASGDWHCDSTWSEGHVTTSTRTWVLPTYNNHLYKRLGESLQ------SNTYNGFSTPWGYFDFNRFHCHFSPRDWQ
AAV5  (190)   ADTMSAGGGGPLGDNNQGADGVGNASGDWHCDSTWMGDRVVTKSTRTWVLPSYNNHQYREIKSGS-VDGSNANAYFGYSTPWGYFDFNRFHSWSPRDWQ
AAV6  (200)   PTTMASGGGAPMADNNEGADGVGNASGNWHCDSTWLGDRVITTSTRTWALPTYNNHLYKQISSAST-GASNDNHYFGYSTPWGYFDFNRFHCHFSPRDWQ
AAV7  (201)   SGTVAAGGGGAPMADNNEGADGVGNASGNWHCDSTWLGDRVITTSTRTWALPTYNNHLYKQISSETAG-STNDNTYFGYSTPWGYFDFNRFHCHFSPRDWQ
AAV8  (201)   PNTMAAGGGAPVADNNEGADGVGSSSGNWHCDSTWLGDRVITTSTRTWALPTYNNHLYKQISNGTSGGATNDNTYFGYSTPWGYFDFNRFHCHFSPRDWQ
AAV9  (200)   SLTMASGGGAPVADNNEGADGVGSSSGNWHCDSTWLGDRVITTSTRTWALPTYNNHLYKQISNSTSGGSSNDNAYFGYSTPWGYFDFNRFHCHFSPRDWQ
AAV10 (201)   SGTMAAGGGAPMADNNEGADGVGSSSGNWHCDSTWLGDRVITTSTRTWALPTYNNHLYKQISNGTSGGSTNDNTYFGYSTPWGYFDFNRFHCHFSPRDWQ
```

FIG. 33C-1

```
                                                                                                                                   400
          301
AAV1  (299)  RLINNNWGFRPKRLNFKLFNIQVKEVTTNDGVTTIANNLTSTVQVFSDSEYQLPYVLGSAHQGCLPFFPADVFMIPQYGYLTLNNGSQA----VGRSSFYC
AAV2  (298)  RLINNNWGFRPKRLNFKLFNIQVKEVTQNDGTTTIANNLTSTVQVFTDSEYQLPYVLGSAHQGCLPFFPADVFMVPQYGYLTLNNGSQA----VGRSSFYC
AAV3  (298)  RLINNNWGFRPKKLSFKLFNIQVRGVTQNDGTTIANNLTSTVQVFTDSEYQLPYVLGSAHQGCLPFFPADVFMVPQYGYLTLNNGSQA----VGRSSFYC
AAV4  (289)  RLINNNWGMRPKAMRVKIFNIQVKEVTTSNGETTVANNLTSTVQIFADSSYELPYVMDAGQEGSLPFFPNDVFMVPQYGYCGLVTGNTSQQQTDRNAFYC
AAV5  (289)  RLINNYWGFRPRSLRVKIFNIQVKEVTVQDSTTTIANNLTSTVQVFTDDDYQLPYTDDYQLPAFFPQVFTLPQYGYATLNRDNTEN-PTERSSFYC
AAV6  (299)  RLINNNWGFRPKRLNFKLFNIQVKEVTTNDGVTTIANNLTSTVQVFSDSEYQLPYVLGSAHQGCLPFFPADVFMIPQYGYLTLNNGSQA----VGRSSFYC
AAV7  (300)  RLINNNWGFRPKRLNFKLRPKLFNIQVKEVTTQNEGTKTIANNLTSTIQVFTDSEYQLPYVLGSAHQGCLPFFPADVFMIPQYGYLTLNNGSQA----VGRSSFYC
AAV8  (301)  RLINNNWGFRPKRLSFKLNFKLFNIQVKEVTQNEGTRTIANNLTSTVQVFTDSDYQLPYLPYTDSDYQLPYLPYVLGSAHQGCLPFFPADVFMIPQYGYLTLNDGSQS----VGRSSFYC
AAV9  (300)  RLINNNWGFRPKRLNFKLFNIQVKEVTDNNNGVKTIANNLTSTIQVFTDSEYQFDSDYQLPYVLGSAHEGCLPFFPADVFMIPQYGYLTLNDGSQA----VGRSSFYC
AAV10 (301)  RLINNNWGFRPKRLNFKLFNIQVKEVTQNEGFRTIANNLTSTIQVFTDSEYQLPYVLGSAHQGCLPFFPADVFMIPQYGYLTLNNGSQA----VGRSSFYC 401                                                                                                                      500
AAV1  (396)  LEYFPSQMLRTGNNFTFSYTFEEVPFHSSYAHSQSLDRLMNPLIDQYLYYLNRTQ-NQSGSAQNKDLLFSRGSPAGMSVQPKNWLPGPCYRQQRVSKTKT
AAV2  (395)  LEYFPSQMLRTGNNFTFSYTFEDVPFHSSYAHSQSLDRLMNPLIDQYLYYLSRTN-TPSGTTTQSRLQFSQAGASDIRDQSRNWLPGPCYRQQRVSKTSA
AAV3  (395)  LEYFPSQMLRTGNNFQFSYTFEDVPFHSSYAHSQSLDRLMNPLIDQYLYYLNRTQGTTSGTTNQSRLLFSQAGPQSMSLQARNWLPGPCYRQQRLSKTAN
AAV4  (389)  LEYFPSQMLRTGNNFEIITYSFEKVPFHSMYAHSQSLDRLMNPLIDQYLWGLQSTTTGTTLNAGTATTNFTKLRPTNFSMFKKNWLPGPSIKQQGFSKTAN
AAV5  (388)  LEYFPSKMLRTGNNFEFTYNFEEVPFHSSYAHSQSLFAPSQNLFKIANPLVDQYIYRFVSTN------NTGGVQFMNKNLAGRYANTYKNWFPGPMGRTQGMNLGSS
AAV6  (396)  LEYFPSQMLRTGNNFTFSYTFEDVPFHSSYAHSQSLDRLMNPLIDQYLYYLNRTQ-NQSGSAQNKDLLFSRGSPAGMSVQPKNWLPGPCYRQQRVSKTKT
AAV7  (397)  LEYFPSQMLRTGNNFEFSYSFEDVPFHSSYAHSQSLDRLMNPLIDQYLYYLLARTQSNPGGTAGNRELQFYQGGPSTMAEQAKNWLPGPCFRQQRVSKTLD
AAV8  (398)  LEYFPSQMLRTGNNFQFTYTFEDVPFHSSYAHSQSLDRLMNPLIDQYLYYLSRTQTT-GGTANTQTLGFSQGGPNTMANQAKNWLPGPCYRQQRVSTTTG
AAV9  (397)  LEYFPSQMLRTGNNFQFSYEFENVPFHSSYAHSQSLDRLMNPLIDQYLYYLSKTING--SGQMQQTLKFSVAGPSNMAVQGRNYIPGPSYRQQRVSTTVT
AAV10 (398)  LEYFPSQMLRTGNNFTFSYQFEDVPFHSSYAHSQSLDRLMNPLIDQYLYYLSRTQST-GGTAGTQQLLFSQAGPNNMSAQAKNWLPGPCYRQQRVSTTLS 501                                                                                            600
AAV1  (495)  DN------NNSNFTWTGASKYNLNGRESIINPGTAMASHKDDEDKFFPMSGVMIFGKE---SAGASNTALDNVMITDEEEIKATNPVATERFGTVAVNFQS
AAV2  (494)  DN------NNSEYSWTGATKYHLNGRDSLVNPGPAMASHKDDEEKFFPMHGNLIFGKE---GSEKTNVDIEKVMITDEEEIRTTNPVATEQYGSVSTNLQR
AAV3  (495)  DN------NNSNFPWTAASKYHLNGRDSLVNPGPAMASHKDDEEKFFPMHGNLIFGKE---GTTASNAELDNVMITDEEEIRTTNPVATEQYGTVANNLQS
AAV4  (489)  QNYKIPATGSDSLIKYETHSTLDGRWSALITPGPMATAGPADSKFS-NSQLIFAGPK---QNGNTATVPGTLIFTSEEELAATNATDTDMWGNLPGGDQS
AAV5  (481)  RASVSAFAFTNRMELEGASYQVPPQPNGMTNNLQGSNTYALENTMIFNSQPANPGTTATYLEGNMLITSESETQPVNRVAYNVGGQMATMNQS
AAV6  (495)  DN------NNSNFTWTGASKYNLNGRESIINPGTAMASHKDDDKFFPMSGVMIFGKE---SAGASNTALDNVMITDEEEIKATNPVATERFGTVAVNLQS
AAV7  (497)  QN------NNSFAWTGATKYHLNGRNSLANPGIAMATHKDDEERFFPSNGLILFGKT---GATNKTTLENVLMTNEEIRPTNPVATEEYGIVSSNLQA
AAV8  (497)  QN------NNSFAWTAGTKYHLNGRNSLANPGLAMATHKDDEERFFPSNGILIFGKQ---NAARIDNADYSDVMLTSEEIKTTNPVATEEYGIVADNLQQ
AAV9  (495)  QN------NNSEFAWPGASSWALNGRNSLMNPGPAMASHKEGEDREFFPLSGSLIFGKQ---GTGRDNVDADKVMITNEEIKTTNPVATESYGVATNHQS
AAV10 (497)  QN------NNSNFAWTGATKYHLNGRDSLVNPGPAMATHKDDEERFFPSSGVLMFGKQ---GAGKDNVDYSSVMLTSEEIKTTNPVATEQYGVVADNLQQ
```

*FIG. 33C-2*

```
         601                                                                                          700
AAV1  (587) SSTDPATGDVHAMGALPGMVWQDRDVYLQGPIWAKIPHTDGHFHPSPLMGGFGLKNPPPQILIKNTPVPANPPAEFSATKFASFITQYSTGQVSVEIEWE
AAV2  (586) GNRQAATADVNTQGVLPGMVWQDRDVYLQGPIWAKIPHTDGHFHPSPLMGGFGLKHPPPQILIKNTPVPANPSTTFSAAKFASFITQYSTGQVSVEIEWE
AAV3  (587) SNTAPTTGTVNHQGALPGMVWQDRDVYLQGPIWAKIPHTDGHFHPSPLMGGFGLKHPPPQIMIKNTPVPANPPTTFSPAKFASFITQYSTGQVSVEIEWE
AAV4  (585) NSNLFTVDRLTALGAVPGMVWQNRDIYYQGPIWAKIPHTDGHFHPSPLIGGFGLKHPPPQIFIKNTPVPANPATTFSSTPVNSFITQYSTGQVSVQIDWE
AAV5  (576) STTAPATGTYNLQEIVPGSVWMERDVYLQGPIWAKIPETGAHFHPSPAMGGFGLKHPSPAMGGFGLKHPPPMLIKNTPVPGN-ITSFSDVPVSSFITQYSTGQVTVEMEWE
AAV6  (587) SSTDPATGDVHAMGALPGMVWQDRDVYLQGPIWAKIPHTDGHFHPSPLMGGFGLKHPPPQILIKNTPVPANPPAEFSATKFASFITQYSTGQVSVEIEWE
AAV7  (588) ANTAAQTQVVNNQGALPGMVWQNRDVYLQGPIWAKIPHTDGNFHPSPLMGGFGLKHPPPQILIKNTPVPANPPEVFTPAKFASFITQYSTGQVSVEIEWE
AAV8  (589) QNTAPQIGTVNSQGALPGMVWQNRDVYLQGPIWAKIPHTDGNFHPSPLMGGFGLKHPPPQILIKNTPVPADPPTTFNQSKLNSFITQYSTGQVSVEIEWE
AAV9  (587) AQAQAQTGWVQNQGILPGMVWQNRDVYLQGPIWAKIPHTDGNFHPSPLMGGFGEMKHPPPQILIKNTPVPADPPTAFNKDKLNSFITQYSTGQVSVEIEWE
AAV10 (589) QNAAPIVGAVNSQGALPGMVWQNRDVYLQGPIWAKIPHTDGNFHPSPLMGGFGLKHPPPQILIKNTPVPADPPTTFSQAKLASFITQYSTGQVSVEIEWE
         701                                                 751
AAV1  (687) LQKENSKRWNPEVQYTSNYAKSANVDFTVDNNGLYTEPRPIGTRYLTRPL- SEQ ID NO:1
AAV2  (686) LQKENSKRWNPEIQYTSNYNKSVNVDFTVDTNGVYSEPRPIGTRYLTRNL- SEQ ID NO:2
AAV3  (687) LQKENSKRWNPEIQYTSNYYKSVNVDFTVDTNGVYSEPRPIGTRYLTRNL- SEQ ID NO:3
AAV4  (685) IQKERSKRWNPEVQFTSNYGQQNSLLWAPDAAGKYTEPRAIGTRYLTHHL- SEQ ID NO:4
AAV5  (675) LKKENSKRWNPEIQYTNNYNDPQFVDFAPDSTGEYRTTRPIGTRYLTRPL- SEQ ID NO:5
AAV6  (687) LQKENSKRWNPEVQYTSNYAKSANVDFTVDNNGLYTEPRPIGTRYLTRPL- SEQ ID NO:6
AAV7  (688) LQKENSKRWNPEIQYTSNFEKQTGVDFAVDSQGVYSEPRPIGTRYLTRNL- SEQ ID NO:7
AAV8  (689) LQKENSKRWNPEIQYTSNYYKSTSVDFAVNTEGVYSEPRPIGTRYLTRNL- SEQ ID NO:8
AAV9  (687) LQKENSKRWNPEIQYTSNYYKSNNVEFAVNTEGVYSEPRPIGTRYLTRNL- SEQ ID NO:9
AAV10 (689) LQKENSKRWNPEIQYTSNYYKSTNVDFAVNTDGTYSEPRPIGTRYLTRNL- SEQ ID NO:10
```

| MUTANT | PACKAGING EFFICIENCY | TRANSDUCTION EFFICIENCY |
|---|---|---|
| AAV2-S261V | ~10-FOLD LOWER | -* |
| AAV2-S264V | NO CHANGE | -* |
| AAV2-S267V | NO DNAse I- RESISTANT PARTICLES | -* |
| AAV2-S276V | ~10-FOLD LOWER | -* |
| AAV2-S384V | ~3-FOLD HIGHER | ~10-FOLD LOWER |
| AAV2-S458V | NO CHANGE | ~4-FOLD HIGHER |
| AAV2-S468V | ~5-FOLD HIGHER | NO CHANGE |
| AAV2-S492V | NO CHANGE | ~2-FOLD HIGHER |
| AAV2-S498V | NO CHANGE | ~10-FOLD LOWER |
| AAV2-S578V | NO CHANGE | ~10-FOLD LOWER |
| AAV2-S658V | ~10-FOLD LOWER | -* |
| AAV2-S662V | NO CHANGE | ~20-FOLD HIGHER |
| AAV2-S668V | NO DNAse I- RESISTANT PARTICLES | -* |
| AAV2-S707V | NO CHANGE | ~10-FOLD LOWER |
| AAV2-S721V | NO CHANGE | NO CHANGE |

*FIG. 34*

| MUTANT | PACKAGING EFFICIENCY | TRANSDUCTION EFFICIENCY |
|---|---|---|
| AAV2-S662V | NO CHANGE | ~20-FOLD HIGHER |
| AAV2-S662A | ~5-FOLD HIGHER | ~3-FOLD HIGHER |
| AAV2-S662D | NO CHANGE | ~8-FOLD HIGHER |
| AAV2-S662F | ~10-FOLD LOWER | NO CHANGE |
| AAV2-S662H | NO CHANGE | ~4-FOLD HIGHER |
| AAV2-S662N | ~10-FOLD LOWER | NO CHANGE |
| AAV2-S662L | ~10-FOLD LOWER | NO CHANGE |
| AAV2-S662I | ~10-FOLD LOWER | NO CHANGE |

SEQUENCE LISTING

```
<160> NUMBER OF SEQ ID NOS: 25

<210> SEQ ID NO 1
<211> LENGTH: 736
<212> TYPE: PRT
<213> ORGANISM: Adeno-associated virus serotype 1

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285
```

-continued

```
His Cys His Phe Ser Pro Arg Asp Trp Gln Arg Leu Ile Asn Asn Asn
            290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
            370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Glu Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
            435                 440                 445
Thr Gln Asn Gln Ser Gly Ser Ala Gln Asn Lys Asp Leu Leu Phe Ser
            450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
            515                 520                 525
Asp Asp Glu Asp Lys Phe Phe Pro Met Ser Gly Val Met Ile Phe Gly
            530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Phe Gln Ser Ser Ser Thr Asp Pro Ala
            580                 585                 590
Thr Gly Asp Val His Ala Met Gly Ala Leu Pro Gly Met Val Trp Gln
            595                 600                 605
Asp Arg Asp Val Tyr Leu Gln Gly Pro Ile Trp Ala Lys Ile Pro His
            610                 615                 620
Thr Asp Gly His Phe His Pro Ser Pro Leu Met Gly Gly Phe Gly Leu
625                 630                 635                 640
Lys Asn Pro Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
            660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Val Gln Tyr Thr Ser Asn
            690                 695                 700
```

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

<210> SEQ ID NO 2
<211> LENGTH: 735
<212> TYPE: PRT
<213> ORGANISM: Adeno-associated virus serotype 2

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
            690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Adeno-associated virus serotype 3

<400> SEQUENCE: 3

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415
```

```
Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
            530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Gly Thr Val Asn His Gln Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 4
<211> LENGTH: 734
<212> TYPE: PRT
<213> ORGANISM: Adeno-associated virus serotype 4

<400> SEQUENCE: 4

```
Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
```

```
                    50                  55                  60
Asn Ala Asp Ala Ala Ala Leu Glu His Asp Lys Ala Tyr Asp Gln
 65                  70                  75                  80
Gln Leu Lys Ala Gly Asp Asn Pro Tyr Leu Lys Tyr Asn His Ala Asp
                     85                  90                  95
Ala Glu Phe Gln Gln Arg Leu Gln Gly Asp Thr Ser Phe Gly Gly Asn
                    100                 105                 110
Leu Gly Arg Ala Val Phe Gln Ala Lys Lys Arg Val Leu Glu Pro Leu
                    115                 120                 125
Gly Leu Val Glu Gln Ala Gly Glu Thr Ala Pro Gly Lys Lys Arg Pro
                    130                 135                 140
Leu Ile Glu Ser Pro Gln Pro Asp Ser Ser Thr Gly Ile Gly Lys
145                 150                 155                 160
Lys Gly Lys Gln Pro Ala Lys Lys Leu Val Phe Glu Asp Glu Thr
                    165                 170                 175
Gly Ala Gly Asp Gly Pro Pro Glu Gly Ser Thr Ser Gly Ala Met Ser
                    180                 185                 190
Asp Asp Ser Glu Met Arg Ala Ala Gly Ala Ala Val Glu Gly
                    195                 200                 205
Gly Gln Gly Ala Asp Gly Val Gly Asn Ala Ser Gly Asp Trp His Cys
                    210                 215                 220
Asp Ser Thr Trp Ser Glu Gly His Val Thr Thr Thr Ser Thr Arg Thr
225                 230                 235                 240
Trp Val Leu Pro Thr Tyr Asn Asn His Leu Tyr Lys Arg Leu Gly Glu
                    245                 250                 255
Ser Leu Gln Ser Asn Thr Tyr Asn Gly Phe Ser Thr Pro Trp Gly Tyr
                    260                 265                 270
Phe Asp Phe Asn Arg Phe His Cys His Phe Ser Pro Arg Asp Trp Gln
                    275                 280                 285
Arg Leu Ile Asn Asn Asn Trp Gly Met Arg Pro Lys Ala Met Arg Val
                    290                 295                 300
Lys Ile Phe Asn Ile Gln Val Lys Glu Val Thr Thr Ser Asn Gly Glu
305                 310                 315                 320
Thr Thr Val Ala Asn Asn Leu Thr Ser Thr Val Gln Ile Phe Ala Asp
                    325                 330                 335
Ser Ser Tyr Glu Leu Pro Tyr Val Met Asp Ala Gly Gln Glu Gly Ser
                    340                 345                 350
Leu Pro Pro Phe Pro Asn Asp Val Phe Met Val Pro Gln Tyr Gly Tyr
                    355                 360                 365
Cys Gly Leu Val Thr Gly Asn Thr Ser Gln Gln Gln Thr Asp Arg Asn
                    370                 375                 380
Ala Phe Tyr Cys Leu Glu Tyr Phe Pro Ser Gln Met Leu Arg Thr Gly
385                 390                 395                 400
Asn Asn Phe Glu Ile Thr Tyr Ser Phe Glu Lys Val Pro Phe His Ser
                    405                 410                 415
Met Tyr Ala His Ser Gln Ser Leu Asp Arg Leu Met Asn Pro Leu Ile
                    420                 425                 430
Asp Gln Tyr Leu Trp Gly Leu Gln Ser Thr Thr Thr Gly Thr Thr Leu
                    435                 440                 445
Asn Ala Gly Thr Ala Thr Thr Asn Phe Thr Lys Leu Arg Pro Thr Asn
                    450                 455                 460
Phe Ser Asn Phe Lys Lys Asn Trp Leu Pro Gly Pro Ser Ile Lys Gln
465                 470                 475                 480
```

Gln Gly Phe Ser Lys Thr Ala Asn Gln Asn Tyr Lys Ile Pro Ala Thr
            485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
            530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
            565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
            595                 600                 605

Asp Ile Tyr Tyr Gln Gly Pro Ile Trp Ala Lys Ile Pro His Thr Asp
            610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
            645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
            675                 680                 685

Arg Ser Lys Arg Trp Asn Pro Glu Val Gln Phe Thr Ser Asn Tyr Gly
            690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
            725                 730

<210> SEQ ID NO 5
<211> LENGTH: 724
<212> TYPE: PRT
<213> ORGANISM: Adeno-associated virus serotype 5

<400> SEQUENCE: 5

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
            50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
            85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe

```
            115                 120                 125
Gly Leu Val Glu Glu Gly Ala Lys Thr Ala Pro Thr Gly Lys Arg Ile
130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
530                 535                 540
```

-continued

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 6
<211> LENGTH: 736
<212> TYPE: PRT
<213> ORGANISM: Adeno-associated virus serotype 6

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

```
Ala Thr Pro Ala Ala Val Gly Pro Thr Thr Met Ala Ser Gly Gly
            195                 200                 205

Ala Pro Met Ala Asp Asn Asn Glu Gly Ala Asp Gly Val Gly Asn Ala
        210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605
```

```
Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                    645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                    725                 730                 735
```

<210> SEQ ID NO 7
<211> LENGTH: 737
<212> TYPE: PRT
<213> ORGANISM: Adeno-associated virus serotype 7

<400> SEQUENCE: 7

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255
```

```
Leu Tyr Lys Gln Ile Ser Ser Glu Thr Ala Gly Ser Thr Asn Asp Asn
                260                 265                 270

Thr Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
            290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Ile Ala Asn
                325                 330                 335

Asn Leu Thr Ser Thr Ile Gln Val Phe Ser Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Met Ile Pro Gln Tyr Gly Tyr Leu Thr Leu Asn Asn
            370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
                450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
            530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
                580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
            610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
                660                 665                 670
```

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
        690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 8
<211> LENGTH: 738
<212> TYPE: PRT
<213> ORGANISM: Adeno-associated virus serotype 8

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

```
Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
```

Asn Leu

<210> SEQ ID NO 9
<211> LENGTH: 736
<212> TYPE: PRT
<213> ORGANISM: Adeno-associated virus serotype 9

<400> SEQUENCE: 9

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
```

```
            355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
    690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735
```

<210> SEQ ID NO 10
<211> LENGTH: 738
<212> TYPE: PRT
<213> ORGANISM: Adeno-associated virus serotype 10

<400> SEQUENCE: 10

-continued

```
Met Ala Ala Asp Gly Tyr Leu Pro Asp Trp Leu Glu Asp Asn Leu Ser
 1               5                  10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
            130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
            165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
            210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
            405                 410                 415

Gln Phe Glu Asp Val Pro Phe His Ser Ser Tyr Ala His Ser Gln Ser
```

420                 425                 430
Leu Asp Arg Leu Met Asn Pro Leu Ile Asp Gln Tyr Leu Tyr Tyr Leu
                435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
        530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
                595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 11
<211> LENGTH: 45
<212> TYPE: DNA
<213> ORGANISM: Artificial Sequence
<220> FEATURE:
<223> OTHER INFORMATION: Forward Oligonucleotide Primer

<400> SEQUENCE: 11
accagaacct gggctctgcc cactttcaac aaccatctct acaag          45

<210> SEQ ID NO 12
<211> LENGTH: 45
<212> TYPE: DNA
<213> ORGANISM: Artificial Sequence
<220> FEATURE:

<223> OTHER INFORMATION: Reverse Oligonucleotide Primer

<400> SEQUENCE: 12
caatcaggag cttcgaacga caaccacttc tttggctaca gcacc        45

<210> SEQ ID NO 13
<211> LENGTH: 45
<212> TYPE: DNA
<213> ORGANISM: Artificial Sequence
<220> FEATURE:
<223> OTHER INFORMATION: Oligonucleotide Primer

<400> SEQUENCE: 13
cttatcgatc agtatctgta cttcctgaac agaacgcaag gaaca        45

<210> SEQ ID NO 14
<211> LENGTH: 48
<212> TYPE: DNA
<213> ORGANISM: Artificial Sequence
<220> FEATURE:
<223> OTHER INFORMATION: Oligonucleotide Primer

<400> SEQUENCE: 14
gctaacgaca acaacaacag taactatcca tggacagcgg ccagcaaa     48

<210> SEQ ID NO 15
<211> LENGTH: 45
<212> TYPE: DNA
<213> ORGANISM: Artificial Sequence
<220> FEATURE:
<223> OTHER INFORMATION: Oligonucleotide Primer

<400> SEQUENCE: 15
tggaatccag agattcagtt cacgtccaac tacaacaagt ctgtt        45

<210> SEQ ID NO 16
<211> LENGTH: 45
<212> TYPE: DNA
<213> ORGANISM: Artificial Sequence
<220> FEATURE:
<223> OTHER INFORMATION: Oligonucleotide Primer

<400> SEQUENCE: 16
gagattcagt acacgtccaa cttcaacaag tctgttaatg tggac        45

<210> SEQ ID NO 17
<211> LENGTH: 44
<212> TYPE: DNA
<213> ORGANISM: Artificial Sequence
<220> FEATURE:
<223> OTHER INFORMATION: Oligonucleotide Primer

<400> SEQUENCE: 17
gtgaacctcg ccctattgga acccggtttc tcacacgaaa cttg         44

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 18
tcccatagta acgccaatag g                                  21

-continued

```
<210> SEQ ID NO 19
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 19
cttggcatat gatacacttg atg                                           23

<210> SEQ ID NO 20
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 20
tcccatagta acgccaatag g                                             21

<210> SEQ ID NO 21
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 21
cttggcatat gatacacttg atg                                           23

<210> SEQ ID NO 22
<211> LENGTH: 145
<212> TYPE: DNA
<213> ORGANISM: Artificial Sequence
<220> FEATURE:
<223> OTHER INFORMATION: Synthetic Sequence

<400> SEQUENCE: 22
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag agagggagtg gccaa                                        145

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 23
ctccatcact agggguttcct                                              20

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 24
ctccatcact aggggttcct                                               20

<210> SEQ ID NO 25
<211> LENGTH: 20
<212> TYPE: DNA
```

```
<213> ORGANISM: Artificial Sequence
<220> FEATURE:
<223> OTHER INFORMATION: Oligonucleotide Primer

<400> SEQUENCE: 25
gaggtagtga tccccaagga                                              20
```

CAPSID-MODIFIED RAAV VECTOR COMPOSITIONS HAVING IMPROVED TRANSDUCTION EFFICIENCIES, AND METHODS OF USE

CROSS-REFERENCE TO RELATED APPLICATIONS

The present application is a continuation-in-part of U.S. patent application Ser. No. 12/595,196, filed Dec. 31, 2009 (to issue May 21, 2013 as U.S. Pat. No. 8,445,267), which was the U.S. national-stage filing of PCT Intl. Patent Appl. No. PCT/US2008/059647 filed Apr. 8, 2008 (nationalized), which claimed priority to U.S. Provisional Patent Appl. No. 60/910,798, filed Apr. 9, 2007. The present application also claims the priority benefit of PCT Intl. Patent Appl. No. PCT/US2013/041234 filed May 15, 2013 (pending), U.S. patent application Ser. No. 13/840,224, filed Mar. 15, 2013), and U.S. Provisional Patent Appl. No. 61/647,318, filed May 15, 2012. The content of each of the aforementioned applications is hereby incorporated in its entirety by express reference thereto.

STATEMENT REGARDING FEDERALLY SPONSORED RESEARCH OR DEVELOPMENT

This invention was made with government support under Contract No. P01 DK-058327 and R01 HL-097088 awarded by the National Institute of Health. The government has certain rights in the invention.

NAMES OF THE PARTIES TO A JOINT RESEARCH AGREEMENT

Not Applicable.

BACKGROUND OF THE INVENTION

Field of the Invention

The present invention relates generally to the fields of molecular biology and virology, and in particular, to the development of gene delivery vehicles. Also disclosed are improved rAAV vector compositions useful in delivering a variety of nucleic acid segments, including those encoding therapeutic proteins polypeptides, peptides, antisense oligonucleotides, and ribozyme constructs to selected host cells for use in various diagnostic and/or therapeutic regimens. Methods are also provided for preparing and using these modified rAAV-based vector constructs in a variety of viral-based gene therapies, and in particular, for the diagnosis, prevention, treatment and/or amelioration of symptoms of human diseases, disorders, dysfunctions, trauma, or injury. The invention also provides mutated rAAV-based viral vector delivery systems with increased transduction efficiency and/or improved viral infectivity of selected mammalian host cells. In particular, the invention provides improved rAAV vectors and virions having particles having amino acid substitutions in one or more surface-exposed residues of a viral capsid protein.

Description of Related Art

Major advances in the field of gene therapy have been achieved by using viruses to deliver therapeutic genetic material. The adeno-associated virus (AAV) has attracted considerable attention as a highly effective viral vector for gene therapy due to its low immunogenicity and ability to effectively transduce non-dividing cells. AAV has been shown to infect a variety of cell and tissue types, and significant progress has been made over the last decade to adapt this viral system for use in human gene therapy.

In its normal "wild type" form, recombinant AAV (rAAV) DNA is packaged into the viral capsid as a single stranded molecule about 4600 nucleotides (nt) in length. Following infection of the cell by the virus, the molecular machinery of the cell converts the single DNA strand into a double-stranded form. Only the double-stranded DNA form is useful to the polypeptides of the cell that transcribe the contained gene or genes into RNA.

AAV has many properties that favor its use as a gene delivery vehicle: 1) the wild type virus is not associated with any pathologic human condition; 2) the recombinant form does not contain native viral coding sequences; and 3) persistent transgenic expression has been observed in many applications.

The transduction efficiency of recombinant adeno-associated virus 2 (AAV) vectors varies greatly in different cells and tissues in vitro and in vivo, which has limited the usefulness of many of them in potential gene therapy regimens. Systematic studies have been performed to elucidate the fundamental steps in the life cycle of AAV. For example, it has been documented that a cellular protein, FKBP52, phosphorylated at tyrosine residues by epidermal growth factor receptor protein tyrosine kinase (EGFR-PTK), inhibits AAV second-strand DNA synthesis and consequently, transgene expression in vitro as well as in vivo. It has also been demonstrated that EGFR-PTK signaling modulates the ubiquitin/proteasome pathway-mediated intracellular trafficking as well as FKBP52-mediated second-strand DNA synthesis of AAV vectors. In those studies, inhibition of EGFR-PTK signaling led to decreased ubiquitination of AAV capsid proteins, which in turn, facilitated nuclear transport by limiting proteasome-mediated degradation of AAV vectors, implicating EGFR-PTK-mediated phosphorylation of tyrosine residues on AAV capsids. What is lacking in the prior art are improved rAAV viral vectors that have enhanced transduction efficiency for infecting selected mammalian cells, and for targeted gene delivery to human cells in particular.

BRIEF SUMMARY OF THE INVENTION

The present invention overcomes limitations and deficiencies inherent in the prior art by providing novel improved rAAV-based genetic constructs that encode one or more therapeutic agents useful in the preparation of medicaments for the prevention, treatment, and/or amelioration of one or more diseases, disorders or dysfunctions resulting from a deficiency in one or more of such polypeptides. In particular, the invention provides VP3 capsid-protein-modified rAAV-based genetic constructs encoding one or more selected molecules, such as, for example, one or more diagnostic or therapeutic agents (including, e.g., proteins, polypeptides, peptides, antibodies, antigen binding fragments, siRNAs, RNAis, antisense oligo- and poly-nucleotides, ribozymes, and variants and/or active fragments thereof), for use in the diagnosis, prevention, treatment, and/or amelioration of symptoms of a variety of mammalian diseases, disorders, dysfunctions, trauma, injury, and such like.

The present invention provides mutated AAV VP3 capsid proteins that include modification of one or more surface-exposed amino acid resides (including, e.g., without limitation, lysine, serine, threonine, and/or tyrosine residues) as compared to wildtype. Also provided are infectious rAAV virions that comprise the mutated AAV capsid proteins of the present invention, as well as nucleic acid molecules and rAAV vectors encoding the mutant AAV capsid proteins of the present invention, and nucleic acids encoding one or more selected diagnostic and/or therapeutic agents for delivery to a selected population of mammalian cells.

Advantageously, the novel rAAV vectors, express constructs, and infectious virions and viral particles comprising them as disclosed herein preferably have an improved efficiency in transducing one or more of a variety of cells, tissues and organs of interest, when compared to wild-type, unmodified, expression constructs, and to the corresponding rAAV vectors and virions comprising them.

The improved rAAV vectors provided herein transduce one or more selected host cells at higher-efficiencies (and often much higher efficiencies) than conventional, wild-type, unmodified rAAV vector constructs. By performing extensive analysis and detailed experiments involved the site-directed mutagenesis of various individual and/or combinations of two, three, four, five, or even more surface-exposed amino acid residues on various AAV capsid proteins from a variety of AAV serotypes (including AAV1-AAV10), the inventors have developed a collection of single- and multi-mutated rAAV vectors having improved properties. The inventors have repeatedly demonstrated that substitution of one or more virion surface-presenting amino acid residues yields improved viral vectors that are capable of higher-efficiency transduction than the corresponding, non-substituted (i.e., unmodified) parent vectors from which the mutants were prepared.

The development of these new capsid-mutant rAAV viral vectors dramatically reduces the number of viral particles needed for conventional gene therapy regimens. In addition to having improved transduction efficiencies for various mammalian cells, the surface-exposed amino acid-modified rAAV vectors described herein are more stable, less immunogenic, and can be produced at much lower cost than the traditional viral vectors currently employed in mammalian gene therapy regimens.

In a particular embodiment the invention provides a modified AAV VP3 capsid protein, that includes: (a) a non-tyrosine amino acid residue at one or more positions corresponding to Y705 and Y731 of the wild-type AAV6 capsid protein as set forth in SEQ ID NO:6; (b) a non-tyrosine amino acid residue at one or more positions corresponding to Y252, Y272, Y444, Y500, Y700, Y704, Y730, and Y731 of the wild-type AAV2 capsid protein as set forth in SEQ ID NO:2; (c) a non-serine amino acid residue at each of two or more positions corresponding to S261, S264, S267, S384, S458, S468, S492, S498, S578, S658, S662, S668, S707, and S721 of the wild-type AAV2 capsid protein as set forth in SEQ ID NO:2; (d) a non-threonine amino acid residue at each of two or more positions corresponding to T251, T329, T330, T454, T455, T491, T503, T550, T592, T597, T581, T671, T659, T660, T701, T713, and T716 of the wild-type AAV2 capsid protein as set forth in SEQ ID NO:2; (e) a non-lysine amino acid residue at each of two or more positions corresponding to K258, K321, K459, K490, K507, K527, K572, K532, K544, K549, K556, K649, K665, K665, and K706 of the wild-type AAV2 capsid protein as set forth in SEQ ID NO:2; (f) (i) a non-tyrosine amino acid residue at position Y252, Y272, Y444, Y500, Y700, Y704, Y730; and (ii) a non-tyrosine amino acid residue at position Y730, a non-threonine amino acid residue at position T491 or T550, or a non-serine amino acid residue at position S492 or S662 of the wild-type AAV2 capsid protein as set forth in SEQ ID NO:2; (g) (1) a non-serine amino acid residue at position S458, S662, or S492; and (2) a non-serine amino acid residue at position S492 or S662 or a non-threonine amino acid residue at position T491 of the wild-type AAV2 capsid protein as set forth in SEQ ID NO:2; (h) (1) a non-threonine amino acid residue at position T455, T550, T659, or T671; and (2) a non-threonine amino acid residue at position T491 of the wild-type AAV2 capsid protein as set forth in SEQ ID NO:2; (i) a combination of three or more amino acid substitutions listed in (b), (c), (d), and (e); each with a non-native amino acid; or (j) a combination of four or more amino acid substitutions listed in (b), (c), (d), and (e); each with a non-native amino acid; or alternatively, wherein each of the amino acid substitutions is at an equivalent amino acid position corresponding thereto in any one of the other wild-type vector serotypes selected from the group consisting of AAV1, AAV3, AAV4, AAV5, AAV7, AAV8, AAV9, and AAV10, as set forth in SEQ ID NO:1, SEQ ID NO:3, SEQ ID NO:4, SEQ ID NO:5, SEQ ID NO:7, SEQ ID NO:8, SEQ ID NO:9, and SEQ ID NO:10, respectively.

Exemplary multi-mutated proteins of the present invention include, but are not limited to, a combination of three or more amino acid substitutions that include a non-native amino acid substitution at each of amino acid residues: (a) Y272, Y444, Y500, and Y730; (b) Y272, Y444, Y500, Y700, and Y730; (c) Y272, Y444, Y500, Y704, and Y730; (d) Y252, Y272, Y444, Y500, Y704, and Y730; (e) Y272, Y444, Y500, Y700, Y704, and Y730; (1) Y252, Y272, Y444, Y500, Y700, Y704, and Y730; (g) Y444, Y500, Y730, and T491; (h) Y444, Y500, Y730, and S458; (i) Y444, Y500, Y730, S662, and T491; (j) Y444, Y500, Y730, T550, and T491; or (k) Y444, Y500, Y730, T659, and T491, of the wild-type AAV2 capsid protein as set forth in SEQ ID NO:2, or at equivalent amino acid positions corresponding thereto in any one of the wild-type AAV1, AAV3, AAV4, AAV5, AAV6, AAV7, AAV8, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:8, SEQ ID NO:9, or SEQ ID NO:10, or any combination thereof.

In the practice of the invention, the non-tyrosine, non-lysine, non-serine, or non-threonine amino acid residues may be any one or more amino acids not normally present at that residue in the wild-type protein, and preferably include one or more non-native amino acid substitutions selected from the group consisting of phenylalanine (F), valine (V), histidine (H), isoleucine (I), alanine (A), leucine (L) aspartic acid (D), asparagine (N). glutamic acid (E), arginine (R), serine (S), and isoleucine (I).

The invention also provides an isolated and purified polynucleotide that encodes one or more of the disclosed VP3 mutant proteins described herein, as well as recombinant adeno-associated viral (rAAV) vectors that include such a polynucleotide. Preferably, the vector constructs of the present invention further include at least one nucleic acid segment that encodes a diagnostic or therapeutic molecule operably linked to a promoter capable of expressing the nucleic acid segment in a suitable host cell comprising the vector. In the practice of the invention, the transduction efficiency of a virion comprising the modified AAV VP3 capsid protein will be higher than that of the corresponding, unmodified, wild-type protein, and as such, will preferably possess a transduction efficiency in a mammalian cell that is at least 2-fold, at least about 4-fold, at least about 6-fold, at least about 8-fold, at least about 10-fold, or at least about 12-fold or higher in a selected mammalian host cell than that of a virion that comprises a corresponding, unmodified, capsid protein. In certain embodiments, the transduction efficiency of the rAAV vectors provided herein will be at least about 15-fold higher, at least about 20-fold higher, at least about 25-fold higher, at least about 30-fold higher, or at least about 40, 45, or 50-fold or more greater than that of a virion that comprises a corresponding, unmodified, capsid protein. Moreover, the infectious virions of the present invention that include one or more modified AAV VP3 capsid proteins are preferably less susceptible to ubiquitination when introduced into a mammalian cell than that of a virion that comprises a corresponding, unmodified, capsid protein.

The present invention also concerns rAAV vectors, wherein the nucleic acid segment further comprises a promoter, an enhancer, a post-transcriptional regulatory sequence, a polyadenylation signal, or any combination thereof, operably linked to the nucleic acid segment that encodes the selected polynucleotide of interest.

Preferably, the promoter is a heterologous promoter, a tissue-specific promoter, a cell-specific promoter, a constitutive promoter, an inducible promoter, or any combination thereof.

In certain embodiments, the nucleic acid segments cloned into the novel rAAV expression vectors described herein will express or encode one or more polypeptides, peptides, ribozymes, peptide nucleic acids, siRNAs, RNAis, antisense oligonucleotides, antisense polynucleotides, antibodies, antigen binding fragments, or any combination thereof.

As noted herein, the therapeutic agents useful in the invention may include one or more agonists, antagonists, anti-apoptosis factors, inhibitors, receptors, cytokines, cytotoxins, erythropoietic agents, glycoproteins, growth factors, growth factor receptors, hormones, hormone receptors, interferons, interleukins, interleukin receptors, nerve growth factors, neuroactive peptides, neuroactive peptide receptors, proteases, protease inhibitors, protein decarboxylases, protein kinases, protein kinase inhibitors, enzymes, receptor binding proteins, transport proteins or one or more inhibitors thereof, serotonin receptors, or one or more uptake inhibitors thereof, serpins, serpin receptors, tumor suppressors, diagnostic molecules, chemotherapeutic agents, cytotoxins, or any combination thereof.

The rAAV vectors of the present invention may be comprised within a virion having a serotype that is selected from the group consisting of AAV serotype 1, AAV serotype 2, AAV serotype 3, AAV serotype 4, AAV serotype 5, AAV serotype 6, AAV serotype 7, AAV serotype 8, AAV serotype 9, AAV serotype 10, AAV serotype 11, or AAV serotype 12, or any other serotype as known to one of ordinary skill in the viral arts.

In related embodiments, the invention further provides populations and pluralities of rAAV vectors, virions, infectious viral particles, or host cells that include one or more nucleic acid segments that encode a mutated VP3 protein.

Preferably, the mammalian host cells will be human host cells, including, for example blood cells, stem cells, hematopoietic cells, CD34+ cells, liver cells, cancer cells, vascular cells, pancreatic cells, neural cells, ocular or retinal cells, epithelial or endothelial cells, dendritic cells, fibroblasts, or any other cell of mammalian origin. Including, for example a cell from the liver, the lung, the heart, the pancreas, the intestines, the kidney, or the brain of a mammal.

The invention further provides composition and formulations that include one or more of the proteins nucleic acid segments viral vectors, host cells, or viral particles of the present invention together with one or more pharmaceutically-acceptable buffers, diluents, or excipients. Such compositions may be included in one or more diagnostic or therapeutic kits, for diagnosing, preventing, treating or ameliorating one or more symptoms of a mammalian disease, injury, disorder, trauma or dysfunction.

The invention further includes a method for providing a mammal in need thereof with a diagnostically- or therapeutically-effective amount of a selected biological molecule, the method comprising providing to a cell, tissue or organ of a mammal in need thereof, an amount of an rAAV vector; and for a time effective to provide the mammal with a diagnostically- or a therapeutically-effective amount of the selected biological molecule.

The invention further provides a method for diagnosing, preventing, treating, or ameliorating at least one or more symptoms of a disease, a disorder, a dysfunction, an injury, an abnormal condition, or trauma in a mammal. In an overall and general sense, the method includes at least the step of administering to a mammal in need thereof one or more of the disclosed rAAV vectors, in an amount and for a time sufficient to diagnose, prevent, treat or ameliorate the one or more symptoms of the disease, disorder, dysfunction, injury, abnormal condition, or trauma in the mammal. In the case of rAAV8 vectors, such disease may preferably include one or more diseases or dysfunctions of the mammalian eye, and in the case of rAAV6 vectors, one or more diseases of stem cells, blood cells, hematopoietic cells, or CD35+ cells, including for example, sickle cell disease, β-thalassemia, and such like.

The invention also provides a method of transducing a population of mammalian cells. In an overall and general sense, the method includes at least the step of introducing into one or more cells of the population, a composition that comprises an effective amount of one or more of the rAAV vectors disclosed herein.

In a further embodiment, the invention also provides isolated nucleic acid segments that encode one or more of the VP3 mutant capsid proteins as described herein, and provides recombinant vectors, virus particles, infectious virions, and isolated host cells that comprise one or more of the improved vector sequences described and tested herein.

Additionally, the present invention provides compositions, as well as therapeutic and/or diagnostic kits that include one or more of the disclosed vectors or AAv compositions, formulated with one or more additional ingredients, or prepared with one or more instructions for their use.

The invention also demonstrates methods for making, as well as methods of using the disclosed improved rAAV capsid-mutated vectors in a variety of ways, including, for example, ex situ, in vitro and in vivo applications, methodologies, diagnostic procedures, and/or gene therapy treatment methods. Because many of the improved vectors are resistant to proteasomal degradation, they possess significantly increased transduction efficiencies in vivo making them particularly suited for viral vector-based human gene therapy regimens, and for delivering one or more genetic constructs to selected mammalian cells in vivo and/or in vitro.

In addition to a variety of single mutation vectors described herein that possess improved properties making them useful in a number of embodiments, the inventors have also surprisingly found that mutation of two or more amino acid residues (and preferably those on or near the outer surface of the capsid proteins) confers even greater transduction efficiency, making them even more suited as delivery vehicles. Exemplary amino acid residues that have been mutated include, for example, but are not limited to, amino acids such as tyrosines, lysine, serine, and threonine found in the surface exposed regions of VP3 protein. Some of the many mutations developed in this method include, without limitation, Tyr252 to Phe272 (Y252F), Tyr272 to Phe272 (Y272F), Tyr444 to Phe444 (Y444F), Tyr500 to Phe500 (Y500F), Tyr700 to Phe700 (Y700F), Tyr704 to Phe704 (Y704F), Tyr730 to Phe730 (Y730F), lysine to glutamic acid (E) or arginine (R) mutations as K258, K321, K459, K490, K507, K527, K572, K532, K544, K549, K556, K649, K655, K665, and/or K706, threonine (T) to valine (V) mutations at T491, T550, T659, or serine (S) to valine mutations at S662, inter alia. Such mutations with one or more non-native amino acids at those positions has resulted in improved transduction efficiency of the rAAV vectors when compared to the corresponding, wild-type, unmodified vectors.

In certain embodiments, one or more surface-exposed lysine residues corresponding to K490, K544, K549, and K556 of the wild-type AAV2 capsid sequence have also been modified. In certain specific embodiments, one or more surface-exposed lysine residue corresponding K490, K544, K549, and K556 of the wild-type AAV2 capsid sequence are modified into glutamic acid (E).

In one embodiment, the present invention provides AAV2 vectors wherein surface-exposed lysine residues corresponding to K544 and K556 residues of the wild-type AAV2 capsid are modified into glutamic acid (E).

In certain embodiments, one or more surface-exposed lysine residues corresponding to K530, K547, and K569 of the wild-type AAV8 capsid sequence are modified. In certain specific embodiments, one or more surface-exposed lysine residue corresponding K530, K547, and K569 of the wild-type AAV2 capsid sequence are modified into glutamic acid (E).

In one embodiment, a combination of surface-exposed lysine, serine, threonine and/or tyrosine residues of the AAV capsid is modified, wherein the modification occurs at positions corresponding to
  (Y444F+Y500F+Y730F+T491V)
  (Y444F+Y500F+Y730F+T491V+ T550V)
  (Y444F+Y500F+Y730F+T491V+ T659V)
  (T491V+ T550V+ T659V)
  (Y440F+Y500F+Y730F)
  (Y444F+Y500F+Y730F+T491V+S662V), and/or
  (Y444F+Y500F+Y730F+T491V+ T550V+ T659V)
of a wild-type AAV capsid sequence [e.g., one or more of SEQ ID NO:1, SEQ ID NO:2. SEQ ID NO:3, SEQ ID NO:4, SEQ ID NO:5, SEQ ID NO:6, SEQ ID NO:7, SEQ ID NO:8, SEQ ID NO:9, or SEQ ID NO:10; and in a particular embodiment, of the capsid protein of wild-type AAV2, AAV6, or AAV8, the sequences of which are shown in SEQ ID NO:2; SEQ ID NO;6 and SEQ ID NO:8, respectively].

In one aspect, the invention provides compositions comprising recombinant adeno-associated viral (AAV) vectors, virions, viral particles, and pharmaceutical formulations thereof, useful in methods for delivering genetic material encoding one or more beneficial or therapeutic product(s) to mammalian cells and tissues. In particular, the compositions and methods of the invention provide a significant advancement in the art through their use in the treatment, prevention, and/or amelioration of symptoms of one or more mammalian diseases. It is contemplated that human gene therapy will particularly benefit from the present teachings by providing new and improved viral vector constructs for use in the treatment of a number of diverse diseases, disorders, and dysfunctions.

In another aspect, the invention concerns modified rAAV vector that encode one or more mammalian therapeutic agents for the prevention, treatment, and/or amelioration of one or more disorders in the mammal into which the vector construct is delivered.

In particular, the invention provides rAAV-based expression constructs that encode one or more mammalian therapeutic agent(s) (including, but not limited to, for example, protein(s), polypeptide(s), peptide(s), enzyme(s), antibodies, antigen binding fragments, as well as variants, and/or active fragments thereof, for use in the treatment, prophylaxis, and/or amelioration of one or more symptoms of a mammalian disease, dysfunction, injury, and/or disorder.

In one embodiment, the invention provides an rAAV vector that comprises at least a first capsid protein comprising at least a first amino acid substitution to a non-native amino acid at one or more surface exposed amino acid residues in an rAAV capsid protein, and wherein the vector further additionally includes at least a first nucleic acid segment that encodes at least a first diagnostic or therapeutic agent operably linked to a promoter capable of expressing the segment in a host cell that contains the expression vector construct.

The surface-exposed amino acid-modified rAAV vectors of the present invention may optionally further include one or more enhancer sequences that are each operably linked to the nucleic acid segment. Exemplary enhancer sequences include, but are not limited to, one or more selected from the group consisting of a CMV enhancer, a synthetic enhancer, a liver-specific enhancer, an vascular-specific enhancer, a brain-specific enhancer, a neural cell-specific enhancer, a lung-specific enhancer, a muscle-specific enhancer, a kidney-specific enhancer, a pancreas-specific enhancer, and an islet cell-specific enhancer.

Exemplary promoters useful in the practice of the invention include, without limitation, one or more heterologous, tissue-specific, constitutive or inducible promoters, including, for example, but not limited to, a promoter selected from the group consisting of a CMV promoter, a β-actin promoter, an insulin promoter, an enolase promoter, a BDNF promoter, an NGF promoter, an EGF promoter, a growth factor promoter, an axon-specific promoter, a dendrite-specific promoter, a brain-specific promoter, a hippocampal-specific promoter, a kidney-specific promoter, an elafin promoter, a cytokine promoter, an interferon promoter, a growth factor promoter, an alpha-1 antitrypsin promoter, a brain-specific promoter, a neural cell-specific promoter, a central nervous system cell-specific promoter, a peripheral nervous system cell-specific promoter, an interleukin promoter, a serpin promoter, a hybrid CMV promoter, a hybrid β-actin promoter, an EF1 promoter, a U1a promoter, a U1b promoter, a Tet-inducible promoter and a VP16-LexA promoter. In exemplary embodiments, the promoter is a mammalian or avian β-actin promoter.

The first nucleic acid segment may also further include one or more post-transcriptional regulatory sequences or one or more polyadenylation signals, including, for example, but not limited to, a woodchuck hepatitis virus post-transcription regulatory element, a polyadenylation signal sequence, or any combination thereof.

Exemplary diagnostic or therapeutic agents deliverable to host cells by the present vector constructs include, but are not limited to, an agent selected from the group consisting of a polypeptide, a peptide, an antibody, an antigen binding fragment, a ribozyme, a peptide nucleic acid, a siRNA, an RNAi, an antisense oligonucleotide, an antisense polynucleotide, and any combination thereof.

In exemplary embodiments, the improved rAAV vectors of the invention will preferably encode at least one diagnostic or therapeutic protein or polypeptide selected from the group consisting of a molecular marker, an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinsase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, a tumor suppressor, and any combination thereof.

In certain applications, the capsid-modified rAAV vectors of the present invention may include one or more nucleic acid segments that encode a polypeptide selected from the group consisting of BDNF, CNTF, CSF, EGF, FGF, G-SCF, GM-CSF, gonadotropin, IFN, IFG-1, M-CSF, NGF, PDGF, PEDF, TGF, TGF-B2, TNF, VEGF, prolactin, somatotropin, XIAP1, IL-1, IL-2, IL-3, IL-4, IL-5, IL-6, IL-7, IL-8, IL-9, IL-10, IL-10(I87A), viral IL-10, IL-11, IL-12, IL-13, IL-14, IL-15, IL-16, IL-17, IL-18, and any combination thereof.

In another embodiment, the invention concerns genetically-modified inproved transduction-efficiency rAAV vectors that include at least a first nucleic acid segment that encodes one or more therapeutic agents that alter, inhibit, reduce, prevent, eliminate, or impair the activity of one or more endogenous biological processes in the cell. In particular embodiments, such therapeutic agents may be those that selectively inhibit or reduce the effects of one or more metabolic processes, dysfunctions, disorders, or diseases. In certain embodiments, the defect may be caused by injury or trauma to the mammal for which treatment is desired. In other embodiments, the defect may be caused the overexpression of an endogenous biological compound, while in other embodiments still; the defect may be caused by the under-expression or even lack of one or more endogenous biological compounds.

When the use of such vectors is contemplated for introduction of one or more exogenous proteins, polypeptides, peptides, ribozymes, siRNAs, and/or antisense oligonucleotides, to a particular cell transfected with the vector, one may employ the modified AAV vectors disclosed herein by incorporating into the vector at least a first exogenous polynucleotide operably positioned downstream and under the control of at least a first heterologous promoter that expresses the polynucleotide in a cell comprising the vector to produce the encoded therapeutic agent, including for example, peptides, proteins, polypeptides, antibodies, ribozymes, siRNAs, and antisense oligo- or polynucleotides. Such constructs may employ one or more heterologous promoters to express the therapeutic agent of interest. Such promoters may be constitutive, inducible, or even cell- or tissue-specific. Exemplary promoters include, but are not limited to, a CMV promoter, a β-actin promoter, a hybrid CMV promoter, a hybrid β-actin promoter, an EF1 promoter, a U1a promoter, a U1b promoter, a Tet-inducible promoter, a VP16-LexA promoter, a joint-specific promoter and a human-specific promoter.

The genetically-modified rAAV vectors and expression systems of the present invention may also further include a second nucleic acid segment that comprises, consists essentially of, or consists of, one or more enhancers, one or more regulatory elements, one or more transcriptional elements, or any combination thereof, that alter, improve, regulate, and/or affect the transcription of the nucleotide sequence of interest expressed by the modified rAAV vectors.

For example, the rAAV vectors of the present invention may further include a second nucleic acid segment that comprises, consists essentially of, or consists of, a CMV enhancer, a synthetic enhancer, a cell-specific enhancer, a tissue-specific enhancer, or any combination thereof. The second nucleic acid segment may also further comprise, consist essentially of, or consist of, one or more intron sequences, one or more post-transcriptional regulatory elements, or any combination thereof.

The improved vectors and expression systems of the present invention may also optionally further include a polynucleotide that comprises, consists essentially of, or consists of, one or more polylinkers, restriction sites, and/or multiple cloning region(s) to facilitate insertion (cloning) of one or more selected genetic elements, genes of interest, or therapeutic or diagnostic constructs into the rAAV vector at a selected site within the vector.

In further aspects of the present invention, the exogenous polynucleotide(s) that may be delivered into suitable host cells by the improved, capsid-modified, rAAV vectors disclosed herein are preferably of mammalian origin, with polynucleotides encoding one or more polypeptides or peptides of human, non-human primate, porcine, bovine, ovine, feline, canine, equine, epine, caprine, or lupine origin being particularly preferred.

The exogenous polynucleotide(s) that may be delivered into host cells by the disclosed capsid-modified viral vectors may, in certain embodiments, encode one or more proteins, one or more polypeptides, one or more peptides, one or more enzymes, or one or more antibodies (or antigen-binding fragments thereof), or alternatively, may express one or more siRNAs, ribozymes, antisense oligonucleotides, PNA molecules, or any combination thereof. When combinational gene therapies are desired, two or more different molecules may be produced from a single rAAV expression system, or alternatively, a selected host cell may be transfected with two or more unique rAAV expression systems, each of which may comprise one or more distinct polynucleotides that encode a therapeutic agent.

In other embodiments, the invention also provides capsid-modified rAAV vectors that are comprised within an infectious adeno-associated viral particle or a virion, as well as pluralities of such virions or infectious particles. Such vectors and virions may be comprised within one or more diluents, buffers, physiological solutions or pharmaceutical vehicles, or formulated for administration to a mammal in one or more diagnostic, therapeutic, and/or prophylactic regimens. The vectors, virus particles, virions, and pluralities thereof of the present invention may also be provided in excipient formulations that are acceptable for veterinary administration to selected livestock, exotics, domesticated animals, and companion animals (including pets and such like), as well as to non-human primates, zoological or otherwise captive specimens, and such like.

The invention also concerns host cells that comprise at least one of the disclosed capsid protein-modified rAAV expression vectors, or one or more virus particles or virions that comprise such an expression vector. Such host cells are particularly mammalian host cells, with human host cells being particularly highly preferred, and may be either isolated, in cell or tissue culture. In the case of genetically modified animal models, the transformed host cells may even be comprised within the body of a non-human animal itself.

In certain embodiments, the creation of recombinant non-human host cells, and/or isolated recombinant human host cells that comprise one or more of the disclosed rAAV vectors is also contemplated to be useful for a variety of diagnostic, and laboratory protocols, including, for example, means for the production of large-scale quantities of the rAAV vectors described herein. Such virus production methods are particularly contemplated to be an improvement over existing methodologies including in particular, those that require very high titers of the viral stocks in order to be useful as a gene therapy tool. The inventors contemplate that one very significant advantage of the present methods will be the ability to utilize lower titers of viral particles in mammalian transduction protocols, yet still retain transfection rates at a suitable level.

Compositions comprising one or more of the disclosed capsid-modified, improved transduction-efficiency rAAV vectors, expression systems, infectious AAV particles, or host cells also form part of the present invention, and particularly those compositions that further comprise at least a first pharmaceutically-acceptable excipient for use in therapy, and for use in the manufacture of medicaments for the treatment of one or more mammalian diseases, disorders, dysfunctions, or trauma. Such pharmaceutical compositions may optionally further comprise one or more diluents, buffers, liposomes, a lipid, a lipid complex; or the tyrosine-modified rAAV vectors may be comprised within a microsphere or a nanoparticle. Pharmaceutical formulations suitable for intramuscular, intravenous, or direct injection into an organ or tissue or a plurality of cells or tissues of a human or other mammal are particularly preferred, however, the compositions disclosed herein may also find utility in administration to discreet areas of the mammalian body, including for example, formulations that are suitable for direct injection into one or more organs, tissues, or cell types in the body. Such injection sites include, but are not limited to, the brain, a joint or joint capsule, a synovium or subsynovium tissue, tendons, ligaments, cartilages, bone, periarticular muscle or an articular space of a mammalian joint, as well as direct administration to an organ such as the heart, liver, lung, pancreas, intestine, brain, bladder, kidney, or other site within the patient's body, including, for example, introduction of the viral vectors via intraabdominal, intrathorascic, intravascular, or intracerebroventricular delivery.

Other aspects of the invention concern recombinant adeno-associated virus virion particles, compositions, and host cells that comprise, consist essentially of, or consist of, one or more of the capsid-modified, improved transduction efficiency, rAAV vectors disclosed herein, such as for example pharmaceutical formulations of the vectors intended for administration to a mammal through suitable means, such as, by intramuscular, intravenous, intra-articular, or direct injection to one or more cells, tissues, or organs of a selected mammal. Typically, such compositions may be formulated with pharmaceutically-acceptable excipients as described hereinbelow, and may comprise one or more liposomes, lipids, lipid complexes, microspheres or nanoparticle formulations to facilitate administration to the selected organs, tissues, and cells for which therapy is desired.

Kits comprising one or more of the disclosed capsid-modified rAAV vectors (as well as one or more virions, viral particles, transformed host cells or pharmaceutical compositions comprising such vectors); and instructions for using such kits in one or more therapeutic, diagnostic, and/or prophylactic clinical embodiments are also provided by the present invention. Such kits may further comprise one or more reagents, restriction enzymes, peptides, therapeutics, pharmaceutical compounds, or means for delivery of the composition(s) to host cells, or to an animal (e.g., syringes, injectables, and the like). Exemplary kits include those for treating, preventing, or ameliorating the symptoms of a disease, deficiency, dysfunction, and/or injury, or may include components for the large-scale production of the viral vectors themselves, such as for commercial sale, or for use by others, including e.g., virologists, medical professionals, and the like.

Another important aspect of the present invention concerns methods of use of the disclosed rAAV vectors, virions, expression systems, compositions, and host cells described herein in the preparation of medicaments for diagnosing, preventing, treating or ameliorating at least one or more symptoms of a disease, a dysfunction, a disorder, an abnormal condition, a deficiency, injury, or trauma in an animal, and in particular, in a vertebrate mammal. Such methods generally involve administration to a mammal in need thereof, one or more of the disclosed vectors, virions, viral particles, host cells, compositions, or pluralities thereof, in an amount and for a time sufficient to diagnose, prevent, treat, or lessen one or more symptoms of such a disease, dysfunction, disorder, abnormal condition, deficiency, injury, or trauma in the affected animal. The methods may also encompass prophylactic treatment of animals suspected of having such conditions, or administration of such compositions to those animals at risk for developing such conditions either following diagnosis, or prior to the onset of symptoms.

As described above, the exogenous polynucleotide will preferably encode one or more proteins, polypeptides, peptides, ribozymes, or antisense oligonucleotides, or a combination of these. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which will provide unique heterologous polynucleotides encoding at least two different such molecules.

Compositions comprising one or more of the disclosed rAAV vectors, expression systems, infectious AAV particles, host cells also form part of the present invention, and particularly those compositions that further comprise at least a first pharmaceutically-acceptable excipient for use in the manufacture of medicaments and methods involving therapeutic administration of such rAAV vectors. Such pharmaceutical compositions may optionally further comprise liposomes, a lipid, a lipid complex; or the rAAV vectors may be comprised within a microsphere or a nanoparticle. Pharmaceutical formulations suitable for intramuscular, intravenous, or direct injection into an organ or tissue of a human are particularly preferred.

Another important aspect of the present invention concerns methods of use of the disclosed vectors, virions, expression systems, compositions, and host cells described herein in the preparation of medicaments for treating or ameliorating the symptoms of various polypeptide deficiencies in a mammal. Such methods generally involve administration to a mammal, or human in need thereof, one or more of the disclosed vectors, virions, host cells, or compositions, in an amount and for a time sufficient to treat or ameliorate the symptoms of such a deficiency in the affected mammal. The methods may also encompass prophylactic treatment of animals suspected of having such conditions, or administration of such compositions to those animals at risk for developing such conditions either following diagnosis, or prior to the onset of symptoms.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 1A, FIG. 1B, and FIG. 1C show the effect of NF-κB pathway inhibitors and activator on AAV vector-mediated EGFP expression in HeLa cells in vitro. Cells were pretreated with various concentrations of inhibitors and activators for 12 hrs and transduced with $2 \times 10^3$ AAV-EGFP vgs per cell. FIG. 1A: Transgene expression was detected by fluorescence microscopy 48 hrs post-infection. Representative images are shown. FIG. 1B: Quantitative analyses of the data from FIG. 1A. Images from five visual fields were analyzed as described. *P<0.001. FIG. 1C: Western blot analysis of HeLa cell extracts transduced with scAAV vectors and in the presence of NF-κB modulators. The samples were analyzed by using anti-p65 and anti-IκB antibodies [classical pathway], anti-p100/p52 antibody [non-canonical pathway] for detection NF-κB signaling in response to AAV exposure. These results are representative of two independent experiments;

FIG. 2A and FIG. 2B show AAV-EGFP vector-mediated transduction of primary human monocytes-derived dendritic cells in the presence of NF-κB modulators. FIG. 2A: Transgene expression was detected by flow cytometry 48 hrs post-transduction. FIG. 2B: Western blot analysis for components of classical and non-canonical pathway of NF-κB activation in nuclear extracts from dendritic cells, mock-transduced or transduced with 2,000 vgs/cell of scAAV vectors and in the presence of NF-κB modulators;

FIG. 4A: Representative images are shown. Original magnification: ×400. FIG. 4B: Quantitative analyses of the data from FIG. 4A. Images from five visual fields were analyzed quantitatively as described in the legend to FIG. 1A;

FIG. 5 demonstrates that AAV genome contains putative binding sites for NF-κB-responsive transcription factors within the inverted terminal repeats (ITRs). The putative NF-κB-responsive transcription factor-binding sites in the AAV-ITRs were identified by in silico analysis using the TRANSFAC database [http://alggen.lsi.upc.es/]. The binding sites for p300, TFIIB, and SpII transcriptions factors are denoted by green, red, and blue underlined fonts, respectively. The boxed sequence represents the 20-nucleotide single-stranded D-sequence within the ITR;

FIG. 6A, FIG. 6B, FIG. 6C, FIG. 6D, and FIG. 6E show the effect of NF-κB activators and inhibitors on transgene expression from an AAV2-EGFP vector in HeLa cells in vitro. Cells were either mock-treated or pretreated with various combinations of inhibitors and activators for 12 hr. Washed cells were infected with $2 \times 10^3$ vg/cell of scAAV2-EGFP (FIG. 6A), ssAAV2-EGFP (FIG. 6B), or TM-scAAV2-EGFP (FIG. 6C). Transgene expression was detected by fluorescence microscopy 48 hrs' postinfection. Representative images are shown; FIG. 6D shows a Western blot analysis of cytoplasmic and nuclear extracts from HeLa cells transduced with scAAV vectors and in the presence of NF-κB modulators. The samples were analyzed by using anti-p100/p52 antibody for detection of NF-κB signaling. Anti-GAPDH and lamin B antibodies were used as appropriate controls. These results are representative of two independent experiments;

FIG. 8A: IL-1α; FIG. 8B: IL-6; FIG. 8C: TNF-α; FIG. 8D: IL-12α, FIG. 8E: KC; and FIG. 8F: RANTES. Values are significant above 2.6 and below 0.38; calculated by determining the variability in the 96-well plates used to measure specific gene expression;

FIG. 11A: Equivalent numbers of T47D and T47D+hHGFR cells were infected with various indicated multiplicity-of-infection (MOI) of scAAV3-CBAp-EGFP vectors under identical conditions. Transgene expression was determined by fluorescence microscopy 72 hrs post-infection. FIG. 11B: T47D+hHGFR cells were transduced with 2,000 vgs/cell of scAAV3 vectors in the absence or the presence of 5 μg/mL of hHGF. Transgene expression was determined by fluorescence microscopy 72 hrs' post-infection;

FIG. 12A: T47D+ hHGFR cells, either mock-treated or treated with various concentration of BMS-777607, were infected with 2,000 vgs/cell of scAAV3-CBAp-EGFP vectors. Transgene expression was determined by fluorescence microscopy 72 hrs' post-infection. FIG. 12B: T47D and T47D+hHGFR cells were infected with 10,000 vgs/cell of scAAV3-CBAp-EGFP vectors in the absence or the presence of 1 μM of BMS-777607. FIG. 12C: T47D and T47D+hHGFR cells were mock-treated or pretreated with BMS-777607 for 2 hrs. Whole-cell lysates were prepared and analyzed on Western blots using various indicated primary antibodies. β-actin was used as a loading control;

FIG. 13A: T47D+hHGFR cells, either mock-treated or treated with 1 μM of BMS-777607, were infected with 2,000 vgs/cell of either scAAV2-, scAAV3- or scAAV4-CBAp-EGFP vectors. FIG. 13B: T47D+hHGFR cells, either mock-treated or treated with 1 μM of BMS-777607, were infected with 2,000 vgs/cell of either scAAV5-, scAAV7-, scAAV8- or scAAV9-CBAp-EGFP vectors. Transgene expression was determined by fluorescence microscopy 72 hrs post-infection;

FIG. 14A: HeLa cells, either mock-treated or treated with 5 μM of MG132, were infected with scAAV2-CBAp-EGFP vectors. FIG. 14B: Huh7 and Hep293TT cells, either mock-treated or treated with various concentration of MG132, were infected with scAAV3-WT-CBAp-EGFP vectors. FIG. 14C: HeLa cells, either mock-treated or treated with 200 μM of Tyr23, were infected by scAAV2-CBAp-EGFP vectors. FIG. 14D: Hep293TT cells, either mock-treated or treated with Tyr23, were infected by scAAV3-CBAp-EGFP vectors. Transgene expression was determined 72 hrs' post-transduction;

FIG. 16A, FIG. 16B, and FIG. 16C illustrate the transduction efficiency of WT and single, double, and triple tyrosine-mutant AAV3 vectors. FIG. 16A: Huh7 cells were transduced with WT or various indicated Y-F mutant scAAV3-CBAp-EGFP vectors under identical conditions. Transgene expression was determined 72 hrs post-transduction. FIG. 16B: Huh7 cells were transduced with 5,000 vgs/cell of WT or Y-F mutant scAAV3 vectors in the absence or the presence of 5 μg/mL of hHGF. Transgene expression was determined by fluorescence microscopy 72 hrs post-infection (FIG. 16C);

FIG. 19A: Transgene expression was detected by fluorescence microscopy 48 hrs post infection. FIG. 19B: Images from three visual fields were analyzed as described. *P<0.005, **P<0.001 vs. WT AAV2;

FIG. 20A: EGFP expression analysis at 48 hrs post-infection at an MOI of $1\times10^3$ vgs/cell. FIG. 20B: Quantitation of transduction efficiency of each of the serine-mutant AAV2 vectors. *P<0.005, **P<0.001 vs. WT AAV2;

FIG. 21 and FIG. 21B illustrate the structure of AAV2. FIG. 21B: The capsid surface of AAV2 shown in blue with serine residues 458, 492, and 662 highlighted in the same colors as in FIG. 3A. S458 and 492 are located adjacent to each other on the outer surface of the protrusions facing the depression surrounding the two-fold axes. S662 is located on the HI loop (colored white) (between the β-H and β-I strands of the core eight-stranded beta-barrel) which lie on the floor of the depression surrounding the icosahedral five-fold axes. The five-fold symmetry related DE loops (between the β-D and β-E strands), which form the channel at the icosahedral 5-fold axes, are colored in brown. The approximate positions of an icosahedral two-fold (2F), three-fold (3F), and five-fold (5F) axes are indicated by the open arrows;

FIG. 22A: EGFP expression analysis at 48 h after infection of 293 cells at an MOI of $1\times10^3$ vgs/cell. FIG. 22B: Quantitation of the transduction efficiency of each of the serine-mutant AAV2 vectors. *P<0.005, **P<0.001 vs. WT AAV2;

FIG. 23A: Quantitation of the transduction efficiency of WT- and S662V-AAV2 vectors in HEK293, HeLa, NIH3T3, H2.35 and moDCs. FIG. 23B: Western blot analysis of lysates from different cell lines for p-p38 MAPK expression levels. Total p38 MAPK and GAPDH levels were measured and used as loading controls. *P<0.005, **P<0.001 vs. WT AAV2;

FIG. 24A: Effect of JNK and p38 MAPK inhibitors, and site-directed substitution of the serine residue at position 662 on EGFP expression. FIG. 24B: Quantitation of the data in FIG. 24A at 48 hrs after infection and initiation of maturation. FIG. 24C: Analysis of expression of co-stimulatory markers such as CD80, CD83, CD86 in moDCs infected with scAAV2-S662V vectors at an MOI of $5\times10^4$ vgs/cell. iDCs—immature dendritic cells, and mDCs—mature dendritic cells, stimulated with cytokines, generated as described herein, were used as negative and positive controls, respectively. A representative example is shown. *P<0.005, **P<0.001 vs. WT AAV2;

FIG. 26A and FIG. 26B show the analysis of EGFP expression after transduction of HEK293 cells with individual site-directed AAV2 capsid mutants. Each of the 17 surface-exposed threonine (T) residues in AAV2 capsid was substituted with valine (V) and evaluated for its efficiency to mediate transgene expression. FIG. 26A: EGFP expression analysis at 48 h post-infection at MOI of $1\times10^3$ vg/cell. FIG. 26B: Quantification of transduction efficiency of each of the threonine-mutant scAAV2 vectors. *P<0.005, **P<0.001 vs. WT AAV2;

FIG. 27A: EGFP expression analysis at 48 hrs' post-infection at MOI of $1\times10^3$ vg/cell. FIG. 27B: Quantitation of transduction efficiency of each of the threonine-mutant AAV2 vectors. *P<0.005, **P<0.001 vs. WT AAV2;

FIG. 28A and FIG. 28B demonstrate the evaluation of EGFP expression in H2.35 cell transduced with capsid optimized AAV2 vectors. The most efficient tyrosine, serine and threonine mutations were combined on single AAV2 capsid to produce several optimized AAV mutants. Efficiency of each vector was estimated on immortalized murine hepatocytes. FIG. 3A: EGFP expression analysis at 48 hrs' post-infection at MOI of $1\times10^3$ vg/cell. FIG. 3B: Quantification of transduction efficiency of each of the optimized scAAV2 vectors. *P<0.005, **P<0.001 vs. WT AAV2;

FIG. 29A: EGFP expression analysis at 16, 24 and 48 hrs' post-infection at MOI of $1\times10^3$ vg/cell. FIG. 29B: Quantification of transduction efficiency of each of the optimized scAAV2 vectors. *P<0.005, **P<0.001 vs. WT AAV2;

FIG. 32A: The capsid surface of AAV2 (grey) with the 17 surface threonine residues mutated in blue (251, 329, 330, 454, 503, 581, 592, 597, 660, 671, 701, 713, 716), green (455), yellow (491), brown (550), and pink (659). The surface location of T329, T330, T713 and T716 are indicated by arrows. The five-fold symmetry related DE loops (between the βD and βE strands) are colored in orange. The HI loops (between the βH and βI strands) are colored white and S662 located in this loop is in red. The white dashed triangle in FIG. 32A depicts a viral asymmetric unit bounded by a five-fold axis and two three-fold axes with a two-fold axis between the three-folds. Dashed ovals delineate the approximate footprints (2/60) of threonine residues that affect transduction when mutated. FIG. 32B: A "Roadmap" projection of the AAV2 capsid surface residues within a viral asymmetric unit. The areas covered by AAV2 surface threonines and 5662 are colored as in FIG. 32A. The residues in the tyrosine triple mutant residues, 444, 500, and 730 are shown in shades of purple. Dashed ovals are as described in FIG. 23A. Dashed rectangle (blue) shows residues previously determined to be important in heparin sulfate receptor binding for AAV2 and AAV6 (Wu et al., 2006; Opie et al., 2003);

Figure 33A-1:
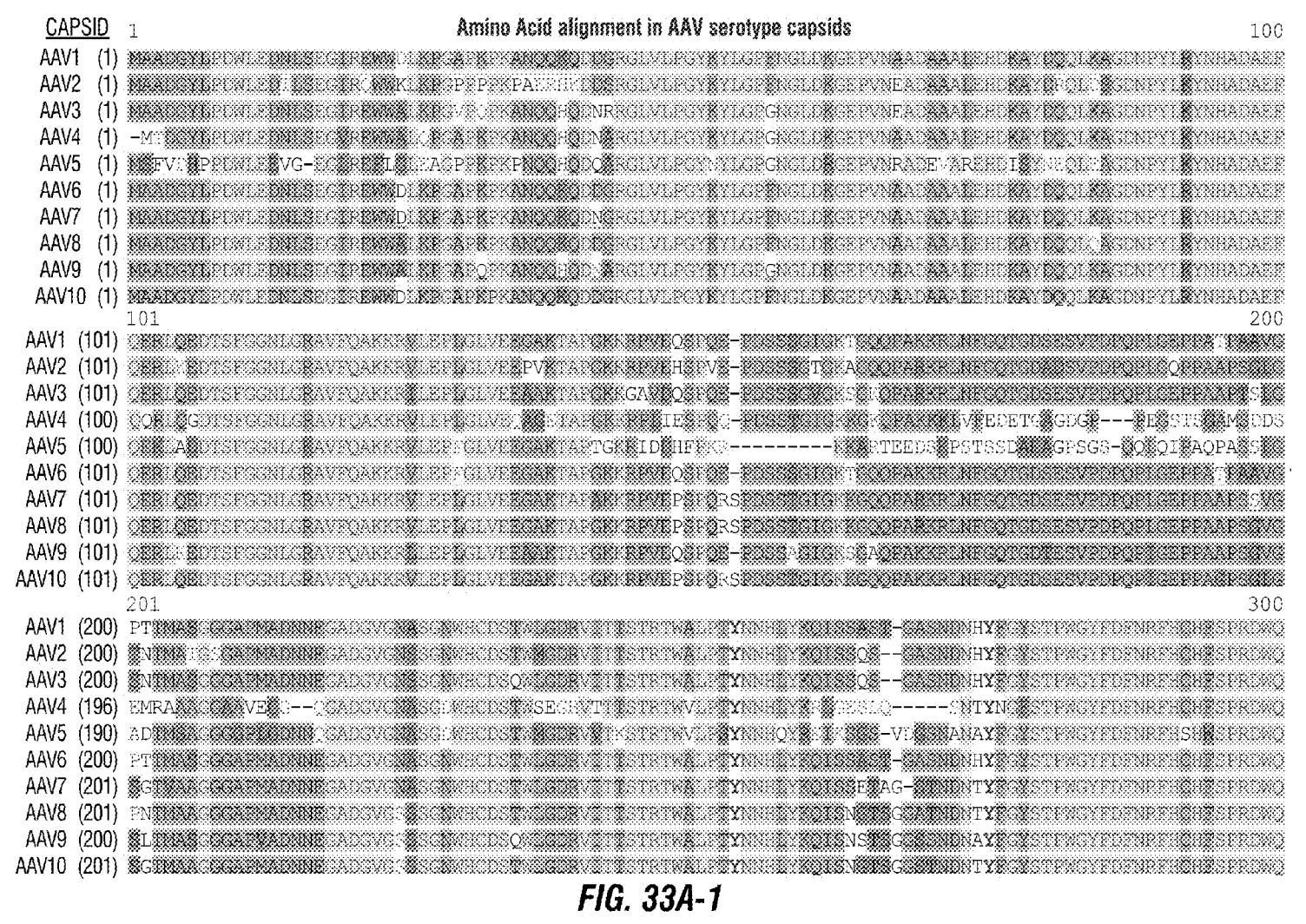
Figure 33A-2:
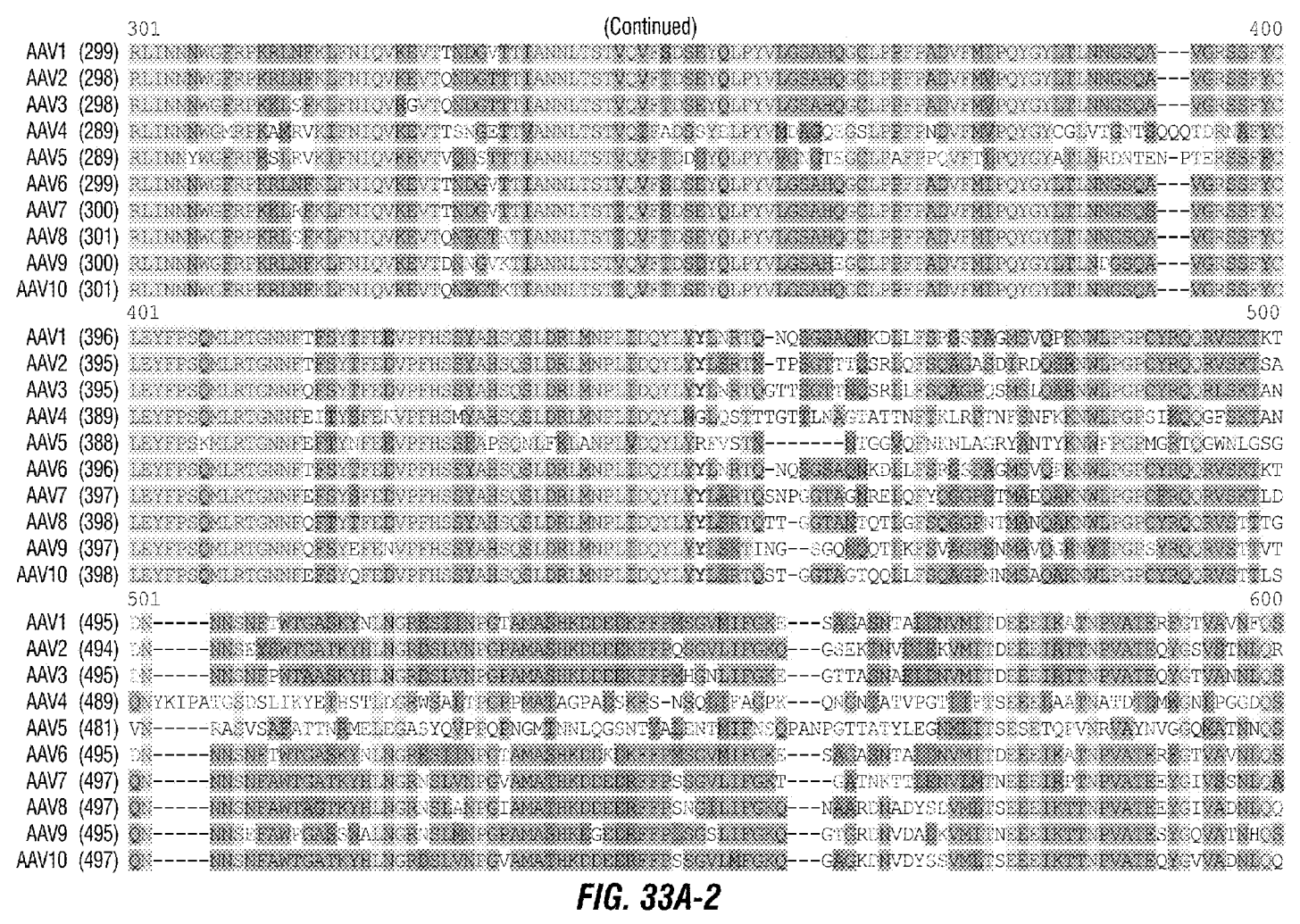
Figure 33A-3:
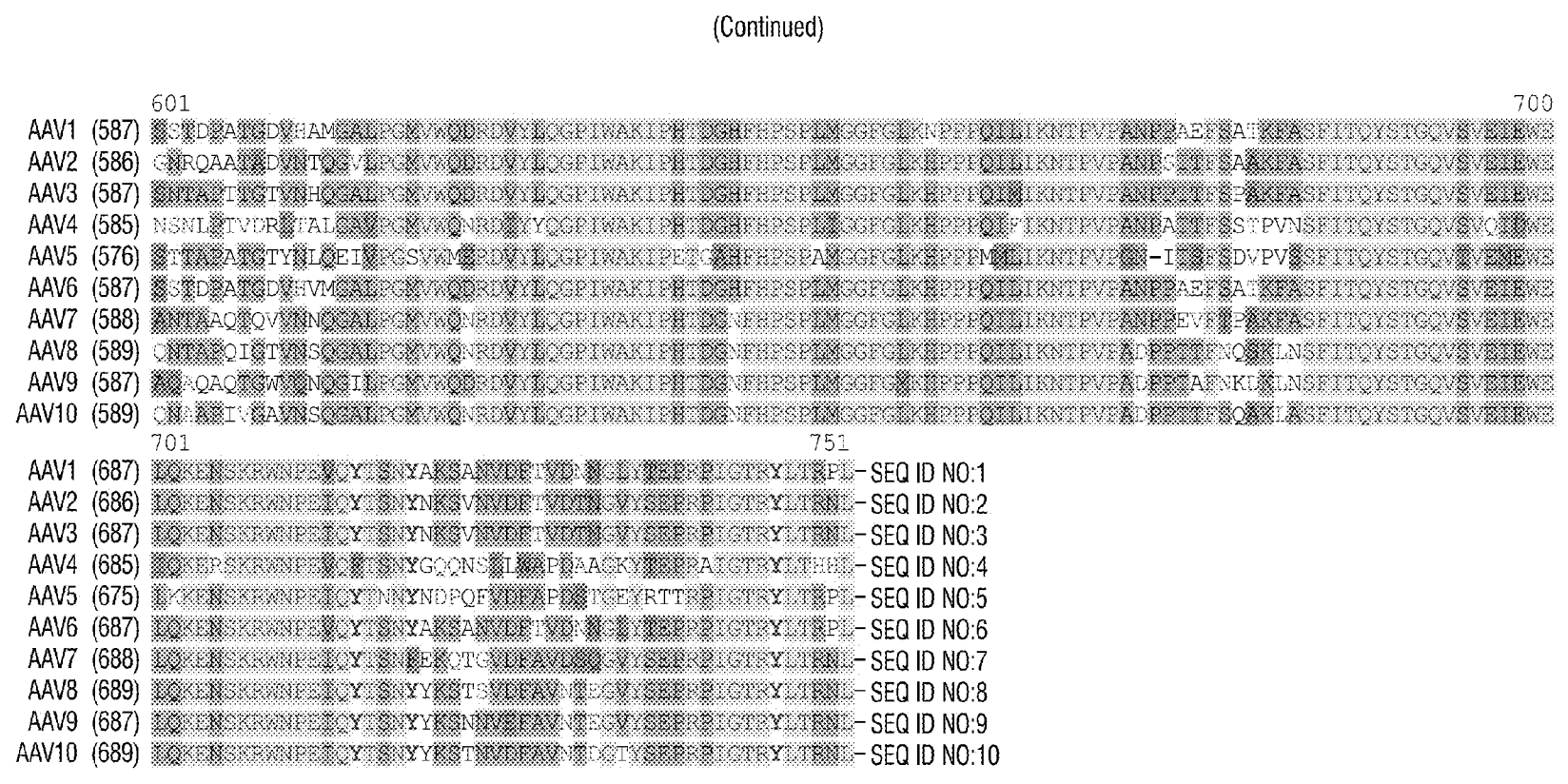
Figure 33B-2:
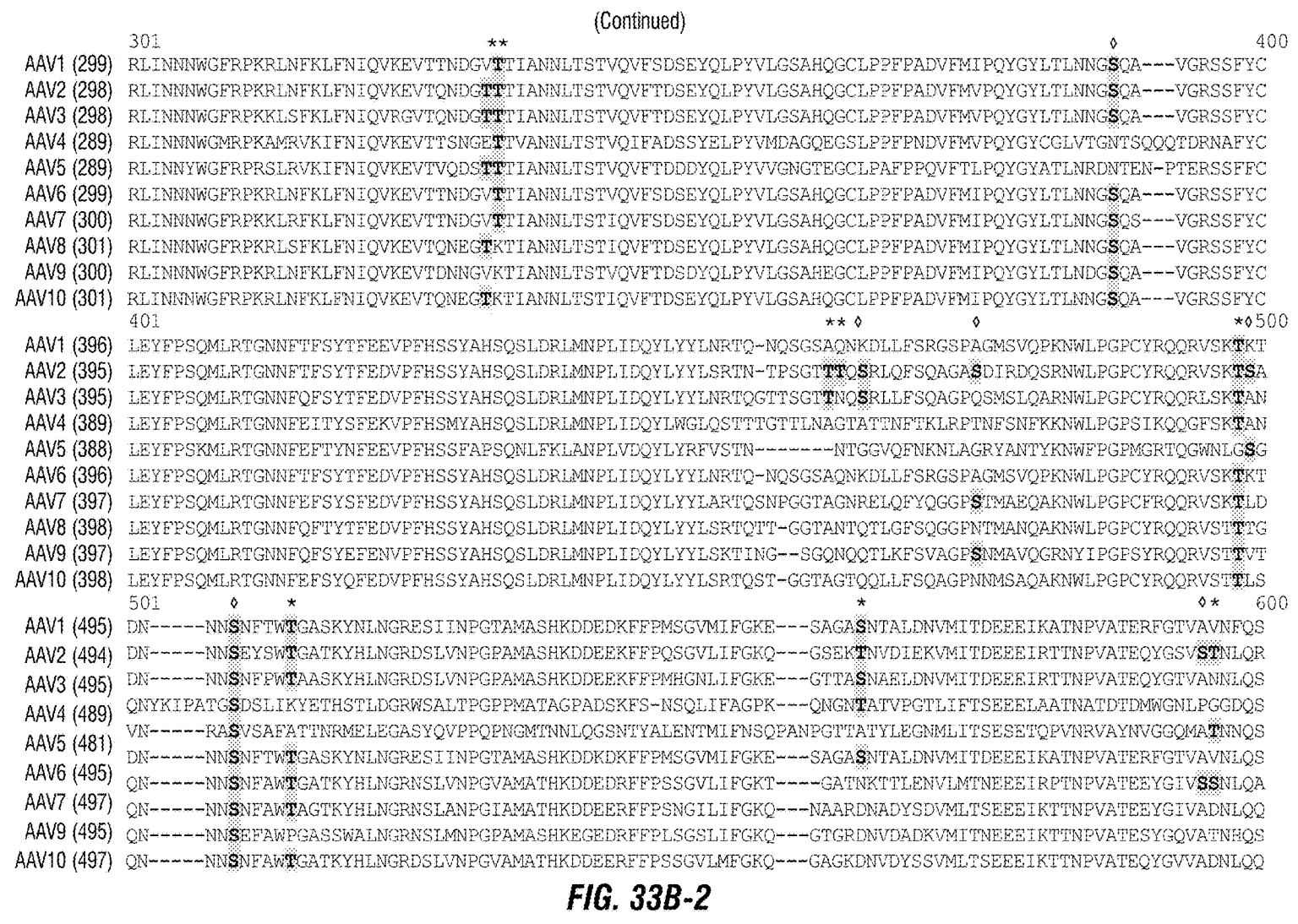

FIG. 33A, FIG. 33B, and FIG. 33C show amino acid alignment of the wild-type AAV1-10 capsids. FIG. 33A shows amino acid alignment of the wild-type AAV1-10 serotype capsids (SEQ ID NO:1 through SEQ ID NO:10). FIG. 33B shows amino acid alignment of the wild-type AAV1-10 serotype capsids, as well as surface-exposed serine and threonine residues that are conserved in among AAV1-10 capsids (conserved, surface-exposed residues are shown in bold); and FIG. 33C shows conserved, surface-exposed tyrosine residues in the wild-type AAV1-12 capsids, as well as embodiments of amino acid modifications. The tyrosine residues conserved among AAV1-12 are shown in bold;

FIG. 34 show packaging and transduction efficiencies of various serine-valine mutant AAV2 vectors relative to WT AAV2 vectors amino acid alignment of the wild-type AAV1-10 capsids; and FIG. 35 shows packaging and transduction efficiencies of serine-mutant vectors replaced with various amino acids relative to WT AAV2 vectors.

BRIEF DESCRIPTION OF THE SEQUENCES

Figure 2B:
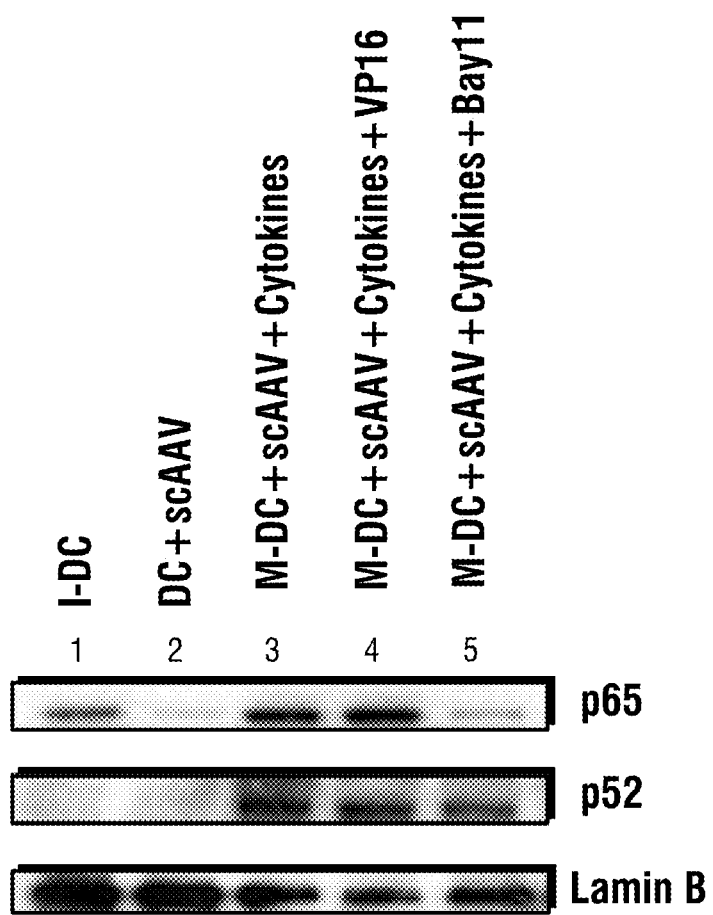

SEQ ID NO:1 is an amino acid sequence of the capsid protein of the wild-type adeno-associated virus serotype 1 (AAV1);

SEQ ID NO:2 is an amino acid sequence of the capsid protein of the wild-type adeno-associated virus serotype 2 (AAV2);

SEQ ID NO:3 is an amino acid sequence of the capsid protein of the wild-type adeno-associated virus serotype 3 (AAV3);

SEQ ID NO:4 is an amino acid sequence of the capsid protein of the wild-type adeno-associated virus serotype 4 (AAV4);

SEQ ID NO:5 is an amino acid sequence of the capsid protein of the wild-type adeno-associated virus serotype 5 (AAV5);

SEQ ID NO:6 is an amino acid sequence of the capsid protein of the wild-type adeno-associated virus serotype 6 (AAV6);

SEQ ID NO:7 is an amino acid sequence of the capsid protein of the wild-type adeno-associated virus serotype 7 (AAV7);

SEQ ID NO:8 is an amino acid sequence of the capsid protein of the wild-type adeno-associated virus serotype 8 (AAV8);

SEQ ID NO:9 is an amino acid sequence of the capsid protein of the wild-type adeno-associated virus serotype 9 (AAV9);

SEQ ID NO:10 is an amino acid sequence of the capsid protein of the wild-type adeno-associated virus serotype 10 (AAV10);

SEQ ID NO:11 is an oligonucleotide primer sequence useful according to the present invention;

SEQ ID NO:12 is an oligonucleotide primer sequence useful according to the present invention;

SEQ ID NO:13 is an oligonucleotide primer sequence useful according to the present invention;

SEQ ID NO:14 is an oligonucleotide primer sequence useful according to the present invention;

SEQ ID NO:15 is an oligonucleotide primer sequence useful according to the present invention;

SEQ ID NO:16 is an oligonucleotide primer sequence useful according to the present invention;

SEQ ID NO:17 is an oligonucleotide primer sequence useful according to the present invention;

SEQ ID NO:18 is an oligonucleotide primer sequence useful according to the present invention;

SEQ ID NO:19 is an oligonucleotide primer sequence useful according to the present invention;

SEQ ID NO:20 is an oligonucleotide primer sequence useful according to the present invention;

SEQ ID NO:21 is an oligonucleotide primer sequence useful according to the present invention;

SEQ ID NO:22 is a nucleic acid sequence containing the putative binding site for NF-kB-responsive transcription factors (See FIG. 5);

SEQ ID NO:23 is a single-stranded nucleic acid sequence probe (See FIG. 10);

SEQ ID NO:24 is a double-stranded nucleic acid sequence probe (See FIG. 10); and SEQ ID NO:25 is a single-stranded nucleic acid sequence probe (See FIG. 10).

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Recombinant adeno-associated virus (AAV) vectors have been used successfully for in vivo gene transfer in numerous pre-clinical animal models of human disease, and have been used successfully for long-term expression of a wide variety of therapeutic genes (Daya and Berns, 2008; Niemeyer et al., 2009; Owen et al., 2002; Keen-Rhinehart et al., 2005; Scallan et al., 2003; Song et al., 2004). AAV vectors have also generated long-term clinical benefit in humans when targeted to immune-privileged sites, i.e., ocular delivery for Leber's congenital amaurosis (Bainbridge et al., 2008; Maguire et al., 2008; Cideciyan et al., 2008). A major advantage of this vector is its comparatively low immune profile, eliciting only limited inflammatory responses and, in some cases, even directing immune tolerance to transgene products (LoDuca et al., 2009). Nonetheless, the therapeutic efficiency, when targeted to non-immune privileged organs, has been limited in humans due to antibody and CD8+ T cell responses against the viral capsid, while in animal models, adaptive responses to the transgene product have also been reported (Manno et al., 2006; Mingozzi et al., 2007; Muruve et al., 2008; Vandenberghe and Wilson, 2007; Mingozzi and High, 2007). These results suggested that immune responses remain a concern for AAV vector-mediated gene transfer.

Based on pre-clinical data from murine models (Snyder et al., 1999), AAV was considered as minimally immunogenic for years, due to absence of prior exposure of these antigens in these models and the presence of variety of tolerance-inducing mechanisms against the vector (Dobrzynski et al., 2004; Cao et al., 2007). This was best illustrated in gene transfer studies in murine and canine models of hemophilia B, which showed remarkable therapeutic efficiency (5-25% of F.IX levels) and long-term (2-8 years) and stable F.IX expression (Snyder et al., 1999). In the first clinical trial using AAV to deliver the human F.IX gene to the liver in subjects with hemophilia B, therapeutic levels (~11.8%) of F.IX expression were observed at a high dose of vector ($2 \times 10^{12}$ vgs/kg body weight) (Manno et al., 2006).

However, 4-6 weeks after gene transfer, an AAV capsid-specific T cell response was observed that coincided with a rise in liver transaminases and a drop in F.IX transgene expression to baseline levels. This CD8+ T cell-mediated immune response was unexpected (Mingozzi et al., 2007), as this had not been observed in any pre-clinical animal models. This study and several others have implicated the host inflammatory and innate immune responses for cytotoxic T-lymphocyte mediated elimination of transduced hepatocytes (Zhu et al., 2009; Li et al., 2009; Madsen et al., 2009). Subsequently, a great deal of effort has been devoted to circumvent the host immune response to AAV vectors. These include the use of alternate naturally occurring AAV serotypes such as AAV1 (Brandy et al., 2009; Cohn et al., 2007) or AAV8 (Nathwani et al., 2006), the use of shuffled capsids (Gray et al., 2010), or surface-exposed tyrosine-mutant AAV2 (Markusic et al., 2010) vectors. In addition, strategies to counter the risks associated with the immune response have included the use of transgene constructs which have targeted expression in the host tissue (Wang et al., 2010), or the development of transient immune-suppression protocols (Jiang et al., 2006).

Although such strategies have incrementally improved the safety of AAV gene transfer, their efficacy in humans remains to be seen. For example, immune suppression with cyclosporine and MMF was effective at lower AAV1 vector dose ($3 \times 10^{11}$ vg/kg) but failed to prevent IFN-α CD8+ T cell responses against capsid at high doses ($1 \times 10^{12}$ vg/kg) during muscle-directed gene transfer in patients with lipoprotein lipase deficiency (Ross et al., 2006). These data underscore the importance of pursuing further studies on the biology of the virus-host cell interactions to identify the first "danger signal" in response to AAV infection. It was reasoned that understanding how the potential activity and the selectivity of proteins associated with inflammatory and innate immune response are regulated in host cells upon transduction with AAV might offer clues to address obstacles of the host immune response against the capsid and/or the transgene product. Although compared with other viral vectors, AAV vectors are inefficient in transducing professional APCs such as DCs, additional signals that activate NF-κB would lead to increased transgene expression in these cells, thereby increasing the risk of adaptive responses to the transgene product.

Recombinant vectors based on AAV serotype 2 are currently in use in a number of gene therapy clinical trials (Daya and Berns, 2008), and have recently shown remarkable efficacy in the treatment of Leber's congenital amaurosis (Bainbridge et al., 2008; Cideciyan et al., 2008; Maguire et al., 2008). However, concerns have been raised with reference to the humoral response to AAV2 vectors based on the high prevalence of sero-positivity in the general population (~80 to 90%) (Boutin et al.; Mendell et al.; Manno et al., 2006). The discovery of many novel AAV serotypes has prompted the development of AAV vectors to circumvent this potential problem (Muramatsu et al., 1996; Chiorini et al., 1997; Chiorini et al., 199; Rutledge et al., 1998; Gao et al., 2002; Gao et al., 2004).

For example, recombinant AAV8 vectors were recently reported to be therapeutic in a mouse model of liver cancer. (Kato et al., 2006) However, several groups have described various strategies to target human liver cancer cells in murine models using AAV2 vectors. (Su et al., 1996; Peng et al., 2000; Su et al., 2000; Ma et al., 2005; Wang et al., 2005; Tse et al., 2008; Zhang et al., 2008; Malecki et al., 2009; Wang et al.) To identify the most efficient AAV serotype to target human liver cancer cells, three different human liver cancer cell lines were shown to be transduced extremely efficiently by AAV3 vectors (Glushakova et al., 2009). Human hepatocyte growth factor receptor (hHGFR) was subsequently identified as a cellular co-receptor for AAV3 infection (Ling et al., 2010). However, the precise role of hHGFR, especially the role of tyrosine kinase activity associated with the intracellular domain of hHGFR, in AAV3-mediated transduction remained unclear. Data in Example 5, below, provide a more-detailed explanation of AAV3-hHGFR interactions, and demonstrate the development of optimized AAV3 vector for use in targeting human liver cancer cells.

rAAV Capsid Proteins

Supramolecular assembly of 60 individual capsid protein subunits into a non-enveloped, T-1 icosahedral lattice capable of protecting a 4.7-kb single-stranded DNA genome is a critical step in the life-cycle of the helper-dependent human parvovirus, adeno-associated virus2 (AAV2). The mature 20-nm diameter AAV2 particle is composed of three structural proteins designated VP1, VP2, and VP3 (molecular masses of 87, 73, and 62 kDa respectively) in a ratio of 1:1:18. Based on its symmetry and these molecular weight estimates, of the 60 capsid proteins comprising the particle, three are VP1 proteins, three are VP2 proteins, and fifty-four are VP3 proteins. The employment of three structural proteins makes AAV serotypes unique among parvoviruses, as all others known package their genomes within icosahedral particles composed of only two capsid proteins. The antiparallel β-strand barreloid arrangement of these 60 capsid proteins results in a particle with a defined tropism that is highly resistant to degradation. Modification of one or more tyrosine residues in one or more of the capsid proteins has been shown by the inventors to achieve superior transfection at lower dose and lower cost than conventional protocols. By site-specifically modifying one or more tyrosine residues on the surface of the capsid, the inventors have achieved significant improvement in transduction efficiency.

Uses for Improved, Capsid-Modified rAAV Vectors

The present invention provides compositions including one or more of the disclosed tyrosine-modified rAAV vectors comprised within a kit for diagnosing, preventing, treating or ameliorating one or more symptoms of a mammalian disease, injury, disorder, trauma or dysfunction. Such kits may be useful in diagnosis, prophylaxis, and/or therapy, and particularly useful in the treatment, prevention, and/or amelioration of one or more symptoms of cancer, diabetes, autoimmune disease, kidney disease, cardiovascular disease, pancreatic disease, intestinal disease, liver disease, neurological disease, neuromuscular disorder, neuromotor deficit, neuroskeletal impairment, neurological disability, neurosensory dysfunction, stroke, ischemia, eating disorder, $\alpha_1$-antitrypsin (AAT) deficiency, Batten's disease, Alzheimer's disease, sickle cell disease, β-thalassamia, Huntington's disease, Parkinson's disease, skeletal disease, trauma, pulmonary disease, or any combination thereof.

The invention also provides for the use of a composition disclosed herein in the manufacture of a medicament for treating, preventing or ameliorating the symptoms of a disease, disorder, dysfunction, injury or trauma, including, but not limited to, the treatment, prevention, and/or prophylaxis of a disease, disorder or dysfunction, and/or the amelioration of one or more symptoms of such a disease, disorder or dysfunction. Exemplary conditions for which rAAV viral based gene therapy may find particular utility include, but are not limited to, cancer, diabetes, sickle cell disease, β-thalassamia, autoimmune disease, kidney disease, cardiovascular disease, pancreatic disease, diseases of the eye, intestinal disease, liver disease, neurological disease, neuromuscular disorder, neuromotor deficit, neuroskeletal impairment, neurological disability, neurosensory dysfunction, stroke, α₁-antitrypsin (AAT) deficiency, Batten's disease, ischemia, an eating disorder, Alzheimer's disease, Huntington's disease, Parkinson's disease, skeletal disease, pulmonary disease, and any combinations thereof.

The invention also provides a method for treating or ameliorating the symptoms of such a disease, injury, disorder, or dysfunction in a mammal. Such methods generally involve at least the step of administering to a mammal in need thereof, one or more of the tyrosine-modified rAAV vectors as disclosed herein, in an amount and for a time sufficient to treat or ameliorate the symptoms of such a disease, injury, disorder, or dysfunction in the mammal.

Such treatment regimens are particularly contemplated in human therapy, via administration of one or more compositions either intramuscularly, intravenously, subcutaneously, intrathecally, intraperitoneally, or by direct injection into an organ or a tissue of the mammal under care.

The invention also provides a method for providing to a mammal in need thereof, a therapeutically-effective amount of the rAAV compositions of the present invention, in an amount, and for a time effective to provide the patient with a therapeutically-effective amount of the desired therapeutic agent(s) encoded by one or more nucleic acid segments comprised within the rAAV vector. Preferably, the therapeutic agent is selected from the group consisting of a polypeptide, a peptide, an antibody, an antigen-binding fragment, a ribozyme, a peptide nucleic acid, an siRNA, an RNAi, an antisense oligonucleotide, an antisense polynucleotide, a diagnostic marker, a diagnostic molecule, a reporter molecule, and any combination thereof.

AAV Vector Compositions

One important aspect of the present methodology is the fact that the improved rAAV vectors described herein permit the delivery of smaller titers of viral particles in order to achieve the same transduction efficiency as that obtained using higher levels of conventional, non-surface capsid modified rAAV vectors. To that end, the amount of AAV compositions and time of administration of such compositions will be within the purview of the skilled artisan having benefit of the present teachings. In fact, the inventors contemplate that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV vector compositions, either over a relatively short, or over a relatively prolonged period, as may be determined by the medical practitioner overseeing the administration of such compositions. For example, the number of infectious particles administered to a mammal may be approximately $10^7$, $10^8$, $10^9$, $10^{10}$, $10^{11}$, $10^{12}$, $10^{13}$, or even higher, infectious particles/mL, given either as a single dose (or divided into two or more administrations, etc., as may be required to achieve therapy of the particular disease or disorder being treated. In fact, in certain embodiments, it may be desirable to administer two or more different rAAV vector-based compositions, either alone, or in combination with one or more other diagnostic agents, drugs, bioactives, or such like, to achieve the desired effects of a particular regimen or therapy. In most rAAV-vectored, gene therapy-based regimens, the inventors contemplate that lower titers of infectious particles will be required when using the modified-capsid rAAV vectors described herein, as compared to the use of equivalent wild-type, or corresponding "un-modified" rAAV vectors.

As used herein, the terms "engineered" and "recombinant" cells are intended to refer to a cell into which an exogenous polynucleotide segment (such as DNA segment that leads to the transcription of a biologically active molecule) has been introduced. Therefore, engineered cells are distinguishable from naturally occurring cells, which do not contain a recombinantly introduced exogenous DNA segment. Engineered cells are, therefore, cells that comprise at least one or more heterologous polynucleotide segments introduced through the hand of man.

To express a therapeutic agent in accordance with the present invention one may prepare a tyrosine-modified rAAV expression vector that comprises a therapeutic agent-encoding nucleic acid segment under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded polypeptide. This is the meaning of "recombinant expression" in this context. Particularly preferred recombinant vector constructs are those that comprise an rAAV vector. Such vectors are described in detail herein.

When the use of such vectors is contemplated for introduction of one or more exogenous proteins, polypeptides, peptides, ribozymes, and/or antisense oligonucleotides, to a particular cell transfected with the vector, one may employ the capsid-modified rAAV vectors disclosed herein to deliver one or more exogenous polynucleotides to a selected host cell.

Pharmaceutical Compositions

The genetic constructs of the present invention may be prepared in a variety of compositions, and may also be formulated in appropriate pharmaceutical vehicles for administration to human or animal subjects. The rAAV molecules of the present invention and compositions comprising them provide new and useful therapeutics for the treatment, control, and amelioration of symptoms of a variety of disorders, and in particular, articular diseases, disorders, and dysfunctions, including for example osteoarthritis, rheumatoid arthritis, and related disorders.

The invention also provides compositions comprising one or more of the disclosed capsid-modified rAAV vectors, expression systems, virions, viral particles, mammalian cells, or combinations thereof. In certain embodiments, the present invention provides pharmaceutical formulations of one or more capsid-modified rAAV vectors disclosed herein for administration to a cell or an animal, either alone or in combination with one or more other modalities of therapy, and in particular, for therapy of human cells, tissues, and diseases affecting man. Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intra-articular, intramuscular administration and formulation.

Exemplary Definitions

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

The term "subject," as used herein, describes an organism, including mammals such as primates, to which treatment with the compositions according to the present invention can be provided. Mammalian species that can benefit from the disclosed methods of treatment include, but are not limited to, apes; chimpanzees; orangutans; humans; monkeys; domesticated animals such as dogs and cats; livestock such as horses, cattle, pigs, sheep, goats, and chickens; and other animals such as mice, rats, guinea pigs, and hamsters.

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, ameliorating or affecting the progression, severity, and/or scope of a disease or condition.

The term "effective amount," as used herein, refers to an amount that is capable of treating or ameliorating a disease or condition or otherwise capable of producing an intended therapeutic effect.

The term "promoter," as used herein refers to a region or regions of a nucleic acid sequence that regulates transcription.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "vector," as used herein, refers to a nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Next Generation rAAV2 Vectors: Point Mutations in Tyrosines Lead to High-Efficiency Transduction at Lower Doses The present example demonstrates that mutations of surface-exposed tyrosine residues on AAV2 capsids circumvents the ubiquitination step, thereby avoiding proteasome-mediated degradation, and resulting in high-efficiency transduction by these vectors in human cells in vitro and murine hepatocytes in vivo, leading to the production of therapeutic levels of human coagulation factor at reduced vector doses. The increased transduction efficiency observed for tyrosine-mutant vectors is due to lack of ubiquitination, and improved intracellular trafficking to the nucleus. In addition to yielding insights into the role of tyrosine phosphorylation of AAV2 capsid in various steps in the life cycle of AAV2, these studies have resulted in the development of novel AAV2 vectors that are capable of high-efficiency transduction at lower doses.

Materials and Methods

Recombinant AAV2 Vectors

Highly purified stocks of scAAV2 vectors containing the enhanced green fluorescence protein (EGFP) gene driven by the chicken β-actin (CBA) promoter (scAAV2-EGFP), and ssAAV2 vectors containing the factor IX (F.IX) gene under the control of the apolipoprotein enhancer/human α-1 antitrypsin (ApoE/hAAT) promoter (ssAAV2-F.IX) were generated using published methods.

Localization of Surface-Tyrosines on the AAV2 Capsid

The crystal structure of AAV2 (PDB accession number 1lp3) was used to localize the tyrosine residues on the AAV2 capsid surface. The icosahedral two-, three- and five-fold related VP3 monomers were generated by applying icosahedral symmetry operators to a reference monomer using Program O on a Silicon graphics Octane workstation. The position of the tyrosine residues were then visualized and analyzed in the context of a viral asymmetric unit using the program COOT, and graphically presented using the program PyMOL Molecular Graphics System (DeLano Scientific, San Carlos, Calif., USA).

Construction of Surface-Exposed Tyrosine Residue Mutant AAV2 Capsid Plasmids

A two-stage procedure, based on QuikChange II® site-directed mutagenesis (Stratagene, La Jolla, Calif., USA) was performed using plasmid pACG-2. Briefly, in stage one, two PCR extension reactions were performed in separate tubes for each mutant. One tube contained the forward PCR primer and the other contained the reverse primer. In stage two, the two reactions were mixed and a standard PCR mutagenesis assay was carried out as per the manufacturer's instructions. PCR primers were designed to introduce changes from tyrosine to phenylalanine residues as well as a silent change to create a new restriction endonuclease site for screening purposes. All mutants were screened with the appropriate restriction enzyme and were sequenced prior to use.

Preparation of Whole Cell Lysates (WCL) and Co-Immunoprecipitations

Approximately $2 \times 10^6$ HeLa cells, mock-treated or treated with MG132, were also subjected to mock-infection or infection with the WT scAAV2-EGFP or Y730F mutant vectors at $5 \times 10^3$ particles/cell for 2 hr at 37° C. For immunoprecipitations, cells were treated with 0.01% trypsin and washed extensively with PBS. WCL were cleared of non-specific binding by incubation with 0.25 mg of normal mouse IgG together with 20 µl of protein G-agarose beads. After preclearing, 2 µg of capsid antibody against intact AAV2 particles (mouse monoclonal IgG$_3$, clone A20; Research Diagnostics, Inc. (Flanders, N.J., USA), or 2 µg of normal mouse IgG (as a negative control) were added and incubated at 4° C. for 1 hr, followed by precipitation with protein G-agarose beads. For immunoprecipitations, resuspended pellet solutions were used for SDS-PAGE. Membranes were treated with monoclonal HRP-conjugated anti-Ub antibody (1:2,000 dilution) specific for ubiquitin (Ub) (mouse monoclonal immunoglobulin G$_1$ γIgG$_1$], clone P4D1; Santa Cruz, Calif., USA). Immuno-reactive bands were visualized using chemiluminescence (ECL-plus, Amersham Pharmacia Biotech, Piscataway, N.J., USA).

Isolation of Nuclear and Cytoplasmic Fractions from HeLa Cells

Nuclear and cytoplasmic fractions from HeLa cells were isolated and mock-infected or recombinant wt scAAV2-EGFP or Y700F vector-infected cells were used to isolate the cytoplasmic and nuclear fractions. The purity of each fraction was determined to be >95%.

Southern Blot Analysis for AAV2 Trafficking

Low-$M_r$ DNA samples from nuclear and cytoplasmic fractions were isolated and electrophoresed on 1% agarose gels or 1% alkaline-agarose gels followed by Southern blot hybridization using a $^{32}$P-labeled EGFP-specific DNA probe.

Recombinant AAV2 Vector Transduction Assays in Vitro

Approximately $1 \times 10^5$ HeLa cells were used for transductions with recombinant AAV2 vectors. The transduction efficiency was measured 48-hr post-transduction by EGFP imaging using fluorescence microscopy. Images from three to five visual fields were analyzed quantitatively by ImageJ analysis software (NIH, Bethesda, Md., USA). Transgene expression was assessed as total area of green fluorescence (pixel$^2$) per visual field (mean±SD). Analysis of variance (ANOVA) was used to compare between test results and the control and they were determined to be statistically significant.

Recombinant AAV2 Vector Transduction Studies In Vivo scAAV2-EGFP vectors were injected intravenously via the tail vein into C57BL/6 mice at $1 \times 10^{10}$ virus particles per animal. Liver sections from three hepatic lobes of the mock-injected and injected mice 2 weeks after injection were mounted on slides. The transduction efficiency was measured by EGFP imaging as described. ssAAV2-F.IX vectors were injected intravenously (via the tail vein) or into the portal vein of C57BL/6, BALB/c, and C3H/HeJ mice at $1 \times 10^{10}$ or $1 \times 10^{11}$ virus particles per animal. Plasma samples were obtained by retro-orbital bleed and analyzed for hF.IX expression by ELISA.

Results

Mutations in Surface-Exposed Tyrosine Residues Significantly Improve Transduction Efficiency of AAV2 Vectors To demonstrate that tyrosine-phosphorylation of AAV2 capsids leads to increased ubiquitination and results in impaired intracellular trafficking, and is therefore unfavorable to viral transduction, surface-exposed tyrosine residues were modified on AAV2 capsids. Inspection of the capsid surface of the AAV2 structure revealed seven surface-exposed tyrosine residues (Y252, Y272, Y444, Y500, Y700, Y704, and Y730). Site-directed mutagenesis was performed for each of the seven tyrosine residues, which were conservatively substituted with phenylalanine residues (tyrosine-phenylalanine, Y-F) (Table 1). scAAV2-EGFP genomes encapsidated in each of the tyrosine-mutant capsids were successfully packaged, and mutations of the surface-exposed tyrosine residues did not lead to reduced vector stability.

TABLE 1

TITERS OF WILDTYPE (WT) AND TYROSINE-MODIFIED
(Y-F MUTANTS) AAV2 VECTORS

| AAV Vectors | 1$^{st}$ packaging titers (vgs/mL) | 2$^{nd}$ packaging titers (vgs/mL) | 3$^{rd}$ packaging titers (vgs/mL) | 4$^{th}$ packaging titers (vgs/mL) |
|---|---|---|---|---|
| WT scAAV2-EGFP | $3.4 \times 10^{11}$ | $1.0 \times 10^{12}$ | $3.2 \times 10^{11}$ | $3.0 \times 10^{11}$ |
| Y252F scAAV2-EGFP | $3.8 \times 10^{11}$ | $4.0 \times 10^{11}$ | ND | ND |
| Y272 scAAV2-EGFP | $7.7 \times 10^{11}$ | $1.0 \times 10^{11}$ | ND | ND |
| Y444F scAAV2-EGFP | $9.7 \times 10^{10}$ | $4.0 \times 10^{10}$ | $6.0 \times 10^9$ | $5.0 \times 10^{10}$ |
| Y500F scAAV2-EGFP | $8.8 \times 10^{10}$ | $2.0 \times 10^9$ | $4.0 \times 10^{10}$ | $6.0 \times 10^{10}$ |
| Y700F scAAV2-EGFP | $1.0 \times 10^{11}$ | $4.0 \times 10^{11}$ | ND | ND |
| Y704F scAAV2-EGFP | $6.0 \times 10^{11}$ | $2.0 \times 10^{11}$ | ND | ND |
| Y730F scAAV2-EGFP | $1.2 \times 10^{11}$ | $5.0 \times 10^{11}$ | $1.2 \times 10^{11}$ | $4.0 \times 10^{11}$ |

ND = Not done.

The transduction efficiency of each of the tyrosine-mutant vectors was analyzed and compared with the WT scAAV2-EGFP vector in HeLa cells in vitro under identical conditions. From the results, it was evident that whereas mock-infected cells showed no green fluorescence, the transduction efficiency of each of the tyrosine-mutant vectors was significantly higher compared with the WT scAAV2-EGFP vector at 2,000 viral particles/cell. Specifically, the transduction efficiency of Y444F, Y500F, Y730F vectors was ~8- to 11-fold higher than the WT vector.

Mutations in Surface-Exposed Tyrosine Residues Dramatically Improve Transduction Efficiency of AAV2 Vectors in Murine Hepatocytes In Vivo The efficacy of WT and tyrosine-mutant scAAV2-EGFP vectors was also evaluated in a mouse model in vivo. The transduction efficiency of tyrosine-mutant vectors was significantly higher, and ranged between 4-29-fold, compared with the WT vector. When other tissues, such as heart, lung, kidney, spleen, pancreas, GI tract (jejunum, colon), testis, skeletal muscle, and brain were harvested from mice injected with $1 \times 10^{10}$ particles of the tyrosine-mutant vectors and analyzed, no evidence of EGFP gene expression was seen. Thus, mutations in the surface-exposed tyrosine residues did not appear to alter the liver-tropism following tail vein injection of these vectors in vivo.

Increased Transduction Efficiency of Tyrosine-Mutant Vectors is Due to Lack of Ubiquitination, and Improved Intracellular Trafficking to the Nucleus To further confirm the hypothesis that EGFR-PTK-mediated phosphorylation of capsid proteins at tyrosine residues is a pre-requisite for ubiquitination of AAV2 capsids, and that ubiquitinated virions are recognized and degraded by cytoplasmic proteasome on their way to the nucleus, leading to inefficient nuclear transport, a series of experiments were performed as follows.

In the first study, HeLa C12 cells, carrying adenovirus-inducible AAV2 rep and cap genes, were mock infected, or infected with WT, Y444F or Y730F scAAV2-EGFP vectors. Whereas mock-infected cells showed no green fluorescence, and ~15% of cells were transduced with the WT scAAV2-EGFP vectors in the absence of co-infection with adenovirus, the transduction efficiency of Y444F and Y730F scAAV2-EGFP vectors was increased by ~9 and ~18-fold, respectively, compared with the WT vector. Interestingly, whereas co-infection with adenovirus led to ~11-fold increase, the transduction efficiency of Y444F and Y730F scAAV2-EGFP vectors was not further enhanced by co-infection with adenovirus. Since adenovirus can improve AAV2 vector nuclear transport in HeLa cells, these data suggested that the surface-exposed tyrosine residues play a role in intracellular trafficking of AAV2, and that their removal leads to efficient nuclear transport of AAV2 vectors.

In a second study, HeLa cells, either mock-treated or treated with Tyr23, a specific inhibitor of EGFR-PTK, or MG132, a proteasome inhibitor, both known to increase the transduction efficiency of AAV vectors, were mock-infected or infected with the WT or Y730F scAAV2-EGFP vectors. Whereas mock-infected cells showed no green fluorescence, and ~5% of cells were transduced with the WT scAAV2-EGFP vectors in mock-treated cells, pretreatment with Tyr23 or MG132 led to an ~9-fold and ~6-fold increase in the transduction efficiency, respectively. Although the transduction efficiency of Y730F scAAV2-EGFP vectors was increased by ~14-fold compared with the WT vector, it was not further enhanced by pretreatment with either Tyr23 or MG132. These data strongly suggest that the absence of surface-exposed tyrosine residues, which prevented phosphorylation of the mutant vectors, likely prevented ubiquitination of the capsid proteins, and these vectors could not be recognized on their way to the nucleus and degraded by the proteasome, which led to their efficient nuclear translocation.

In a third study, HeLa cells, either mock-treated or treated with MG132, were mock-infected or infected with the WT, Y730F, or Y444F scAAV2-EGFP vectors. WCL were prepared 4 hrs post-infection and equivalent amounts of proteins were immunoprecipitated first with anti-AAV2 capsid antibody (A20) followed by Western blot analyses with anti-Ub monoclonal antibody. Whereas ubiquitinated AAV2 capsid proteins (Ub-AAV2 Cap) were undetectable in mock-infected cells, the signal of ubiquitinated AAV2 capsid proteins was weaker in untreated cells, and a significant accumulation of ubiquitinated AAV2 capsid proteins occurred following treatment with MG132. Interestingly, infections with Y730F or Y444F vectors dramatically decreased the extent of accumulation of MG132-induced ubiquitinated AAV2 capsid proteins. These results substantiate that mutation in tyrosine residues circumvents proteasome-mediated degradation of the vectors.

In a fourth study, the fate of the input WT, Y444F, and Y730F vector viral DNA was determined in HeLa cells. Southern blot analysis of low-$M_r$ DNA samples isolated from cytoplasmic [C] and nuclear [N] fractions and densitometric scanning of autoradiographs, revealed that ~36% of the input scAAV2 DNA was present in the nuclear fraction in cells infected with the WT vector. Interestingly, however, the amount of input Y730F and Y444F scAAV2 vector DNA in the nuclear fraction was increased to ~72% and ~70%, respectively. These results further documented that mutations in the surface-exposed tyrosine residues prevent ubiquitination of AAV2 capsids, resulting in a decrease of proteasome-mediated degradation, and in turn, facilitate nuclear transport of AAV2 vectors.

Tyrosine-Mutant Vectors Express Therapeutic Levels of Human Factor IX Protein at ~10-Fold Reduced Vector Dose in Mice It was important to examine whether tyrosine-mutant AAV2 vectors were capable of delivering a therapeutic gene efficiently at a reduced vector dose in vivo. To this end, a single-stranded, hepatocyte-specific human Factor IX (h.FIX) expression cassette was encapsidated in the Y730F vector, and the efficacy of this vector was tested in three different strains of mice (BALB/c, C3H/HeJ, and C57BL/6). Consistently in all three strains, Y730F vector achieved ~10-fold higher circulating hF.IX levels compared with the WT vector following tail vein or portal vein administration, with the latter being the more effective route. These results clearly indicated that the Y730F vectors expressed therapeutic levels of human F.IX protein (~50 ng/mL) at ~10-fold reduced vector dose ($10^{10}$ particles/mouse) in C57BL/6 mice by port vein injection. It should be noted that hepatic viral gene transfer in C57BL/6 mice is generally more efficient than in the other two strains.

These results demonstrated here are consistent with the interpretation that EGFR-PTK-induced tyrosine phosphorylation of AAV2 capsid proteins promotes ubiquitination and degradation of AAV2, thus leading to impairment of viral nuclear transport and decrease in transduction efficiency. Mutational analyses of each of the seven surface-exposed tyrosine residues yield AAV2 vectors with significantly increased transduction efficiency in vitro as well as in vivo. Specifically, Y444F and Y730F mutant vectors bypass the ubiquitination step, which results in a significantly improved intracellular trafficking and delivery of the viral genome to the nucleus.

Despite long-term therapeutic expression achieved in preclinical animal models by AAV2 vectors composed of the WT capsid proteins, in a recent gene therapy trial, two patients with severe hemophilia B developed vector dose-dependent transaminitis that limited duration of hepatocyte-derived hF.IX expression to <8 weeks. Subsequent analyses demonstrated presence of memory CD8$^+$ T cells to AAV capsids in humans and an MHC I-restricted, capsid-specific cytotoxic T lymphocyte (CTL) response in one of the hemophilia B patients, which mirrored the time course of the transaminitis. It was concluded that this CD8$^+$ T cell response to input capsid eliminated AAV2-transduced hepatocytes. These data demonstrated that a lower capsid antigen dose is sufficient for efficient gene transfer with the Y730F vector, and show much-reduced ubiquitination of AAV-Y730F compared to WT capsid, a prerequisite for MHC I presentation. Thus, the T-cell response to AAV2 capsid (a serious hurdle for therapeutic gene transfer in the liver), may be avoided by using the surface-exposed tyrosine-mutant AAV2 vectors.

Dramatically increased transduction efficiency of tyrosine-mutant vectors have also been observed in primary human neuronal and hematopoietic stem cells in vitro and in various tissues and organs in mice in vivo. Double, triple, and quadruple tyrosine-mutants have also been constructed to examine whether such multiple mutants are viable, and whether the transduction efficiency of these vectors can be augmented further. It is noteworthy that with a few exceptions (Y444 positioned equivalent to a glycine in AAV4 and arginine in AAV5; Y700 positioned equivalent to phenylalanine in AAV4 and AAV5; and Y704 positioned equivalent to a phenylalanine in AAV7), these tyrosine residues are highly conserved in AAV serotypes 1 through 10.

Example 2—Activation of the NF-κB Pathway by rAAV Vectors

Since the in silico analysis with human transcription factor database demonstrated the presence of several binding sites for NF-κB, a central regulator of cellular immune and inflammatory responses, in the adeno-associated virus (AAV) genome, the present example investigates whether AAV utilizes NF-κB during its life cycle. Small molecule modulators of NF-κB were used in HeLa cells transduced with recombinant AAV vectors. VP16, an NF-κB activator, augmented AAV vector-mediated transgene expression up to 25-fold. Of the two NF-κB inhibitors (Bay11), which blocks both the canonical and the non-canonical NF-κB pathways, totally ablated the transgene expression, whereas pyrrolidone dithiocarbamate (PDTC), which interferes with the classical NF-κB pathway, had no effect. Western blot analyses confirmed the abundance of the nuclear p52 protein component of the non-canonical NF-κB pathway in the presence of VP16, which was ablated by Bay11, suggesting that the non-canonical NF-κB pathway is triggered during AAV infection. Similar results were obtained with primary human dendritic cells (DCs) in vitro, in which cytokines-induced expression of DC maturation markers, CD83 and CD86, was also inhibited by Bay11. Administration of Bay11 prior to gene transfer in normal C57BL/6 mice in vivo resulted in up to 7-fold decrease in AAV vector-induced production of pro-inflammatory cytokines and chemokines such as, IL-1β, IL-6, TNFα, IL-12β, KC, and RANTES. These studies suggested that transient immuno-suppression with NF-κB inhibitors prior to transduction with AAV vectors leads to a dampened immune response, which has significant implications in the optimal use of AAV vectors in human gene therapy.

Recent studies have begun to define the initial activation signals that result from AAV gene transfer. One study found AAV-induced signaling through the Toll-like receptor 9 (TLR9)-myeloid differentiation factor 88 (MyD88) pathway to induce a type I interferon response in plasmacytoid dendritic cells (pDCs), thereby driving subsequent adaptive immune responses to the vector and transgene product upon gene transfer to murine skeletal muscle (Zhu et al., 2009). These data indicate sensing of the DNA genome by the endosomal TLR9 receptor in pDCs. No evidence for induction of pro-inflammatory cytokines following in vitro pulsing of DCs or macrophages with AAV was found. Still, earlier reports demonstrated a rapid, albeit highly transient, Kupffer cell-dependent innate response to AAV vectors in the liver, which included expression of several inflammatory cytokines (Zaiss and Muruve, 2008; Zaiss et al., 2008; Zaiss and Muruve, 2005; Zaiss et al., 2002).

Interestingly, the role of NF-κB, a key cellular responder to many stress- and pathogen-derived signals and regulator of pro-inflammatory cytokine expression (Hayden and Ghosh, 2004; Hiscott et al., 2006; Li and Verma, 2002), has not been previously studied in the AAV life cycle. In this example, it is shown that infection of human cells with AAV can lead to activation of the non-canonical NF-κB pathway. In addition, activation of NF-κB substantially increases transgene expression (including in DCs), while inhibition of NF-κB blunts expression. Prevention of inflammatory cytokine induction by transient inhibition of NF-κB reveals a role for NF-κB in the innate response to AAV in vivo, and importantly, does not interfere with long-term transgene expression.

Results

AAV-ITRs Contain Binding Sites for NF-κB-Responsive Transcription Factors

The existence of a cellular protein which interacts specifically with the single-stranded DH-sequence in the left inverted terminal repeat (ITR) of the AAV2 genome has been previously described (Qing et al., 1997). Since the ssDH-sequence in the right ITR is complementary to the ssD[−]-sequence in the left ITR, it was reasoned that a putative cellular protein might also exist, and interact with the ssD[+]-sequence in the right ITR. In electrophoretic mobility-shift assays, using the ssD[+]-sequence probe, a distinct cellular protein was indeed detected, which was designated as ssD[+]-sequence binding protein (ssD[+]-BP) (Qing et al., 1997). Following purification and mass spectrometry, ssD[+]-BP was found to have partial amino acid homology to a cellular NF-κB repressing factor, a negative regulator of transcription. Additional in silico analysis with human transcription factor database [TRANSFAC, http://alggen.lsi.upc.es/] demonstrated the presence of several binding sites for NF-κB binding co-factors, such as p300, TFIIB, and SpII. One of these is the p300/CREB transcription factor that has been recently shown to be associated with the AAV genome (Dean et al., 2009). Although it is not known whether the NF-κB signaling is activated by AAV binding to the cell surface receptors/co-receptors, recent studies have demonstrated that the innate immune response could be triggered either a) through the Toll like receptor 9 (TLR9)-myeloid differentiation factor 88 (MYD88) pathway, or b) through the activation of the CD40 ligand on the cell surface in mouse models in vivo (Zhu et al., 2009; Mays et al., 2009). Both of these ligands are known to interact down-stream with NF-κB transcription factors during their biological activation (Mineva et al., 2007; Loiarro et al., 2005). The following data demonstrated that the NF-κB is involved in the AAV life cycle.

AAV Infection Activates Non-Canonical NF-κB Pathway in Human Cells

Figure 6A:
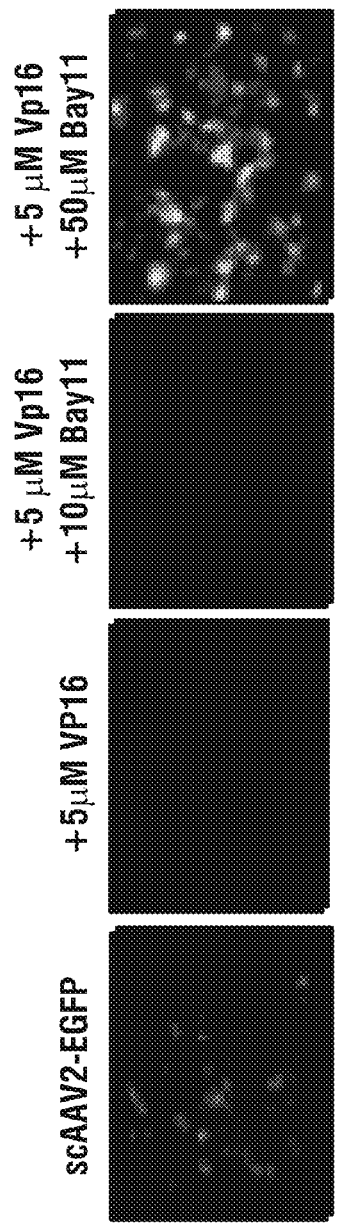
Figure 6B:
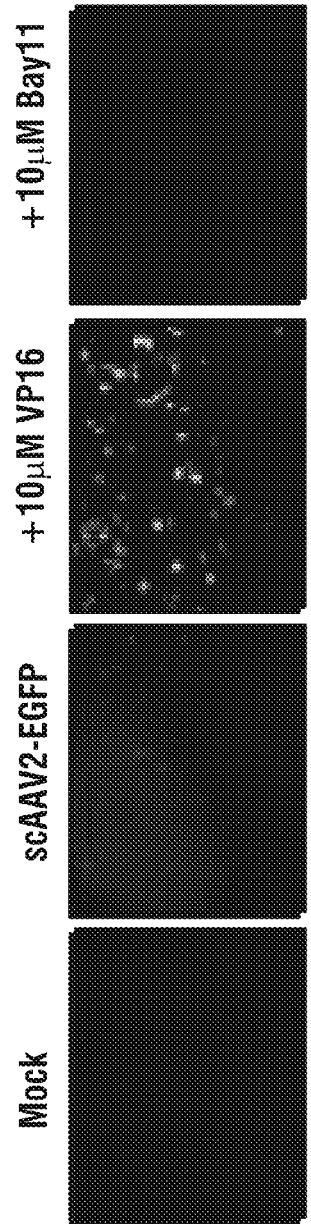
Figure 6C:
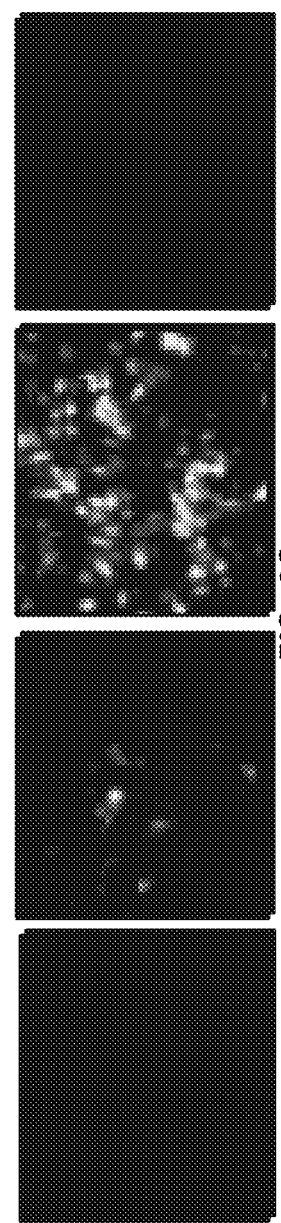

Small molecule activators and inhibitors of NF-κB signaling were used in HeLa cells transduced with a self-complementary serotype 2 vector expressing EGFP (scAAV-EGFP). VP16, an NF-κB activator (Wu and Miyamoto, 2008), augmented EGFP expression by ~25-fold (FIG. 1A and FIG. 1B). Between the two inhibitors tested, Bay11, that blocks the activity of both IKKκ and IKKκ, totally ablated EGFP expression, whereas PDTC, which inhibits IKB degradation by blocking IKB ubiquitin ligase in the classical pathway (Cuzzocrea et al., 2002), had no noticeable effect on EGFP expression (FIG. 1A and FIG. 1B). Furthermore, VP16-mediated augmented transgene expression was completely ablated by Bay11, but not by PDTC (FIG. 6A). Similar results were obtained with both ssAAV vectors (FIG. 6B) and with the tyrosine triple-mutant scAAV vector (Y730+500+444F; TM-AAV), which were described in the previous examples (Markusic et al., 2010) (FIG. 6C). It was concluded, therefore, that transgene expression from the AAV vector was regulated by the alternative (non-canonical) pathway of NF-κB. This conclusion was confirmed by Western blot analysis (FIG. 6D and FIG. 6E), which revealed an increase in the cytosolic p100 and the nuclear p52 protein components of the non-canonical NF-κB pathway by ~3- to 6-fold in the presence of VP16. Moreover, transduction with AAV vector by itself (i.e., in the absence of activator) increased p100 and p52 (FIG. 1C), indicating that infection of the cell activated the alternative NF-κB pathway. This increase was ablated by Bay11 treatment, while p65, the marker used for the classical NF-κB pathway, was unaffected (FIG. 1C).

Figure 7:
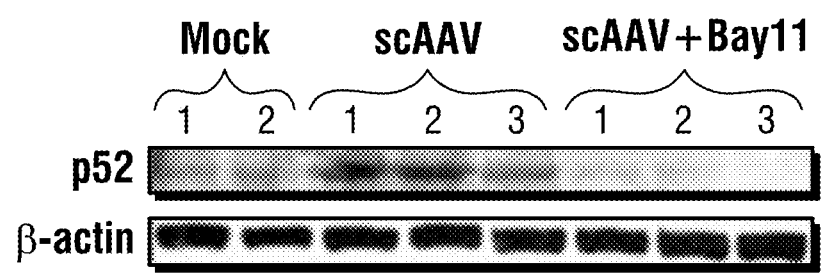
FIG. 7 is a Western blot analysis of liver homogenates from mice following mock-injections (n=2), or injections with scAAV vectors, with and without prior administration of Bay11 (n=3 each). The samples were analyzed by using anti-p52 antibody for detection NF-κB signaling in response to AAV exposure. Anti-β-actin antibody was used as a loading control.
Figure 8A:
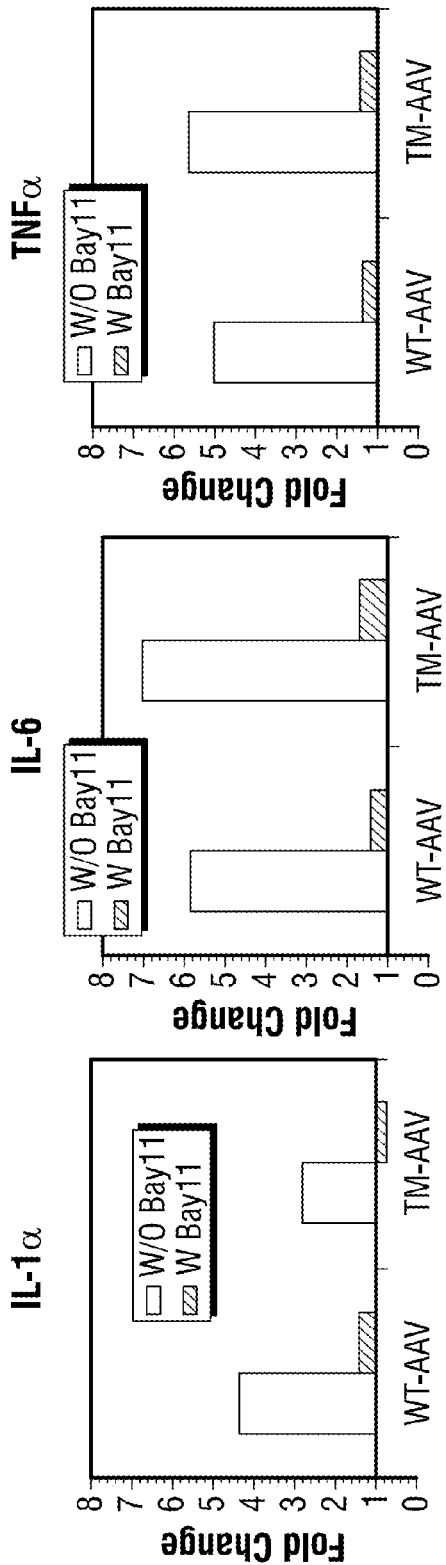
FIG. 8A FIG. 8B, FIG. 8C, FIG. 8D, FIG. 8E, and FIG. 8F show fold changes in gene expression of various cytokines/chemokines from total mRNA collected from liver samples from animals injected with the WT-AAV or the TM-AAV vectors, following PBS- or Bay11-pre-treatment.
Figure 8B:
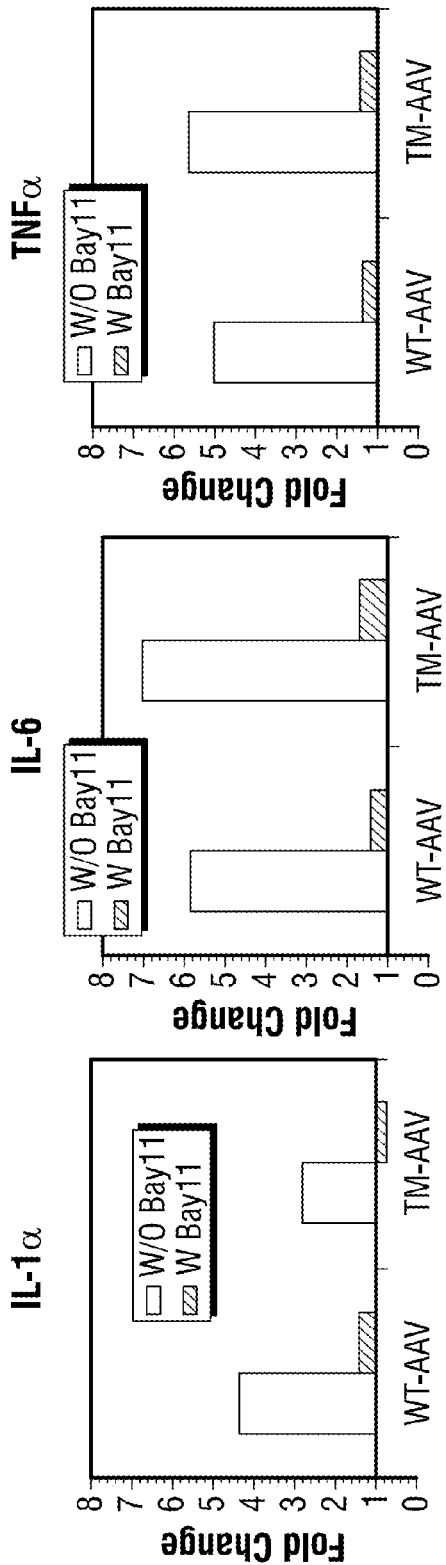
Figure 8C:
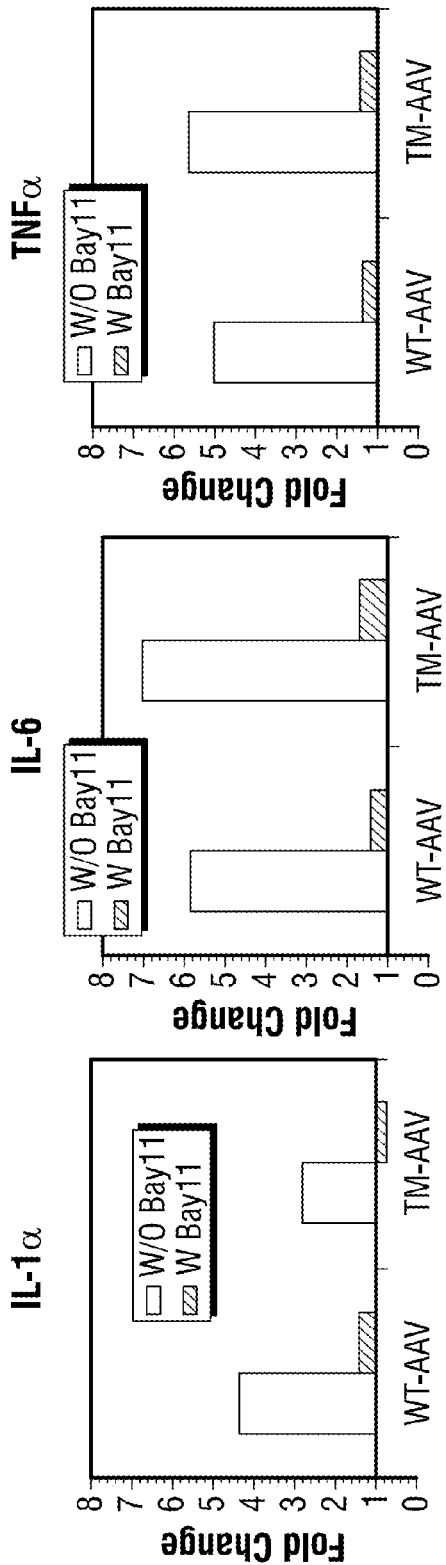
Figure 8D:
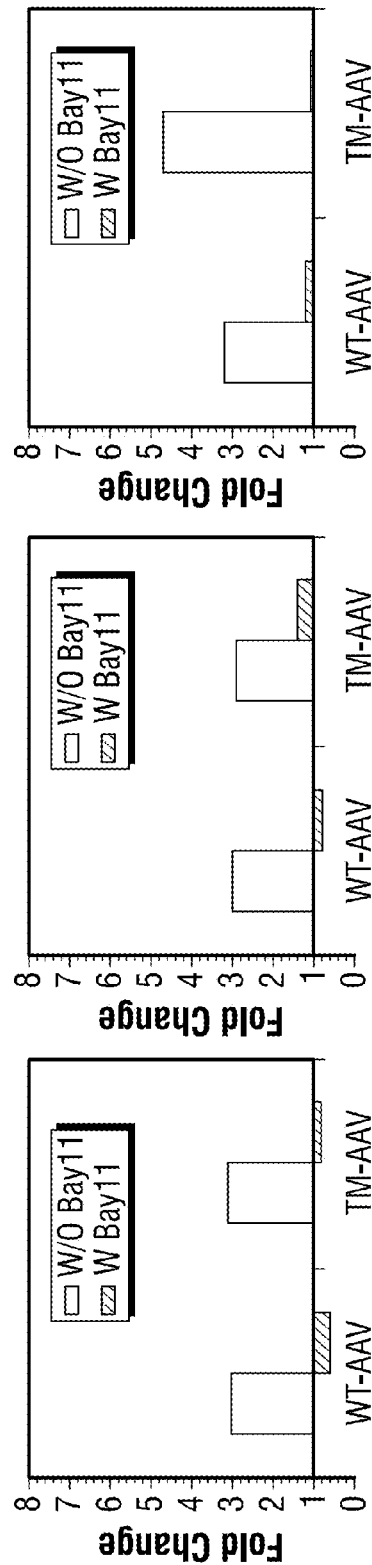
Figure 8E:
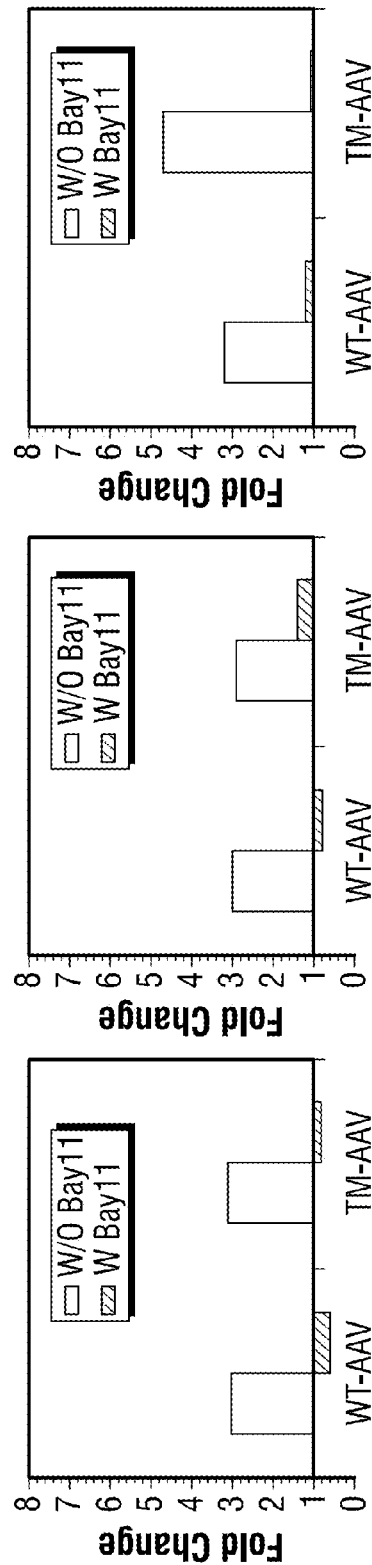
Figure 8F:
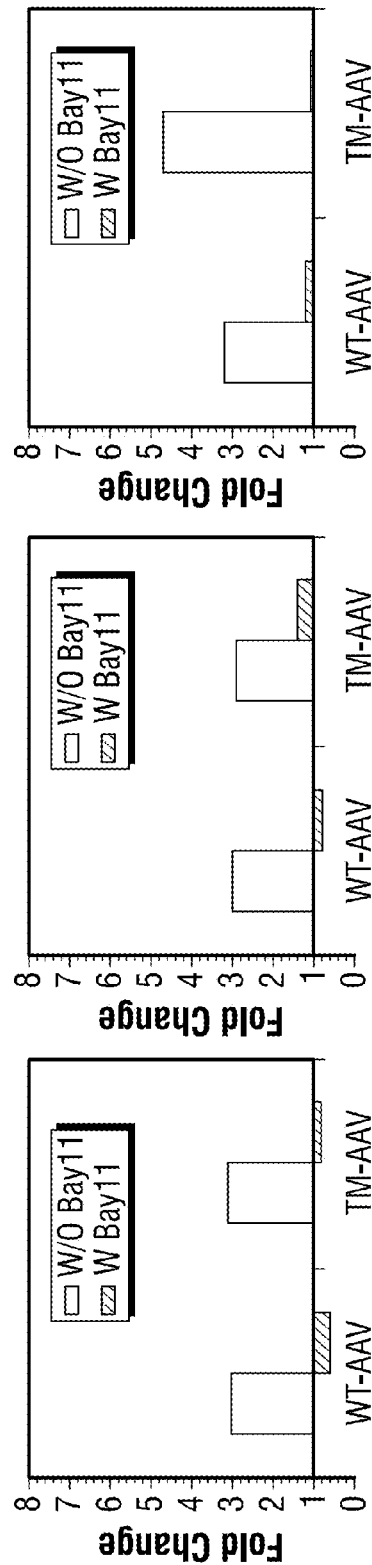

NF-κB Pathway is Operational in Primary Human Antigen-Presenting Cells Following AAV Infection In primary human dendritic cells (DCs), on the other hand, while transgene expression was again substantially increased with the NF-κB activator (FIG. 2A), AAV infection by itself did not activate NF-κB (FIG. 2B). In the presence of VP16, ~20-fold increase in EGFP expression was observed compared with scAAV vector-transduced DCs. Treatment with cytokines (TNF-α, IL-6, IL-1β, PGE2), known to activate the NF-κB pathway, led to a further increase in transgene expression to ~26%, which was reduced to ~12% following treatment with Bay11 (FIG. 2A). Western blot analyses of nuclear fractions further corroborated that the alternative pathway of NF-κB activation (accumulation of p52 proteins) was operational (FIG. 2B). Similar results were obtained following scAAV vector-mediated gene delivery to murine livers in vivo (FIG. 7). The inventors also tested the capability of NF-κB modulators to induce phenotypic changes in DCs. Flow cytometric analyses of two DC maturation markers, CD83 and CD86 indicated that VP16 alone was not able to induce maturation or enhance the expression of co-stimulatory molecules when used together with the cytokines cocktail. However, treatment with Bay11 led to inhibition of cytokine-mediated maturation of APCs, further implicating the involvement of NF-κB (Table 2). This reduction of maturation markers expression diminishes the main function of DCs to process antigenic material and reduces T-cell activation and proliferation. Thus, it was hypothesized that suppression of NF-κB activation prior to vector administration might lead to a dampened innate immune response against AAV.

TABLE 2

FACS ANALYSES OF MARKERS OF MATURATION OF PRIMARY HUMAN DENDRITIC CELLS

| Group | Geometric means of levels of expression in cells expressing | |
|---|---|---|
| | CD83 | CD86 |
| Immature DCs | 10.38 | 7.04 |
| DCs - No maturation supplement | 18.08 | 13.63 |
| Mature DCs + Cytokines | 20.60 | 26.80 |
| DCs + AAV | 18.29 | 12.65 |
| DCs + VP16 | 16.48 | 13.70 |
| Mature DCs + AAV + Cytokines | 24.25 | 23.75 |
| Mature DCs + AAV + Cytokines + VP16 | 19.92 | 21.92 |
| Mature DCs + AAV + Cytokines + Bay11 | 16.88 | 10.11 |

Data from a representative experiment are shown (n = 3).

Figure 3A:
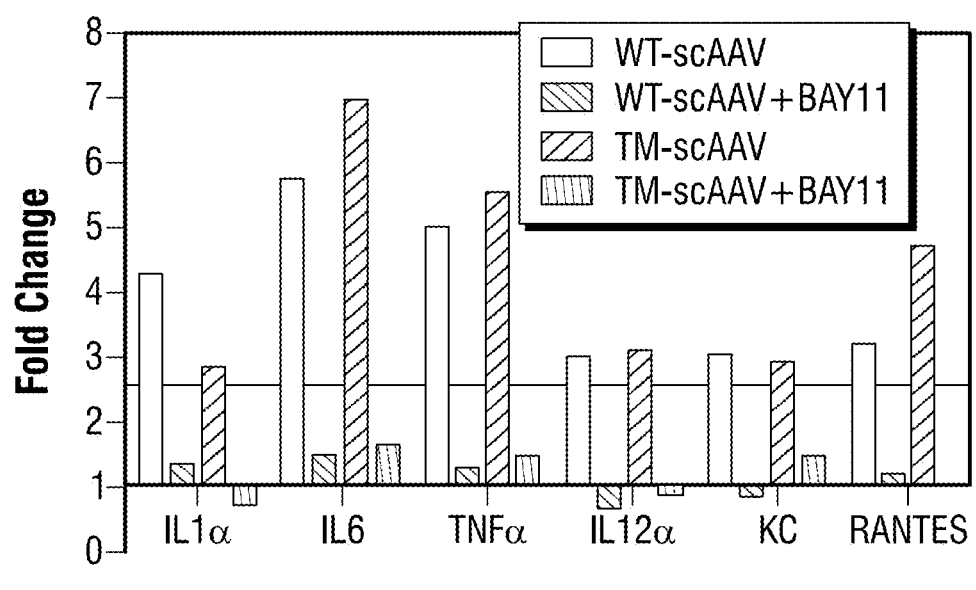
FIG. 3A and FIG. 3B show AAV vector-induced innate immune and NF-κB response in mice in vivo. Gene expression profiling of innate immune mediators (FIG. 3A) or NF-κB activation (FIG. 3B) was performed as described. The data for fold changes in gene expression at the 2 hrs time-point comparing AAV vectors with Bay11 (hatched or open bars) with AAV vectors without Bay11 (black or grey bars) are shown. The minimal threshold fold-increase (horizontal black line) was 2.5 (FIG. 3A) or 3.0 (FIG. 3B) by measuring the variability of duplicate ΔCT (compared to GAPDH, $2^{-\Delta CT(variability)}$)
Figure 3B:
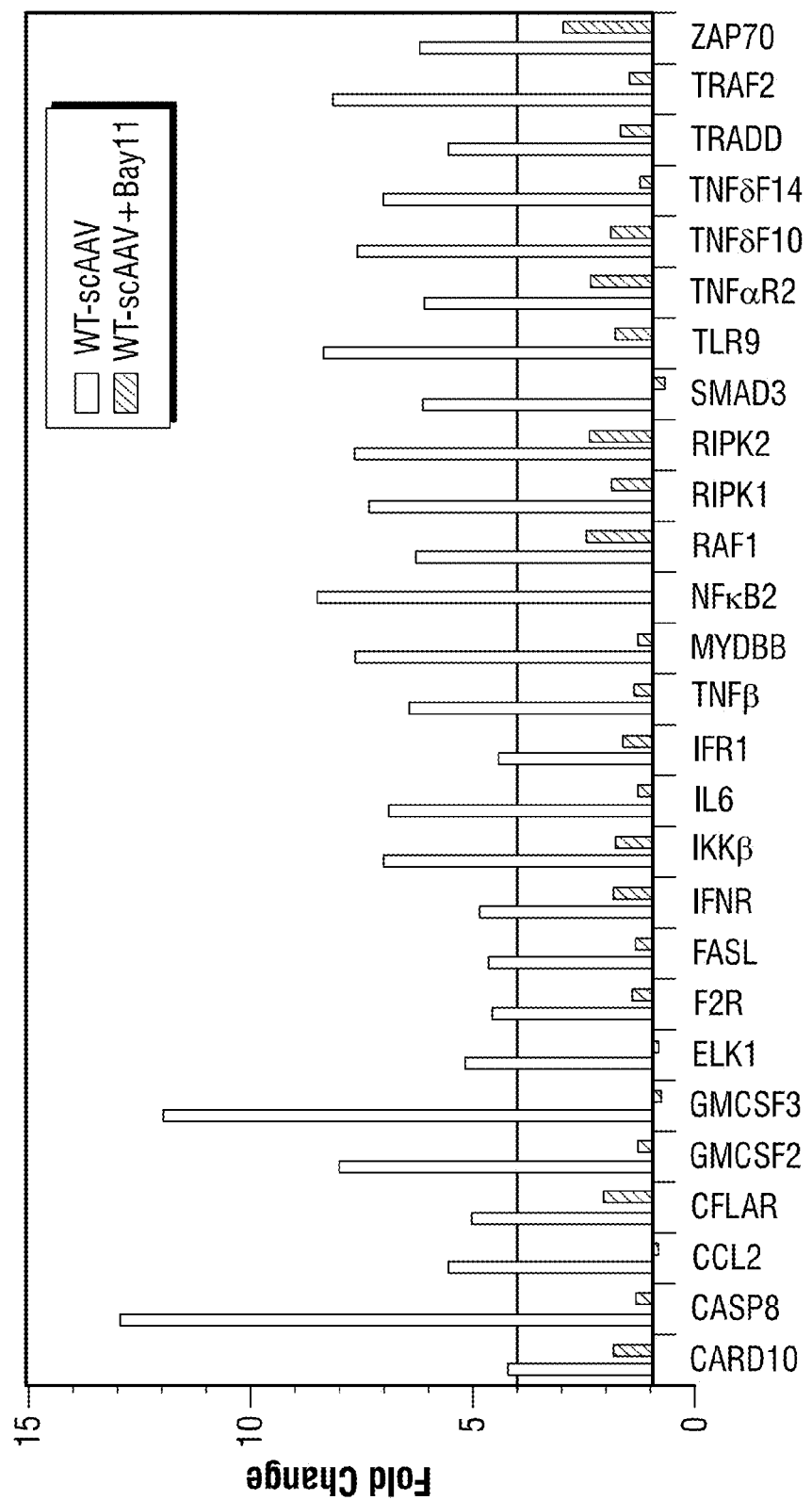
Figure 9:
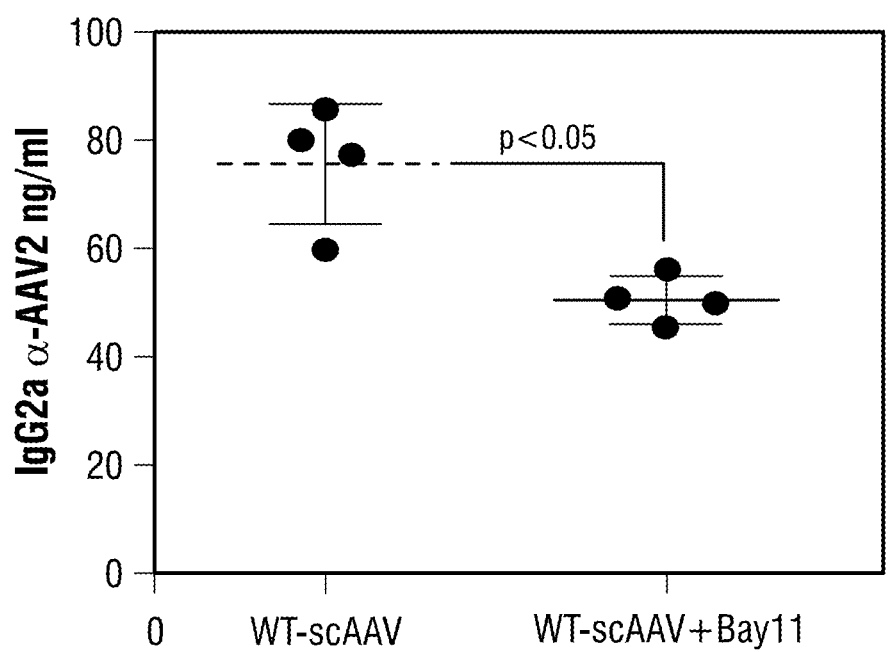
FIG. 9 demonstrates humoral response to AAV vectors in the absence or presence of NF-kB inhibitor. Anti-AAV2 IgG2a levels were determined in peripheral blood from mice at day 10 following injections with scAAV vectors, with and without prior administration of Bay11 (n=4 each)

Inhibition of NF-κB Activation Leads to Suppression of Pro-Inflammatory Cytokine Production Prior to AAV Vector-Mediated Gene Transfer in Mice In Vivo In in vivo studies, a single dose of Bay11 at 20 mg/kg body weight was administered intra-peritoneally (i.p.) 12 hrs prior to vector administration in C57BL/6 mice. Transcript levels from liver homogenates of innate immune mediators (FIG. 3A) or for activation of NF-κB (FIG. 3B) genes were measured from Bay11- and vector-injected groups and compared with sham-injected mice. These data revealed that 2 hrs post-vector administration, mice injected with Bay11+ AAV vector had significantly reduced levels of pro-inflammatory cytokines or chemokines including IL-1α, IL-6, TNFα, IL-12a, KC, and RANTES, compared with sham- and AAV vector-injected animals (FIG. 3A), and additionally, the up-regulation of the NF-κB gene expression profile was prevented (FIG. 3B). A similar down-regulation trend of these innate immune response markers was seen in mice injected with the more efficacious tyrosine triple-mutant AAV vector (Y730+500+444F; TM-AAV). The up-regulation of type I interferon expression by both wild-type (WT-AAV) and TM-AAV vectors was unaffected by Bay11 (FIG. 8A, FIG. 8B, FIG. 8C, FIG. 8D, FIG. 8E, and FIG. 8F). Administration of Bay11 also significantly reduced the anti-AAV2 antibody response in these mice (FIG. 9). The sum of these results implies that the transient inflammatory cytokine response, typically seen during in vivo hepatic AAV gene transfer, is mediated by NF-κB activation.

AAV Vector-Mediated Transgene Expression in Murine Hepatocytes

Figure 4A:
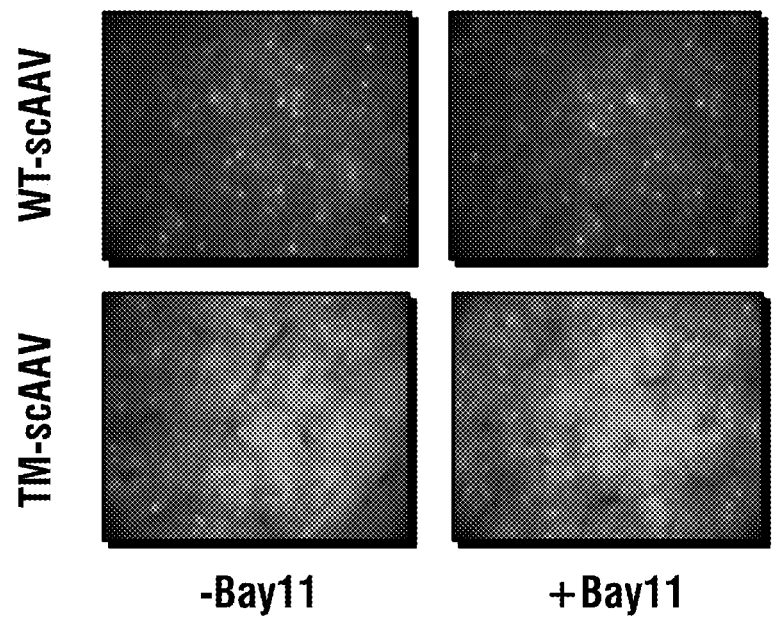
FIG. 4A and FIG. 4B illustrate transgene expression in murine hepatocytes 10 days post-injection of $1 \times 10^{11}$ vgs each of WT-scAAV-EGFP or TM-scAAV-EFGP vectors/animal via the tail-vein.
Figure 4B:
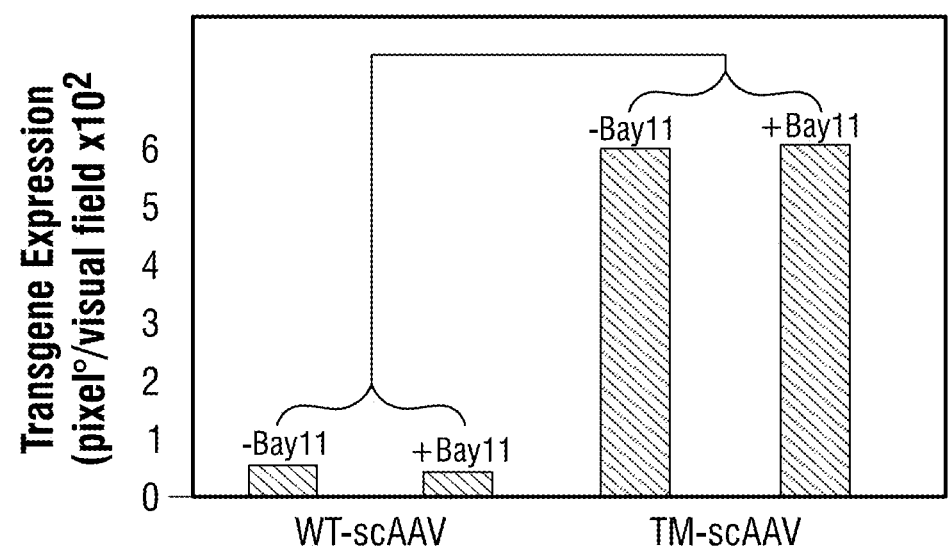

In view of the observation that Bay11 strongly inhibits AAV-mediated transgene expression in HeLa cells in vitro 48 hrs post-transduction (FIG. 1A and FIG. 1B), which would be counter-productive to achieve long-term transgene expression in vivo, it was important to examine the effect of Bay11 in mice. As can be seen in FIG. 4A, animals injected with or without Bay11 had similar levels of EGFP expression from either vector when analyzed 2 weeks after gene transfer. Transduction efficiency of the TM-AAV vector was ~12-fold higher than that of the WT-AAV vector (FIG. 4B), consistent with recently published studies (Markusic et al., 2010). These data suggested that Bay11 administration could safely and effectively down-regulate mediators of innate immune response without compromising long-term transgene expression.

Materials and Methods

Recombinant AAV Vectors

Highly purified stocks of self-complementary (sc) AAV2 vectors were generated containing either the wild-type (WT)

plasmid or the triple tyrosine-mutant (TM; Y730+500+444F) plasmid and the enhanced green fluorescence protein (EGFP) gene driven by the chicken β-actin (CBA) promoter (WT-scAAV2-EGFP, TM-scAAV2-EGFP) by triple transfection of HEK-293 cells. The vectors were then purified by CsCl gradient centrifugation, filter sterilized, and quantified by slot-blot hybridization as described (Liu et al., 2003; Kube and Srivastava, 1997). The tyrosine-mutant pACG2-Y730+500+444F-Rep/Cap plasmid has been described recently (Markusic et al., 2010).

Recombinant AAV Vector Transduction Assays In Vitro

Optimal concentration of NF-κB-modulating compounds was determined by a cell viability assay with tenfold-dilutions from the $IC_{50}$ or were used as described previously (Wu and Miyamoto, 2008; Kumar et al., 2008). VP16 or Bay11 (10 or 5 μM, final concentration), and PDTC (50 or 25 μM final concentration) were used either alone or in activator/inhibitor combinations. For transduction experiments, approximately $1\times10^5$ HeLa cells were either pre-treated with these compounds 24 hrs prior to vector infection. Cells were transduced with 500 or 2,000 vector genomes (vgs) per cell of recombinant WT-AAV or TM-AAV vectors encoding the EGFP transgene as described previously (Markusic et al., 2010). After 7 days of culture, primary human dendritic cells were transduced with AAV vectors at 2000 vgs/cell and incubated for 48 hrs. Transgene expression was assessed as total area of green fluorescence ($pixel^2$) per visual field (mean±SD), or by flow cytometry. Analysis of variance (ANOVA) was used to compare between test results and the control and they were determined to be statistically significant.

Recombinant AAV Vector Transduction Studies In Vivo

Groups of 6-weeks old normal C57BL/6J mice (Jackson Laboratories, Bar Harbor, Me., USA) were administered intra-peritoneally, with a single dose (20 mg/kg) of NF-κB inhibitor Bay11, in a 200-μL volume diluted in DMSO (day 0). Animals injected with only the DMSO carrier solvent were considered as baseline (mock) group (n=75) and animals injected with Bay11 were the test group (n=75). At this point, the animals from mock and Bay11 groups were randomized to receive either phosphate buffered saline (PBS, pH 7.4) or WT-AAV or TM-AAV vectors (n=25 mice each group). On day 1, ~$1\times10^{11}$ viral genome (vg) particles of WT-AAV2-EGFP or TM-AAV2-EGFP vectors or PBS were administered intravenously via the tail vein. To measure the modulation of immune response to AAV, 5 animals each from PBS-, WT-AAV-, or TM-AAV vector-injected groups were sacrificed by carbon-dioxide inhalation at different time points post-vector administration (2, 6, 10, 24 hrs and day 10). Hepatic lobes were collected, cross-sectioned and mounted on slides to study the effect of Bay11 on AAV-mediated EGFP expression (from day 10 mice). All animal studies were conducted in accordance with institutional animal care and use committee guidelines.

Gene-Expression Analysis of Innate Immune Response by RT-PCR Assay

Groups of 6-weeks old normal C57BL/6J mice were administered intra-peritoneally, with a single dose (20 mg/kg) of NF-κB inhibitor, Bay11, in a 200-μL volume diluted in DMSO (day 0). On day 1, mice were injected with either phosphate-buffered saline (PBS, pH 7.4), or with ~$1\times10^{11}$ vgs of the wild-type (WT) AAV-EGFP vectors, or the tyrosine triple-mutant (TM) AAV-EGFP vectors intravenously via the tail-vein (n=5 mice each group). At 2 hr post-vector administration, gene expression profiling of the innate immune response was performed that included Toll-like receptors 1-9, MyD88, MIP-1, IL-1α, IL-1β, IL-12α, IL6, KC, TNFα, RANTES, MCP-1, IFNα, IFNβ, and IP-10. Data were captured and analyzed using an ABI Prism 7500 Sequence Detection System with v1.1 Software (Applied Biosystems). The baseline was determined automatically for the 18S rRNA and for other genes. Thresholds were determined manually for all genes. Gene expression was measured by the comparative threshold cycle (Ct) method. The parameter threshold cycle (Ct) was defined as the cycle number at which the reporter fluorescence generated by the cleavage of the probe passed a fixed threshold above baseline. Cytokine gene expression was normalized using the endogenous reference 18S rRNA gene and mock-infected murine mRNA were used as reference sample. Relative gene expression was determined for each group of treated and untreated animals and values >2.6 and <0.38 were considered as significant up-regulations and down-regulations between the groups and was calculated by assessing the variability in the 96 well plates used to measure specific gene expression.

Cells, Antibodies and Chemicals

HeLa cells were obtained from the American Type Culture Collection (Rockville, Md., USA) and maintained as monolayer cultures in Iscove's-modified Dulbecco's medium (IMDM, Invitrogen Carlsbad, Calif., USA) supplemented with 10% newborn calf serum (NCS) (Lonza, Inc., Basel, Switzerland) and antibiotics. Leukapheresis-derived PBMCs were resuspended in serum-free AIM-V medium (Lonza) and semi-adherent cell fractions were incubated in serum-free AIM-V medium supplemented with recombinant human IL-4 (500 U/mL) and GM-CSF (800 U/mL) (R&D Systems, MN, USA). Cells were treated with NF-κB modulators (10 mM VP16 or 10 mM Bay11), and cytokines cocktail including 10 ng/mL TNF-α, 10 ng/mL IL-1, 10 ng/mL IL-6, 1 mg/mL PGE2 (R&D Systems) for 20 hr. Cells were harvested, characterized to ensure they met the typical phenotype of mature DCs (CD83, RPE, murine IgG1, CD86, FITC, murine IgG1; Invitrogen). All primary and secondary antibodies were purchased from Cell Signaling Technology, Inc. (Danvers, Mass., USA) or Santa Cruz Biotechnology, Inc (Santa Cruz, Calif., USA). NF-kB activators [Etoposide (VP16), Aphidicolin, Hydroxyurea (HU)] and NF-kB inhibitors [Bay11-7082 (Bay11), Pyrrolidine dithiocarbamate (PDTC)] were purchased from Sigma-Aldrich Co. (St. Louis, Mo., USA). These compounds were re-suspended in either DMSO (Sigma-Aldrich) or in sterile, DNAase-, RNAase-free water (Invitrogen) as per the manufacturer's instructions.

Western Blot Analyses

Homogenized lysates of the cell pellets from ~$2\times10^6$ HeLa cells or DCs, mock or pre-treated with the optimal concentration of NF-κB activators or inhibitors were used for sample preparation. Whole cell proteins were isolated using the RIPA lysis buffer (Sigma-Aldrich) and cytoplasmic and nuclear proteins were extracted using a commercial kit (NE-PER Extraction Reagent Kit, Pierce Biotech, Rockford, Ill., USA) as per the manufacturer's protocol in the presence of a protease inhibitor cocktail (Halt™ Protease Inhibitor Cocktail Kit, Pierce Biotech). The protein extracts were boiled for 5 min under reducing conditions [SDS-sample buffer containing 62.5 mM Tris-HCl (pH 6.8 at 25° C.), 2% wt./vol. SDS, 10% glycerol, 50 mM DTT, 0.01% wt./vol. bromo-phenol blue (Cell Signaling Technology, Inc.)] and stored at −86° C. until further analysis. Equal volumes of samples were run on 4-15% SDS-PAGE (Bio-Rad, Hercules, Calif., USA). Gels were transferred onto a 0.2-μm nitrocellulose membrane (Bio-Rad) and typically incubated overnight with 1:1000 dilution of primary antibodies [p100/52, p65, inhibitory kinase-IκBκ, glyceraldehyde 3-phosphate dehydrogenase (GAPDH), Lamin B (Cell Signaling Technology, Inc.), β-actin (Santa Cruz Biotechnology)]. The next day, blots were incubated with 1:2,000-1:5,000 of the appropriate anti-idiotypic HRP labeled IgG secondary antibody (Santa Cruz Biotechnology). Immunoblot detection was performed using the ECL plus Western blotting detection kit (Amersham Biosciences, Piscataway, N.J., USA). The intensity of the protein bands was measured with Adobe Photoshop CS3 Software® and normalized to proteins levels from the housekeeping gene products used as loading controls.

Figures 10A, 10B:
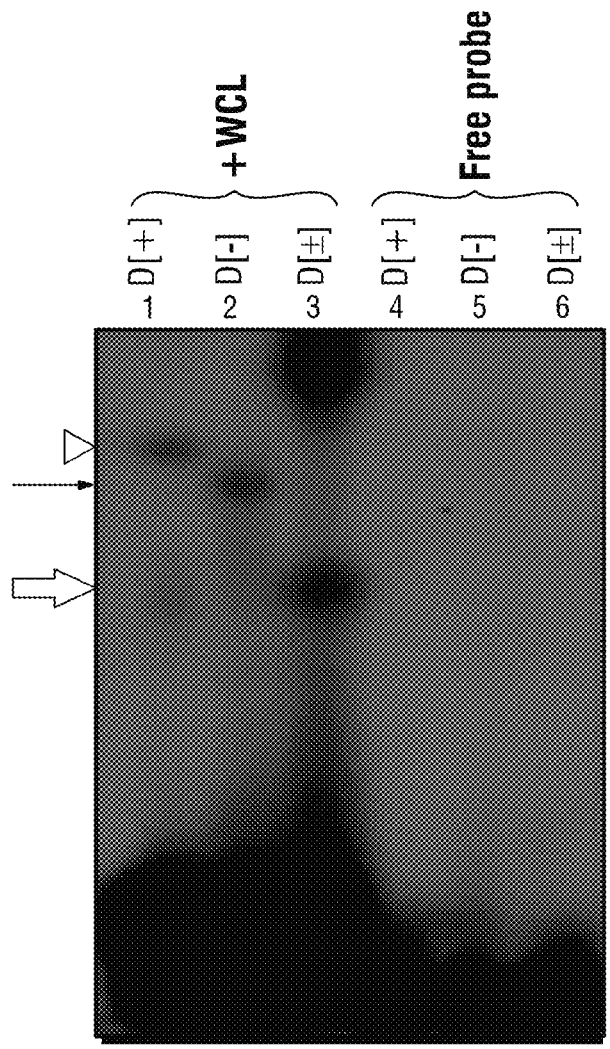
FIG. 10A and FIG. 10B illustrate electrophoretic mobility-shift assays carried out with whole-cell extracts prepared from HeLa cells and $^{32}$P-labeled single-stranded DM-sequence probe (lane 1), which interacted with a host cell protein (lane 3, arrowhead). Single-stranded D[−]-sequence (lane 2) probe was used as an appropriate control, which also interacted with a cellular protein, FKBP52 (lane 4, arrow). Binding assays were also carried out using biotin-labeled ssD[+]-sequence probe followed by selection with streptavidin-beads, and fractionation by SDS-polyacrylamide gel electrophoresis. The relevant protein band was visualized by silver staining, excised from the gel, and subjected to mass spectrometry, and one of the unique peptides was found to share homology with the NF-κB-repressing factor (NRF)

The basis for the present study was the finding that the host cellular NF-κB can bind to the 20-bp D-sequence present in the AAV inverted terminal repeats (ITRs) (Qing et al., 1997), which was identified by electrophoretic mobility-shift assays followed by mass-spectrometry (FIG. 10A and FIG. 10B). The data presented in this example provide the first evidence of the involvement of NF-κB in AAV infection. Using a variety of pharmacological modulators, which have been extensively used by other investigators (Wu and Miyamoto, 2008; Kumar et al., 2008) to study the NF-κB signaling pathway, it was shown that the non-canonical NF-κB pathway is up-regulated following AAV infection. This is significant considering that activation of the NF-κB transcriptional program is a fundamental immediate early step of inflammatory and immune activation (Li and Verma, 2002), and NF-κB signaling represents a prime candidate for viral susceptibility or interference (Hiscott et al., 2006). Viruses which activate NF-κB have been shown to be susceptible to innate immune response through an interferon response (Vesicular stomatitis virus, Measles virus) (Hiscott et al., 2003), toll-like receptor (TLR) dependent (Ebola virus, Respiratory syncytial virus) (Okumura et al., 2010; Lizundia et al., 2008), and TLR-independent signaling pathway (Cytomegalovirus, Hepatitis C virus) (Castanier et al., 2010; Gourzi et al., 2007). On the other hand, many viruses disrupt the innate immune responses and NF-κB using multifunctional viral decoy proteins that target specific aspects of the NF-κB pathway. Viruses, including human immunodeficiency virus type I (HIV-I), human T-cell leukemia virus type 1 (HTLV-1), Human herpesvirus 8 (HHV8) and Epstein-Barr virus (EBV), have incorporated aspects of NF-κB signaling into their life cycle and pathogenicity, and thus utilize NF-κB activation to promote their survival (Hiscott et al., 2006).

In contrast, it stands to reason that the non-canonical pathway of NF-κB is activated following AAV infection both because the non-canonical NF-κB activation is known to be important for innate and adaptive immune response (Gilmore, 2006), and AAV vectors lack complex structural gene elements necessary to develop any NF-κB-like decoy proteins. The exacerbated activation of the non-canonical pathway has been associated to a wide range of inflammatory disorders like rheumatoid arthritis, ulcerative colitis or B cell lymphomas (Dejardin, 2006). Monarch-1, a pyrin-containing protein expressed exclusively in cells of myeloid lineage suppresses pro-inflammatory cytokines and chemokines through inhibition of NF-κB inducing kinase (NIK) necessary to activate non-canonical NF-κB pathway (Lich et al., 2007). The activation of non-canonical pathway of NF-κB activation has been shown to result in maturation and T-cell priming activity of DCs over-expressing a mutated IκBκ which blocks activation of the classical pathway (Lind et al., 2008). In alymphoplasia (Aly) mouse deficient in NIK, the cross-priming of CD8+ T cells to exogenous antigens in DCs is affected suggesting the importance of this pathway in adaptive immunity (Lind et al., 2008). Mice deficient in non-canonical pathway components are also deficient in secondary lymphoid organ development and homeostasis (Guo et al., 2008). It is not known whether AAV-binding activates the NF-κB signaling to a cell surface receptor. Recent studies have demonstrated that the innate immune response to AAV could be triggered through the TLR9-MYD88 pathway or through activation of the CD40 ligand on cell surface in murine models in vivo (Zhu et al., 2009; Mays et al., 2009). It is interesting to note that while both rely on NF-κB signaling down-stream for mounting an innate immune response (Mineva et al., 2007; Loiarro et al., 2005), activation of TNF super family receptors such as CD40L can activate the non-canonical NF-κB pathway (Qing et al., 2005).

Based on the evidence that the first "danger-signal" or "trigger" to immune surveillance directed against AAV vectors may be the activation of alternative NF-κB signaling pathway, it was reasoned that transient blocking of NF-κB during AAV vector administration could dampen the host immune response. One possible strategy to negate the NF-κB-priming by AAV is to generate targeted mutations against the NF-κB responsive transcription factor binding sites in the AAV-ITRs. However, given the pleiotropic functions of NF-κB proteins in cellular physiology (Hayden and Ghosh, 2004), it is possible that different NF-κB-responsive cytokine promoter-binding transcription factors might be operational in different cell types. Alternatively, a protocol for transient immuno-suppression by targeting the NF-κB pathway might be universally applicable. The selective NF-κB inhibitor, Bay11, can markedly reduce markers of inflammation and innate immune response to AAV vectors yet does not affect its transgene expression in vivo. Bay11 was able to down-regulate the activity of several key regulators namely, IL-1α, IL-6, TNFα, IL-12α, KC and RANTES, suggesting the benefit of using this pharmacologic modulator to selectively down-regulate the inflammatory and innate immune response against AAV vectors. Interestingly, NIK that is critical for activation of the non-canonical NF-κB pathway, is also known induce activation of IL-1α, IL-6, IL-12α, TNFα and RANTES in response to a variety of viral infections (DiPaolo et al., 2009; Yanagawa and Onoe, 2006; Andreakos et al., 2006; Habib et al., 2001). In addition, it is well recognized that NIK is pivotal to the activation and function of the quiescent professional antigen presenting cells, the DCs, whose activity is critical for priming of the antigen specific CD4+ helper T cells, leading to immune responses to relevant targets such as the delivery vector (Andreakos et al., 2006; Habib et al., 2001; Martin et al., 2003; Brown and Lillicrap, 2002). In vitro, NIK increases DC antigen presentation by potently activating NF-κB and consequently up-regulating the expression of cytokines (TNFα, IL-6, IL-12, IL-15, and IL-18), chemokines {IL-8, RANTES, macrophage inflammatory protein-1α, monocyte chemo-attractant protein-1, and monocyte chemo-attractant protein-3}, MHC antigen-presenting molecules (class I and II), and co-stimulatory molecules (CD80 and CD86) (Andreakos et al., 2006). In vivo, NIK enhances immune responses against a vector-encoded antigen and shifts them toward a T helper 1 immune response with increased IgG2a levels, T-cell proliferation, IFN-γ production, and cytotoxic T lymphocyte responses more potently than complete Freund's adjuvant (Andreakos et al., 2006). Bay11, used in this study, prevents the activity of IKKα and β, which are the substrates for NIK in the non-canonical pathway (Pierce et al., 1997). These data indicate the high specificity of Bay11 in targeting the non-canonical NF-κB pathway as well as its ability to prevent the activation of major modulators of immune response.

A protocol for transient immuno-suppression by targeting the NF-κB pathway might be universally applicable to limit immuno-toxicities. Indeed, a recent report showed decreased AAV capsid antigen presentation by the use of a proteasomal inhibitor, Bortezomib [Velcade®] (Finn et al., 2010). Bortezomib has a considerable anti-myeloma efficacy (Kube and Srivastava, 1997), which is likely in large part due to repression of NF-κB signaling. It may therefore be possible to simultaneously block MHC I presentation of capsid and inflammatory signals or use more selective NF-κB-targeted therapies, such as Bay11 in this study, or the newer IKK inhibitors in order to further enhance the safety and therapeutic efficacy of AAV vectors.

Example 3—Development of Optimized AAV3 Serotype Vectors: Mechanism of High-Efficiency Transduction of Human Liver Cancer Cells Adeno-associated virus 2 (AAV2), a non-pathogenic human parvovirus, contains a single-stranded DNA genome, and possesses a wide tissue-tropism that transcends the species barrier (Muzyczka, 1992). Recombinant AAV2 vectors have gained attention as a promising vector system for the potential gene therapy of a variety of human diseases, and are currently in use in a number of gene therapy clinical trials (Daya and Berns, 2008). More recently, several additional AAV serotypes have been isolated, and have been shown to transduce specific cell types efficiently (Muramatsu et al., 1996; Chiorini et al., 1997; Chiorini et al., 1999; Rutledge et al., 1998; Gao G P et al., 2002; Vandenberghe et al., 2004). Whereas various steps in the life cycle of AAV2 are reasonably well understood (Summerford and Samulski 1998; Qing et al., 1999; Summerford et al. 1999; Hansen et al., 2000; Hansen et al., 2001; Sanlioglu et al., 2000; Douar et al., 2001; Zhao et al., 2006; Thomas et al. 2004; Zhong et al. 2004; Ferrari et al., 1996; Fisher et al. 1996; Qing et al., 2004; Zhong et al., 2004; Thong et al., 2004; Thong et al., 2008; McCarty et al., 2004; Bainbridge et al., 2008), less is known about the other serotypes.

Of the 10 commonly used AAV serotypes, AAV3 has been reported to transduce cells and tissues poorly (Zincarelli et al.; Zincarelli et al., 2008). However, recent studies revealed that AAV3 vectors transduce established human hepatoblastoma (HB) and human hepatocellular carcinoma (HCC) cell lines as well as primary human hepatocytes extremely efficiently (Glushakova et al., 2009). Subsequently, it was documented that AAV3 infection was strongly inhibited by hepatocyte growth factor (HGF), HGF receptor (HGFR) specific siRNA, and anti-HGFR antibody, which suggested that AAV3 utilizes HGFR as a cellular receptor/co-receptor for viral entry (Ling et al., 2010).

The ubiquitin-proteasome pathway plays a crucial role in intracellular trafficking of AAV vectors (Douar et al., 2001; Zhong et al., 2007; Duan et al., 2000). Intact AAV2 capsids can be phosphorylated at tyrosine residues by epidermal growth factor receptor protein tyrosine kinase (EGFR-PTK), and that tyrosine-phosphorylation of AAV capsids negatively affects viral intracellular trafficking and transgene expression. These observations led to the suggestion that tyrosine-phosphorylation is a signal for ubiquitination of AAV capsids followed by proteasome-mediated degradation (Duan et al., 2000; Zhong et al., 2008). This led to the hypothesis that mutations of the surface-exposed tyrosine residues (Y) to phenylalanine (F) might allow the vectors to evade phosphorylation, ubiquitination and proteasome-mediated degradation. Indeed, mutations of the surface-exposed tyrosine residues in AAV2 vectors led to high-efficiency transduction at lower doses both in HeLa cells in vitro and murine hepatocytes in vivo (Thong et al., 2008). Therapeutic levels of expression of human factor IX have been obtained in several different strains of mice using the single and multiple tyrosine-mutant AAV2 vectors (Thong et al., 2008; Markusic et al., 2010). Additional studies have corroborated that similar Y-to-F mutations in AAV serotypes 6, 8 and 9 also lead to augmented transgene expression (Petrs-Silva et al., 2009; Qiao et al., 2010; Taylor and Ussher, 2010). Six of seven surface-exposed tyrosine residues in AAV2 are also conserved in AAV3, but their involvement in AAV3-mediated transduction has not been evaluated.

This example demonstrates that: (i) AAV3 vector-mediated transduction is dramatically increased in T47D cells, a human breast cancer cell line that expresses undetectable levels of the endogenous hHGFR (Abella et al., 2005), following stable transfection and over-expression of hHGFR; (ii) the tyrosine kinase activity associated with hHGFR negatively affects the transduction efficiency of AAV3 vectors; (iii) the use of proteasome inhibitors significantly improves AAV3 vector-mediated transduction; (iv) site-directed mutagenesis of three surface-exposed tyrosine residues on the AAV3 capsid leads to improved transduction efficiency; (v) a specific combination of two tyrosine-mutations further improves the extent of transgene expression; and (vi) AAV3 vectors efficiently transduce human HB and HCC tumors in a murine xenograft model in vivo, following both intratumoral or systemic administration. These optimized AAV3 vectors provide improved tools for gene therapy, and particularly for the therapy of liver cancer in humans.

Materials and Methods

Cell Lines and Cultures

Human cervical cancer (HeLa) and hepatocellular carcinoma (Huh7) cell lines were purchased from American Type Culture Collection (Manassas, Va., USA), and maintained in complete DMEM medium (Mediatech, Inc., Manassas, Va., USA) supplemented with 10% heat-inactivated fetal bovine serum (FBS, Sigma-Aldrich, St. Louis, Mo., USA), 1% penicillin and streptomycin (P/S, Lonza, Walkersville, Md., USA). A newly established human hepatoblastoma (Hep293TT) cell line (Chen et al., 2009) was maintained in complete RPMI medium 1640 (Invitrogen, Camarillo, Calif., USA) supplemented with 15% heat-inactivated FBS (Sigma-Aldrich), 1% penicillin and streptomycin (P/S, Lonza, Walkersville, Md.). Cells were grown as adherent cultures in a humidified atmosphere at 37° C. in 5% $CO_2$ and were sub-cultured after treatment with trypsin-versene mixture (Lonza) for 2-5 min at room temperature, washed and re-suspended in complete medium. A human breast cancer cell line, T47D, and T47D cells stably transfected with a hHGFR expression plasmid (T47D+hHGFR), were maintained in complete DMEM medium (Mediatech, Inc.) with or without 600 μg/mL of G418, supplemented with 10% heat-inactivated fetal bovine serum (FBS, Sigma-Aldrich, St. Louis, Mo., USA), 1% penicillin and streptomycin (Lonza).

Recombinant AAV Plasmids and Vectors

Recombinant AAV3 packaging plasmid and recombinant AAV2-CBAp-EGFP vector plasmid were generously provided respectively by Drs. R. Jude Samulski and Xiao Xiao, University of North Carolina at Chapel Hill, Chapel Hill, N.C. Highly purified stocks of scAAV2 and scAAV3 vectors containing the enhanced green fluorescent protein (EGFP)

gene driven by the chicken β-actin promoter (CBAp) were packaged by the calcium phosphate triple-plasmid transfection protocol described previously (Wu et al., 2007; Kube and Srivastava, 1997). The physical particle titers of recombinant vector stocks were determined by quantitative DNA slot-blot analyses (Kube and Srivastava, 1997).

Construction of Surface-Exposed Tyrosine Residue Mutant AAV3 Capsid Plasmids

A two-stage procedure, based on QuikChange II® site-directed mutagenesis (Stratagene) was performed by using plasmid pAAV3 as described previously (Glushakova et al., 2009; Ling et al., 2010). Briefly, in stage one, two PCR extension reactions were performed in separate tubes for each mutant. One tube contained the forward PCR primer and the other contained the reverse primer (Table 3).

In stage two, the two reactions were mixed and a standard PCR mutagenesis assay was carried out as the manufacturer's instructions. PCR primers were designed to introduce changes from tyrosine to phenylalanine residues and a silent change to create a new restriction endonuclease site for screening purposes (Table 3). All mutants were screened with the appropriate restriction enzyme and were sequenced before use.

Rad) and equal amounts (50 μs) of whole cell lysates were resolved by SDS-PAGE. After electrophoresis, samples were electro-transferred to a nitrocellulose membrane (Bio-Rad), probed with relevant primary antibodies at 4° C. overnight, incubated with horseradish peroxidase-conjugated secondary antibodies (Jackson ImmunoResearch, West Grove, Pa., USA), and detected with an enhanced chemi-luminescence substrate (Amersham). Antibodies against phospho-c-Met (Y1234/1235), total c-Met, phospho-Akt (S473) and phospho-ERK (T202/Y204) were purchased from Cell Signaling, and anti-β-actin (AC-74) antibody was obtained from Sigma-Aldrich.

Recombinant AAV3 Vector Transduction Studies in Mouse Xenograft Models

Groups of 6-weeks old NSG mice (Jackson Laboratories) were injected subcutaneously with $5 \times 10^6$ Hep293TT or Huh7 cells. Four-week post-injection, indicated numbers of AAV3 vector genomes (vgs) were administered either intra-tumorally or through tail-vein. Four days post-vector administration, tumors were resected, cross-sectioned and evaluated for EGFP expression using a fluorescent microscope. Sections were also stained with DAPI to visualize the cell

TABLE 3

NUCLEOTIDE SEQUENCES OF PRIMERS USED FOR SITE-DIRECTED MUTAGENESIS

| Mutants | Primer Sequences (5' to 3') |
|---|---|
| Y252F | ACCAGAACCTGGGCtCTGCCCACTT*T*CAACAACCATCTCTACAAG (SEQ ID NO: 11)<br>　　　　ApaI　　　Tyr→Phe |
| Y272F | CAATCAGGAGCTTCgAACGACAACCACT*T*CTTTGGCTACAGCACC (SEQ ID NO: 12)<br>　　　　+BstBI　　　Tyr→Phe |
| Y444F | CTTATcGATCAGTATCTGTACT*T*CCTGAACAGAACGCAAGGAACA (SEQ ID NO: 13)<br>　+ClaI　　　Tyr→Phe |
| F501Y | GCTAACGACAACAACAACAGTAACT4TCCaTGGACAGCGGCCAGCAAA (SEQ ID NO: 14)<br>　　　　　　Phe→Tyr +NcoI |
| Y701F | TGGAATCCAGAGATTCAGT*T*CACgTCCAACTACAACAAGTCTGTT (SEQ ID NO: 15)<br>　　　　Tyr→Phe +BmgBI |
| Y705F | GAGATTCAGTACACgTCCAACT*T*CAACAAGTCTGTTAATGTGGAC (SEQ ID NO: 16)<br>　　　+AflIII  Tyr→Phe |
| Y731F | GTGAACCTCGCCCTATTGGAACCCGGT*T*TCTCACACGAAACTTG (SEQ ID NO: 17)<br>　　　　　　Tyr→Phe |

The codon triplets are shown in bold; red fonts denote the mutations from tyrosine to phenylalanine residues, and green fonts indicate the silent mutations to eliminate/create the restriction enzyme sites (underlined), which were used to identify the desired clones.

AAV Vector Transduction Assays

Huh7 or HeLa cells were seeded in 96-well plates at a concentration of 5,000 cells per well in complete DMEM medium. AAV infections were performed in serum- and antibiotic-free DMEM medium. Hep293TT cells were seeded in 96-well plates at a concentration of 10,000 cells per well in complete RPMI medium. The infections were performed in serum- and antibiotic-free RPMI medium. The expression of EGFP was analyzed by direct fluorescence imaging 72 hrs' post-transduction.

Western Blot Analyses

Cells were harvested and disrupted in a radio-immuno-precipitation assay (RIPA) lysis buffer (50 mM Tris-HCl, pH 8.0, 150 mM NaCl, 0.1% SDS, 1% NP-40, 0.25% sodium deoxycholate and 1 mM EDTA with protease inhibitor cocktail, 1 mM NaF and 1 mM $Na_3VO_4$). Total protein concentration was measured using a Bradford reagent (Bionucleus. All animal studies were conducted in accordance with approved institutional guidelines.

Statistical Analysis

Results are presented as mean±standard deviation (SD). Differences between groups were identified using a grouped-unpaired two-tailed distribution of Student's T test. P values <0.05 were considered statistically significant.

Results

Human HGFR is Required/or AAV3 Infectivity

Figure 11A:
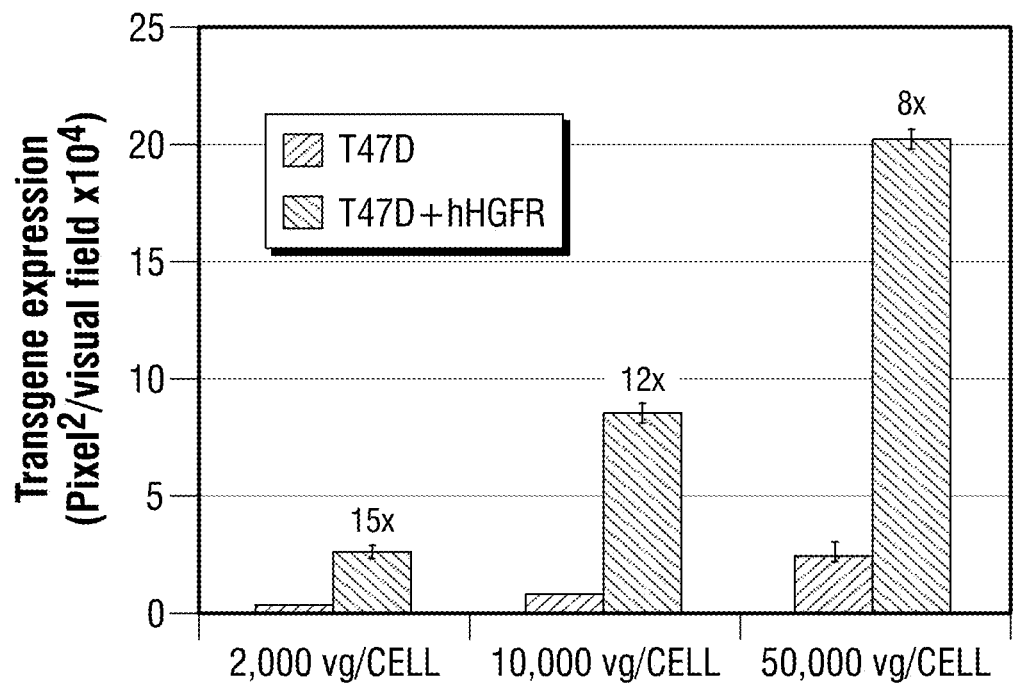
FIG. 11A and FIG. 11B show the analysis of AAV3-mediated transgene expression in T47D and T47D+hHGFR cells.
Figure 11B:
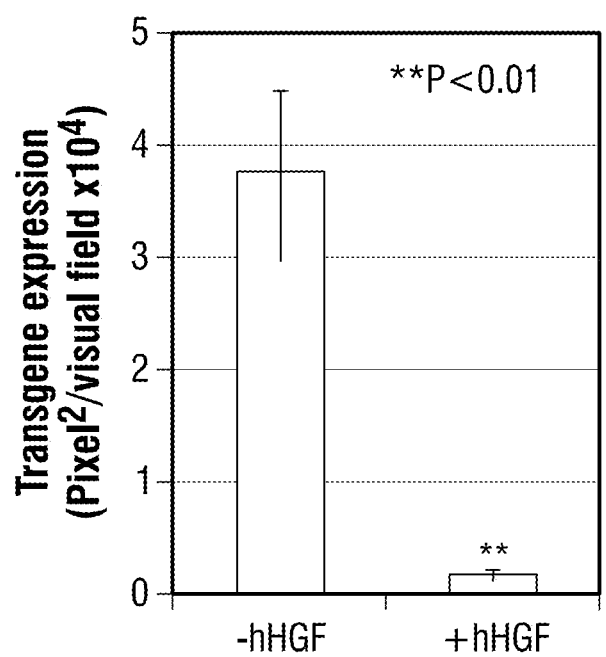

AAV3 utilizes human hepatocyte growth factor receptor (HGFR) as a cellular co-receptor (Ling et al., 2010). To unequivocally corroborate this finding, a human breast cancer cell line, T47D, was used that expresses undetectable levels of hHGFR (Abella et al., 2005), as well as T47D cells stably transfected with hHGFR expression plasmids (T47D+ hHGFR) (Abella et al., 2005). The expression of hHGFR protein in the established cell line T47D+hHGFR was confirmed by Western blot analysis (see FIG. 12C). Equivalent numbers of T47D and T47D+hHGFR cells were transduced with various multiplicities-of-infection (MOI) of self-complementary (sc) AAV3-CBAp-EGFP vectors under identical conditions and transgene expression was determined 72 hr post-transduction. These results, shown in FIG. 11A, document that the transduction efficiency of AAV3 vectors is ~8-13-fold higher in cells that express hHGFR than those that do not. AAV3 vector-mediated transduction of T47D+hHGFR cells could be completely blocked in the presence of 5 µg/mL of hHGF (FIG. 11B). Taken together, these data provide conclusive evidence that cell surface expression of hHGFR is required for successful transduction by AAV3 vectors.

Figure 12A:
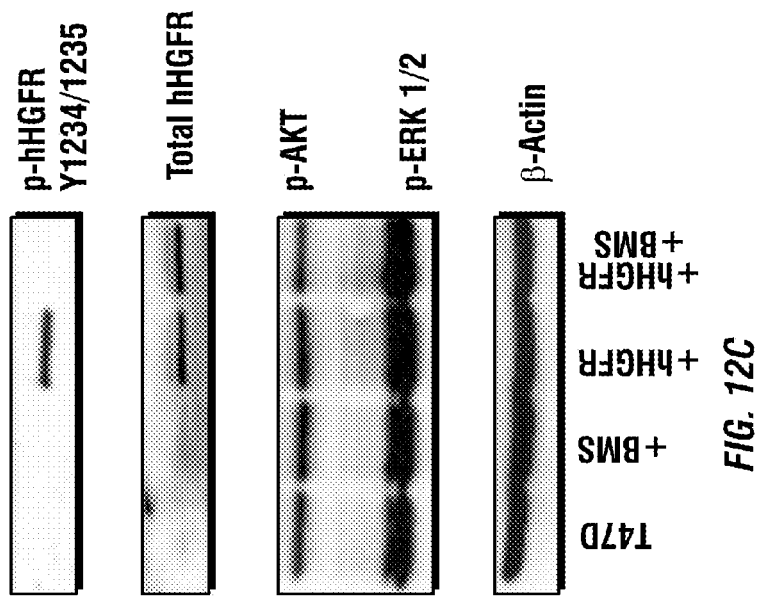
FIG. 12A, FIG. 12B and FIG. 12C show the effect of BMS-777607 on AAV3-mediated transgene expression.
Figure 12B:
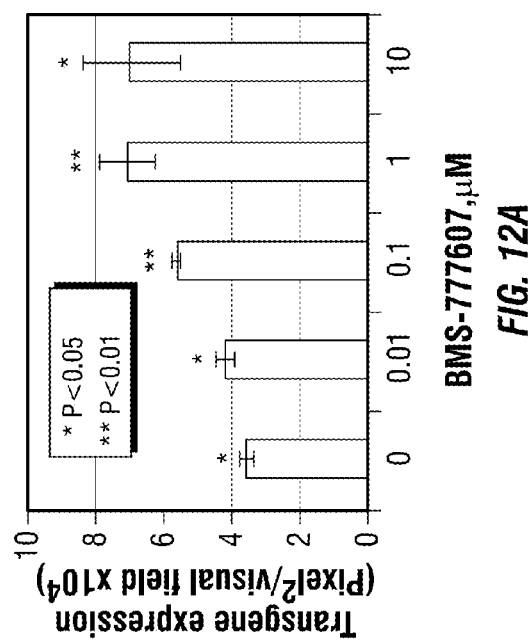
Figure 12C:
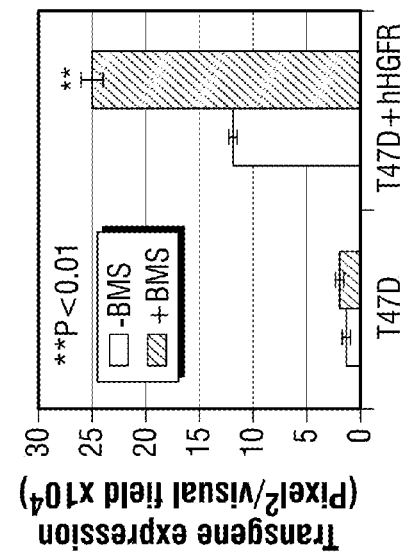

Inhibition of HGFR Protein Tyrosine Kinase Activity Enhances Transduction Efficiency of AAV3 Vectors To examine whether in addition to the extracellular domain, the intracellular domain of HGFR, which contains protein tyrosine kinase activity, is also involved in AAV3 infection, a further study was performed. Binding of its ligand, HGF, results in dimerization of the receptor and intermolecular trans-phosphorylation of multiple tyrosine residues in the intracellular domain (Nguyen et al., 1997). T47D+hHGFR cells were treated for two hrs with increasing concentrations of a specific HGFR kinase inhibitor, BMS-77760707 (BMS) (Schroeder et al., 2009; Dai and Siemann, 2010). Cells were subsequently infected with scAAV3 vectors at 2,000 vgs/cell. These results are shown in FIG. 12A. It is evident that BMS-777607-treatment led to ~2-fold increase in AAV3 transduction efficiency. Although the p-value is higher when BMS-777607 was used at the highest concentration of 10 µM, compared with the lower concentration of 1 µM, this change is most likely due to drug toxicity. In previous studies, it was reported that BMS-777607 treatment had no significant effect on cell growth at doses ≤1 µM. However, doses of 10 µM did result in significant reduction in cell proliferation, which suggests that this concentration is toxic to cells (Dai and Siemann, 2010). In the next experiment, to rule out any possible non-specific nature of this drug, the parental T47D cells were included as a control. Both cell types were treated with 1 µM BMS-777607 for 2 hr and then infected with scAAV3 vectors at 10,000 vg/cell. The results, shown in FIG. 12B, indicated that whereas BMS-777607-treatment significantly enhanced AAV3 infectivity in T47D+hHGFR cells, it had no effect in T47D cells that lack expression of hHGFR.

To examine whether inhibition of the HGFR kinase led to alterations in the phosphorylation status of specific cellular proteins involved in the downstream signaling pathway total and phosphorylation levels of the HGFR protein in both T47D and T47D+hHGFR lysates were determined following a 2-hr drug-incubation period. Activation of signaling pathways downstream from HGFR kinase, ERK1/2 and Akt, were analyzed using phosphorylation-specific antibodies. These results, shown in FIG. 12C, confirmed that whereas little expression of hHGFR occurs in T47D cells, the level of expression is significantly higher in T47D+hHGFR cells for both total HGFR and phosphorylated HGFR, which is consistent with previously published reports (Abella et al., 2005). Treatment of T47D+hHGFR cells with BMS-777607 completely blocked the phosphorylation of HGFR, but not total HGFR. In addition, BMS-777607-treatment had no effect on the expression of phosphorylated AKT and ERK1/2. These results suggest that the enhancement of AAV3 vector infectivity by the BMS-777607-treatment is due to inhibition of HGFR kinase.

Figure 13A:
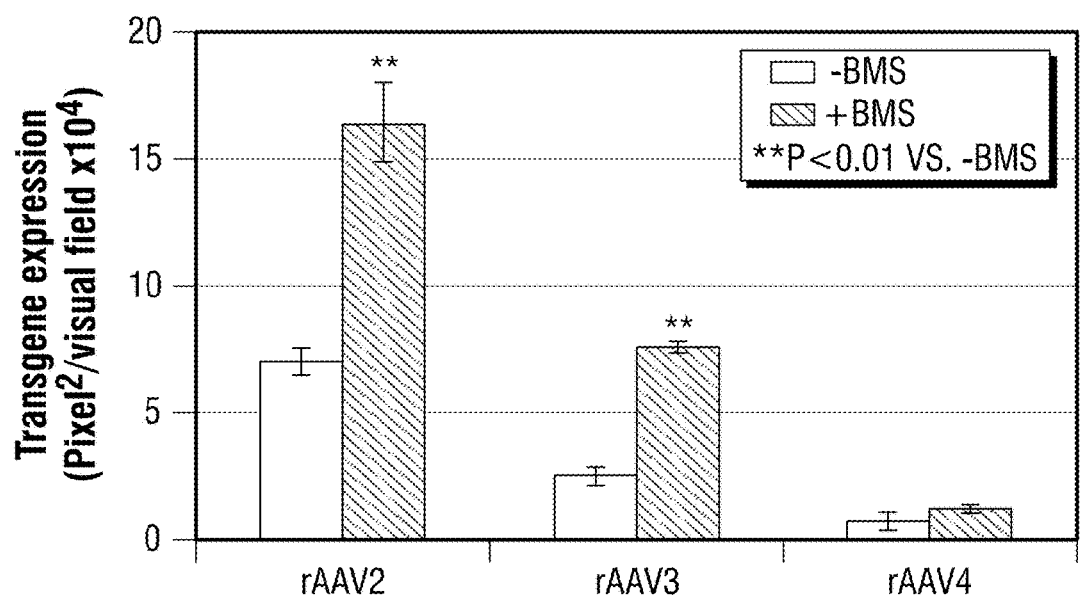
FIG. 13A and FIG. 13B show the effect of BMS-777607 on various AAV serotype-mediated transgene expression.
Figure 13B:
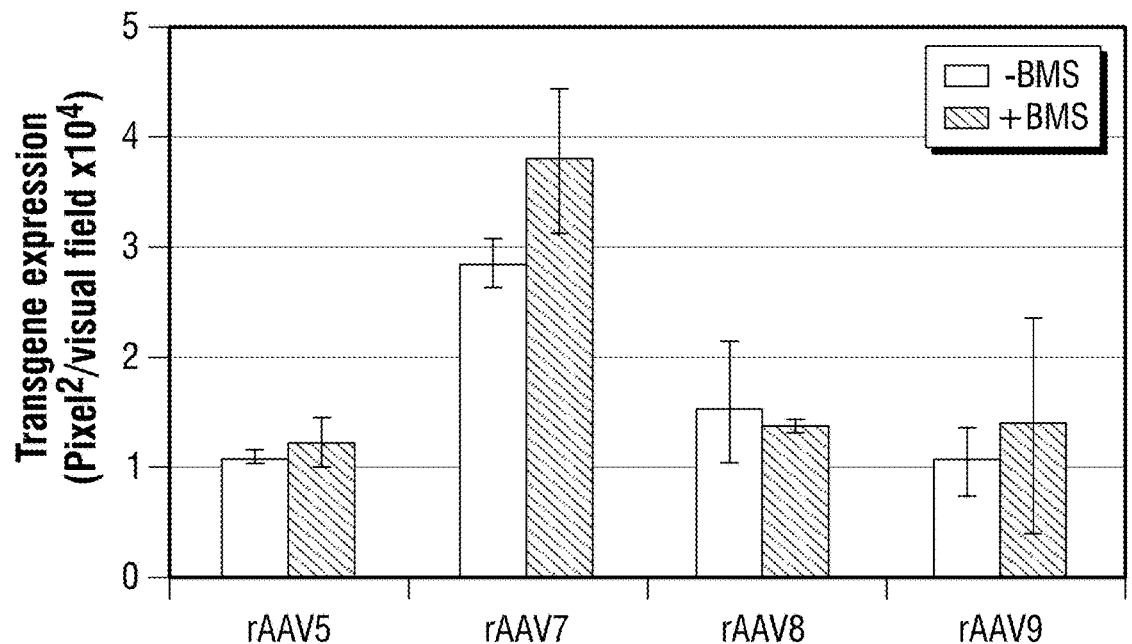

To date, only AAV2 has been reported to use hHGFR as a co-receptor (Yan et al., 2002). The roles of hHGFR and hHGFR kinase inhibitor on other AAV serotypes are not known. To rule out any non-specific enhancement of transduction by BMS-777607, other serotypes of AAV, which are not dependent on HGFR, as well as AAV2 vectors, were compared for transduction efficiency following treatment of cells with BMS-777607. These results, shown in FIG. 13, indicate that whereas AAV2 and AAV3 vectors can efficiently transduce T47D+hHGFR cells, other serotypes (AAV4-AAV9) can only transduce these cells at a very low efficiency. This result suggests that hHGFR is not involved in the life cycle of these AAV serotypes. Treatment of cells with BMS-777607 significantly increased the transduction efficiency of both AAV2 and AAV3 vectors, but not the other AAV serotypes, which suggested that the effect of the BMS-777607-treatment is AAV serotype-specific.

Proteasome Inhibitors Increase the Transduction Efficiency of AAV3 Vectors

Figure 14A:
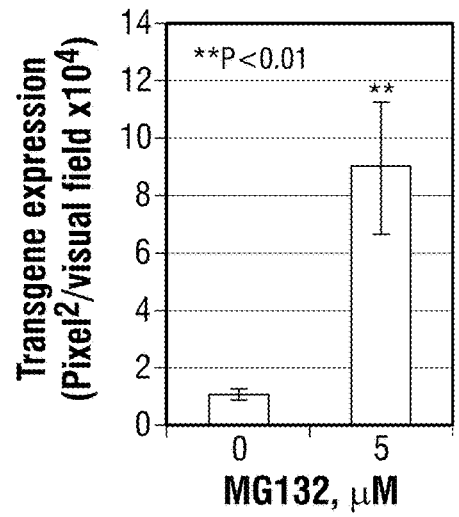
FIG. 14A, FIG. 14B, FIG. 14C and FIG. 14D show the comparative analyses of AAV3-mediated transduction efficiency in Huh7 and Hep293TT cells with or without treatment with MG132.
Figure 14B:
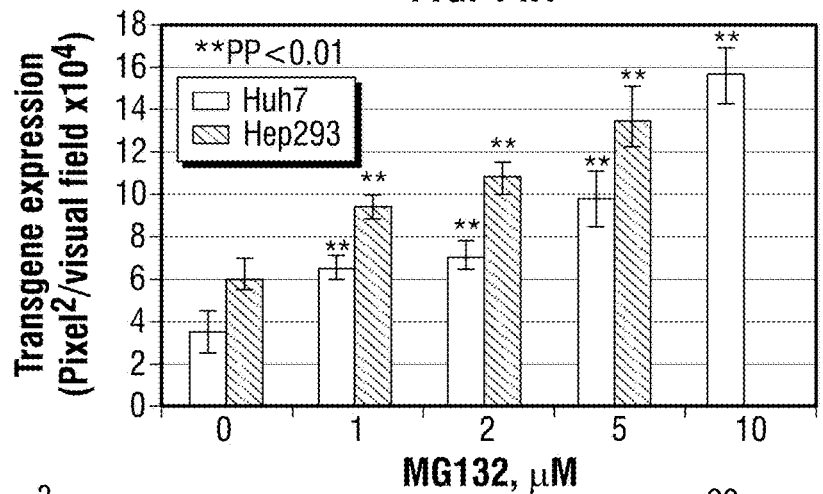

Previous studies have shown that proteasome inhibitors, such as MG132, can significantly enhance the transduction efficiency of AAV2 vectors by facilitating intracellular trafficking (Thong et al., 2007; Yan et al., 2002). To evaluate whether MG132 can also improve AAV3 trafficking in target cells, Huh7, a well-established human hepatocellular carcinoma cell line (Nakabayashi et al., 1982), and Hep293TT, a recently established human hepatoblastoma cell line (Chen et al., 2009), were either mock-treated or treated with increasing concentrations of MG132. Following a two-hour treatment, cells were infected with scAAV3-EGFP vectors. HeLa cells, treated with 5 µM MG132 and transduced with scAAV2 vectors, were included as a positive control. Transgene expression was determined by fluorescence microscopy 72 hrs post-transduction. These data are shown in FIG. 14A and FIG. 14B. As can be seen, pretreatment with MG132 significantly increased the transduction efficiency of scAAV2 vectors in HeLa cells, which is consistent with previously results (Zhong et al., 2008). Interestingly, a dose-dependent increase in the transduction efficiency of scAAV3 vectors in both Huh7 and Hep293TT cells occurred following MG132-treatment, suggesting that AAV3 vectors also undergo ubiquitination followed by proteasome-mediated degradation.

Figure 14C:
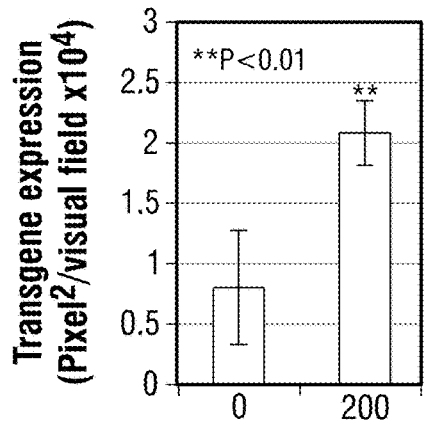
Figure 14D:
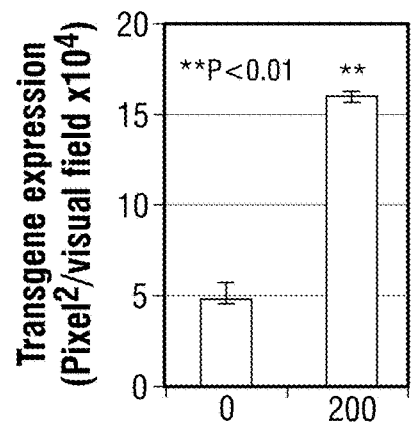

Previous studies have also shown that inhibition of EGFR-PTK signaling by Tyrphostin 23 (Tyr23), a specific inhibitor of EGFR-PTK (May et al., 1998), modulates the Ub/proteasome pathway, which in turn, facilitates intracellular trafficking and transgene expression mediated by AAV2 vectors (Zhong et al., 2007). Hep293TT cells were mock-treated or treated with Tyr23 for 2 hr and transduced with scAAV3 vectors. HeLa cells, pretreated with Tyr23 and transduced with scAAV2 vectors, were included as appropriate controls. Transgene expression was determined 72 hr post-transduction. These results, shown in FIG. 14C and FIG. 14D, indicate that Tyr23-treatment led to a significant increase in the transduction efficiency of both scAAV2 and scAAV3 vectors. The increased transgene expression was independent of vector entry, since there was no significant difference in the amounts of internalized viral DNA in the presence or absence of either MG132 or Tyr23. These results further corroborate the involvement of the host cell Ub/proteasome machinery in the life cycle of AAV3 vectors as well.

Site-directed Mutagenesis of Surface-Exposed Tyr Residues Significantly Improves Transduction Efficiency of scAAV3 Vectors In the preceding examples, the inventors have demonstrated that there are seven surface-exposed tyrosine residues (Y252, Y272, Y444, Y500, Y700, Y704 and Y730) on AAV2 capsids that are phosphorylated by EGFR-PTK and negatively affect the transduction efficiency of AAV2 vectors (Zhong et al., 2008). Alignment of amino acid sequences from AAV2 and AAV3 capsids indicated that six of seven tyrosine residues (Y252, Y272, Y444, Y701, Y705 and Y731) are conserved in AAV3 capsid (Table 4).

TABLE 4

SURFACE-EXPOSED TYR RESIDUES ON AAV CAPSIDS, & SITE-DIRECTED MUTAGENESIS TO CONVERT THEM TO PHENYLALANINE RESIDUES

| AAV2 | AAV3 |
| --- | --- |
| Y252 | Y252→F |
| Y272 | Y272→F |
| Y444 | Y444→F |
| Y500 | F501 |
| Y700 | Y701→F |
| Y704 | Y705→F |
| Y730 | Y731→F |

The surface-exposed tyrosine (Y) residues on AAV2 and AAV3 capsids are shown; arrows denote the site-directed mutations from Y to phenylalanine (F) residues on AAV3 capsids.

Figure 15A:
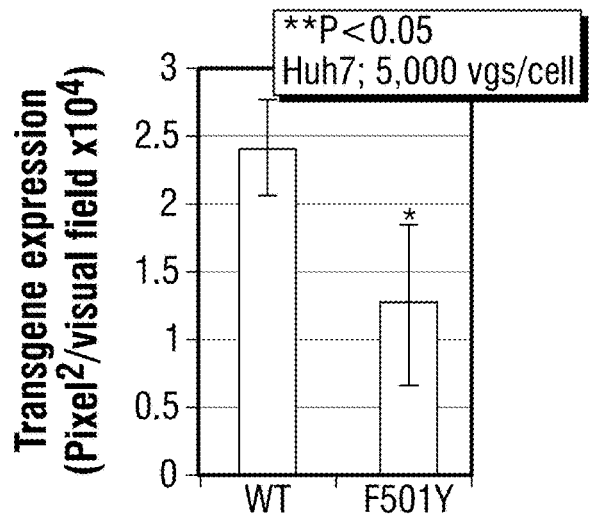
FIG. 15A, FIG. 15B and FIG. 15C show the site-directed mutational analyses of surface-exposed tyrosine residues on AAV3 capsids. Huh7 cells were transduced with WT or F501Y scAAV3-CBAp-EGFP vectors under identical conditions, and transgene expression was determined 72 hrs' post-transduction. Transduction efficiency of WT (FIG. 15A) and various Y-F scAAV3-mediated transgene expression in Huh7 (FIG. 15B) and Hep293TT (FIG. 15C) cells. Transgene expression was determined 72 hrs post-transduction.

One tyrosine residue, Y500 in AAV2, is present as F501 in AAV3. Since it has been shown that Y to F mutations in several AAV serotypes enhance transgene expression by circumventing ubiquitination and proteasome-mediated degradation (Zhong et al., 2008; Petrs-Silva et al., 2009; Qiao et al., 2010; Taylor and Ussher et al., 2010), it was reasoned that mutation of F501 back to a tyrosine residue would reduce the transduction efficiency of AAV3 vectors. This hypothesis was tested by generating a mutant AAV3 vector in which the phenylalanine residue was substituted with a tyrosine residue (F501Y). The transduction efficiency of the mutant vector was compared with its wild-type (WT) AAV3 counterpart using Huh7 cells under identical conditions. As can be seen in FIG. 15A, the extent of the transgene expression mediated by the F501Y mutant vector was reduced by ~50% compared with the WT AAV3 vector.

Figure 15B:
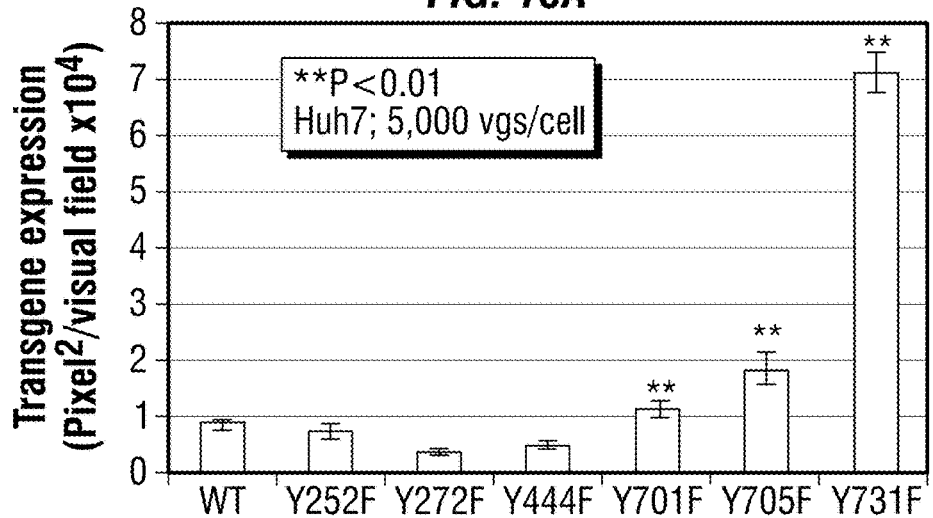
Figure 15C:
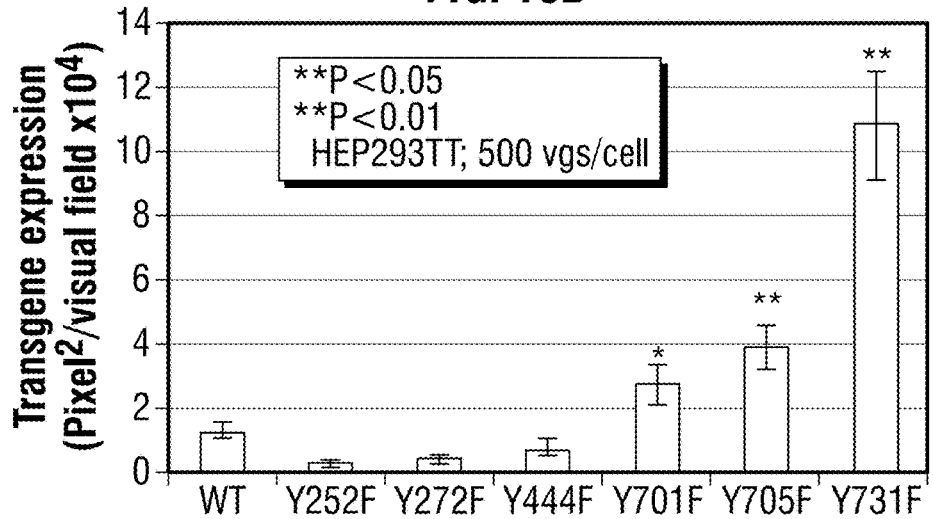

To further test the hypothesis that tyrosine-mutations on AAV3 capsids would lead to decreased EGFR-PTK-mediated phosphorylation followed by reduced ubiquitination and impaired proteasome-mediated degradation resulting in increased transgene expression, all six surface-exposed tyrosine residues on AAV3 capsids were modified and substituted with phenylalanine residues (tyrosine-phenylalanine, Y-F). Each of the single tyrosine-mutant vectors encapsidating scAAV2-CBAp-EGFP genomes could be successfully packaged. Vector titers for each of the mutants were determined by both quantitative DNA slot blots and qPCR, and no significant differences in the packaging efficiency were observed. The transduction efficiency of each of the tyrosine-mutant vectors was analyzed and compared with the WT scAAV3-CBAp-EGFP vector in both Huh7 (FIG. 15B) and Hep293TT (FIG. 15C) cells under identical conditions. From these results, it is evident that, the transduction efficiency of three of the tyrosine-mutant vectors (Y701F, Y705F and Y731F) is significantly higher compared with the WT scAAV3 vector. Specifically, the transduction efficiency of Y731F vector was ~8-fold higher than the WT vector, followed by Y705F (~3-fold) and Y701F (~2-fold) vectors.

Multiple-Mutations in Surface-Exposed Tyrosine Residues Further Improve the Transduction Efficiency of AAV3 Vectors In the prior examples involving Y-F mutant AAV2 vectors, it was observed that specific combinations of the most efficient single-mutations of surface-exposed tyrosine residues further augmented the transduction efficiency of AAV2 vectors (Markusic et al., 2010). To examine whether a similar enhancement could be achieved with AAV3 vectors, the following double- and triple-mutant AAV3 vectors were constructed: Y701+731F, Y705+731F, and Y701+705+ 731F. Each of these mutant vectors was packaged to similar titers, as determined by both quantitative DNA slot blots and qPCR. The transduction efficiency of these multiple-mutants was compared with the WT and the Y731F single-mutant AAV3 vectors in Huh7 cells under identical conditions. These results are shown in FIG. 16A. As can be seen, whereas the Y731F mutation significantly increased the transduction efficiency of AAV3 vectors, as observed before, only one of the double-mutations (Y705+731F) led to an additional significant increase in transgene expression. Interestingly, the transduction efficiency of both the double mutant (Y701+731F) and the triple mutant (Y701+705+ 731F) vectors was reduced to levels similar to the WT AAV3 vector. The best-performing single and multiple tyrosine-mutants on human liver cancer cells were then evaluated for transduction of T47D and T74D+hHGFR cells (FIG. 16B). Similar to human liver cancer cells, the tyrosine-mutant rAAV3 vectors led to high-efficiency transduction of both cell types, with or without hHGFR expression.

To examine the possibility whether the observed enhanced transduction efficiency of the Y-F mutant vectors was due to the involvement of one or more additional putative cellular receptor/co-receptor functions, the WT, Y731F, and Y705+731F mutant scAAV3-CBAp-EGFP vectors were used to transduce Huh7 cells in the absence or the presence of 5 µg/ml hHGF under identical conditions. These results are shown in FIG. 16C. As is evident, the presence of hHGF dramatically inhibited the transduction efficiency and transgene expression of all three AAV3 vectors, which is consistent with the interpretation that the tyrosine-mutant vectors also utilize hHGFR as a cellular receptor/co-receptor for viral entry.

AAV3 Vectors Transduce Human Liver Tumors in Murine Xenograft Models

Figure 17A:
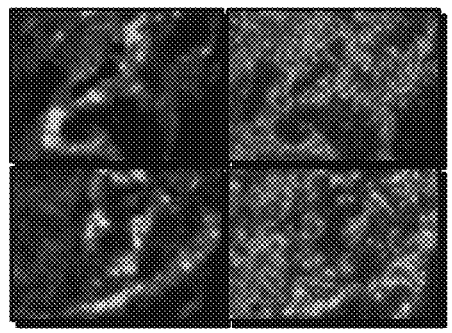
FIG. 17A, FIG. 17B, FIG. 17C and FIG. 17D show the transduction efficiency of AAV3 vectors in vivo following direct intra-tumor injections. Transduction efficiency of WT-AAV3 vectors in Huh7- (FIG. 17A) and Hep293TT- (FIG. 17B) derived tumors in NSG mice. Transduction efficiency of WT- (FIG. 17C) and Y705+731F-AAV3 (FIG. 17D) vectors in Hep293TT-derived tumors in NSG mice. EGFP fluorescence (green) and DAPI staining (blue) of two representative tumor sections from each set of mice is shown.
Figure 17B:
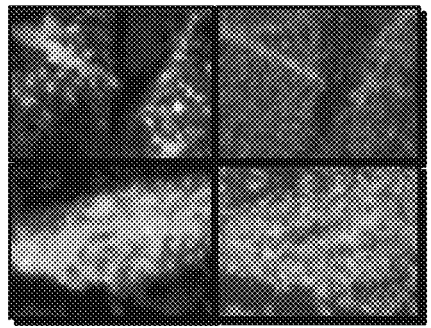

To demonstrate AAV3 vectors could also transduce human HB and HCC tumors in a xenograft mouse model in vivo, ~5×10$^6$ HCC (Huh7) or HB (Hep293TT) cells were injected sub-cutaneously in NOD/Scid gamma (NSG) mice. Four-weeks later, when tumors were clearly visible and palpable in both groups of animals, ~2×10$^{10}$ vgs of scAAV3-CBAp-EGFP vectors were injected directly into tumors. Four-days post-vector injections, tumors were excised and thin sections were examined under a fluorescence microscope. These results indicated that AAV3 vectors were effective to transduce both human HCC (FIG. 17A) and HB (FIG. 17B) tumors in vivo. Consistent with the in vitro data, the transduction efficiency of AAV3 vectors was higher in Hep293TT cell-derived tumors than that in Huh7 cell-derived tumors.

Figure 17C:
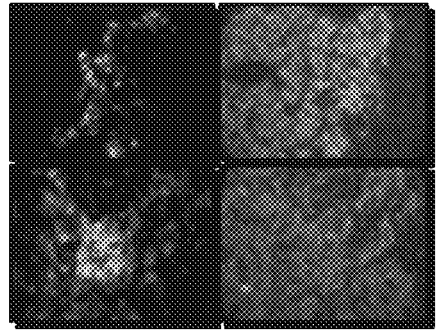
Figure 17D:
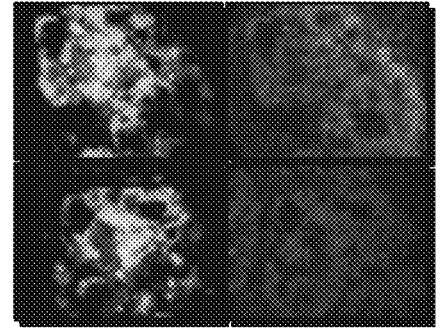

Optimized Tyrosine-Mutant AAV3 Vectors are Highly Efficient in Transducing Human Liver Tumors in Marine Xenografts Next, the best performing double tyrosine-mutant AAV3 vectors were further evaluated in vivo for xenograft human liver tumors gene transfer. In the first set of studies, ~5×10$^{10}$ vgs of either the wild-type (WT) scAAV3- or Y705+731F-AAV3-CBAp-EGFP vectors were intratumorally injected in NSG mice bearing human HB (Hep293TT) tumors. Four-days post-vector injections, tumors were excised, and thin sections were examined under a fluorescence microscope (FIG. 17C). As can be seen, tumors injected with the WT-AAV3 vectors exhibited detectable levels expression of EGFP. The transduction efficiency of the double tyrosine-mutant AAV3 vectors was significantly higher compared with the WT AAV3 vectors, which is consistent with the in vitro data.

Figures 18A, 18B, 18C:
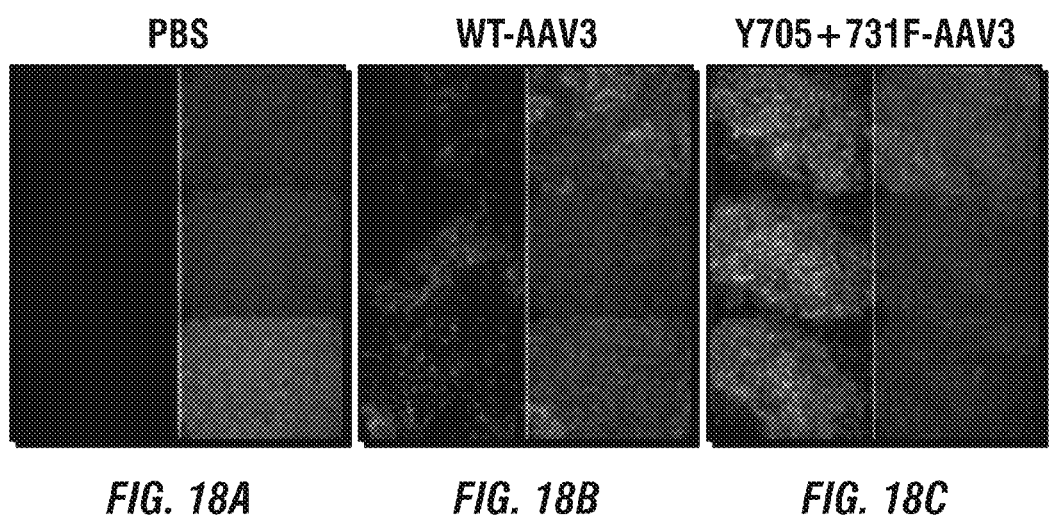
FIG. 18A, FIG. 18B and FIG. 18C show the transduction efficiency of WT- and Y705+731F-AAV3 vectors in Hep293TT-derived tumors in NSG mice following tail-vein injections. EGFP fluorescence (green) and DAPI staining (blue) of tumor in three representative tumor sections from each set of mice injected with PBS (FIG. 18A), WT-AAV3 (FIG. 18B), or Y705+731F-AAV3 (FIG. 18C) vectors is shown.

In the second set of studies, ~5×10$^{11}$ vgs of either the WT-scAAV3- or the Y705+731F-scAAV3-CBAp-EGFP vectors were injected via the tail-vein in NSG mice bearing human HB (Hep293TT) tumors. Phosphate-buffered saline (PBS) injections were used as an appropriate control. Whereas little transgene expression occurred in tumors from mice injected with pBS (FIG. 18A), direct tumor-targeting could be achieved following systemic administration of AAV3 vectors. The transduction efficiency of the optimized tyrosine-mutant AAV3 vectors (FIG. 18C), once again, was significantly higher than that of the WT AAV3 vectors (FIG. 18B). These data suggest that the observed increased transduction efficiency of tyrosine-mutant AAV3 vectors was independent of viral administration route.

HGFR is a trans-membrane receptor tyrosine kinase, and binding of its ligand, HGF, results in dimerization of the receptor and intermolecular trans-phosphorylation of multiple tyrosine residues in the intracellular domain. (Liu et al., 2008) Whereas it is clear that AAV3 capsid interacts with the extracellular domain of hHGFR, it is less clear, whether AAV3-binding to hHGFR also triggers its activation and phosphorylation of the downstream target proteins. The data does indeed demonstrate that suppression of the hHGFR-PTK activity leads to a modest increase in AAV3 vector-mediated transgene expression. In this context, it is of interest to note that the transduction efficiency of AAV3 vectors is significantly higher in a more recently established human hepatoblastoma (HB) cell line, Hep293TT, compared with that in a HB cell line, Huh6, which was established nearly three decades ago. Although subtle differences might exist between the two cell lines, specific mutations have been identified in the tyrosine kinase domain of hHGFR in Hep293TT cells, which render it inactive, and that the hHGFR-specific kinase inhibitor, BMS-777607, which augments the transduction efficiency in Huh6 cells, has little effect on AAV3 transduction efficiency in Hep293TT cells.

Despite the utilization of two distinct cellular growth factor receptors as co-receptors by AAV2 (hFGFR1) and AAV3 (hHGFR), the two serotypes appear to share certain post-receptor entry and intracellular trafficking pathways. For example, both capsids become phosphorylated at tyrosine residues by EGFR-PTK, presumably in the late endosomes, followed by ubiquitination, which leads to proteasome-mediated degradation. (Thong et al., 2008) However, although 6 of 7 surface-exposed tyrosines in AAV2 are conserved in AAV3, the patterns of behavior of the corresponding Y-F mutants are somewhat divergent. For example, Y730F (for AAV2) and Y731F (for AAV3) are the most efficient single-mutants, followed by 114F (for AAV2), and Y705F (for AAV3), the transduction efficiency of Y444F (for AAV3) remains unaltered. Similarly, whereas the transduction efficiency of the Y730+444F double-mutant (for AAV2) is not significantly different from that of Y730F, the transduction efficiency of the Y705+731F double-mutant (for AAV3) is significantly higher than Y731F. Furthermore, the Y730+500+444F triple-mutant (for AAV2) is the most efficient, the Y731+501+705F triple-mutant (for AAV3) is the most efficient, the Y501 residue having already been mutated in the WT AAV3 capsid. Interestingly, even the WT AAV3 vectors were able to transduce human liver tumors reasonably well in a mouse xenograft model in vivo following intratumor injection. However, evidence that the tyrosine-mutant vector resulted in higher gene transfer efficiency in vivo has been demonstrated.

Human liver cancer, especially hepatocellular carcinoma (HCC), is one of the most aggressive malignant tumors. The major obstacle to survival with HCC is recurrence after HCC resection. (Tang, 2005) Thus, transduction of 100% of target cells is desirable in order to completely eliminate the tumor. In previous studies, it was observed that melittin, a toxic peptide derived from bee venom, inhibits the viability and motility of HCC cells both in vitro and in vivo via the suppression of Rac1-dependent pathway (Liu et al., 2008) and up-regulation of mitochondria membrane protein 7A6. (Zhang et al., 2007) Melittin has been shown to induce apoptosis of HCC cells potentially by activating CaMKII/TAK1/JNK/p38 signaling pathway. (Wang et al., 2009)

Based on previous studies with recombinant adenovirus vectors containing the melittin gene driven by a liver cancer cell-specific promoter to achieve specific killing of liver cancer cells both in vitro and in vivo (Ling et al., 2005), this example provides optimized tyrosine-mutant AAV3-melittin vectors under the control of a liver cancer cell-specific promoter that can be used to selectively target both primary and metastatic liver cancer.

Example 4—High-Efficiency Transduction of Human Monocyte-Derived Dendritic Cells by Capsid-Modified Recombinant AAV2 Vectors Dendritic cells (DCs) are antigen-presenting cells (APCs), which play a critical role in the regulation of the adaptive immune response. DCs are unique APCs and have been referred to as "professional" APCs, since the principal function of DCs is to present antigens, and because only DCs have the ability to induce a primary immune response in resting naïve T lymphocytes. (Banchereau and Steinman, 1998) Although a naturally occurring anti-tumor immune response is detectable in patients, this response fails to control tumor growth. On the other hand, monocyte-derived DCs (moDCs) generated ex vivo in the presence of granulocyte-macrophage colony-stimulating factor (GM-CSF) and interleukin 4 (IL-4) possess the capacity to stimulate antigen-specific T-cells after endogenous expression of antigens. (Chapuis et al., 1997; den Brok et al., 2005) For this reason, genetically-modified DCs have been extensively studied and numerous Phase I and II clinical trials evaluating the efficacy of DCs in patients with cancer have been initiated. (Figdor et al., 2004; Palucka et al., 2011) However, current methods for DC loading are inadequate in terms of cell viability, uncertainty regarding the longevity of antigen presentation, and the restriction by the patient's haplotype. (Palucka et al., 2011)

The possibility of manipulating viral genomes by biotechnological techniques, together with the recent identification of many tumor-associated antigens (TAAs), has sparked an interest in using recombinant viruses to express TAAs in the hope of inducing a protective antitumor immune response in patients. (Liu, 2010; Robert-Guroff, 2007) Among different methods for gene delivery, vectors based on a human parvovirus, the adeno-associated virus serotype 2 (AAV2), have attracted much attention mainly because of the non-pathogenic nature of this virus, and its ability to mediate long-term, sustained therapeutic gene expression. (Daya and Berns, 2008; Mueller and Flotte, 2008; Srivastava, 2008) Successful transduction of different subsets of DCs by different commonly used serotypes of AAV vectors has been demonstrated and the potential advantage of an AAV-based antitumor vaccine discussed. (Pannazhagan et al., 2001; Veron et al., 2007; Mahadevan et al., 2007; Shin et al., 2008; Taylor and Ussher, 2010) However, further improvements in gene transfer by recombinant AAV vectors to DCs in terms of specificity and transduction efficiency are warranted to achieve a significant impact when used as an anti-tumor vaccine.

Cellular epidermal growth factor receptor protein tyrosine kinase (EGFR-PTK) negatively impacts nuclear transport and subsequent transgene expression by recombinant AAV2 vectors primarily due to phosphorylation of capsids at surface tyrosine residues. (Thong et al., 2007) These studies resulted in the development of next generation recombinant AAV2 vectors containing point mutations in surface exposed tyrosine residues that transduce various cells and tissues with high-efficiency at lower doses compared to the wild-type (WT) vector. (Zhong et al., 2008) However, such single or multiple tyrosine-mutant AAV vectors failed to increase the transduction efficiency of monocyte-derived DCs (moDCs) more than 2-fold, most likely due to lower levels of expression and/or activity of EGFR-PTK compared with that in HeLa cells or hepatocytes. (Taylor and Ussher, 2010)

Serine/threonine protein kinases are involved in a wide variety of cellular processes such as differentiation, transcription regulation, and development of many cell types including immune cells. Such kinases can also negatively regulate the efficiency of recombinant AAV vector-mediated gene transfer by phosphorylating the surface-exposed serine and/or threonine residues on the viral capsid and target the vectors for proteasome-mediated degradation. In the present example, the following were documented: (i) Site-directed mutagenesis of the 15 surface-exposed serine (S) residues on the AAV2 capsid to valine (V) residues leads to improved transduction efficiency of S458V, S492V, and S662V mutant vectors compared with the WT AAV2 vector; (ii) The S662V mutant vector efficiently transduces human monocyte-derived dendritic cells (moDCs), a cell type not readily amenable to transduction by the conventional AAV vectors; (iii) High-efficiency transduction of moDCs by S662V mutant does not induce any phenotypic changes in these cells; and (iv) Recombinant S662V-vectors encoding a truncated human telomerase (hTERT) gene, used to transduced DCs result in rapid, specific T-cell clone proliferation and generation of robust CTLs, which leads to specific cell lysis of K562 cells.

Materials and Methods

Cells and Antibodies

HEK293, HeLa and NIH3T3 cells were obtained from the American Type Culture Collection and maintained as monolayer cultures in DMEM (Invitrogen) supplemented with 10% FBS (Sigma) and antibiotics (Lonza). Leukapheresis-derived peripheral blood mononuclear cells (PBMCs) (All-Cells) were purified on Ficoll-Paque (GEHeathCare), resuspended in serum-free AIM-V medium (Lonza), and semi-adherent cell fractions were incubated for 7 days with recombinant human IL-4 (500 U/mL) and GM-CSF (800 U/mL) (R&D Systems). Cell maturation was initiated with a cytokine mixture including 10 ng/mL TNF-α, 10 ng/mL IL-1, 10 ng/mL IL-6, and 1 mg/mL PGE2 (R&D Systems) for 48 hrs. Prior to EGFP expression cells were characterized for co-stimulatory molecules expression to ensure that they met the typical phenotype of mature dendritic cells (mDC) (CD80, RPE, murine IgG1; CD83, RPE, murine IgG1; CD86, FITC, murine IgG1; Invitrogen). (Jayandharan et al., 2011)

Site-Directed Mutagenesis

A two-stage PCR was performed with plasmid pACG2 as described previously (Wang and Malcolm, 1999) using Turbo Pfu Polymerase (Stratagene). Briefly, in stage one, two PCR extension reactions were performed in separate tubes for the forward and reverse PCR primer for 3 cycles. In stage two, the two reactions were mixed and a PCR reaction was performed for an additional 15 cycles, followed by DpnI digestion for 1 hr. Primers were designed to introduce changes from serine (TCA or AGC) to valine (GTA or GTC) for each of the residues mutated.

Production of Recombinant AAV Vectors

Recombinant AAV2 vectors containing the EGFP gene driven by the chicken β-actin promoter were generated as described previously (Zologukhin et al., 2002). Briefly, HEK293 cells were transfected using polyethelenimine (PEI, linear, MW 25,000, Polyscinces, Inc.). Seventy-two hrs post transfection, cells were harvested and vectors were purified by iodixanol (Sigma) gradient centrifugation and ion exchange column chromatography (HiTrap Sp Hp 5 mL, GE Healthcare). Virus was then concentrated and the buffer exchanged in three cycles to lactated Ringer's using centrifugal spin concentrators (Apollo, 150-kDa cut-off, 20-mL capacity, CLP) (Cheng et al., 2011). Ten μL of purified virus was treated with DNAse I (Invitrogen) for 2 hr at 37° C., then an additional 2 hr with proteinase K (Invitrogen) at 56° C. The reaction mixture was purified by phenol/chloroform, followed by chloroform treatment. Packaged DNA was precipitated with ethanol in the presence of 20 μg glycogen (Invitrogen). DNAse I-resistant AAV particle titers were determined by RT-PCR with the following primer-pair, specific for the CBA promoter:

```
                                    (SEQ ID NO: 18)
    Forward 5'-TCCCATAGTAACGCCAATAGG-3', (SEQ ID NO: 19)
    Reverse 5'-CTTGGCATATGATACACTTGATG-3'
``` and SYBR Green PCR Master Mix (Invitrogen). (Aslanidi et al., 2009).

Recombinant AAV Vector Transduction Assays In Vitro

HEK293 or monocyte-derived dendritic cells (moDCs), were transduced with AAV2 vectors with 1,000 vgs/cell or 2,000 vgs/cell respectively, and incubated for 48 hr. Alternatively, cells were pretreated with 50 μM of selective serine/threonine kinase inhibitors 2-(2-hydroxyethylamino)-6-aminohexylcarbamic acid tert-butyl ester-9-isopropylpurine (for CaMK-II), anthra[1,9-cd]pyrazol-6(2H)-one, 1,9-pyrazoloanthrone (for JNK), and 4-(4-fluorophenyl)-2-(4-methylsulfinylphenyl)-5-(4-pyridyl)1H-imidazole (for MAPK) (CK59, JNK inhibitor 2, PD 98059, Calbiochem), 1 hr before transduction. Transgene expression was assessed as the total area of green fluorescence (pixel2) per visual field (mean±SD) as described previously (Markusic et al., 2011; Jayandharan et al., 2011). Analysis of variance was used to compare test results and the control, which were determined to be statistically significant.

Western Blot Analysis

Western blot analysis was performed as described previously. (Akache et al., 2006) Cells were harvested by centrifugation, washed with PBS, and resuspended in lysis buffer containing 50 mM TrisHCl, pH 7.5, 120 mM NaCl, 1% Nonidet P-40, 10% glycerol, 10 mM Na4P2O7, 1 mM phenylmethylsulfonyl fluoride (PMSF), 1 mM EDTA, and 1 mM EGTA supplemented with protease and phosphotase inhibitors mixture (Set 2 and 3, Calbiochem). The suspension was incubated on ice for 1 hr and clarified by centrifugation for 30 min at 14,000 rpm at 4° C. Following normalization for protein concentration, samples were separated using 12% polyacrylamide/SDS electrophoresis, transferred to a nitrocellulose membrane, and probed with primary antibodies, anti p-p38 MAPK (Thr180/Tyr182) rabbit mAb, total p38 MAPK rabbit mAb and GAPDH rabbit mAb (1:1000, CellSignaling), followed by secondary horseradish peroxidase-linked linked antibodies (1:1000, CellSignaling).

Specific Cytotoxic T-Lymphocytes Generation and Cytotoxicity Assay

Monocyte-derived dendritic cells (moDCs) were generated as described above. Immature DCs were infected with AAV2-S662V vectors encoding human telomerase cDNA, separated into two overlapping ORF—hTERT838-2229 and hTERT2042-3454 at MOI 2,000 vgs/cell of each. Cells were then allowed to undergo stimulation with supplements to induce maturation. After 48 hr, the mature DCs expressing hTERT were harvested and mixed with the PBMCs at a ratio of 20:1. CTLs were cultured in AIM-V medium containing recombinant human IL-15 (20 IU/mL) and IL-7 (20 ng/mL) at $20 \times 10^6$ cells in 25 $cm^2$ flasks. Fresh cytokines were added every 2 days. After 7 days post-priming, the cells were harvested and used for killing assays (Heiser et al., 2002). A killing curve was generated and specific cell lysis was determined by FACS analysis of live/dead cell ratios as described previously (Mattis et al., 1997). Human immortalized myelogenous leukemia cell line, K562, was used as a target.

Statistical Analysis

Results are presented as mean±S.D. Differences between groups were identified using a grouped-unpaired two-tailed distribution of Student's T-test. P-values <0.05 were considered statistically significant.

Results

Figure 19A:
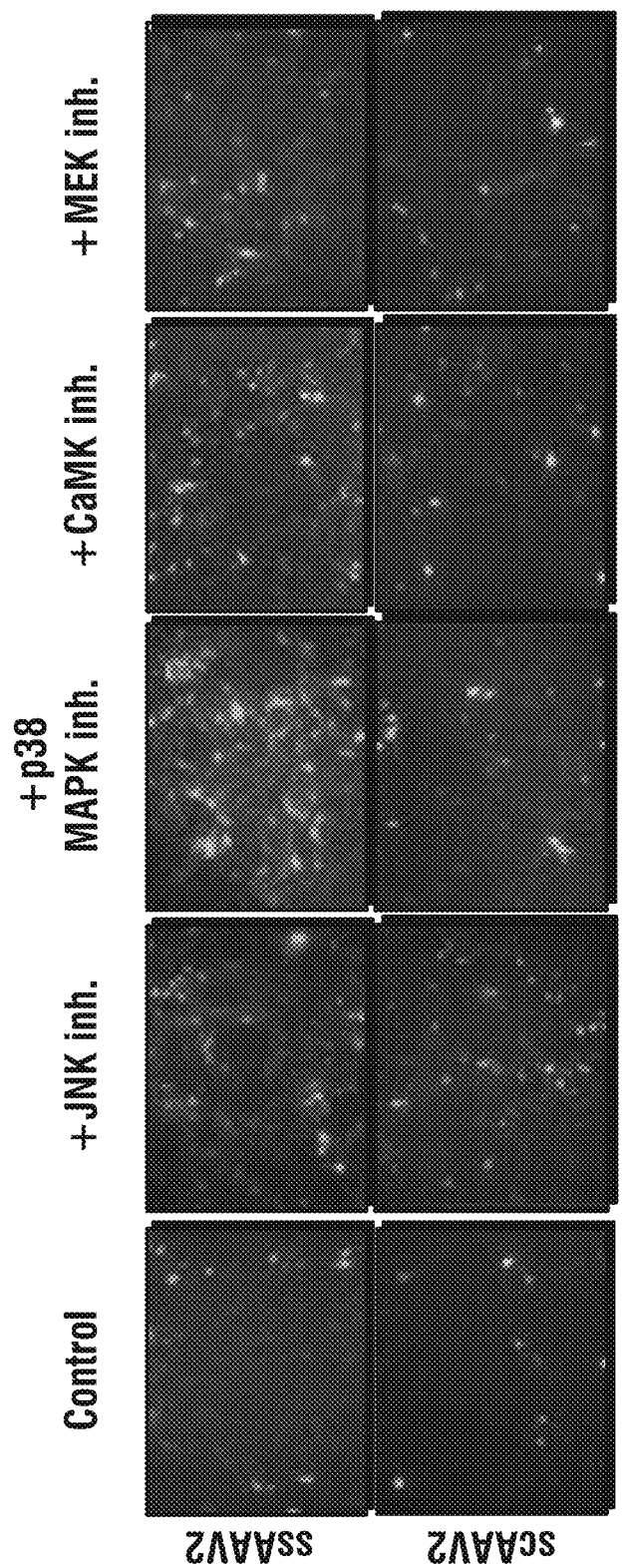
FIG. 19A and FIG. 19B show the effect of various kinase inhibitors on ssAAV and scAAV mediated EGFP expression in HEK293 cells. Cells were pretreated with inhibitors for 1 hr before infection then transduced with $1\times10^3$ vgs/cell.
Figure 19B:
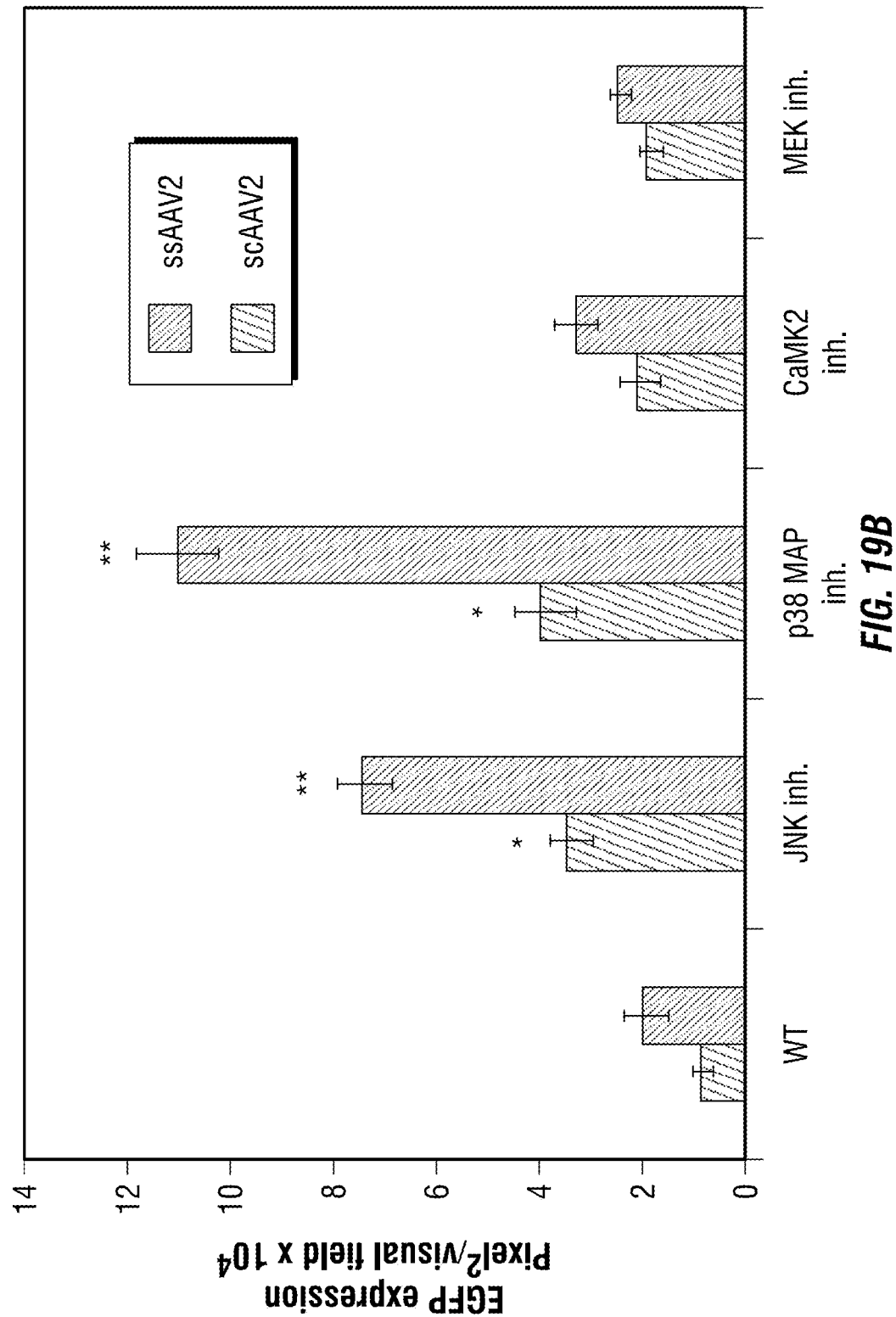

Inhibition of Specific Cellular Serine/Threonine Kinase Increases Transduction Efficiency of rAAV2 Vectors In previous studies, inhibition of cellular epidermal growth factor receptor protein tyrosine kinase (EGFR-PTK) activity and site-directed mutagenesis of the 7 surface-exposed tyrosine residues was shown to significantly increase to the transduction efficiency of AAV2 vectors by preventing phosphorylation of these residues, thereby circumventing ubiquitination and subsequent proteasome-mediated degradation of the vectors (Thong et al., 2008). However, AAV2 capsids also contain 15 surface-exposed serine residues, which can potentially be phosphorylated by cellular serine/threonine kinases widely expressed in various cell types and tissues. To test the hypothesis that inhibition of such kinase activity can prevent phosphorylation of surface-exposed serine residues and thus improve intracellular trafficking and nuclear transport of AAV2 vectors, several commercially available specific inhibitors of cellular serine/threonine kinases were used, including calmodulin-dependent protein kinase II (CamK-II), c-Jun N-terminal kinase (JNK); and mitogen-activated protein kinase (p38 MAPK). HEK293 cells were pre-treated with specific inhibitors, such as 2-(2-hydroxyethylamino)-6-aminohexylcarbamic acid tert-butyl ester-9-isopropylpurine (for CaMK-II), anthra[1,9-cd]pyrazol-6(2H)-one, 1,9-pyrazoloanthrone (for JNK), and 4-(4-fluorophenyl)-2-(4-methylsulfinylphenyl)-5-(4-pyridyl)1H-imidazole (for p38 MAPK) for 1 hr at various concentrations. Cells were subsequently transduced with either single-stranded (ss) or self-complementary (sc) AAV2 vectors at 1,000 vector genomes (vgs) per cell. These results indicated that all inhibitors at an optimal concentration of 50 µM significantly increased the transduction efficiency of ssAAV2 and scAAV2 vectors, the p38 MAPK inhibitor being the most effective (FIG. 19A and FIG. 19B). This observation suggests, albeit does not prove, that the increase in the transduction efficiency was most likely due to prevention of phosphorylation of vector capsids rather than improved viral second-strand DNA synthesis.

Figure 20A:
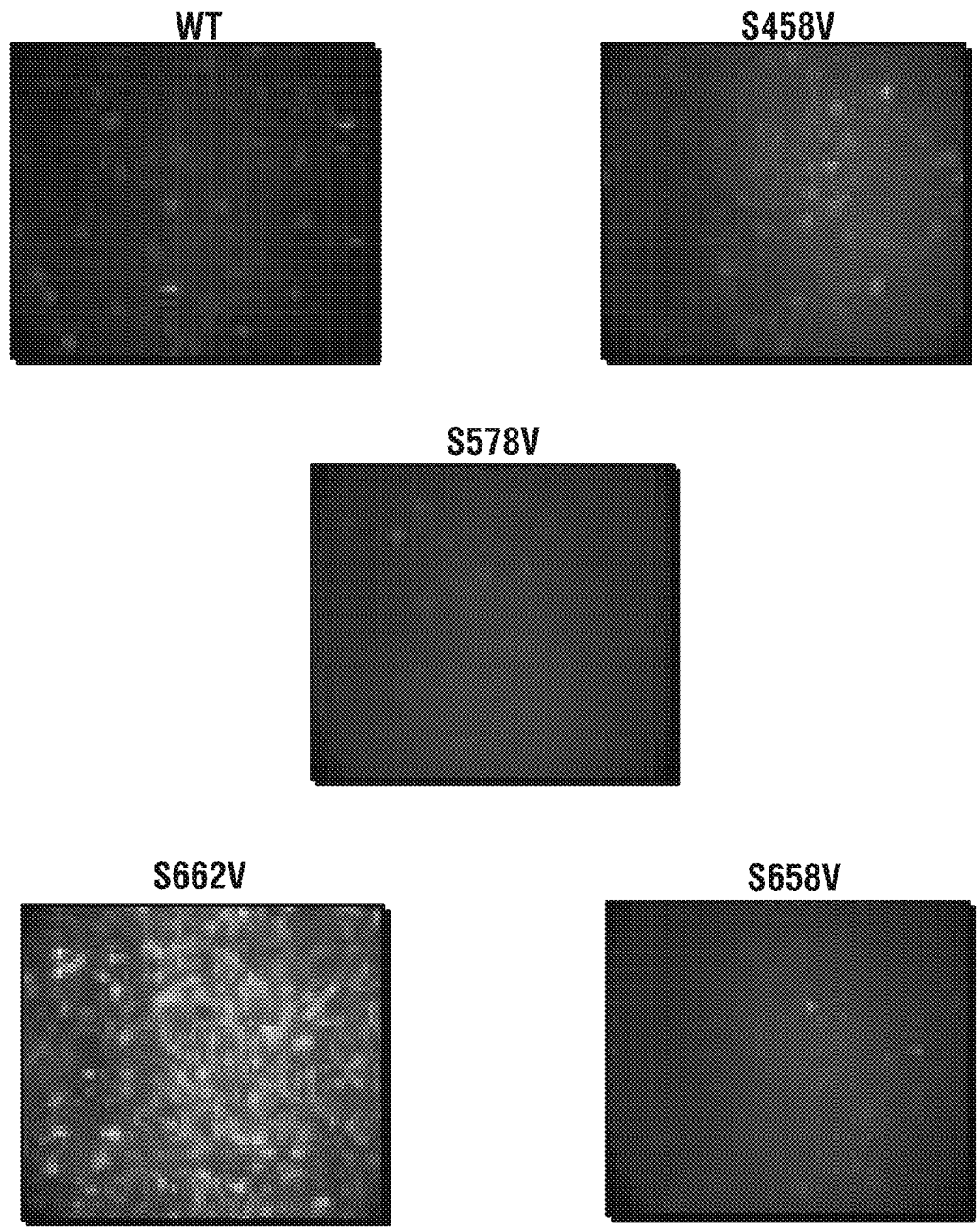
FIG. 20A and FIG. 20B show the analysis of EGFP expression after transduction of HEK293 cells with individual site-directed scAAV2 capsid mutants. Each of the 15 surface-exposed serines (S) in AAV2 capsid was substituted with valine (V) and evaluated for its efficiency to mediate transgene expression.
Figure 20B:
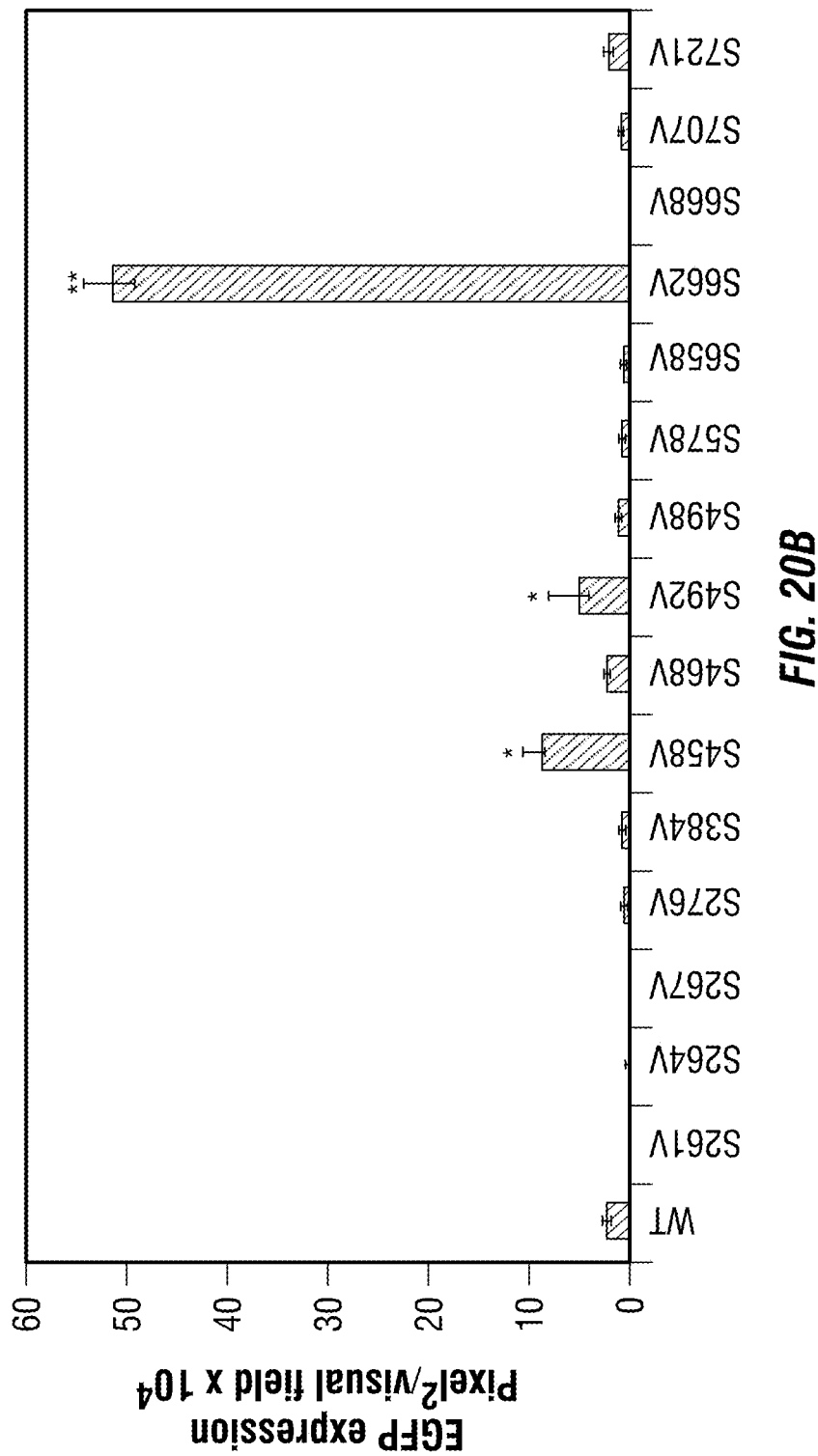
Figure 21A:
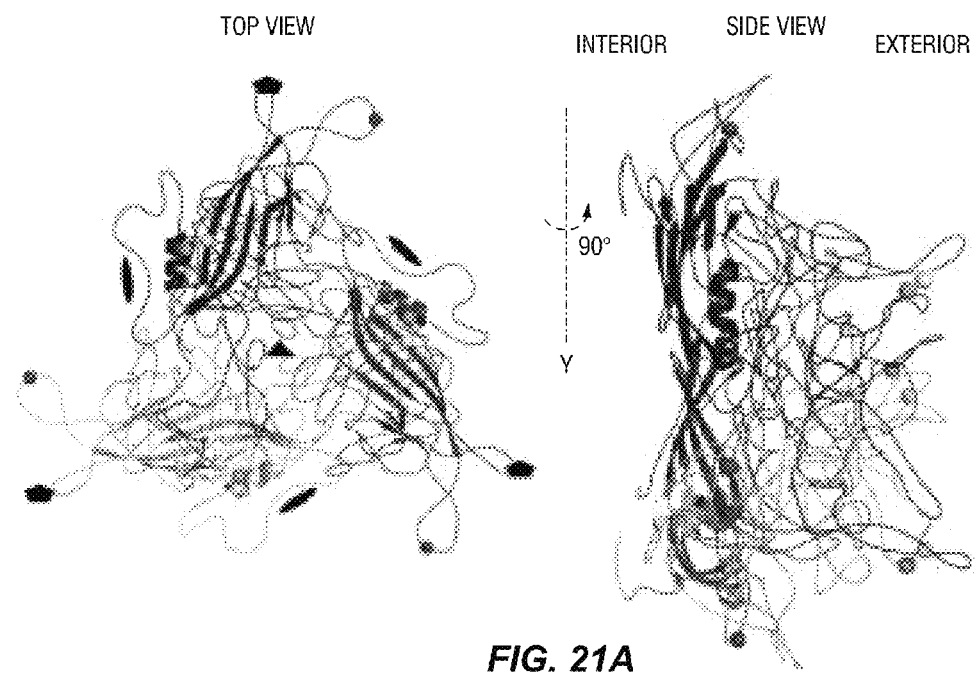
FIG. 21A: A trimer of the AAV2 VP3 shown in ribbon representation and viewed down the icosahedral threefold axis (left) and rotated 90° (right) with VP monomers colored in blue, purple and light blue showing the location of serine residues 458, 492, and 662 in the yellow, green, and red spheres, respectively. The approximate positions of the icosahedral two-, three-, and five-fold axes are depicted by the filled oval, triangle, and pentagon, respectively.
Figure 21B:
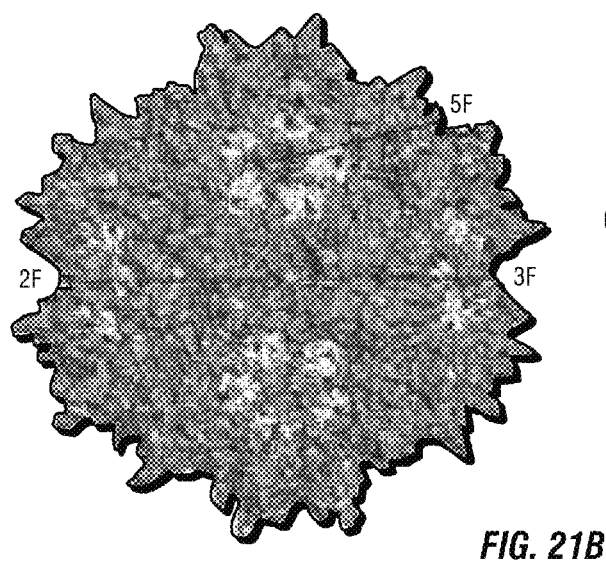

Site-Directed Mutagenesis of Surface-Exposed Serine Residues on AAV2 Capsid Improves AAV2 Vector-Mediated Transgene Expression The AAV2 capsid contains 50 serine (S) residues in the viral protein 3 (VP3) common region of the three capsid VPs, of which 15 (S261, S264, S267, S276, S384, S458, S468, S492, S498, S578, S658, S662, S668, S707, S721) are surface-exposed. (Xie et al., 2002) Each of the 15 S residues was substituted with valine (V) by site-directed mutagenesis as described (Thong et al., 2008). Most mutants could be generated at titers similar to the WT AAV2 vectors, with the exception of S261V, S276V, and S658V, which were produced at ~10 times lower titers, and S267V and S668V, which produced no detectable levels of DNAse I-resistant vector particles. The titers of S468V and S384V mutants were ~3-5 times higher than the WT AAV2 vectors. Each of the S-V mutant vectors was evaluated for transduction efficiency in HEK293 cells. These results, shown in FIG. 20, indicate that of the 15 mutants, the S662V mutant transduced HEK293 cells ~20-fold more efficiently than its WT counterpart did. The transduction efficiency of the S458V and the S492V mutant vectors was increased by ~4- and 2-fold, respectively. The positions of these three critical surface exposed serine residues on the AAV2 capsid are shown in FIG. 21A and FIG. 21B. No further increase in transduction efficiency was observed with the double-mutants (S458+662V and S492+662V), or the triple-mutant (S458+492+662V), indicating that unlike some of the tyrosine-mutants, combining multiple mutations in the serine residues was neither additive nor synergistic. Interestingly, the transduction efficiency of the S468V and the S384V mutants, which were produced at titers higher than the WT AAV2 vectors, remained unchanged (S468V) or were reduced ~10-fold (S384V) at the same multiplicity of infection (MOI). These data are summarized in FIG. 34.

Figure 22A:
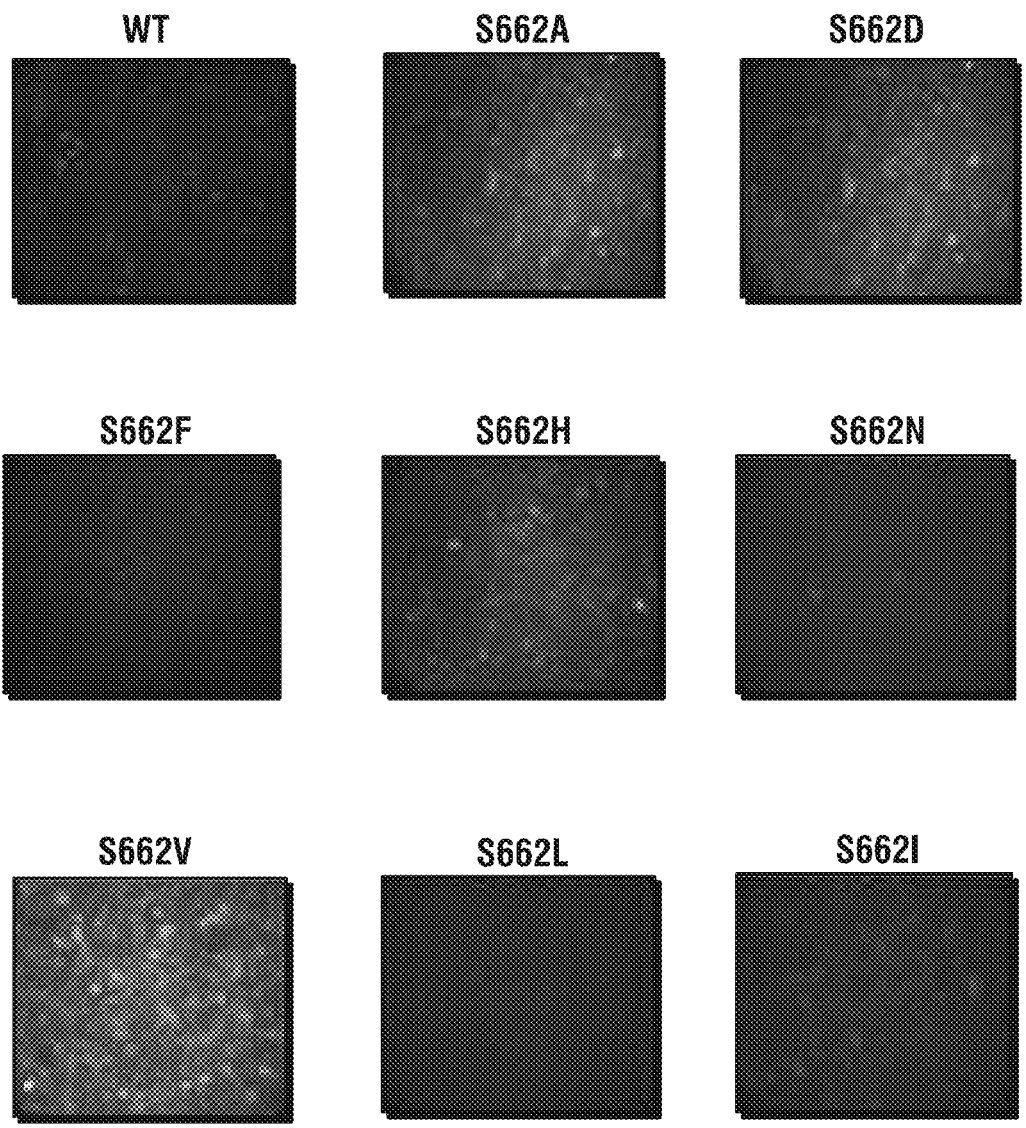
FIG. 22A and FIG. 22B show the evaluation of the effect of serine substitution at position 662 in the scAAV2 capsid with different amino acids in mediating transgene expression. The following 8 serine mutants were generated with different amino acids: S662→Valine (V), S662→Alanine (A), S662→Asparagine (N), S662→Aspartic acid (D), S662→Histidine (H), S662→Isoleucine (I), S662→Leucine (L), and S662→Phenylalanine (F), and their transduction efficiency in 293 cells was analyzed.
Figure 22B:
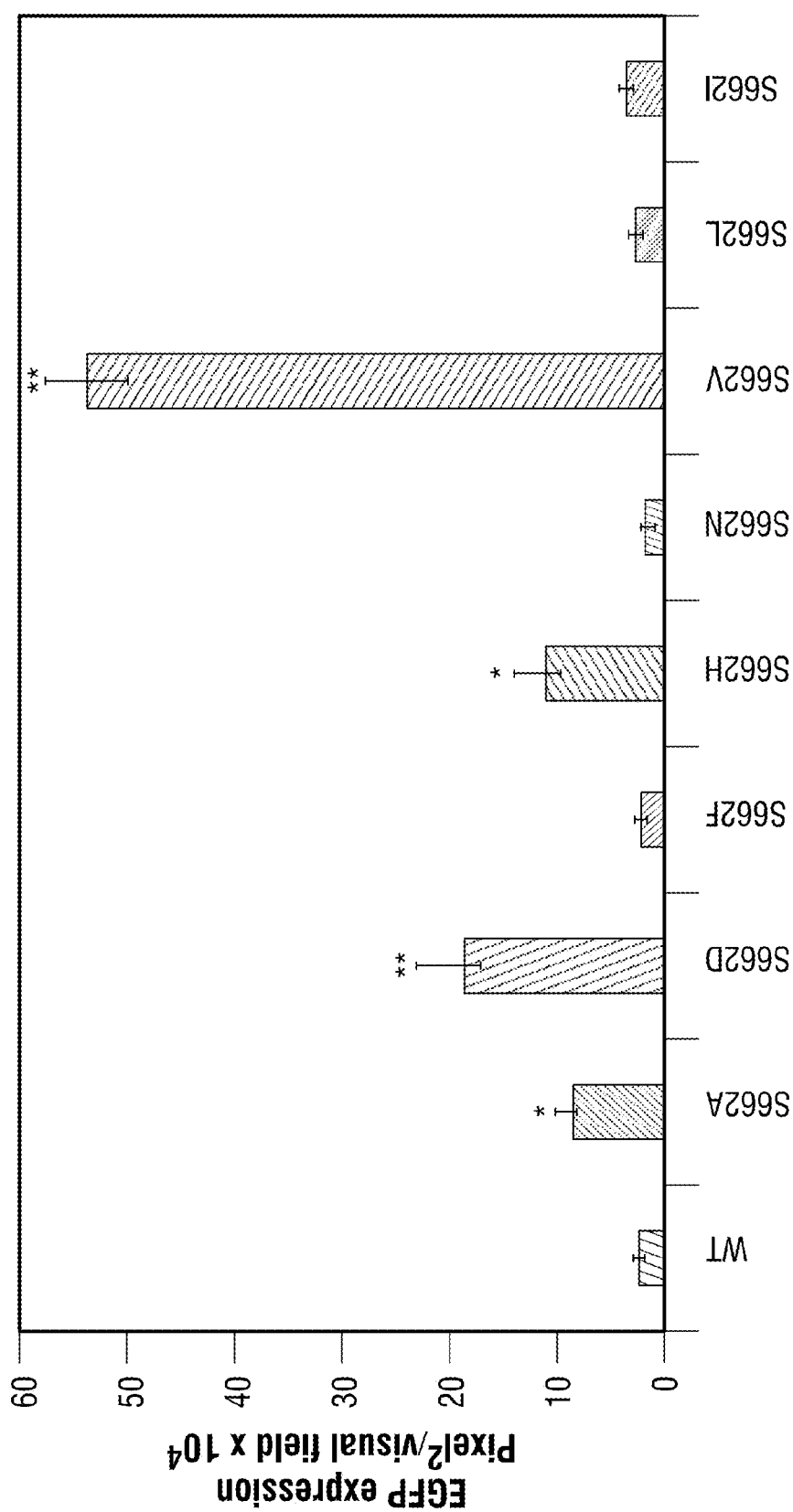

Substitution of S662 with Different Amino Acids has Diverse Effects on AAV2 Capsid Assembly and AAV2 Vector-Mediated Transgene Expression In addition to S-to-V substitution at position 662, the following 7 mutants with different amino acids were also generated: S662→Alanine (A), S662→Asparagine (N), S662→Aspartic acid (D), S662→Histidine (H), S662→Isoleucine (I), S662→Leucine (L), and S662→Phenylalanine (F), and evaluated their transduction efficiency in 293 cells. These results, shown in FIG. 22 and summarized in FIG. 35, demonstrate that the substitution of S with V led to the production of the most efficient mutant without any change in vector titers. Replacement of S with N, I, L, or F decreased the packaging efficiency ~10-fold with no significant effect on the transduction efficiency, whereas substitution with D or H increased the transduction efficiency ~8-fold and ~4-fold, respectively, with no effect on vector titers. Interestingly, substitution of S to A increased the viral titer up to ~5-fold, and enhanced the transgene expression ~3-fold compared with the WT AAV2 vector. The observed variability in titers and infectivity of the serine-mutants at position 662 suggests the critical role each of the amino acids plays in modulating both AAV2 packaging efficiency and biological activity.

Transduction Efficiency of S662V Vectors Correlate with p38 MAPK Activity

Figure 23A:
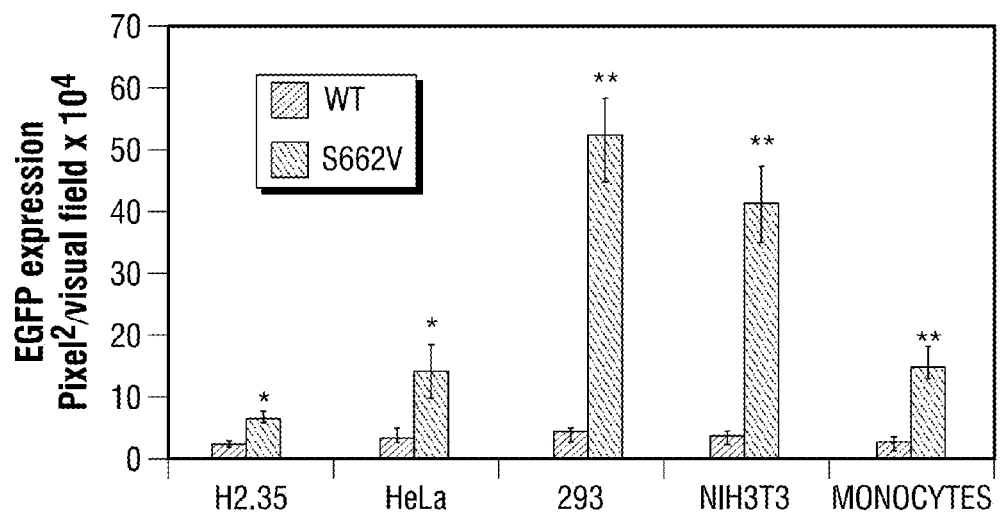
FIG. 23A and FIG. 23B show the analysis of correlation of transduction efficiency of scAAV2-S662V vectors with p38 MAPK activity in various cell types.
Figure 23B:
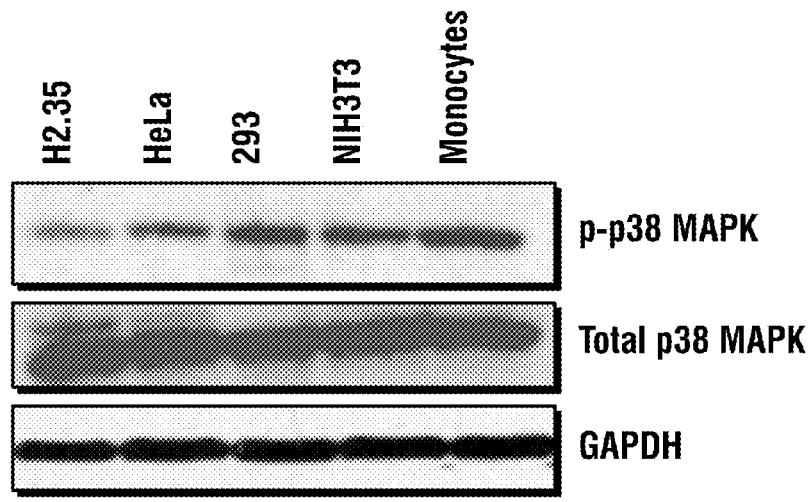

Since all of the S662V vector-mediated transgene expression data thus far were derived using 293 cells, these studies were extended to include the following cells types: (i) NIH3T3 (mouse embryonic fibroblasts), (ii) H2.35 (mouse fetal hepatocytes), (iii) HeLa (human cervical cancer cells), and (iv) primary human monocyte-derived dendritic cells (moDCs). These cell types were transduced with WT scAAV2-EGFP or S662V scAAV2-EGFP vectors at an MOI of 2,000 vgs per cell under identical conditions. EGFP gene expression was evaluated 48 hrs post-infection (p.i.) for HeLa, 293 and moDCs, and 5 days p.i. for H2.35 and NIH3T3 cells. These results are shown in FIG. 23A. As can be seen, although the absolute differences in the transduction efficiency between WT and S662V mutant vectors ranged from ~3-fold (in H2.35 cells) to ~20-fold (in 293 cells) the mutant vector was consistently more efficient in each cell type tested. Since pre-treatment of cells with an inhibitor of cellular p38 MAPK was the most effective in increasing the transduction efficiency (FIG. 19A and FIG. 19B), the inventors examined whether or not the observed differences in the transduction efficiency of the WT and the mutant vectors was due to variations in the levels of expression and/or activity of the cellular p38 MAPK. Cell lysates prepared from each cell type were analyzed on Western blots probed with specific antibodies to detect both total p38 MAPK and phospho-p38 MAPK levels. GAPDH was used as a loading control. These results, shown in FIG. 23B, indicate that whereas the p38 MAPK protein levels were similar, the kinase activity, as determined by the level of phosphorylation, varied significantly among different cell types, and the transduction efficiency of the S662V mutant vector correlated roughly with the p38 MAPK activity. These approximate correlations between p38 MAPK activity and the efficiency of the S662V mutant vector can probably be explained by different cell susceptibilites for AAV infection, the overall number of viral particles entered cell after primary infection. It remains unclear as to which precise steps in the life cycle of AAV are modulated by p38 MAPK-mediated phosphorylation. It is also possible that other serine/threonine kinases contributing to the difference in efficiency of transduction by S662V and WT vectors. Interestingly, however, transduction by the WT-AAV2 vectors did not lead to up regulation of phosphorylation of p38 MAPK in 293 cells or in moDC, further supporting a previous report that AAV does not induce robust phenotypic changes in moDCs (Markusic et al., 2011).

Figure 24A:
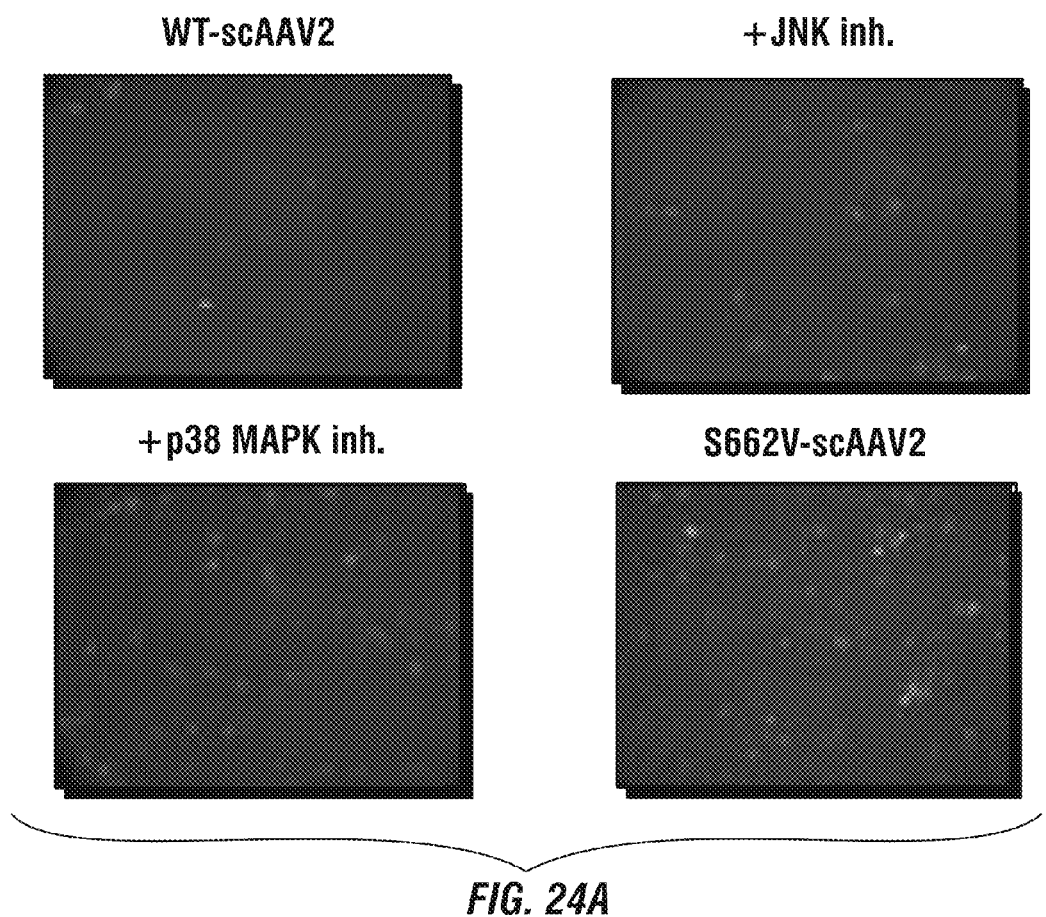
FIG. 24A, FIG. 24B, and FIG. 24C illustrate scAAV vector-mediated transgene expression in monocyte-derived dendritic cells (moDCs).
Figure 24B:
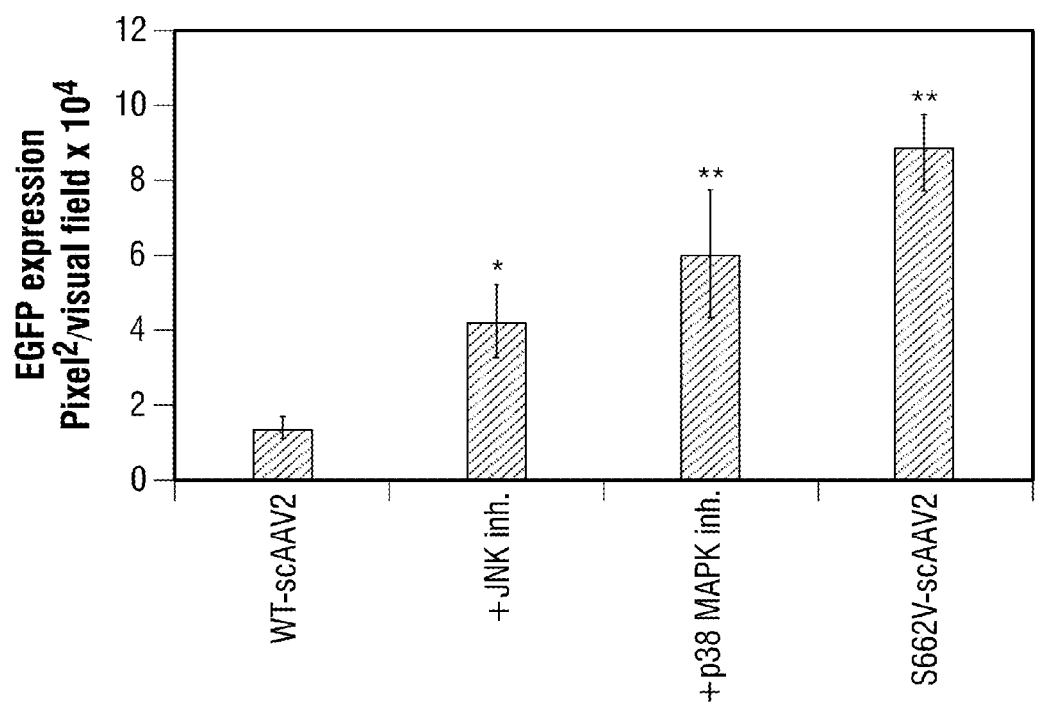
Figure 24C:
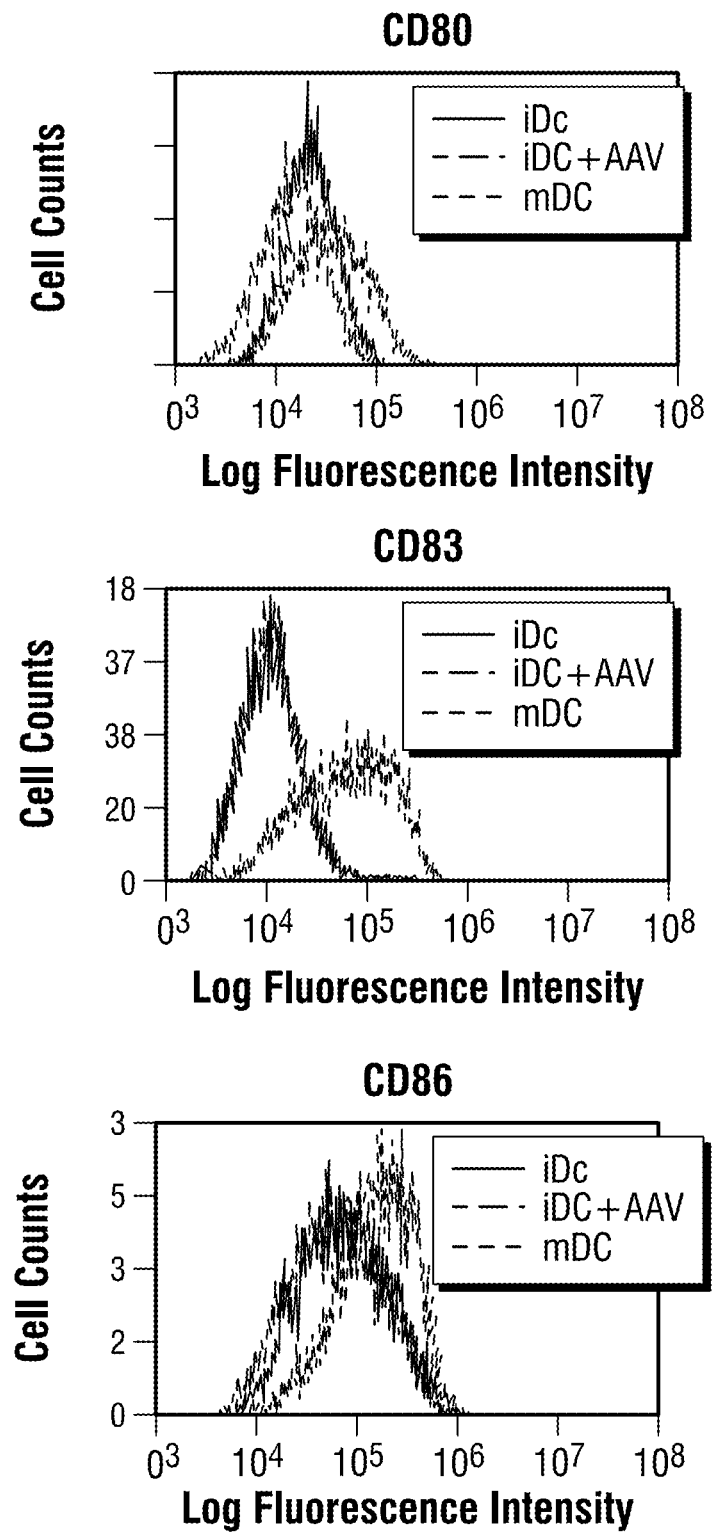

S662V Vector-Mediated Transduction of Primary Human moDCs does not Lead to Phenotypic Alterations MAPK family members play important roles in the development and maturation of APCs. moDCs, isolated from healthy donor leukapheresis, were treated with 50 µM selective kinase inhibitors as described above and then transduced with WT scAAV2-EGFP vectors. Two hrs p.i., cells were treated with supplements (TNF-α, IL-1β, 11-6, PGE2) to induce maturation. EGFP transgene expression was evaluated 48 hrs p.i. by fluorescence microscopy. Pre-treatment of moDCs with specific inhibitors of JNK and p38 MAPK increased EGFP expression levels ~2-fold and ~3-fold, respectively, and the transduction efficiency was enhanced by ~5-fold with the S662V mutant vectors (FIG. 24). Since inhibition of these kinases has previously been reported to prevent maturation of dendritic cells (Beisleve et al., 2005; Nakahara et al., 2006; Nakahara et al., 2004; Harley, 2008), the capability of S662V mutant to induce phenotypic changes in DCs also was evaluated. moDC were infected with an increasingly higher MOI up to 50,000 vgs per cell, harvested at 48 hrs p.i., and analyzed by fluorescence-activated cell sorting (FACS) for up regulation of surface co-stimulatory molecules. Flow cytometric analyses of DC maturation markers such as CD80, CD83 and CD86 indicated that, similar to WT AAV2 vectors, the S662V mutant vectors also did not induce the maturation of moDCs (FIG. 24C). This observation supports the previously described low immunogenicity of AAV vectors. (Shin et al., 2008; Jayandharan et al., 2011)

hTERT-Specific CTL Generation by moDC Transduced with AAV2-S662V Vectors

Figure 25:
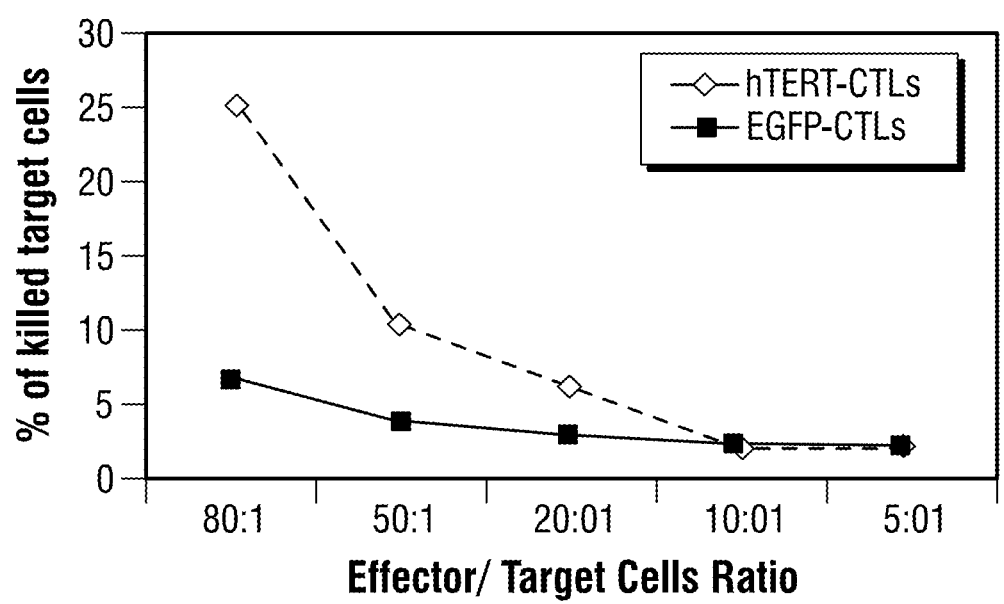
FIG. 25 shows the analysis of hTERT-specific cytotoxic T-lymphocytes (CTLs) killing activity on K562 cells. CTLs were generated after transduction of moDCs by scAAV2-S662V vectors encoding the truncated human telomerase (hTERT). scAAV2-S662V-EGFP vector-traduced moDCs were used to generate non-specific CTLs. Pre-stained with 3,3-dioctadecyloxacarbocyanine (DiOC18(3)), a green fluorescent membrane stain, $1\times10^5$ target K562 cells were co-cultured overnight with different ratios of CTLs (80:1, 50:1, 20:1, 10:1, 5:1). Membrane-permeable nucleic acid counterstain, propidium iodide, was added to label the cells with compromised plasma membranes. Percentages of killed, double stain-positive cells were analyzed by flow cytometry.

Since the serine-mutant AAV2 vector-mediated transgene expression in moDC was significantly improved compared with the WT-AAV2 vectors, the ability of S662V-loaded moDCs to stimulate the generation of cytotoxic T-lymphocytes and effect specific killing of the target cell was examined. Given that human telomerase is recognized as a unique anti-cancer target (Harley, 2008; Beatty and Vonderheide, 2008) commonly expressed in most cancer cells, a truncated human telomerase (hTERT) gene was cloned under the control of the chicken β-actin promoter and packaged the DNA into the AAV2 S662V mutant. Non-adherent peripheral blood mononuclear cells (PBMC) containing up to 25% of CD8 positive cells were stimulated once with moDC/hTERT delivered by the S662V vector. An immortalized myelogenous leukemia cell line, K562, was used for a two-color fluorescence assay of cell-mediated cytotoxicity to generate a killing curve with subsequently reduced effector to target cell ratio. Result of these experiments, shown in FIG. 25, suggest that moDC loaded with hTERT can effectively stimulate specific T cell clone proliferation and killing activity compared with moDC expressing GFP. Thus, since immunization strategies that generate rapid and potent effector responses are essential for effective immunotherapy, these results support the efficacy of AAV-based delivery methods for vaccination studies.

Discussion

Although the possibility of genetically-modified dendritic cells stimulating a specific anti-tumor cytotoxic T cell response has been proven in a number of clinical trials, a reliable method for therapeutic antigen loading, control of expression, and antigen presentation has not yet been previously developed (O'Neill and Bhardwaj, 2007; Tacken et al., 2007). Since the first attempts to transduce dendritic cells with conventional ssAAV vectors nearly a decade ago (Pannazhagan et al., 2001), significant progress has been made in increasing the transduction efficiency of these vectors. For example, the development of self-complementary AAV (scAAV) vectors has circumvented a major rate-limiting step of viral second-strand DNA synthesis, which dramatically increases transgene expression levels in different subsets of dendritic cells. (Shin et al., 2008; Aldrich et al., 2006; Wang et al., 2003) AAV vector-based antigen delivery to dendritic cells has successfully been utilized for several cancer models. (Mahadevan et al., 2007; Eisold et al., 2007; Yu et al., 2008)

The natural flexibility of AAV structural and regulatory viral components promotes rapid molecular evolution and formation of numerous serologically distinct serotypes (Gao et al., 2003; Vandenberghe et al., 2009; Wu et al., 2006). Several studies have shown that one can take advantage of such plasticity of AAV to generate new vectors with different cell and tissue tropism (Wu et al., 2000; Girod et al., 1999). Other studies revealed that substitution of a single amino acid on the viral capsid can strongly affect viral titer, interaction with cellular receptor, tissue-tropism and trafficking from endosome to the nucleolus (Zhong et al., 2008; Wu et al., 2006). Wu et al. (2006) have reported that replacement of lysine to glutamine at position 531 (K531E) on AAV6 capsid reduces gene transfer to mouse hepatocytes in vivo and affinity for heparin. The reverse mutation (E531K) on AAV1 capsid increased liver transduction and imparted heparin binding.

Data with AAV2 serotype vectors indicate that a single substitution of tyrosine to phenylalanine (Y→F) dramatically improves viral trafficking from endosome to the nucleolus by preventing capsid phosphorylation, subsequent ubiquitination and degradation via proteasome (Zhong et al., 2008). These studies have led to the generation of a number of vectors with increased transduction efficiency in different cell types and tissues. Such vectors were used to improve F.IX gene transfer to murine hepatocytes for the phenotypic correction of hemophilia B (Markusic et al., 2011). These tyrosine-mutant AAV vectors also led to high efficiency transduction of mouse retina for the potential treatment of ocular diseases (Petrs-Zilva et al., 2009). Although AAV6 serotype has shown higher transduction efficiency than AAV2 in dendritic cells (Veron et al., 2007; Taylor and Ussher, 2010), these studies have focused on AAV2 because these vectors have been studied more extensively in both basic research and clinical settings, however AAV6 vectors may be developed with a similar strategy as described herein.

It has become abundantly clear that phosphorylation of surface-exposed tyrosine-residues on AAV2 capsids negatively impacts the transduction efficiency of these vectors, which can be dramatically augmented by the use of specific inhibitors of cellular EGFR-PTK, known to phosphorylate these residues (Zhong et al., 2008). In the present example, the role of phosphorylation of serine residues in the life cycle of AAV2 vectors was more fully delineated.

Indeed, the transduction efficiency of both ssAAV and scAAV vectors could be augmented by pre-treatment of cells with specific inhibitors of JNK and p38 MAPK, implying that one or more surface-exposed serine and/threonine residues on the AAV2 capsid becomes phosphorylated inside the host cell and that this modification is detrimental to capsid trafficking to the nucleus.

Next, each of 15 surface-exposed serine residues was mutated individually, but only three of these mutations led to an increase in transduction efficiency in different cell types, which ranged from ~2-fold to ~20-fold. However, unlike the tyrosine-mutants (Markusic et al., 2011), combining multiple mutations did not augment the transduction efficiency of either the double-mutants (S458+662V and S492+662V), or the triple-mutant (S458+492+662V) AAV2 vectors in vitro. In this context, it is noteworthy that in a report by DiPrimio et al., (DiPrimio et al., 2008), in which the HI loop located between the H and I strands of the conserved core β-barrel and contains residue S662 was characterized, both site-directed mutagenesis and peptide substitutions showed that this capsid region plays a crucial role in AAV capsid assembly and viral genome packaging (FIG. 22A and FIG. 22B) (Xie et al., 2002). Although the S662 residue was not specifically targeted in those studies, the transduction efficiency of most of these mutants was either unchanged, or was reduced by up to 27-fold. The HI loop, which forms interactions between icosahedral five-fold symmetry related VPs and lies on the floor of the depression surrounding this axis, was also proposed to undergo a conformational re-arrangement that opens up the channel located at the icosahedral fivefold axis following heparin binding by AAV2 (Levy et al., 2009). Residues S458 and 492 are located adjacent to each other (contributed from symmetry related VPs) on the outer surface of the protrusions (surrounding the icosahedral three-fold axes) facing the depression at the two-fold axes. Previous mutation of residues adjacent to S458A, S492A and S492T had no effect on capsid assembly and resulted in no effect on transduction efficiency (Lochrie et al., 2006), which confirms the critical role that particular amino acids plays in packaging efficiency and biological activity of AAV. Additional structural analyses of these data revealed the following: For the three mutants with low yields, the side-chain of the residues interact with main-chain atoms from the same VP monomer, and S267V with a low titer, interacts with D269 from the same monomer. For another capsid mutant, S668V, which is located in the HI loop and shown to play a role in capsid assembly (DiPrimio et al., 2008), no obvious disruption of interaction was observed with the substitution. Interestingly, all of these residues, regardless of assembly phenotype, are at interface positions but only 458 and 492 involved in inter-VP interactions. The other residues are only involved in intra-VP interactions, if any. Thus, it is possible that the changes in the no capsid or low capsid yield mutants result in misfolding for their VPs or the abrogation of formation of multimers formation required for assembly when changed to alanine.

In the setting of tumor immunotherapy, the time of T cell activation and the potency and longevity of CD8 T cell responses are crucial factors in determining therapeutic outcome. Thus, the investors further evaluated whether increased transduction efficiency of moDC by the serine-mutant AAV2 vectors correlated with superior priming of T cells. Human telomerase was used as a specific target since it has been shown in numerous studies and clinical trials to be an attractive candidate for a broadly expressed rejection antigen for many cancer patients (Harley, 2008; Beatty and Vonderheide, 2008). These results suggest that modification of the AAV2 capsid might be beneficial in terms of producing more specific and effective vectors for gene delivery.

It is also important that one of the main obstacles, the induction of immuno-competition in cellular immune responses against vector-derived and transgene-derived epitopes, can probably be overcome not only by the replication-deficiency and lack of viral proteins expressed by recombinant AAV2, but also the fact that less capsid of modified viral particles will be degraded by host proteosomes and thus, provide less material for presentation.

Example 5—Optimization of the Capsid of rAAV2 Vectors

Adeno-associated virus (AAV) vectors are currently in use in a number of Phase I/II clinical trials as delivery vehicles to target a variety of tissues to achieve sustained expression of therapeutic genes (Daya and Berns 2008; Mueller and Flotte 2008; Srivastava 2008; Asokan et al., 2012; Flotte et al., 2012). However, large vector doses are needed to achieve therapeutic benefits. The requirements for sufficient amounts of the vector pose a production challenge, as well as the risk of initiating the host immune response to the vector (High and Aubourg, 2011; Mendell et al., 2012, Mingozzi and High, 2011). More specifically, recombinant vectors based on AAV2 serotype were initially used in a clinical trial for the potential gene therapy of hemophilia B, but in this trial, therapeutic level of expression of human Factor IX (hF.IX) was not achieved at lower vector doses, and at higher vector doses, the therapeutic level of expression of hF.IX was short-lived due to a cytotoxic T cell (CTL) response against AAV2 capsids (Manno et al., 2006; Mingozzi and High, 2007; Mingozzi et al., 2007).

In a more recent trial with recombinant vectors based on AAV8 serotype, therapeutic levels of expression of hF.IX were been achieved, but an immune response to AAV8 capsid proteins was observed (Aslanidi et al., 2012). Thus, it is critical to develop novel AAV vectors with high transduction efficiency that can be used at lower doses. Cellular epidermal growth factor receptor protein tyrosine kinase (EGFR-PTK) negatively affects transgene expression from recombinant AAV2 vectors primarily due to phosphorylation of AAV2 capsids at tyrosine residues, and tyrosine-phosphorylated capsids are subsequently degraded by the host proteasome machinery (Zhong et al., 2008; Markusic et al., 2010). Selective inhibitors of JNK and p38 MAPK serine/threonine kinases also improved the transduction efficiency of AAV2 vectors, suggesting that phosphorylation of certain surface-exposed serine and/or threonine residues might also decrease the transduction efficiency of these vectors. These studies led to the development of tyrosine- and serine-mutant AAV2 vectors, which has been shown to transduce various cell types with significantly higher efficiency than the WT vectors. (Aslanidi et al., 2012; Zhong et al., 2008; Markusic et al., 2010; Petrs-Silva et al., 2009) In addition to the tyrosine and serine residues, the elimination of surface-exposed threonine residues by site-directed mutagenesis also led to an increase in the transduction efficiency at lower vector doses. In this example, each of the 17 surface-exposed threonine residues was substituted with valine (V) residues by site-directed mutagenesis, and four of these mutants, T455V, T491V, T550V, T659V, were shown to increase the transduction efficiency between ~2-4-fold in human HEK293 cells. Because the tyrosine triple-mutant (Y730F+500+444F) vector transduced murine hepatocytes most efficiently than WT (Aslanidi et al., 2012; Zhong et al., 2008; Markusic et al., 2010; Petrs-Silva et al., 2009), these mutations were subsequently combined with the best-performing single serine-mutant (S662V) and single threonine-mutant (T491V) to generate the following vectors: two quadruple (Y444+500+730F+S662V; Y730+500+44F+T491V) and one quintuple (Y444+500+730F+S662V+T491V). The quadruple-mutant (Y444+500+730F+T491V) vector efficiently transduced a murine hepatocyte cell line in vitro as well as primary murine hepatocytes in vivo at reduced doses, which implicated the use of these vectors in human gene therapy in general, and hemophilia in particular.

Materials and Methods

Cells

Human embryonic kidney cell line, HEK293, and murine hepatocyte cell line, H2.35, cells were obtained from the American Type Culture Collection (Manassas, Va., USA), and maintained as monolayer cultures in DMEM (Invitrogen) supplemented with 10% fetal bovine serum (FBS; Sigma) and antibiotics (Lonza).

Production of Recombinant Vectors

Recombinant AAV2 vectors containing either EGFP (scAAV2-GFP) or firefly luciferase gene (Fluc) (ssAAV2-Fluc) driven by the chicken β-actin promoter (CBA) were generated as described previously (Aslanidi et al., 2012; Aslanidi et al., 2009; Zolotukhin et al., 2002; Kohlbrenner et al., 2005). Briefly, HEK293 cells were transfected using polyethylenimine (PEI, linear, MW 25,000, Polysciences, Inc.). Seventy-two hrs' post-transfection, cells were harvested and vectors were purified by iodixanol (Sigma) gradient centrifugation and ion exchange column chromatography (HiTrap Sp Hp 5 mL, GE Healthcare). Virus was then concentrated and buffer exchanged into Lactated Ringer's solution in three cycles using centrifugal spin concentrators (Apollo, 150-kDa cut-off, 20-mL capacity, CLP). To determine genome titers, ten μl of purified virus were incubated with DNase I (Invitrogen) at 37° C. for 2 hr, then with Proteinase K (Invitrogen) at 55° C. for an additional 2 hr. The reaction mixture was purified by phenol/chloroform, followed by chloroform extraction. Packaged DNA was precipitated O/N with ethanol in the presence of 20 μg glycogen (Invitrogen). DNase I-resistant AAV2 particle titers were determined by qPCR with the following primer-pairs specific for the CBA promoter:

```
                                      (SEQ ID NO: 20)
Forward: 5'-TCCCATAGTAACGCCAATAGG-3', (SEQ ID NO: 21)
Reverse: 5'-CTTGGCATATGATACACTTGATG-3',
``` and SYBR GreenER PCR Master Mix (Invitrogen) (Aslanidi et al., 2012; Aslanidi et al., 2009).

Site-Directed Mutagenesis

A two-stage PCR was performed with plasmid pACG2 as described previously (Aslanidi et al., 2012; Wang and Malcolm, 1999) using Turbo Pfu Polymerase (Stratagene). Briefly, in stage one, two PCR extension reactions were performed in separate tubes for the forward and reverse PCR primers for 3 cycles. In stage two, the two reactions were mixed and a PCR reaction was performed for an additional 15 cycles, followed by DpnI digestion for 1 hr. Primers were designed to introduce changes from threonine (ACA) to valine (GTA) for each of the residues mutated.

Recombinant AAV Vector Transduction Assays In Vitro

Human HEK293 were transduced with $1 \times 10^3$ vgs/cell, and murine hepatocytes H2.35 cells were transduced with $2 \times 10^3$ vgs/cell with WT and mutant scAAV2-GFP vectors, respectively, and incubated for 48 hr. Transgene expression was assessed as the total area of green fluorescence (pixel2) per visual field (mean±SD) as described previously (Aslanidi et al., 2012; Zhong et al., 2008; Markusic et al., 2010). Analysis of variance was used to compare test results and the control, which were determined to be statistically significant.

Analysis of Vector Genome Distribution in Cytoplasm and Nuclear Fractions

Approximately $1 \times 10^6$ H2.35 cells were infected by either WT or mutant scAAV2-GFP vectors with MOI $1 \times 10^4$ vgs/cell. Cells were collected at various time points by trypsin treatment to remove any adsorbed and un-adsorbed viral particles and then washed extensively with PBS. Nuclear and cytoplasmic fractions were separated with Nuclear and Cytoplasmic Extraction Reagents kit (Thermo Scientific) according to manufacturer instruction. Viral genome was extracted and detected by qPCR analysis with the CBA specific primers described above. The difference in amount of viral genome between cytoplasmic and nuclear fractions was determined by the following rule: $C_T$ values for each sample from cells treated with virus were normalized to corresponding $C_T$ from mock treated cells ($\Delta C_T$). For each pairwise set of samples, fold change in packaged genome presence was calculated as fold change=$2^{-(\Delta CT\text{-}cytoplasm - \Delta CT\text{-}nucleus)}$. Data from three independent experiments were presented as a percentage of the total amount of packaged genome in the nuclear and cytoplasmic fractions.

In Vivo Bioluminescence Imaging

All animal experiments were performed per institutional policies, and all procedures were done in accordance with the principles of the National Research Council's Guide for the Care and Use of Laboratory Animals. All efforts were made to minimize suffering. Ten-week-old C57BL/6 male mice (Jackson Laboratory, Bar Harbor, Me.) were injected intravenously with $1 \times 10^{10}$ vgs/animal of WT and mutant ssAAV2-Fluc vectors (n=3). Luciferase activity was analyzed two weeks post injection using a Xenogen IVIS Lumina System (Caliper Life Sciences). Briefly, mice were anesthetized with 2% isofluorane and injected intraperitoneally with luciferin substrate (Beetle luciferin, Caliper Life Sciences) at a dose of 150 µg/g of body weight. Mice were placed in a light-tight chamber and images were collected at 5 min after the substrate injection. Images were analyzed by the Living Image 3.2 software (Caliper Life Sciences) to determine relative signal intensity.

Visualization of the Position of the Mutant Residues on the AAV2 Capsid

The atomic coordinates for the AAV2 VP3 crystal structure (residues 217 to 735, VP1 numbering) (Protein Data Bank (PDB) accession no. 11p3; [Xie et al., 2002]) was downloaded and used to generate a complete capsid model using the Oligomer generator application in VIPERdb (Carrillo-Trip et al., 2009). This generates 60 VP3 copies for creating the T=1 icosahedral capsid via matrix multiplication. The structure was viewed with the program COOT (Xie et al., 2002) and figures were generated using either of the computer programs, PyMOL (Schrodinger, LLC) and RIVEM (Xiao and Rossman, 2007).

Statistical Analysis

Results are presented as mean±S.D. Differences between groups were identified using a grouped-unpaired two-tailed distribution of Student's t-test. P-values <0.05 were considered statistically significant.

Results

Site-Directed Mutagenesis of Surface-Exposed Threonine Residues on AAV2 Capsid

Figure 26B:
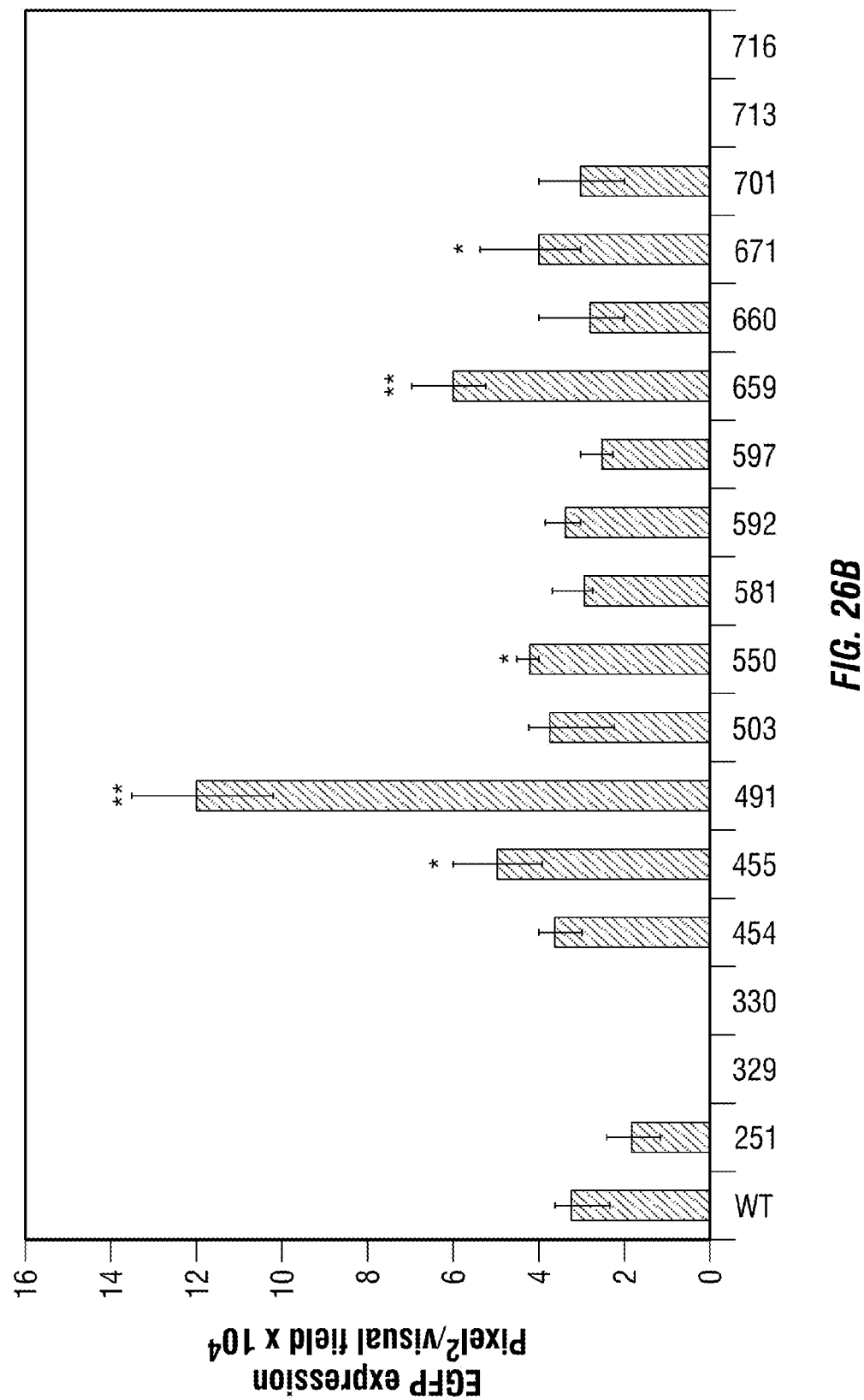

The AAV2 capsid contains 45 threonine (T) residues in the capsid viral protein 3 (VP3) common region of the three capsid VPs, VP1, VP2, and VP3. Seventeen of these (251, 329, 330, 454, 455, 503, 550, 592, 581, 597, 491, 671, 659, 660, 701, 713, 716) are surface-exposed. (Xie et al., 2002) Each of the 17 T residues was substituted with valine (V) by site-directed mutagenesis as described previously (Aslanidi et al., 2012; Zhong et al., 2008). Most mutants could be generated at titers similar to the WT AAV2 vectors, with the exception of T329V and T330V that were produced at ~10-fold lower titers, and T713V and T716V, which produced no detectable levels of DNase I-resistant vector particles. Each of the T-V mutant vectors was evaluated for transduction efficiency in HEK293 cells. These results, shown in FIG. 26A and FIG. 26B, indicate that of the 17 mutants, the T491V mutant transduced HEK293 cells ~4-fold more efficiently than its WT counterpart did. The transduction efficiency of the T455V, T550V, T659V mutant vectors were increased by ~2-fold. These data indicated that phosphorylation of specific tyrosine, serine, and threonine residues on AAV2 capsid by cellular kinases is a critical determinant of the transduction efficiency of these vectors.

Figure 27A:
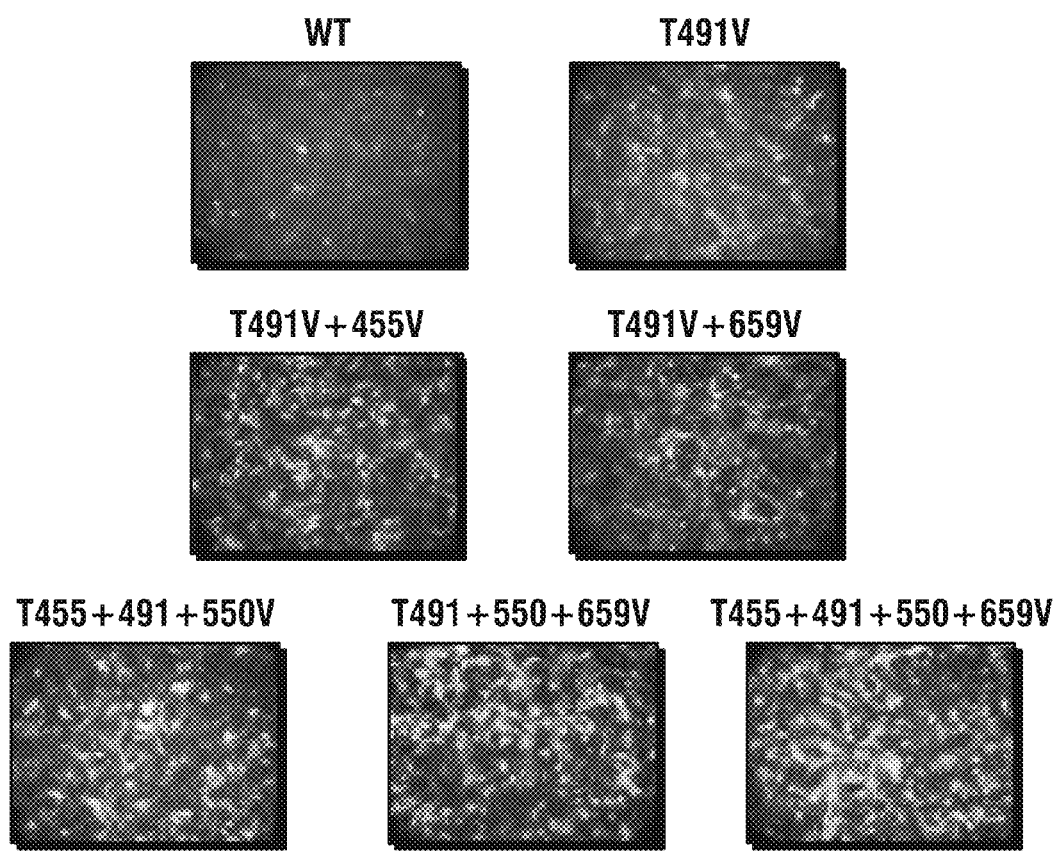
FIG. 27A and FIG. 27B show the analysis of EGFP expression in HEK293 cells infected with multiple site-directed AAV2 capsid mutants. Several most efficient threonine mutations were combined on single AAV2 capsid to produce double- and triple-mutant and efficiency of each vector was evaluated.
Figure 27B:
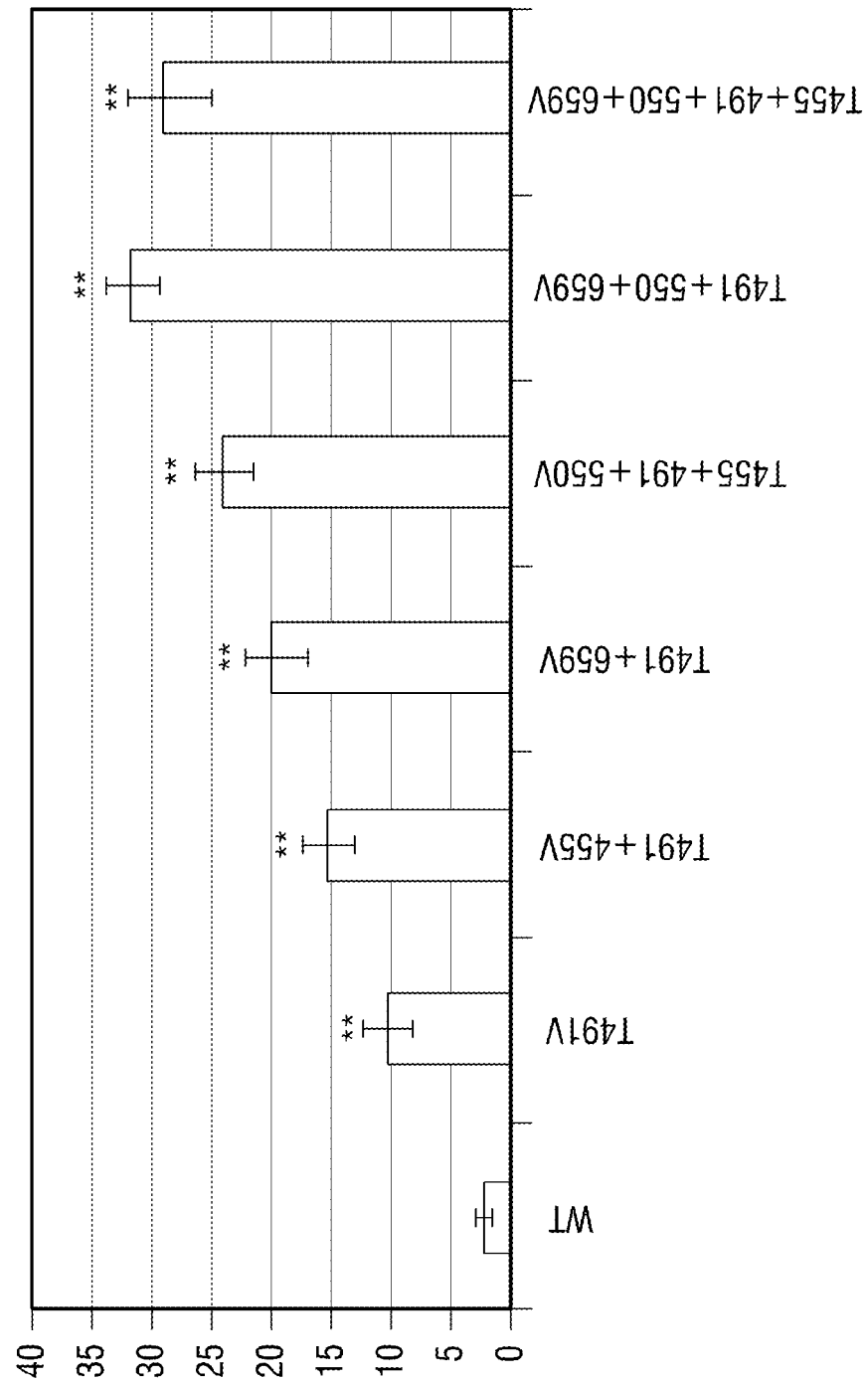

Multiple Mutations of Surface-Exposed Threw/the Residues Further Improve Transduction Efficiency of AAV2 Vectors To evaluate whether the transduction efficiency of the threonine-mutant AAV2 vectors could be enhanced further, the following multiple-mutant vectors were generated: three double-mutants (T455+491V; T550+491V; T659+491V), two triple-mutants (T455+491+550V; T491+550+659V), and one quadruple-mutant (T455+491+550+659V). Each of the multiple-mutant vectors packaged genome titers similar to the WT AAV2 vectors. In side-by-side comparisons, each of the multiple-mutant vectors was shown to transduce HEK293 more efficiently than the WT and the single-threonine mutant AAV2 vectors (FIG. 27A and FIG. 27B). The best performing vector was identified to be the triple-mutant (T491+550+659V), with the transduction efficiency ~10-fold higher than the WT vector, and ~3-fold higher than the best single-mutant (T491V) vector. These data confirmed that combining several threonine-mutations on a single viral capsid led to a synergetic effect in augmenting the transduction efficiency.

Optimized Threonine-Mutant AAV2 Vectors Efficiently Transduce Murine Hepatocytes in Vitro The tyrosine triple-mutant (Y444+550+730F) vector described in previous examples has been shown to be efficient in transducing murine hepatocytes in a comparison of vectors containing up to 7 surface tyrosine to phenylalanine changes (Markusic et al. 2010; Jayandharan et al., 2011). Thus, it was of interest to evaluate whether combining the best performing single-serine (S662V) and single-threonine (T491V) mutations with the triple-tyrosine mutant could further increase the transduction efficiency of these vectors to produce even further improved expression vectors in accordance with the methods described herein.

Figure 28B:
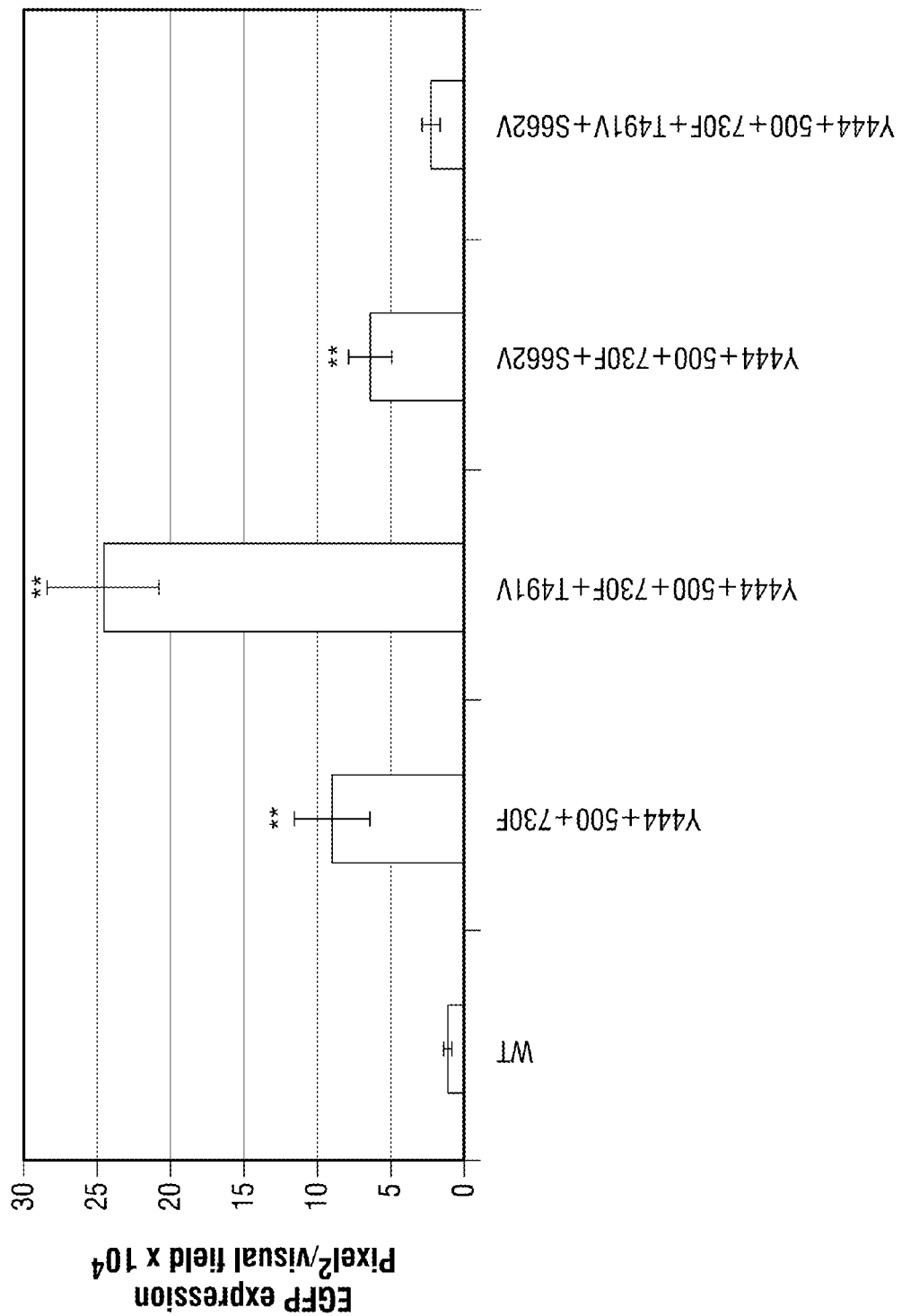

To that end, several multiple-mutants were generated as follows: two quadruple (Y444+500+730F+T491V; Y444+500+730F+S662V), and one quintuple (Y444+500+730F+T491V+S662V) mutant vectors. Comparison of the transduction efficiency of these mutants with the WT and the tyrosine triple-mutant AAV2 vectors in H2.35 cells showed that the expression level from the Y444+500+730F+T491V mutant was ~2-3-fold higher than for the tyrosine triple-mutant AAV2 vector, and ~24-fold higher than the WT AAV2 vector (FIG. 28A and FIG. 28B). Interestingly, combining the S662V mutation with the tyrosine triple-mutant vector, or with the tyrosine-threonine quadruple-mutant vector, negatively affected their transduction efficiency. Addition of several other threonine mutations, such as T550V and T659V, also did not augment the transduction efficiency of the Y444+500+730F+T491V quadruple-mutant AAV2 vector. Additional studies are warranted to gain a better understanding of the complex interactions among these surface-exposed Y, S, and T residues as well as their phosphorylation status.

Figure 29A:
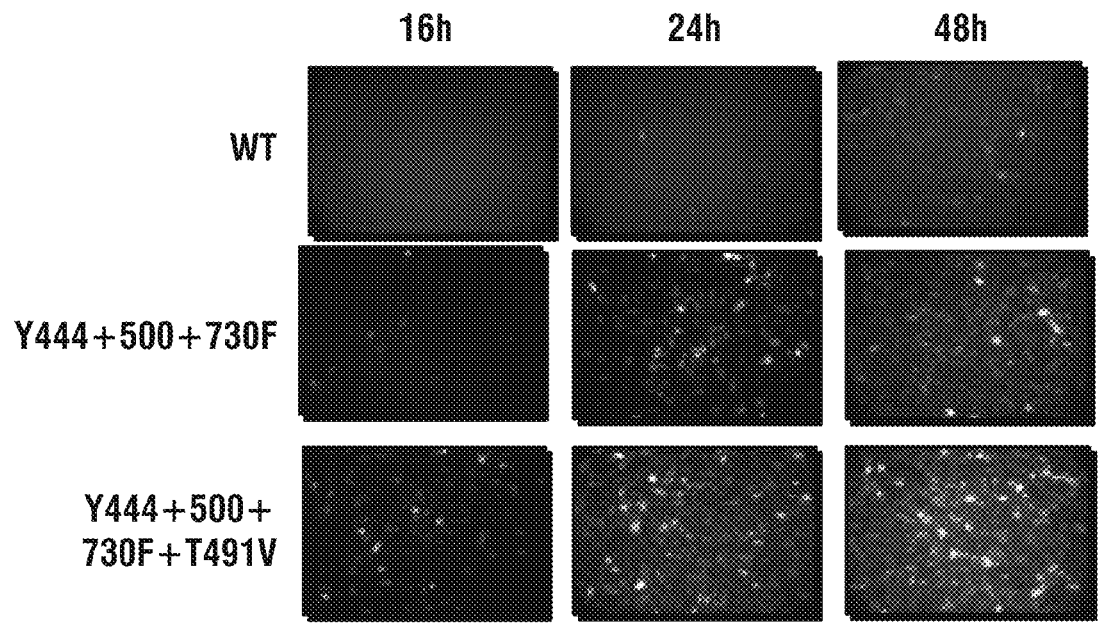
FIG. 29A and FIG. 29B illustrate the kinetics of EGFP expression in H2.35 cell mediated by capsid optimized AAV vectors.
Figure 29B:
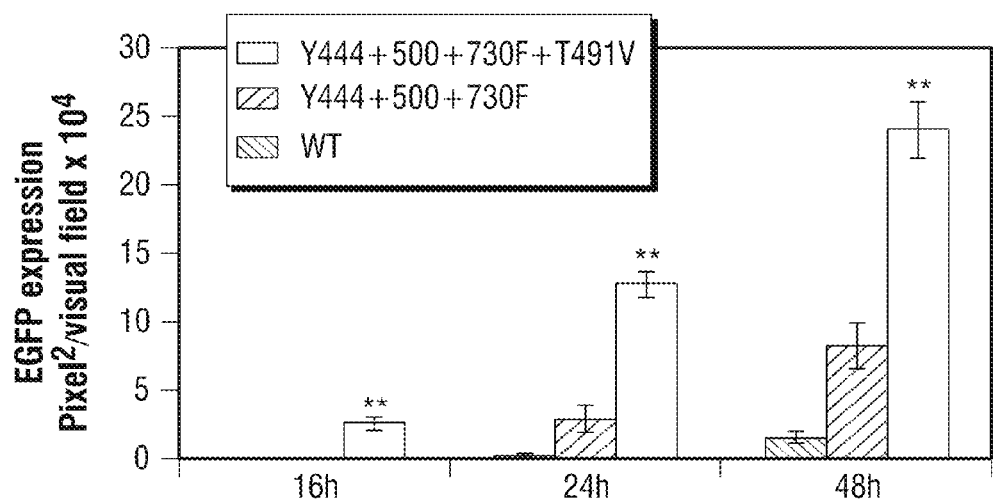
Figure 30A:
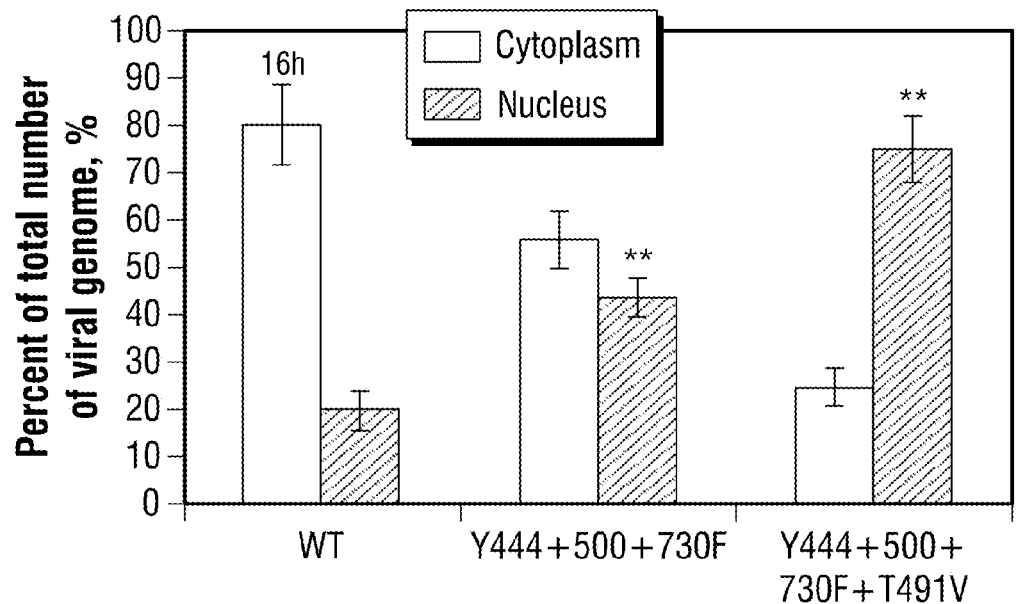
FIG. 30A and FIG. 30B show the analysis of intracellular trafficking of AAV multiple mutant vectors to the nucleus. Nuclear and cytoplasmic fraction of H2.35 cell infected with AAV2-WT, AAV2-Y444+500+730F and AAV2-Y444+500+730F+T491V mutant were separated and qPCR analysis was performed to evaluate vector genome distribution within cells at 16 hr (FIG. 30A) and 48 hr (FIG. 30B) post infection. ** P<0.001 vs. WT in nucleus was considered as significant.
Figure 30B:
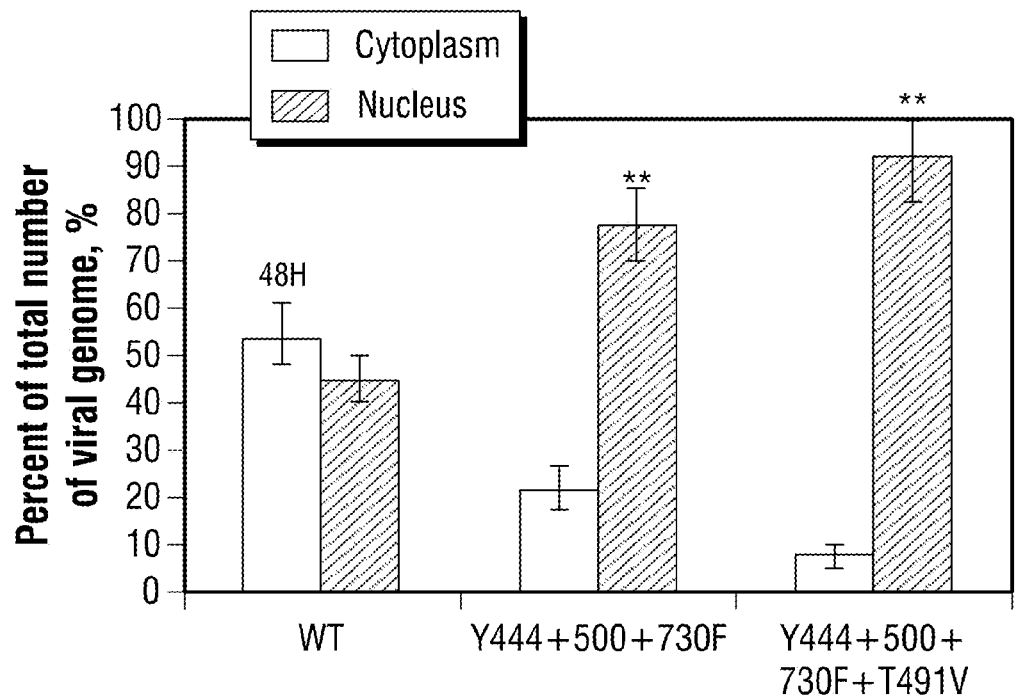

Multiple-Mutations Enhance Intracellular Trafficking and Nuclear Translocation of AAV2 Vectors Prevention of phosphorylation of surface-exposed tyrosine residues on the AAV2 capsid improved intracellular trafficking of tyrosine-mutant vectors and increases the number of the viral genomes translocated to the nucleus (Zhong et al., 2008; Zhong et al., 2008). In this example, the addition of the T491V mutant to the tyrosine triple-mutant vector was assigned for its ability to augment this transduction efficiency by further increasing nuclear transport of these vectors. To this end, the kinetics of transgene expression in H2.35 cells mediated by the Y444+500+730F+T491V quadruple-mutant were evaluated and compared to the Y444+500+730F triple-mutant and the WT AAV2 vectors. These results are shown in FIG. 29A and FIG. 29B. As can be seen, EGFP expression from the tyrosine-threonine quadruple-mutant vector was ~2-3 fold higher at each tested time point, and could be detected as early as 16 hr post-infection. These results suggested that the early-onset of transgene expression from the quadruple-mutant vectors could be due to more efficient nuclear transport of these vectors. To test this possibility experimentally, qPCR analy sis was used to quantitate the vector genomes in cytoplasmic and nuclear fractions of H2.35 cells infected with the WT and the two mutant AAV2 vectors at different time points. The vector genome ratios in the two cellular fractions are shown in FIG. 30A and FIG. 30B. Whereas ~20% of the genomes from the WT AAV2 vectors, and ~45% of the genomes from the triple-mutant vectors were detected in the nuclear fraction 16 hr post-infection, more than 70% of the vector genomes from the quadruple-mutant were detected at the same time-point. Similarly, only ~45% of the genomes from the WT AAV2 vectors were detected in the nuclear fraction 48 hr post-infection, ~80% of the genomes from the triple-mutant vectors, and ~90% of the vector genomes from the quadruple-mutant were detected in the nuclear fraction at the same time-point. Thus, these data corroborated the hypothesis that combining the threonine (T491V) mutation with the tyrosine triple-mutant (Y444+500+730F) vector leads to a modest improvement in the nuclear translocation of these vectors, which correlated with a faster onset of gene expression and the observed improvement in the transduction efficiency.

Figure 31A:
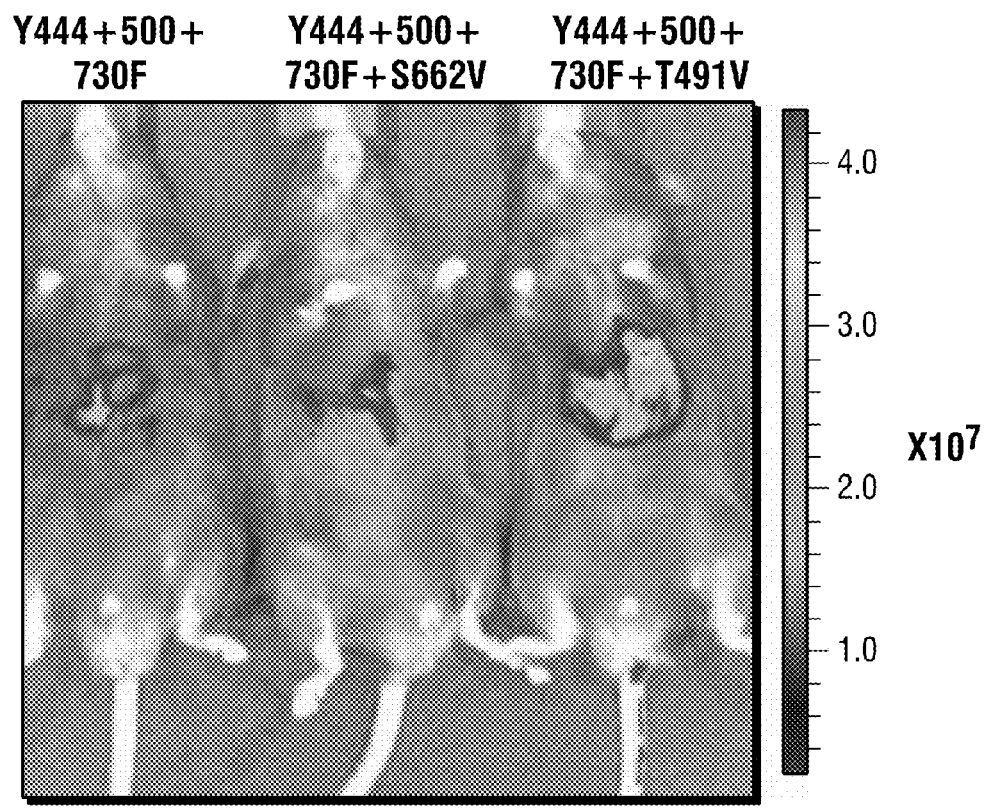
FIG. 31A and FIG. 31B show the in vivo imaging of luciferase gene expression following tail vein injection of multiple site-directed AAV2 capsid mutants. C57BL/6 mice were injected with $1\times10^{10}$ vg/animal of several most efficient mutant scAAV vectors carrying luciferase gene. Live images were taken to analyses difference in luciferase activity. The visual output represents the number of photons emitted/second/cm2 as a false color image where the maximum is red and the minimum is blue (FIG. 31A) and relative signal intensity (FIG. 31B) *P<0.005 was considered as significant.
Figure 31B:
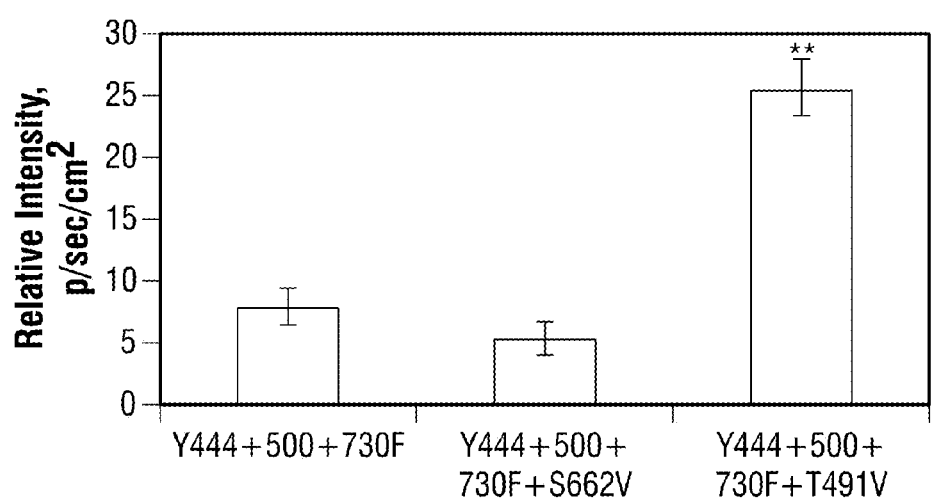

Optimized AAV2 Vectors are Highly Efficient in Transducing Murine Hepatocytes In Vivo The transduction efficiency of the optimized AAV2 vectors was evaluated in a murine model in vivo. Each of multiple-mutant vectors was packaged with a single-stranded firefly luciferase (Fluc) AAV2 genome, and $\sim 1 \times 10^{10}$ vgs of each vectors were injected intravenously into C57BL/6 mice (n=3 for each group). Levels of expression of Fluc gene, assessed two weeks post-injection by bioluminescence imaging, showed that expression from the Y444+500+730F+T491V quadruple-mutant vector was ~3-fold higher than that from the tyrosine triple-mutant vector. One representative animal from each group and the quantification of these data are presented in FIG. 31A and FIG. 31B. Consistent with the data obtained in vitro, the addition of S662V mutation had a negative effect on the transduction efficiency of both the tyrosine-triple-mutant and the tyrosine-threonine quadruple-mutant vectors. Exemplary single and multiple-mutation capsid proteins of the present invention include, but are not limited to, those illustrated in Table 5:

TABLE 5

SUMMARY OF EXEMPLARY MUTATIONS OF SURFACE-EXPOSED TYROSINE (Y), SERINE (S), AND THREONINE (T) RESIDUES ON THE AAV2 CAPSID

| Single Mutations | Double Mutations | Triple Mutations | Multiple Mutations |
|---|---|---|---|
| Y252F | Y252F + Y730F | Y444 + 500 + 730F | Y272 + 444 + 500 + 730F |
| Y272F | Y272F + Y730F | Y730F + S662V + T491V | Y272 + 444 + 500 + 730F |
| Y444F | Y444F + Y730F | S458 + 492 + 662V | Y272 + 444 + 500 + 730F |
| Y500F | Y500F + Y730F | T455 + 550 + 491V | Y272 + 444 + 500 + 700 + 730F |
| Y700F | Y700F + Y730F | T550 + 659 + 491V | Y272 + 444 + 500 + 704 + 730F |
| Y704F | Y704F + Y730F | | Y252 + 272 + 444 + 500 + 704 + 730F |
| Y730F | Y444F + T550F | | Y272 + 444 + 500 + 700 + 704 + 730F |
| S261V | S458V + S492V | | Y252 + 272 + 444 + 500 + 700 + 704 + 730F |
| S264V | S458V + S662V | | Y444 + 500 + 730F + T491V |
| S267V | S492V + S662V | | Y444 + 500 + 730F + S458V |
| S276V | T455 + T491V | | Y444 + 500 + 730F + S662V + T491V |
| S384V | T550 + T491V | | Y444 + 500 + 730F + T550 + T491V |
| S458V | T659 + T491V | | Y444 + 500 + 730F + T659 + T491V |
| S468V | T671 + T491V | | |
| S492V | Y730F + T491V | | |
| S498V | S662V + T491V | | |
| S578V | Y730F + S662V | | |
| S658V | | | |
| S662V | | | |
| S662A | | | |
| S662D | | | |
| S662F | | | |
| S662H | | | |
| S662N | | | |
| S662L | | | |
| S662I | | | |
| S668V | | | |
| S707V | | | |
| S721V | | | |
| T251V | | | |
| T329V | | | |
| T330V | | | |
| T454V | | | |
| T455V | | | |
| T491V | | | |
| T503V | | | |
| T550V | | | |
| T592V | | | |
| T597V | | | |
| T581V | | | |
| T671V | | | |
| T659V | | | |
| T660V | | | |
| T701V | | | |
| T713V | | | |
| T716V | | | |

The first letter corresponds to the amino acid in the wild-type AAV2 capsid, the number is the VP3 amino acid position that was mutated, and the last letter is the mutant amino acid.

Discussion

Recombinant AAV-based vectors are attractive delivery vehicles for gene replacement therapy as a potential treatment for a variety of genetic disorders. Although AAV vectors have been used successfully in many animal models, and recently shown efficacy in several clinical trials, a number of steps in the life cycle of AAV continue to appear to limit the effectiveness of these vectors in gene therapy. Some of these steps include intracellular trafficking, nuclear transport, uncoating, and viral second-strand DNA synthesis (Ding et al., 2005; Harbison et al., 2005; Nonnenmacher and Weber, 2012).

The simple organization and natural plasticity of AAV structural and regulatory components provide a unique opportunity to manipulate the viral capsid and the genome to develop customized recombinant vectors with distinctive features. Significant progress has been made in the past decade to improve the specificity and the transduction efficiency of recombinant AAV vectors. For example, specific mutations in the viral inverted terminal repeat (ITR) sequences have led to development of self-complementary AAV (scAAV) vectors, which overcome the rate-limiting step of viral second-strand DNA synthesis, and dramatically increase transgene expression levels in various types of the cells and tissues (McCarty et al., 2003; Wang et al., 2003). Additional studies on capsid structure analyses, combined with a wealth of information emanating from mutagenesis studies on the capsid genes, have led to the identification of specific regions which play a critical role in vector encapsidation, tissue-tropism, and intracellular trafficking of these vectors (Lochire et al., 2006; Muzyczka and Warrington, 2005; Wu et al., 2006; Gao et al., 2003; Vandenberghe et al., 2009; Wu et al., 2006).

In the previous examples, it was shown that substitution of surface-exposed specific tyrosine (Y) and serine (S) residues on AAV2 capsids significantly increased the transduction efficiency of these vectors, both in vitro and in vivo, presumably by preventing phosphorylation, subsequent ubiquitination, and proteasome-mediated degradation. Since surface-exposed specific threonine (T) residues on AAV2 capsids would likewise be expected to undergo phosphorylation, in this example each of the 17 surface-exposed T residues were systematically mutagenized, and several single-mutant vectors were identified that could increase the transduction efficiency up to 4-fold. Combinations of multiple T mutations on a single capsid identified modifications that further augmented the transduction efficiency up to ~10-fold, compared with that of the WT AAV2 vector in HEK293 cells.

Two independent groups have previously reported mutations of specific T residues on AAV2 capsids. For example, Lochrie et al., 2006, targeted the T residues at positions 330, 454, 455, 491, 503, and 550 in a tour de force effort to identify surface regions that bind antibodies, and DiPrimio et al. (2008), targeted the T residue at position 659 in an effort to identify regions critical for capsid assembly and genome packaging. In both studies, the T residues were substituted with either alanine (A), serine (S), or lysine (K) residues, or by peptide substitution. However, no increase in the transduction efficiency of any of the mutant vectors was observed. In contrast, in the example, the surface-exposed T residues were substituted with valine residues. This further corroborates the recent observation for the critical role played by specific amino acid type in modulating the biological activity of AAV vectors (Aslanidi et al., 2012; Li et al., 2012).

When the most efficient threonine-mutation (T491V) was combined with a previously reported tyrosine triple-mutation (Y444+500+730F) (Markusic et al. 2010) to generate a Y-T quadruple-mutant (Y444+500+730F+T491V) vector, the transduction efficiency of this vector was ~2-3-fold higher than the tyrosine triple-mutant vector in murine hepatocytes, both in vitro and in vivo. However, combining the most efficient S-mutation (S662V) (Aslanidi et al., 2012) with the tyrosine triple-mutation negatively affected the transduction efficiency of the Y-S quadruple mutant (Y444+500+730F+S662V) vector as well as the Y-S-T pentuple-mutant (Y444+500+730F+S662V+ T491V) vector. Although several other combinations showed greater transduction efficiency compared with the WT AAV2 vector, neither combination of similar (quadruple, pentuple or sextuple-tyrosine; and triple and quadruple-threonine mutants), nor combination of the best performing YST mutations reached the level of expression from the triple-tyrosine mutant vector. In view of the large number of combinations of mutations tested, only the mutations that significantly increased the transduction efficiency over the triple-tyrosine mutant vector were characterized in detail here.

Figure 32A:
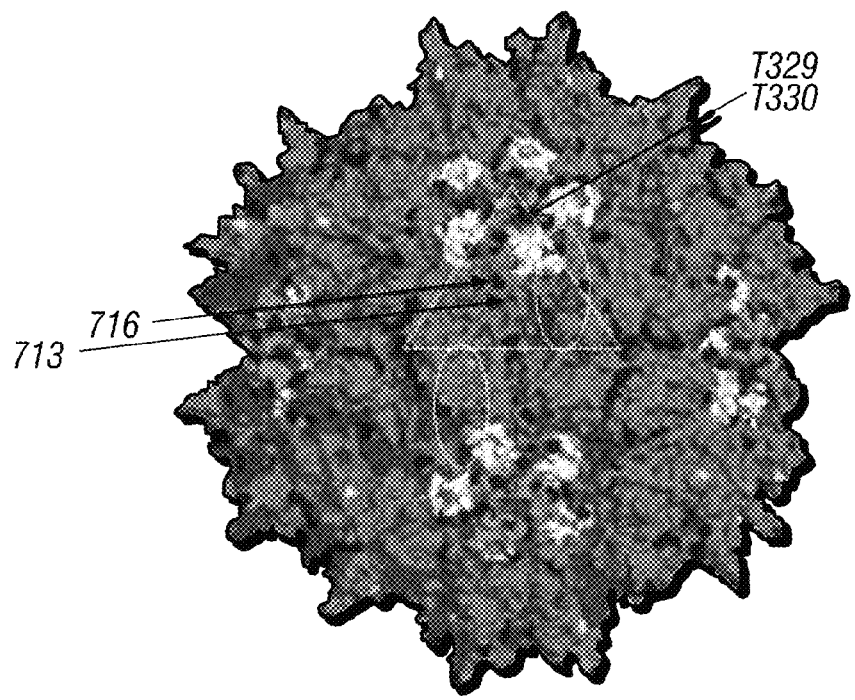
FIG. 32A and FIG. 32B illustrate the AAV2 capsid surface.
Figure 32B:
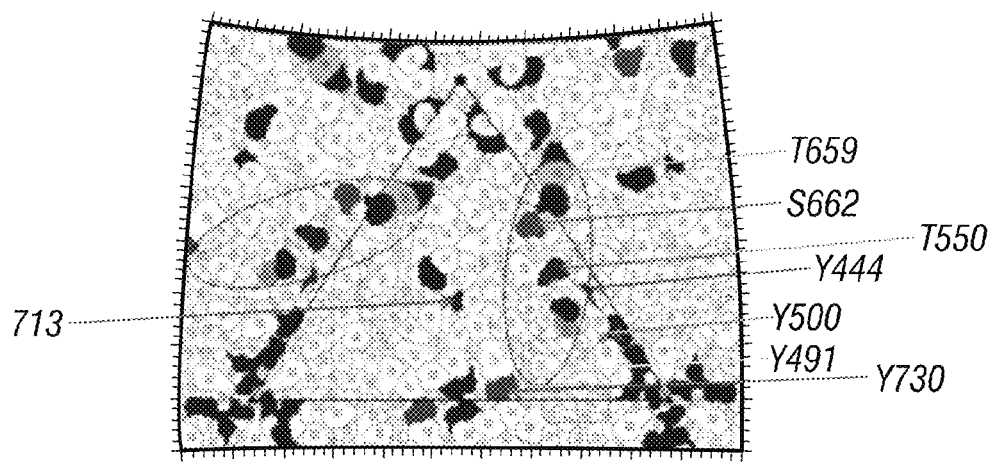

The 17 AAV2 surface-exposed threonine residues are scattered throughout the capsid. Four of the mutations (T329V, T330V, T713V, and T716V) resulted in significant defects in assembly and vector production, and they could not be further characterized. Residues 329 and 330 are located in the α-surface loop (DE loop) located between the βD and βE strands of the core β-barrel of the AAV2 VP3 structure (Xie et al., 2002). Five of these loops, from icosahedral five-fold symmetry related VP3s assembly a channel at this axis which connects the interior and exterior surfaces of the capsid (FIG. 32A). As was observed in a previous study (Bleker et al., 2006), titers for these mutants were significantly reduced consistent with a role for the channel in genome packaging. Residues 713 and 716 are located on the wall/raised capsid region between the depressions at and surrounding the icosahedral two- and five-fold axes, respectively (FIG. 32A and FIG. 32B). Their side-chains participate in polar interactions with symmetry related VP3 monomers and it is likely that mutation results in a defect in capsid assembly. A role in capsid assembly for residues located at the icosahedral two-fold axis is consistent with a recent report in which they observe that the AAV2 residues that mediated the interaction with the assembly-activating protein (AAP) were located at this capsid region (Naumer et al., 2012).

Residues T455, T491, T550, and T659, showing an increased transduction phenotype when mutated to valine or alanine, are located on the protrusions which surround the icosahedral three-fold axis (T455, T491, and T550) or on the HI loop (between βH and βI of the core β-barrel) (T659) which is lies on the depression surrounding the channel at the icosahedral five-fold axis of the AAV2 capsid. The residues on the protrusion, a prominent feature on the capsid assembled from two VP3 monomers, are located close to the top (455), side facing the two-fold depression (491), and side facing the depression surrounding the five-fold (550), respectively, of the protrusions. This AAV region contains the most variability in sequence and structure, and with the exception of residue 659, the other three threonine residues are located to define VP3 variable regions (VRs) (Govindasamy et al., 2006). Along with T659, these residues form a footprint on the capsid surface that extends over the top of the protrusion towards the depression surrounding the icosahedral five-fold axis (FIG. 32A and FIG. 32B). Their surface exposure is consistent with the potential to interact with host molecules, which could include kinases. Interestingly, this footprint is flanked by the residues in the triple-tyrosine mutant, Y444, Y500, and Y730, with T491 located proximal to tyrosine residue Y730 in a depiction of the capsid surface amino acids (FIG. 32B). This residue, which sits in the depression at the icosahedral axis of the capsid, showed the highest increase in transduction compared to WT AAV2 when of the seven surface-exposed tyrosines where mutated to phenylanine residues (Zhong et al. 2008). Significantly, the two-fold capsid region is observed to undergo pH-mediated structural transitions when the homologous AAV8 was examined at the conditions encountered during trafficking in the endocytic pathway (Nam et al., 2011). It is possible that the mutations of the AAV2 improve transduction efficiency through altered receptor binding mechanisms. Residues mediating AAV2 and AAV6 interaction with heparan sulfate receptors, R585 and R588, and K531 (structurally equivalent to E530 in AAV2), respectively, are close to this foot (FIG. 26B), and residues 491 and 500, in VRV, are located in one of two large regions on the surface of the AAV2 capsid that has been implicated in binding to the LamR receptor in AAV8 (Akache et al., 2006). Amino acids in VRV also play a role in the AAV9 capsid binding to its glycan receptor, galactose.

The decreased transduction efficiency phenotype of the mutants containing the S662V mutations is difficult to explain given the location of this residue within the footprint delineated by the residues which enhance transduction when mutated to eliminate potential phosphorylation (FIG. 32A and FIG. 32B). In addition, it has been shown that a mutation of this residue to valine improved transduction relative to WT AAV2 (Aslanidi et al., 2012). Residue S662, like T659, is located in the HI loop that extends over adjacent five-fold symmetry related VP3 monomers and likely plays a role in stabilizing the pentameric subunits. However, the serine side-chain is not engaged in any inter- or intra-subunit interactions, and while the HI loop has been reported to be a determinant of capsid assembly and genome packaging (DiPrimio et al., 2008), it tolerated single amino acid substitution (Aslanidi et al., 2012). Thus, its effect is likely due to the abrogation of a capsid interaction utilizing the footprint containing the triple-tyrosine mutant residues and T491. Significantly, the phenotypes for mutations in nearby amino acids that make up the HI loop, for example, amino acid residue 664, substituting either serine (mut45subSer14) or a FLAG epitope (mut45SubFLAG10), were non-infectious or not assembled into viral capsid (Wu et al., 2000). However, an HA insertion at the same position produced capsids that were partially defective, yet still bound heparin (Wu et al., 2000).

Whereas only ~45% of the vector genomes delivered by the WT AAV2 vectors were present in the nucleus at 48 h post infection, >90% of the vector genomes delivered by the Y-T quadruple-mutant vector were present at the same time point. This indicates improved trafficking kinetics for the mutant that would be consistent with reduced re-direction to the proteasome. The modest (~2-3-fold) increase in the transduction efficiency of these vectors compared to the tyrosine triple-mutant vectors is also consistent with the ~10% increase in nuclear vector genome delivery, i.e. ~90% compared to ~80%.

The various combinations of surface tyrosine, serine, and threonine modifications clearly showed that there is an optimal combination to achieve maximal augmentation. These studies also highlighted the requirement for specific residue types in AAV interactions during infection and for enhancing transduction. It is possible that the individual mutations, which did not show a significant increase in the transduction efficiency as single changes, can form superior vectors when combined in a single capsid.

TABLE 6

COMPARISON OF TYROSINE RESIDUES IN AAV SEROTYPES

| AAV1 | AAV2 | AAV3 | AAV4 | AAV5 | AAV6 | AAV7 | AAV8 | AAV9 | AAV10 | AAV11 | AAV12 |
|---|---|---|---|---|---|---|---|---|---|---|---|
| Y6 | Y6 | Y6 | Y5 | NA | Y6 | Y6 | Y6 | Y6 | Y6 | Y6 | Y6 |
| Y50 | Y50 | Y50 | Y49 | Y49 | Y50 | Y50 | Y50 | Y50 | Y50 | Y50 | Y50 |
| Y52 | Y52 | Y52 | Y51 | Y51 | Y52 | Y52 | Y52 | Y52 | Y52 | Y52 | Y52 |
| Y79 | Y79 | Y79 | Y78 | Y78 | Y79 | Y79 | Y79 | Y79 | Y79 | Y79 | Y79 |
| Y90 | Y90 | Y90 | Y89 | Y89 | Y90 | Y90 | Y90 | Y90 | Y90 | Y90 | Y90 |
| Y93 | Y93 | Y93 | Y92 | Y92 | Y93 | Y93 | Y93 | Y93 | Y93 | Y93 | Y93 |
| Y252* | Y252* | Y252* | Y246* | Y242* | Y252* | Y253* | Y253* | Y252* | Y253* | Y246* | Y255* |
| Y257 | Y257 | Y257 | Y251 | Y247 | Y257 | Y258 | Y258 | Y257 | Y258 | Y251 | Y260 |
| Y273* | Y272* | Y272* | Y263* | Y263* | Y273* | Y274* | Y275* | Y274* | Y275* | Y263* | Y272* |
| Y276 | Y275 | Y275 | NA | Y266 | Y276 | Y277 | Y278 | Y277 | Y278 | NA | NA |
| Y282 | Y281 | Y281 | Y272 | Y272 | Y282 | Y283 | Y284 | Y283 | Y284 | Y272 | Y281 |
| NA | NA | NA | NA | Y294 | NA | NA | NA | NA | NA | NA | NA |
| Y349 | Y348 | Y348 | Y339 | Y339 | Y349 | Y350 | Y351 | Y350 | Y351 | Y339 | Y348 |
| Y353 | Y352 | Y352 | Y343 | Y343 | Y353 | Y354 | Y355 | Y354 | Y355 | Y343 | Y352 |
| Y376 | Y375 | Y375 | Y366 | Y366 | Y376 | Y377 | Y378 | Y377 | Y378 | Y366 | Y375 |
| Y378 | Y377 | Y377 | Y368 | Y368 | Y378 | Y379 | Y380 | Y379 | Y380 | Y368 | Y377 |
| Y394 | Y393 | Y393 | Y387 | NA | Y394 | Y395 | Y396 | Y395 | Y396 | Y386 | Y395 |
| Y398 | Y397 | Y397 | Y391 | Y390 | Y398 | Y399 | Y400 | Y399 | Y400 | Y390 | Y399 |
| Y414 | Y413 | Y413 | Y407 | Y406 | Y414 | Y415 | Y416 | Y415 | Y416 | Y406 | Y415 |
| Y425 | Y424 | Y424 | Y418 | NA | Y425 | Y426 | Y427 | Y426 | Y427 | Y417 | Y426 |
| Y442* | Y441* | Y441* | Y435* | Y434* | Y442* | Y443* | Y444* | Y443* | Y444* | Y434* | Y443* |
| NA | NA | NA | NA | Y436 | NA | NA | NA | NA | NA | NA | NA |
| Y444* | Y443* | Y443* | NA | NA | Y444* | Y445* | Y446* | Y445* | Y446* | Y446* | NA |
| Y445* | Y444* | Y444* | NA | NA | Y445* | Y446* | Y447* | Y446* | Y447* | NA | NA |
| NA | NA | NA | NA | NA | NA | NA | NA | NA | NA | NA | Y465 |
| NA | NA | NA | NA | NA | NA | Y466 | NA | NA | NA | NA | NA |
| NA | NA | NA | NA | Y457 | NA | NA | NA | NA | NA | NA | NA |
| NA | NA | NA | NA | NA | NA | NA | NA | NA | NA | NA | Y475 |
| NA | NA | NA | NA | NA | NA | NA | NA | NA | NA | Y467 | Y476 |

TABLE 6-continued

COMPARISON OF TYROSINE RESIDUES IN AAV SEROTYPES

| AAV1 | AAV2 | AAV3 | AAV4 | AAV5 | AAV6 | AAV7 | AAV8 | AAV9 | AAV10 | AAV11 | AAV12 |
|---|---|---|---|---|---|---|---|---|---|---|---|
| NA | NA | NA | NA | Y461 | NA | NA | NA | NA | NA | NA | NA |
| NA | NA | NA | NA | NA | NA | NA | NA | Y478 | NA | NA | NA |
| Y484 | Y483 | Y484 | NA | NA | Y484 | NA | Y486 | Y484 | Y486 | NA | NA |
| NA | NA | NA | Y491* | NA | NA | NA | NA | NA | NA | Y490* | Y499* |
| NA | Y500* | NA | NA | NA | NA | NA | NA | NA | NA | NA | NA |
| NA | NA | NA | Y504* | NA | NA | NA | NA | NA | NA | Y503* | Y512* |
| Y509 | Y508 | Y509 | NA | NA | Y509 | Y511 | Y511 | NA | Y511 | Y507 | NA |
| NA | NA | NA | NA | Y502 | NA | NA | NA | NA | NA | NA | NA |
| NA | NA | NA | NA | Y521* | NA | NA | NA | NA | NA | NA | NA |
| NA | NA | NA | NA | Y542* | NA | NA | Y557* | NA | Y557* | NA | NA |
| NA | NA | NA | NA | Y563* | NA | NA | NA | NA | NA | NA | NA |
| NA | Y576 | Y577 | NA | NA | NA | Y578 | Y579 | Y577 | Y579 | NA | NA |
| NA | NA | NA | NA | Y585* | NA | NA | NA | NA | NA | NA | NA |
| Y613* | Y612* | Y613* | Y611* | Y602* | Y613* | Y614* | Y615* | Y613* | Y615* | Y610* | Y619* |
| NA | NA | NA | Y612 | NA | NA | NA | NA | NA | NA | Y611 | Y620 |
| Y674* | Y673* | Y674* | Y672* | Y662* | Y674* | Y675* | Y676* | Y674* | Y676* | Y671* | Y680* |
| Y701* | Y700-S | Y701* | NA | Y689* | Y701* | Y702* | Y703* | Y701* | Y703* | NA | NA |
| Y705* | Y704* | Y705* | Y703* | Y693* | Y705* | NA | Y707* | Y705* | Y707* | Y702* | Y711* |
| NA | NA | NA | NA | NA | NA | NA | Y708 | Y706 | Y708 | NA | NA |
| Y721 | Y720 | Y721 | Y719 | Y709 | Y721 | Y722 | Y723 | Y721 | Y723 | Y717 | Y727 |
| Y731* | Y730* | Y731* | Y729* | Y719* | Y731* | Y732* | Y733* | Y731* | Y733* | Y728* | NA |

(Surface exposed residues are shown with an "*" following their amino acid position)

TABLE 7

COMPARISON OF LYSINE RESIDUES IN AAV SEROTYPES

| AAV1 | AAV2 | AAV3 | AAV4 | AAV5 | AAV6 | AAV7 | AAV8 | AAV9 | AAV10 | AAV11 | AAV12 |
|---|---|---|---|---|---|---|---|---|---|---|---|
| NA | K24 | NA | NA | NA | NA | NA | NA | NA | NA | NA | NA |
| K26 | K26 | K26 | NA | NA | K26 | K26 | K26 | K26 | K26 | K26 | K26 |
| K31 | NA | NA | K30 | K30 | K31 | K31 | K31 | NA | K31 | K31 | NA |
| K33 | K33 | K33 | K32 | K32 | K33 | K33 | K33 | K33 | K33 | K33 | K33 |
| K38 | NA | NA | NA | NA | K38 | K38 | K38 | NA | K38 | K38 | NA |
| NA | K39 | NA | NA | NA | NA | NA | NA | NA | NA | NA | NA |
| K51 | K51 | K51 | K50 | NA | K51 | K51 | K51 | K51 | K51 | K51 | K51 |
| K61 | K61 | K61 | K60 | NA | K61 | K61 | K61 | K61 | K61 | K61 | K61 |
| K77 | K77 | K77 | K76 | NA | K77 | K77 | K77 | K77 | K77 | K77 | K77 |
| NA | NA | NA | NA | NA | NA | NA | NA | NA | NA | NA | K81 |
| K84 | NA | K84 | K83 | NA | K84 | K84 | NA | K84 | K84 | K84 | NA |
| NA | K92 | K92 | K91 | K91 | NA | NA | NA | K92 | NA | NA | K92 |
| NA | NA | NA | NA | K102 | NA | NA | NA | NA | NA | NA | NA |
| NA | K105 | NA | NA | NA | NA | NA | NA | K105 | NA | NA | NA |
| NA | NA | NA | NA | K115 | NA | NA | NA | NA | NA | NA | NA |
| K122 | K122 | K122 | K121 | K121 | K122 | K122 | K122 | K122 | K122 | K122 | K122 |
| K123 | K123 | K123 | K122 | K122 | K123 | K123 | K123 | K123 | K123 | K123 | K123 |
| K137 | K137 | K137 | NA | K136 | K137 | K137 | K137 | KI37 | K137 | K137 | K137 |
| K142 | K142 | K142 | K141 | NA | K142 | K142 | K142 | K142 | K142 | K142 | K142 |
| K143 | K143 | K143 | K142 | K142 | K143 | K143 | K143 | K143 | K143 | K143 | K142 |
| NA | NA | NA | NA | NA | NA | NA | NA | NA | NA | NA | K148 |
| NA | NA | NA | NA | K150 | NA | NA | NA | NA | NA | NA | NA |
| NA | NA | NA | NA | K152 | NA | NA | NA | NA | NA | NA | NA |
| NA | NA | NA | NA | K153 | NA | NA | NA | NA | NA | NA | K160 |
| K161 | K161 | K161 | K160 | NA | K161 | K162 | K162 | K161 | K162 | K160 | K164 |
| NA | NA | NA | K161 | NA | NA | K163 | K163 | NA | K163 | K161 | K165 |
| NA | NA | NA | NA | NA | NA | NA | NA | NA | NA | NA | K166 |
| NA | NA | K164 | K163 | NA | NA | NA | NA | NA | NA | K163 | NA |
| NA | NA | NA | NA | K161 | NA | NA | NA | NA | NA | NA | K168 |
| K168 | NA | NA | K167 | NA | K168 | NA | NA | K168 | K169 | NA | NA |
| K169 | K169 | K169 | K168 | NA | K169 | K170 | K170 | K169 | K170 | K168 | NA |
| NA | NA | NA | K169 | NA | NA | NA | NA | NA | NA | NA | NA |
| NA | NA | NA | NA | K2321 | NA | NA | NA | NA | NA | NA | NA |
| K258* | K258 | K258* | K252 | NA | K258* | K259* | K259* | K258* | K259* | NA | NA |
| NA | NA | NA | NA | K251* | NA | NA | NA | NA | NA | NA | NA |
| K310 I | K309 | K309 I | K300 I | NA | K310 I | K311 I | K312 I | K311 I | K312 I | K300 I | K309 I |
| NA | NA | K310 I | NA | NA | NA | K312 I | NA | NA | NA | NA | NA |
| K315 I | K314 | K314 I | K305 I | K305 I | K315 I | K316 I | K317 I | K316 I | K317 I | K305 I | K314 I |
| K322 I | K321 | K321 I | K312 I | K312 I | K322 I | K323 I | K324 I | K323 I | K324 I | K312 I | K321 I |
| NA | NA | NA | NA | NA | NA | NA | K333* | K332* | K333* | NA | NA |
| NA | NA | NA | NA | NA | NA | NA | NA | NA | NA | NA | K384 I |
| NA | NA | NA | NA | K394 I | NA | NA | NA | NA | NA | NA | NA |
| NA | NA | NA | K411 I | NA | NA | NA | NA | NA | NA | K410 I | K419 I |
| NA | NA | NA | NA | K425 I | NA | NA | NA | NA | NA | NA | NA |

TABLE 7-continued

COMPARISON OF LYSINE RESIDUES IN AAV SEROTYPES

| AAV1 | AAV2 | AAV3 | AAV4 | AAV5 | AAV6 | AAV7 | AAV8 | AAV9 | AAV10 | AAV11 | AAV12 |
|---|---|---|---|---|---|---|---|---|---|---|---|
| NA | NA | NA | NA | NA | NA | NA | NA | K449* | NA | NA | NA |
| K459 I | NA | NA | NA | NA | K459 I | NA | NA | NA | NA | NA | NA |
| NA | NA | NA | NA | NA | NA | NA | NA | K462* | NA | NA | NA |
| NA | NA | NA | K459 I | K451 I | NA | NA | NA | NA | NA | K458 I | K467 I |
| NA | NA | NA | K469 I | NA | NA | NA | NA | NA | NA | NA | NA |
| K476 I | NA | NA | K470 I | K462 I | K476 I | K478 I | K478 I | NA | K478 I | K469 I | K478 I |
| NA | NA | NA | K479 I | NA | NA | NA | NA | NA | NA | K478 I | K487 I |
| NA | NA | NA | NA | NA | NA | NA | NA | NA | NA | NA | K490 I |
| K491* | K490 | K491* | K485* | NA | K491* | K493* | NA | NA | NA | K484* | K490* |
| K493* | NA | NA | NA | NA | K493* | NA | NA | NA | NA | NA | NA |
| NA | NA | NA | K492* | NA | NA | NA | NA | NA | NA | K491* | K493* |
| NA | NA | NA | K503* | NA | NA | NA | NA | NA | NA | K502* | K511* |
| K508* | K507 | K508* | NA | NA | K508* | K510* | K510* | NA | K510* | NA | NA |
| K528* | K527 | K528* | NA | NA | K528* | K530* | K530* | K528* | K530* | NA | NA |
| NA | NA | NA | NA | NA | K531* | NA | NA | NA | NA | NA | NA |
| K533* | K532 | K533* | NA | NA | K533* | NA | NA | NA | NA | NA | NA |
| NA | NA | NA | K532* | NA | NA | NA | NA | NA | NA | NA | NA |
| K545* | K544 | K545* | NA | NA | K545* | K547* | K547* | K545* | K547* | NA | NA |
| NA | NA | NA | K544* | NA | NA | NA | NA | NA | NA | NA | NA |
| NA | K549 | NA | NA | NA | NA | NA | NA | NA | NA | NA | NA |
| NA | NA | NA | NA | NA | NA | K553* | NA | NA | NA | NA | NA |
| NA | K556 | NA | NA | NA | NA | NA | NA | K557* | NA | NA | NA |
| K567*- | NA | NA | NA | NA | K567* | NA | K569* | K567* | K569* | NA | NA |
| K621 I | K620 | K621 I | K619 I | K610 I | K621 I | K622 I | K623 I | K621 I | K623 I | K618 I | K627 I |
| K641 I | K640 | K641 I | K639 I | K630 I | K641 I | K642 I | K643 I | K641 I | K643 I | K638 I | K647 I |
| K650 I | K649 | K650 I | K648 I | K639 I | K650 I | K651 I | K652 I | K650 I | K652 I | K647 I | K656 I |
| NA | NA | NA | NA | NA | NA | NA | NA | K664 I | NA | NA | NA |
| K666* | K665 | K666* | NA | NA | K666* | K667* | K668* | K666* | K668* | NA | NA |
| NA | NA | NA | K676 I | NA | NA | NA | NA | NA | NA | NA | NA |
| K689 I | K688 | K689 I | K687 I | K677 I | K689 I | K690 I | K691 I | K689 I | K691 I | K686 I | K695 I |
| K693 I | K692 | K693 I | K691 I | K681 I | K693 I | K694 I | K695 I | K693 I | K695 I | K690 I | K699 I |
| K707* | K706 | K707* | NA | NA | K707* | K708* | K709* | K707* | K709* | NA | NA |
| NA | NA | NA | K718 I | NA | NA | NA | NA | NA | NA | K717 I | NA |

(Surface exposed residues are shown with an "*" following their amino acid position)
Residues in bold are surface-associated lysines = *
Residues that are located on the interior of the capsid = I
No homologous lysine at that position for that serotype = NA
Residues not visible in the crystal structure of AAVs are columns 1-6 in Table 6 and columns 1-32 in Table 7; however, biochemical data suggests that these amino acids are located inside the AAV capsid until some point in the virus life cycle when they are then externalized.

REFERENCES

The following references, to the extent that they provide exemplary procedural or other details supplementary to those set forth herein, are specifically incorporated herein by reference:

Abella, J V et al., "Met/hepatocyte growth factor receptor ubiquitination suppresses transformation and is required for Hrs phosphorylation," Molec. Cell. Biol., 25:9632-9645 (2005).

Akache, B et al., "The 37/67-kilodalton laminin receptor is a receptor for adeno-associated virus serotypes 8, 2, 3, and 9," J. Virol., 80:9831-9836 (2006).

Aldrich, W A et al., "Enhanced transduction of mouse bone marrow-derived dendritic cells by repetitive infection with self-complementary adeno-associated virus 6 combined with immunostimulatory ligands," Gene Ther., 13(1):29-39 (2006).

Andreakos, E et al., "Activation of NF-κB by the intracellular expression of NF-κB-inducing kinase acts as a powerful vaccine adjuvant," Proc. Natl. Acad. Sci. USA, 103(39):14459-14464 (2006).

Aslanidi, G et al., "An inducible system for highly efficient production of recombinant adeno-associated virus (rAAV) vectors in insect Sf9 cells," Proc. Natl. Acad. Sci. USA, 106(13):5059-5064 (2009).

Aslanidi, G et al., "Ectopic expression of wnt10b decreases adiposity and improves glucose homeostasis in obese rats", Am. J. Physiol. Endocrinol. Metab., 293(3):E726-E36 (2007).

Aslanidi, G V et al., "High-efficiency transduction of human monocyte-derived dendritic cells by capsid-modified recombinant AAV2 Vectors", Vaccine, 30:3908-3917 (2012).

Asokan, A et al., "The AAV vector toolkit: poised at the clinical crossroads", Mol. Ther., 20:699-708 (2012).

Bainbridge, J W et al., "Effect of gene therapy on visual function in Leber's congenital amaurosis," N. Engl. J. Med., 358(21):2231-2239 (2008).

Banchereau, J and Steinman, R M, "Dendritic Cells and the Control of Immunity", Nature, 392(6673):245-252 (1998).

Beatty, G L and Vonderheide, R H, "Telomerase as a universal tumor antigen for cancer vaccines", Exp. Rev. Vaccines, 7(7):881-887 (2008).

Bleker, S et al., "Impact of capsid conformation and Rep-capsid interactions on adeno-associated virus type 2 genome packaging", J. Virol., 80:810-820 (2006).

Boisleve, F et al., "Implication of the MAPK pathways in the maturation of human dendritic cells induced by nickel and TNF-α," Toxicology, 206(2):233-244 (2005).

Boutin, S et al., "Prevalence of serum IgG and neutralizing factors against adeno-associated virus (AAV) types 1, 2, 5, 6, 8, and 9 in the healthy population: implications for gene therapy using AAV vectors", *Hum. Gene Ther.,* 21:704-712 (2010).

Brantly, M L et al., "Sustained transgene expression despite T lymphocyte responses in a clinical trial of rAAV1-AAT gene therapy," *Proc. Natl. Acad. Sci. USA,* 106(38): 16363-16368 (2009).

Brown, B D and Lillicrap, D "Dangerous liaisons: the role of 'danger' signals in the immune response to gene therapy," *Blood,* 100(4):1133-1140 (2002).

Cao, O et al., "Induction and role of regulatory CD4+CD25+ T cells in tolerance to the transgene product following hepatic in vivo gene transfer," *Blood,* 110(4):1132-1140 (2007).

Carrillo-Tripp, M et al., "VIPERdb2: An enhanced and web API enabled relational database for Structural Virology", *Nucl. Acids Res.,* 37:D436-442 (2009).

Castanier, C et al., "Mitochondrial dynamics regulate the RIG-I-like receptor antiviral pathway," *EMBO Rep.,* 11(2):133-138 (2010).

Chapuis, F et al., "Differentiation of Human Dendritic Cells from Monocytes in vitro", *Eur. J. Immunol.,* 27(2):431-441 (1997).

Chen, T T et al., "Establishment and characterization of a cancer cell line derived from an aggressive childhood liver tumor", *Ped. Blood Cancer,* 53:1040-1047 (2009).

Cheng, B et al., "Development of optimized AAV3 serotype vectors: mechanism of high-efficiency transduction of human liver cancer cells", *Gene Ther.,* 19(4):375-384 (2011).

Chiorini, J A et al., "Cloning and characterization of adeno-associated virus type 5", *J. Virol.,* 73:1309-1319 (1999).

Chiorini, J A et al., "Cloning of adeno-associated virus type 4 (AAV4) and generation of recombinant AAV4 particles", *J. Virol.,* 71:6823-6833 (1997).

Cideciyan, A V et al., "Human gene therapy for RPE65 isomerase deficiency activates the retinoid cycle of vision but with slow rod kinetics," *Proc. Natl. Acad. Sci. USA,* 105(39):15112-15117 (2008).

Cohn, E F et al., "Efficient induction of immune tolerance to coagulation factor IX following direct intramuscular gene transfer," *J. Thromb. Haemost.,* 5(6):1227-1236 (2007).

Cuzzocrea, S et al., "Pyrrolidine dithiocarbamate attenuates the development of acute and chronic inflammation," *Br. J. Pharmacol.,* 135(2):496-510 (2002).

Dai, Y and Siemann D W, "BMS-777607, a Small-Molecule Met Kinase Inhibitor, Suppresses Hepatocyte Growth Factor-Stimulated Prostate Cancer Metastatic Phenotype In vitro", *Molec. Cancer Therapeut.,* 9:1554-1561 (2010).

Daya, S and Berns, K I "Gene therapy using adeno-associated virus vectors," *Clin. Microbiol. Rev.,* 21(4):583-593 (2008).

Dean, J et al., "Role of cyclic AMP-dependent kinase response element-binding protein in recombinant adeno-associated virus-mediated transduction of heart muscle cells," *Hum. Gene Ther.,* 20(9):1005-1012 (2009).

Dejardin, E "The alternative NF-kappaB pathway from biochemistry to biology: pitfalls and promises for future drug development," *Biochem. Pharmacol.,* 72(9):1161-1179 (2006).

den Brok, M H et al., "Dendritic Cells: Tools and Targets for Antitumor Vaccination", *Exp. Rev. Vaccines,* 4(5):699-710 (2005).

Ding, W et al., "Intracellular Trafficking of Adeno-Associated Viral Vectors", *Gene Ther.,* 12:873-880 (2005).

DiPaolo, N C et al., "Virus binding to a plasma membrane receptor triggers interleukin-1 alpha-mediated proinflammatory macrophage response in vivo," *Immunity,* 31(1): 110-121 (2009).

DiPrimio, N et al., "Surface Loop Dynamics in Adeno-Associated Virus Capsid Assembly", *J. Virol.,* 82(11): 5178-5189 (2008).

Dobrzynski, E et al., "Induction of antigen-specific CD4+ T-cell anergy and deletion by in vivo viral gene transfer," *Blood,* 104(4):969-977 (2004).

Douar, A M et al., "Intracellular Trafficking of Adeno-Associated Virus Vectors: Routing to the Late Endosomal Compartment and Proteasome Degradation", *J. Virol.,* 75:1824-1833 (2001).

Duan D et al., "Endosomal Processing Limits Gene Transfer to Polarized Airway Epithelia by Adeno-Associated Virus", J. Clin. Invest., 105:1573-1587 (2000).

Eisold, S et al., "Induction of an Antitumoral Immune Response by Wild-Type Adeno-Associated Virus Type 2 in an in vivo model of pancreatic carcinoma", *Pancreas,* 35(1):63-72 (2007).

Emsley, P and Cowtan K, "Coot: Model-Building Tools for Molecular Graphics", *Acta Crystallogr. D. Biol. Crystallogr.,* 60:2126-2132 (2004).

Ferrari, F K et al., "Second-Strand Synthesis is a Rate-Limiting Step for Efficient Transduction by Recombinant Adeno-Associated Virus Vectors", *J. Virol.,* 70:3227-3234 (1996).

Figdor, C G et al., "Dendritic Cell Immunotherapy: Mapping the Way", *Nat. Med.,* 10(5):475-480 (2004).

Finn, J D et al., "Proteasome inhibitors decrease AAV2 capsid derived peptide epitope presentation on MHC class I following transduction," *Mol. Ther.,* 18(1):135-142 (2010).

Fisher, K J et al., "Transduction with Recombinant Adeno-Associated Virus for Gene Therapy is Limited by Leading-Strand Synthesis," *J. Virol.,* 70:520-532 (1996).

Flotte, T R et al., "Phase 2 Clinical Trial of a Recombinant Adeno-Associated Viral Vector Expressing Alpha1-Antitrypsin: Interim Results", *Hum Gene Ther;* 22:1239-1247 (2012).

Gao, G P et al., "Novel Adeno-Associated Viruses from Rhesus Monkeys as Vectors for Human Gene Therapy", *Proc. Natl. Acad. Sci. USA,* 99:11854-11859 (2002).

Gao, G P et al., "Adeno-Associated Viruses Undergo Substantial Evolution in Primates During Natural Infections", *Proc Natl Acad of Sci USA;* 100(10):6081-6086 (2003).

Gao, G P et al., "Clades of Adeno-Associated Viruses are Widely Disseminated in Human Tissues", *J. Virol.,* 78:6381-6388 (2004).

Gilmore, T D "Introduction to NF-κB: players, pathways, perspectives," *Oncogene,* 25(51):6680-6684 (2006).

Girod, A et al., "Genetic Capsid Modifications Allow Efficient Re-Targeting of Adeno-Associated Virus Type 2", *Nature Med.,* 5(12):1438 (1999).

Glushakova, L G et al., "AAV3-Mediated Transfer and Expression of the Pyruvate Dehydrogenase E1 Alpha Subunit Gene Causes Metabolic Remodeling and Apoptosis of Human Liver Cancer Cells", *Molec. Genet. Metabol.,* 98:289-299 (2009).

Gotoh, A and Ohyashiki, K "Role of bortezomib in the treatment of multiple myeloma," *Nippon Rinsho,* 65(12): 2309-2314 (2007).

Gourzi, P et al., "Viral induction of AID is independent of the interferon and the Toll-like receptor signaling pathways but requires NF-κB," *J. Exp. Med.,* 204(2):259-265 (2007).

Govindasamy, L et al., "Structurally Mapping the Diverse Phenotype of Adeno-Associated Virus Serotype 4", *J. Virol.*, 80:11556-11570 (2006).

Gray, S J et al., "Directed evolution of a novel adeno-associated virus (AAV) vector that crosses the seizure-compromised blood-brain barrier (BBB)," *Mol. Ther.*, 18(3):570-578 (2010).

Guo, F et al., "Lack of nuclear factor-κB2/p100 causes a RelB-dependent block in early B lymphopoiesis," *Blood*, 112(3):551-559 (2008).

Habib, A A et al., "The epidermal growth factor receptor engages receptor interacting protein and nuclear factor-kappa B (NF-κB)-inducing kinase to activate NF-κB. Identification of a novel receptor-tyrosine kinase signalosome," *J. Biol. Chem.*, 276(12):8865-8874 (2001).

Hansen, J et al., "Adeno-Associated Virus Type 2-Mediated Gene Transfer: Altered Endocytic Processing Enhances Transduction Efficiency in Murine Fibroblasts", *J. Virol.*, 75:4080-4090 (2001).

Hansen, J et al., "Impaired Intracellular Trafficking of Adeno-Associated Virus Type 2 Vectors Limits Efficient Transduction of Murine Fibroblasts", *J. Virol.*, 74:992-996 (2000).

Harbison, C E et al., "The Parvovirus Capsid Odyssey: from the Cell Surface to the Nucleus", *Trends Microbiol.*, 16:208-214 (2008).

Harley, C B, "Telomerase and Cancer Therapeutics", *Nat. Rev. Cancer*, 8(3):167-179 (2008).

Hayden, M S and Ghosh, S, "Signaling to NF-kB," *Genes Develop.*, 18(18):2195-2224 (2004).

Heiser, A et al., "Autologous Dendritic Cells Transfected with Prostate-Specific Antigen RNA Stimulate CTL Responses Against Metastatic Prostate Tumors", *J. Clin. Invest.*, 109(3):409-417 (2002).

High, K A and Aubourg, P, "rAAV Human Trial Experience", *Methods Mol. Biol.*, 807:429-457 (2011).

Hiscott, J et al., "Convergence of the NF-κB and interferon signaling pathways in the regulation of antiviral defense and apoptosis," *Ann. N.Y. Acad. Sci.*, 1010:237-248 (2003).

Hiscott, J et al., "Manipulation of the nuclear factor-kappaB pathway and the innate immune response by viruses," *Oncogene*, 25(51):6844-6867 (2006).

Jayandharan, G R et al., "Activation of the NF-kB Pathway by Adeno-Associated Virus (AAV) Vectors and Its Implications in Immune Response and Gene Therapy. *Proc Natl Acad Sci USA*, 108(9):3743-3748 (2011).

Jiang, H et al., "Effects of transient immunosuppression on adenoassociated, virus-mediated, liver-directed gene transfer in rhesus macaques and implications for human gene therapy," *Blood*, 108(10):3321-3328 (2006).

Kashiwakura, Y et al., "Hepatocyte Growth Factor Receptor is a Coreceptor for Adeno-Associated Virus Type 2 Infection", *J. Virol.*, 79:609-614 (2005).

Keen-Rhinehart, E et al., "AAV-mediated leptin receptor installation improves energy balance and the reproductive status of obese female Koletsky rats," *Peptides*, 26(12): 2567-2578 (2005).

Kohlbrenner, E et al., "Successful Production of Pseudotyped rAAV Vectors Using a Modified Baculovirus Expression System", *Mol. Ther.*, 12:1217-1225 (2005).

Kota, J et al., "Therapeutic MicroRNA Delivery Suppresses Tumorigenesis in a Murine Liver Cancer Model", *Cell*, 137:1005-1017 (2009).

Kube, D M and Srivastava, A "Quantitative DNA slot blot analysis: inhibition of DNA binding to membranes by magnesium ions," *Nucl. Acids Res.*, 25(16):3375-3376 (1997).

Kumar, N et al., "NF-κB signaling differentially regulates influenza virus RNA synthesis," *J. Virol.*, 82(20):9880-9889 (2008).

Levy, H C et al., "Heparin Binding Induces Conformational Changes in Adeno-Associated Virus Serotype 2", *J. Struct. Biol.*, 165(3):146-156 (2009).

Li, C et al., "Cellular immune response to cryptic epitopes during therapeutic gene transfer," *Proc. Natl. Acad. Sci. USA*, 106(26):10770-10774 (2009).

Li, C et al., "Single Amino Acid Modification of Adeno-Associated Virus Capsid Changes Transduction and Humoral Immune Profiles", *J. Virol.*, 86:7752-7759 (2012).

Li, Q and Verma, I M, "NF-κB regulation in the immune system," *Nat. Rev. Immunol.*, 2(10):725-734 (2002).

Lich, J D et al., "Monarch-1 suppresses non-canonical NF-kappaB activation and p52-dependent chemokine expression in monocytes," *J. Immunol.*, 178(3):1256-1260 (2007).

Lind, E F et al., "Dendritic cells require the NF-κB2 pathway for cross-presentation of soluble antigens," *J. Immunol.*, 181(1):354-363 (2008).

Ling, C et al., "Human Hepatocyte Growth Factor Receptor is a Cellular Co-Receptor for AAV3", *Hum. Gene Ther.*, 21:1741-1747 (2010).

Ling, C Q et al., "Inhibitory Effect of Recombinant Adenovirus Carrying Melittin Gene on Hepatocellular Carcinoma", *Ann. Oncol.*, 16:109-115 (2005).

Liu, M A, "Immunologic Basis of Vaccine Vectors", *Immunity*, 33(4):504-515 (2010).

Liu, S et al., "Melittin prevents liver cancer cell metastasis through inhibition of the Rac1-dependent pathway", *Hepatology* (Baltimore, Md.), 47:1964-1973 (2008).

Liu, X et al., "Targeting the c-MET Signaling Pathway for Cancer Therapy", *Exp. Opin. Invest. Drugs*, 17:997-1011 (2008).

Liu, Y L et al., "Optimized production of high-titer recombinant adeno-associated virus in roller bottles," *Biotechniques*, 34(1):184-189 (2003).

Lizundia, R et al., "Host species-specific usage of the TLR4-LPS receptor complex," *Innate Immun.*, 14(4):223-231 (2008).

Lochrie, M A et al., "Mutations on the External Surfaces of Adeno-Associated Virus Type 2 Capsids that Affect Transduction and Neutralization", *J. Virol.*, 80(2):821-834 (2006).

LoDuca, P A et al., "Hepatic gene transfer as a means of tolerance induction to transgene products," *Curr. Gene Ther.*, 9(2):104-114 (2009).

Loiarro, M et al., "Peptide-mediated interference of TIR domain dimerization in MyD88 inhibits interleukin-1-dependent activation of NF-κB," *J. Biol. Chem.*, 280(16):15809-15814 (2005).

Ma, H et al., "Oral Adeno-Associated Virus-sTRAIL Gene Therapy Suppresses Human Hepatocellular Carcinoma Growth in Mice", *Hepatology* (Baltimore, Md.), 42:1355-1363 (2005).

Madsen, D et al., "AAV-2 induces cell mediated immune responses directed against multiple epitopes of the capsid protein VP1," *J. Gen. Virol.*, 90(11):2622-2633 (2009).

Maguire, A M et al., "Safety and efficacy of gene transfer for Leber's congenital amaurosis," *N. Engl. J. Med.*, 358(21):2240-2248 (2008).

Mah, C et al., "Adeno-Associated Virus Type 2-Mediated Gene Transfer: Role of Epidermal Growth Factor Receptor Protein Tyrosine Kinase in Transgene Expression", *J. Virol.*, 72:9835-9843 (1998).

Mahadevan, M et al., "Generation of Robust Cytotoxic T Lymphocytes Against Prostate Specific Antigen by Transduction of Dendritic Cells Using Protein and Recombinant Adeno-Associated Virus", *Cancer Immunol. Immunother.*, 56(10):1615-1624 (2007).

Malecki, M et al., "Recombinant Adeno-Associated Virus Derived Vectors (rAAV2) Efficiently Transduce Ovarian and Hepatocellular Carcinoma Cells—Implications for Cancer Gene Therapy", *Acta Poloniae Pharmaceutica*, 66:93-99 (2009).

Manno, C S et al., "Successful transduction of liver in hemophilia by AAV-Factor IX and limitations imposed by the host immune response," *Nat. Med.*, 12(3):342-347 (2006).

Markusic, D M et al., "High-efficiency transduction and correction of murine hemophilia B using AAV2 vectors devoid of multiple surface-exposed tyrosines," *Mol. Ther.*, 18(12):2048-2056 (2010).

Martin, E et al., "Antigen-specific suppression of a primed immune response by dendritic cells mediated by regulatory T cells secreting interleukin-10," *Immunity*, 18(1): 155-167 (2003).

Mattis A E et al., "Analyzing Cytotoxic T Lymphocyte Activity: A Simple and Reliable Flow Cytometry-Based Assay", *J. Immunol. Methods*, 204(2):135-142 (1997).

Mays, L E et al., "Adeno-associated virus capsid structure drives CD4-dependent CD8+ T cell response to vector encoded proteins," *J. Immunol.*, 182(10):6051-6060 (2009).

McCarty, D M et al., "Integration of Adeno-Associated Virus (AAV) and Recombinant AAV Vectors", *Annu. Rev. Genet.*, 38:819-845 (2004).

McCarty, D M et al., "Adeno-Associated Virus Terminal Repeat (TR) Mutant Generates Self-Complementary Vectors to Overcome the Rate-Limiting Step to Transduction In Vivo", *Gene Ther.*, 10:2112-2118 (2003).

Mendell, J R et al., "Dystrophin immunity in Duchenne's Muscular Dystrophy", *N. Engl. J. Med.*, 363:1429-1437 (2010).

Mendell, J R et al., "Gene Therapy for Muscular Dystrophy: Lessons Learned and Path forward", *Neurosci. Lett.*, 12:341-355 (2012).

Mineva, N D et al., "CD40 ligand-mediated activation of the de novo RelB NF-κB synthesis pathway in transformed B cells promotes rescue from apoptosis," *J. Biol. Chem.*, 282(24): 17475-17485 (2007).

Mingozzi, F and High K A, "Therapeutic In Vivo Gene Transfer for Genetic Disease Using AAV: Progress and Challenges", *Nat. Rev. Genet.*, 12:341-355 (2011).

Mingozzi, F and High, K A, "Immune responses to AAV in clinical trials," *Curr. Gene Ther.*, 7(5):316-324 (2007).

Mingozzi, F et al., "CD8(+) T-cell responses to adeno-associated virus capsid in humans," *Nat. Med.*, 13(4):419-422 (2007).

Mueller, C and Flotte, T R, "Clinical Gene Therapy Using Recombinant Adeno-Associated Virus Vectors", *Gene Ther.*, 15(11):858-863 (2008).

Muramatsu S et al., "Nucleotide Sequencing and Generation of an Infectious Clone of Adeno-Associated Virus 3", *Virology*, 221:208-217 (1996).

Muruve, D A et al., "The inflammasome recognizes cytosolic microbial and host DNA and triggers an innate immune response," *Nature*, 452(7183):103-107 (2008).

Muzyczka, N and Warrington, K H, "Custom Adeno-Associated Virus Capsids: The Next Generation of Recombinant Vectors with Novel Tropism", *Hum. Gene Ther.*, 16:408-416 (2005).

Muzyczka, N, "Use of Adeno-Associated Virus as a General Transduction Vector for Mammalian Cells", *Curr. Top. Microbiol. Immunol.*, 158:97-129 (1992).

Nakabayashi, H et al., "Growth of Human Hepatoma Cells Lines with Differentiated Functions in Chemically Defined Medium", *Cancer Res.*, 42:3858-3863 (1982).

Nakahara, T et al., "Differential Role of MAPK Signaling in Human Dendritic Cell Maturation and Th1/Th2 Engagement", *J. Dermatol. Sci.*, 42(1):1-11 (2006).

Nakahara, T et al., "Role of c-Jun N-Terminal Kinase on Lipopolysaccharide Induced Maturation of Human Monocyte-Derived Dendritic Cells", *Int. Immunol.*, 16(12):1701-1709 (2004).

Nam, H J et al., "Structural Studies of Adeno-Associated Virus Serotype 8 Capsid Transitions Associated with Endosomal Trafficking", *J. Virol.*, 85:11791-11799 (2011).

Nathwani, A C et al., "Self-complementary adeno-associated virus vectors containing a novel liver-specific human factor IX expression cassette enable highly efficient transduction of murine and nonhuman primate liver," *Blood*, 107(7):2653-2661 (2006).

Naumer, M et al., "Properties of the Adeno-Associated Virus Assembly-Activating Protein", *J. Virol.*, 86:13038-13048 (2012).

Nguyen, L et al., "Association of the Multisubstrate Docking Protein Gab1 with the Hepatocyte Growth Factor Receptor Requires a Functional Grb2 Binding Site Involving Tyrosine 1356", *J. Biol. Chem.*, 272:20811-20819 (1997).

Niemeyer, G P et al., "Long-term correction of inhibitor-prone hemophilia B dogs treated with liver-directed AAV2-mediated factor IX gene therapy," *Blood*, 113(4): 797-806 (2009).

Nonnenmacher, M and Weber T, "Intracellular Transport of Recombinant Adeno-Associated Virus Vectors", *Gene Ther.*, 19:649-658 (2012).

Okumura, A et al., "Interaction between Ebola virus glycoprotein and host toll-like receptor 4 leads to induction of proinflammatory cytokines and SOCS1," *J. Virol.*, 84(1): 27-33 (2010).

O'Neill, D W and Bhardwaj, N, "Exploiting Dendritic Cells for Active Immunotherapy of Cancer and Chronic Infections", *Mol. Biotechnol.*, 36(2):131-141 (2007).

Opie, S R et al., "Identification of Amino Acid Residues in the Capsid Proteins of Adeno-Associated Virus Type 2 that Contribute to Heparan Sulfate Proteoglycan Binding", *J. Virol.*, 77:6995-7006 (2003).

Owen, R T et al. "Gene therapy for pyruvate dehydrogenase E1alpha deficiency using recombinant adeno-associated virus 2 (rAAV2) vectors," *Mol. Ther.*, 6(3):394-399 (2002).

Palucka, K et al., "Recent Developments in Cancer Vaccines", *J. Immunol.*, 186(3):1325-1331 (2011).

Pearson and Lipman, "Improved tools for biological sequence comparison," *Proc. Natl. Acad. Sci. USA*, 85(8): 2444-8 (1988).

Peng, D et al., "Transduction of Hepatocellular Carcinoma (HCC) Using Recombinant Adeno-Associated Virus (rAAV): In vitro and In vivo effects of genotoxic agents", *J. Hepatol.*, 32:975-985 (2000).

Petrs-Silva, H et al., "High-Efficiency Transduction of the Mouse Retina by Tyrosine-Mutant AAV Serotype Vectors", *Mol. Ther.*, 17:463-471 (2009).

Pierce, J W et al., "Novel inhibitors of cytokine-induced IκBα phosphorylation and endothelial cell adhesion molecule expression show anti-inflammatory effects in vivo," *J. Biol. Chem.*, 272(34):21096-21103 (1997).

Ponnazhagan, S et al., "Adeno-Associated Virus Type 2-Mediated Transduction of Human Monocyte-Derived Dendritic Cells: Implications for Ex Vivo Immunotherapy", *J. Virol.*, 75(19):9493-501 (2001).

Qiao, C et al., "AAV6 Capsid Tyrosine to Phenylalanine Mutations Improve Gene Transfer to Skeletal Muscle", *Hum. Gene Ther.*, 21:1343-1348 (2010).

Qing, G et al., "Stabilization of basally translated NF-kappaB-inducing kinase (NIK) protein functions as a molecular switch of processing of NF-kappaB2 p100," *J. Biol. Chem.*, 280(49):40578-40582 (2005).

Qing, K et al., "Adeno-Associated Virus Type 2-Mediated Gene Transfer: Role of Cellular FKBP52 Protein in Transgene Expression", *J. Virol.*, 75:8968-8976 (2001).

Qing, K et al., "Human Fibroblast Growth Factor Receptor 1 is a Co-Receptor for Infection by Adeno-Associated Virus 2", *Nature Med.*, 5:71-77 (1999).

Qing, K et al., "Role of tyrosine phosphorylation of a cellular protein in adeno-associated virus 2-mediated transgene expression," *Proc. Natl. Acad. Sci. USA*, 94(20): 10879-10884 (1997).

Robert-Guroff M, "Replicating and Non-Replicating Viral Vectors for Vaccine Development", *Curr. Opin. Biotechnol.*, 18(6):546-556 (2007).

Ross, C J et al., "Correction of feline lipoprotein lipase deficiency with adeno-associated virus serotype 1-mediated gene transfer of the lipoprotein lipase S447X beneficial mutation," *Hum. Gene Ther.*, 17(5):487-499 (2006).

Rutledge, E A et al., "Infectious Clones and Vectors Derived from Adeno-Associated Virus (AAV) Serotypes Other Than AAV Type 2", *J. Virol.*, 72:309-319 (1998).

Sanlioglu, S et al., "Endocytosis and Nuclear Trafficking of Adeno-Associated Virus Type 2 are Controlled by Rac1 and Phosphatidylinositol-3 Kinase Activation", *J. Virol.*, 74:9184-9196 (2000).

Scallan, C D et al., "Sustained phenotypic correction of canine hemophilia A using an adeno-associated viral vector," *Blood*, 102(6):2031-2037 (2003).

Schroeder, G M et al., "Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily", *J. Med. Chem.*, 52:1251-1254 (2009).

Shin, O et al., "Effective Transduction by Self-Complementary Adeno-Associated Viruses of Human Dendritic Cells with No Alteration of Their Natural Characteristics", *J. Gene Med.*, 10(7):762-769 (2008).

Snyder, R O et al., "Correction of hemophilia B in canine and murine models using recombinant adeno-associated viral vectors," *Nature Med.*, 5(1):64-70 (1999).

Song, S et al., "Recombinant adeno-associated virus-mediated alpha-1 antitrypsin gene therapy prevents type I diabetes in NOD mice," *Gene Ther.*, 11(2):181-186 (2004).

Srivastava, A, "Adeno-Associated Virus-Mediated Gene Transfer", *J. Cell. Biochem.*, 105(1):17-24 (2008).

Su, H et al., "Adeno-Associated Viral-Mediated Gene Transfer to Hepatoma: Thymidine Kinase/Interleukin 2 is More Effective in Tumor Killing in Non-Ganciclovir (GCV)-Treated than in GCV-Treated Animals", *Mol. Ther.*, 1:509-515 (2000).

Su, H et al., "Selective Killing of AFP-Positive Hepatocellular Carcinoma Cells by Adeno-Associated Virus Transfer of the Herpes Simplex Virus Thymidine Kinase Gene", *Hum. Gene Ther.*, 7:463-470 (1996).

Summerford C et al., "AlphaVbeta5 Integrin: A Co-Receptor for Adeno-Associated Virus Type 2 Infection", *Nature Med.*, 5:78-82 (1999).

Summerford, C and Samulski, R J, "Membrane-Associated Heparan Sulfate Proteoglycan is a Receptor for Adeno-Associated Virus Type 2 Virions", *J. Virol.*, 72:1438-1445 (1998).

Tacken, P J et al., "Dendritic-Cell Immunotherapy: From ex vivo Loading to in vivo Targeting", *Nat. Rev. Immunol.*, 7(10):790-802 (2007).

Tang, Z Y, "Hepatocellular Carcinoma Surgery—Review of the Past and Prospects for the 21st Century", *J. Surg. Oncol.*, 91:95-96 (2005).

Taylor, J and Ussher, J E, "Optimized Transduction of Human Monocyte-Derived Dendritic Cells by Recombinant Adeno-Associated Virus Serotype 6 (rAAV6)", *Hum. Gene Ther.*, 21:1675-1686 (2010).

Thomas, C E et al., "Rapid Uncoating of Vector Genomes is the Key to Efficient Liver Transduction with Pseudotyped Adeno-Associated Virus Vectors", *J. Virol.*, 78:3110-3122 (2004).

Tse, L Y et al., "Adeno-Associated Virus-Mediated Expression of Kallistatin Suppresses Local and Remote Hepatocellular Carcinomas", *J. Gene Med.*, 10:508-517 (2008).

Vandenberghe, L H and Wilson, J M "AAV as an immunogen," *Curr. Gene Ther.*, 7(5):325-333 (2007).

Vandenberghe, L H et al., "Tailoring the AAV vector capsid for gene therapy", *Gene Ther.*, 16(3):311-319 (2009).

Veron P et al., "Major Subsets of Human Dendritic Cells Are Efficiently Transduced by Self-Complementary Adeno-Associated Virus Vectors 1 and 2", *J. Virol.*, 81(10):5385-5394 (2007).

Wang, C et al., "Melittin, a Major Component of Bee Venom, Sensitizes Human Hepatocellular Carcinoma Cells to Tumor Necrosis Factor-Related Apoptosis-Inducing Ligand (TRAIL)-Induced Apoptosis by Activating CaMKII-TAK1-JNK/p38 and Inhibiting IkappaBalpha Kinase-NFkappaB", *J. Biol. Chem.*, 284:3804-3813 (2009).

Wang, L et al., "The pleiotropic effects of natural AAV infections on liver-directed gene transfer in macaques," *Mol. Ther.*, 18(1):126-134 (2010).

Wang, W and Malcolm, B A, "Two-Stage PCR Protocol Allowing Introduction of Multiple Mutations, Deletions and Insertions Using QuikChange Site-Directed Mutagenesis", *Biotechniques;* 26(4):680-682 (1999).

Wang, Y et al., "Potent antitumor effect of TRAIL mediated by a novel adeno-associated viral vector targeting to telomerase activity for human hepatocellular carcinoma", *J. Gene Med.*, 10:518-526 (2008).

Wang, Y et al., "The Efficacy of Combination Therapy Using Adeno-Associated Virus-TRAIL Targeting to Telomerase Activity and Cisplatin in a Mice Model of Hepatocellular Carcinoma", *J. Cancer Res. Clin. Oncol.*, 136:1827-1837 (2010).

Wang, Z et al., "Rapid and Highly Efficient Transduction by Double-Stranded Adeno-Associated Virus Vectors in vitro and in vivo", *Gene Ther.*, 10(26):2105-2111 (2003).

Wu, J et al., "Self-complementary recombinant adeno-associated viral vectors: packaging capacity and the role of Rep proteins in vector purity", *Hum. Gene Ther.*, 18:171-182 (2007).

Wu, P et al., "Mutational Analysis of the Adeno-Associated Virus Type 2 (AAV2) Capsid Gene and Construction of AAV2 Vectors with Altered Tropism", *J. Virol.*, 74(18): 8635-47 (2000).

Wu, Z et al., "Adeno-associated virus serotypes: vector toolkit for human gene therapy", *Mol. Ther.*, 14(3):316-327 (2006).

Wu, Z et al., "Single Amino Acid Changes Can Influence Titer, Heparin Binding, and Tissue Tropism in Different Adeno-Associated Virus Serotypes", *J. Virol.*, 80(22): 11393-11397 (2006).

Wu, Z H and Miyamoto, S "Induction of a pro-apoptotic ATM-NF-kappaB pathway and its repression by ATR in response to replication stress," *EMBO J.*, 27:1963-1973 (2008).

Xiao, C and Rossmann, M G, "Interpretation of electron density with stereographic roadmap projections", *J. Struct. Biol.*, 158:182-187 (2007).

Xiao, W et al., "Adenovirus-facilitated nuclear translocation of adeno-associated virus type 2", *J. Virol.*, 76:11505-11517 (2002).

Xie, Q et al, "The Atomic Structure of Adeno-Associated Virus (AAV-2), A Vector for Human Gene Therapy", *Proc Natl Acad Sci USA*; 99(16):10405-10410 (2002).

Yan, Z et al., "Ubiquitination of both adeno-associated virus type 2 and 5 capsid Proteins affects the transduction efficiency of recombinant vectors", *J. Virol.*, 76:2043-2053 (2002).

Yanagawa, Y and Onoe, K "Distinct regulation of CD40-mediated interleukin-6 and interleukin-12 productions via mitogen-activated protein kinase and nuclear factor kappaB-inducing kinase in mature dendritic cells," *Immunology*, 117(4):526-535 (2006).

Yu, Y et al. rAAV/Her-2/neu loading of dendritic cells for a potent cellular-mediated MHC class I restricted immune response against ovarian cancer," *Viral Immunol.*, 21(4): 435-42 (2008).

Zaiss, A K and Muruve, D A "Immune responses to adeno-associated virus vectors," *Curr. Gene Ther.*, 5(3):323-331 (2005).

Zaiss, A K and Muruve, D A "Immunity to adeno-associated virus vectors in animals and humans: a continued challenge," *Gene Ther.*, 15(11):808-816 (2008).

Zaiss, A K et al., "Complement is an essential component of the immune response to adeno-associated virus vectors," *J. Virol.*, 82(6):2727-2740 (2008).

Zaiss, A K et al., "Differential activation of innate immune responses by adenovirus and adeno-associated virus vectors," *J. Virol.*, 76(9):4580-4590 (2002).

Zhang, C et al., "Effects of Melittin on Expressions of Mitochondria Membrane Protein 7A6, Cell Apoptosis-Related Gene Products Fas and Fas Ligand in Hepatocarcinoma Cells]", *J. Chinese Integrat. Med.*, 5:559-563 (2007).

Zhang, Y et al., "AAV-Mediated TRAIL Gene Expression Driven by hTERT Promoter Suppressed Human Hepatocellular Carcinoma Growth in Mice", *Life Sci.*, 82:1154-1161 (2008).

Zhao, W et al., "Role of Cellular FKBP52 Protein in Intracellular Trafficking of Recombinant Adeno-Associated Virus 2 Vectors", *Virology*, 353:283-293 (2006).

Zhong, L et al., "Heat-Shock Treatment-Mediated Increase in Transduction by Recombinant Adeno-Associated Virus 2 Vectors is Independent of the Cellular Heat-Shock Protein 90", *J. Biol. Chem.*, 279:12714-12723 (2004).

Zhong, L et al., "A Dual Role of EGFR Protein Tyrosine Kinase Signaling in Ubiquitination of AAV2 Capsids and Viral Second-Strand DNA Synthesis", *Mol. Ther.*, 15(7): 1323-30 (2007).

Zhong, L et al., "Impaired Nuclear Transport and Uncoating Limit Recombinant Adeno-Associated Virus 2 Vector-Mediated Transduction of Primary Murine Hematopoietic Cells", *Hum. Gene Ther.*, 15:1207-1218 (2004).

Zhong, L et al., "Improved Transduction of Primary Murine Hepatocytes by Recombinant Adeno-Associated Virus 2 Vectors In Vivo", *Gene Ther.*, 11:1165-1169 (2004).

Zhong, L et al., "Next Generation of Adeno-Associated Virus 2 Vectors: Point Mutations in Tyrosines Lead to High-Efficiency Transduction at Lower Doses", *Proc. Natl. Acad. Sci. USA*, 105(22):7827-7832 (2008).

Zhong, L et al., "Single-Polarity Recombinant Adeno-Associated Virus 2 Vector-Mediated Transgene Expression In vitro and In Vivo: Mechanism of Transduction," *Mol. Ther.*, 16:290-295 (2008).

Zhong, L et al., "Tyrosine-phosphorylation of AAV2 vectors and its consequences on viral intracellular trafficking and transgene expression", *Virology*, 381:194-202 (2008).

Zhu, J et al., "The TLR9-MyD88 pathway is critical for adaptive immune responses to adeno-associated virus gene therapy vectors in mice," *J. Clin. Invest.*, 119(8): 2388-2398 (2009).

Zincarelli, C et al., "Analysis of AAV serotypes 1-9 mediated gene expression and Tropism in Mice After Systemic Injection", *Mol. Ther.*, 16:1073-1080 (2008).

Zincarelli, C et al., "Comparative cardiac gene delivery of adeno-associated virus serotypes 1-9 reveals that AAV6 mediates the most efficient transduction in mouse heart," *Clin. Translat. Sci.*, 3:81-89 (2008).

Zolotukhin, S et al., "Production and purification of serotype 1, 2, and 5 recombinant adeno-associated viral vectors", *Methods*, 28(2):158-67 (2002).

It should be understood that the examples and embodiments described herein are for illustrative purposes only and that various modifications or changes in light thereof will be suggested to persons skilled in the art and are to be included within the spirit and purview of this application and the scope of the appended claims.

All references, including publications, patent applications and patents, cited herein are hereby incorporated by reference to the same extent as if each reference was individually and specifically indicated to be incorporated by reference and was set forth in its entirety herein.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order, unless otherwise indicated herein, or otherwise clearly contradicted by context.

The use of any and all examples, or exemplary language (e.g., "such as") provided herein, is intended merely to better illustrate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically and/or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A modified AAV VP3 capsid protein, comprising: a non-tyrosine amino acid residue at one or more positions corresponding to Y705 and Y731 of the wild-type AAV6 capsid protein as set forth in SEQ ID NO:6.

2. The modified AAV VP3 capsid protein of claim 1, wherein the modified AAV VP3 capsid protein is a modified AAV6 capsid protein.

3. The modified AAV VP3 capsid protein of claim 1, wherein the non-tyrosine amino acid residue is selected from the group consisting of serine (S), phenylalanine (F), valine (V), histidine (H), alanine (A), leucine (L) aspartic acid (D), asparagine (N), glutamic acid (E), arginine (R), and isoleucine (I).

4. A composition comprising:
(I)(a) a modified AAV VP3 capsid protein that comprises: a non-tyrosine amino acid residue at one or more positions corresponding to Y705 and Y731 of the wild-type AAV6 capsid protein as set forth in SEQ ID NO:6;
(b) a nucleic acid segment that encodes the protein of (a), or
(c) a viral particle that comprises the protein of (a); and
(II) a pharmaceutically-acceptable buffer, diluent, or excipient.

5. The composition of claim 4, comprised within a kit for diagnosing, preventing, treating or ameliorating one or more symptoms of a mammalian disease, injury, disorder, trauma or dysfunction, including, but not limited to sickle cell disease, β-thalassemia, or a combination thereof.

6. The modified AAV VP3 capsid protein of claim 2, wherein the non-tyrosine amino acid residue is phenylalanine (F).

7. The modified AAV VP3 capsid protein of claim 3, wherein the non-tyrosine amino acid residue is phenylalanine (F).

8. The composition of claim 4, wherein the non-tyrosine amino acid residue is phenylalanine (F).

9. The composition of claim 4, wherein the modified AAV VP3 capsid protein is a modified AAV6 capsid protein.

10. The composition of claim 9, wherein the non-tyrosine amino acid residue is phenylalanine (F).

* * * * *

UNITED STATES PATENT AND TRADEMARK OFFICE
CERTIFICATE OF CORRECTION

PATENT NO. : 9,920,097 B2
APPLICATION NO. : 13/899481
DATED : March 20, 2018
INVENTOR(S) : Li Zhong et al.

Page 1 of 1

It is certified that error appears in the above-identified patent and that said Letters Patent is hereby corrected as shown below:

In the Specification

At Column 1, Lines 27-30, the text:
This invention was made with government support under Contract No. P01 DK-058327 and R01 HL-097088 awarded by the National Institute of Health. The government has certain rights in the invention.

Should be replaced with the text:
--The invention was made with government support under Grant Nos. DK058327, HL051811, HL059412, HL078810, DK062302, EB002073, GM082946, HL065570, HL076901, and HL097088 awarded by the National Institutes of Health. The government has certain rights in the invention.--

Signed and Sealed this
Twelfth Day of March, 2019

Andrei Iancu
*Director of the United States Patent and Trademark Office*